(12) United States Patent
Hingwing et al.

(10) Patent No.: US 11,221,332 B2
(45) Date of Patent: Jan. 11, 2022

(54) MICROFLUIDIC DEVICE

(71) Applicant: TEL-ARRAY DIAGNOSTICS INC., Vancouver (CA)

(72) Inventors: Kyla Rose Hingwing, Vancouver (CA); Xiaoqing Shi, Vancouver (CA); Danny Chan, Vancouver (CA); Hong Zhang, Vancouver (CA); Kenneth Maccallum, Victoria (CA); Gene Wey, Victoria (CA); Aaron Philippsen, Victoria (CA); Ron L. Bardell, St Louis Park, MN (US)

(73) Assignee: TEL-ARRAY DIAGNOSTICS INC., Vancouver (CA)

( * ) Notice: Subject to any disclaimer, the term of this patent is extended or adjusted under 35 U.S.C. 154(b) by 291 days.

(21) Appl. No.: 16/338,137

(22) PCT Filed: Sep. 30, 2017

(86) PCT No.: PCT/IB2017/056047
§ 371 (c)(1),
(2) Date: Mar. 29, 2019

(87) PCT Pub. No.: WO2018/060973
PCT Pub. Date: Apr. 5, 2018

(65) Prior Publication Data
US 2019/0331676 A1    Oct. 31, 2019

Related U.S. Application Data

(60) Provisional application No. 62/402,087, filed on Sep. 30, 2016.

(51) Int. Cl.
*G01N 33/543* (2006.01)
*B01L 3/00* (2006.01)
*B01J 19/00* (2006.01)

(52) U.S. Cl.
CPC .... *G01N 33/54366* (2013.01); *B01J 19/0046* (2013.01); *B01L 3/502707* (2013.01);
(Continued)

(58) Field of Classification Search
CPC .............. G01N 33/54366; G01N 33/48; B01J 19/0046; B01L 3/502707; B01L 3/502715;
(Continued)

(56) References Cited

U.S. PATENT DOCUMENTS

2004/0037739 A1* 2/2004 McNeely ................ B01L 9/527
422/417
2007/0166200 A1* 7/2007 Zhou ....................... F04B 43/14
422/400
(Continued)

FOREIGN PATENT DOCUMENTS

| GA | 2898477 A1 | 8/2014 |
|---|---|---|
| WO | 2002072264 A1 | 9/2002 |

(Continued)

OTHER PUBLICATIONS

Adam et al, "D-dimer antigen: current concepts and future prospects." Blood 113.13 (2009): 2878-2887.
(Continued)

*Primary Examiner* — Matthew D Krcha
*Assistant Examiner* — Sophia Y Lyle
(74) *Attorney, Agent, or Firm* — Leason Ellis LLP

(57) ABSTRACT

The present disclosure provides, in part, a microfluidic apparatus for detecting target molecules. More specifically, the present disclosure relates to a protein microarray-integrated microfluidic system for detecting target molecules.

19 Claims, 39 Drawing Sheets

(52) U.S. Cl.
CPC ... *B01L 3/502715* (2013.01); *B01L 2200/028* (2013.01); *B01L 2200/0631* (2013.01); *B01L 2200/0684* (2013.01); *B01L 2300/0636* (2013.01); *B01L 2300/0816* (2013.01)

(58) Field of Classification Search
CPC ....... B01L 2200/028; B01L 2200/0631; B01L 2200/0684; B01L 2300/0636; B01L 2300/0816; B01L 2200/10; C40B 60/12; C40B 30/04
See application file for complete search history.

(56) References Cited

U.S. PATENT DOCUMENTS

| | | | |
|---|---|---|---|
| 2008/0311585 A1* | 12/2008 | Gao | B01L 3/502738 435/6.19 |
| 2011/0201099 A1* | 8/2011 | Anderson | G01F 23/292 435/287.2 |
| 2012/0178091 A1* | 7/2012 | Glezer | B01L 7/525 435/6.12 |

FOREIGN PATENT DOCUMENTS

| | | | | |
|---|---|---|---|---|
| WO | WO-2007130549 A1 * | 11/2007 | | G01N 33/57449 |
| WO | WO2010040103 A1 | 4/2010 | | |
| WO | 2010118427 A1 | 10/2010 | | |
| WO | WO2010144683 A2 | 12/2010 | | |
| WO | WO2011094577 A2 | 8/2011 | | |
| WO | 2013106458 A2 | 7/2013 | | |
| WO | WO-2013106458 A2 * | 7/2013 | | B01L 3/50273 |
| WO | WO2015160863 A1 | 10/2015 | | |
| WO | 2016019701 A1 | 2/2016 | | |

OTHER PUBLICATIONS

Alexander et al. "Effect of age and cigarette smoking on carcinoembryonic antigen levels" Journal of American Medicine 235.18 (1976): 1975-1979.
Algarra et al. "Current analytical strategies for C-reactive protein quantification in blood." Clinica Chimica Acta 415 (2013): 1-9.
Arribas et al. "HER2 fragmentation and breast cancer stratification." Clinical Cancer Research 16.16 (2010): 4071-4073.
Ay et al. "D-dimer and prothrombin fragment 1+ 2 predict venous thromboembolism in patients with cancer: results from the Vienna Cancer and Thrombosis Study." Journal of Clinical Oncology 27.25 (2009): 4124-4129.
Beauchemin et al. "Carcinoembryonic antigen-related cell adhesion molecules (CEACAMs) in cancer progression and metastasis." Cancer and Metastasis Reviews 32.3-4 (2013): 643-671.
Begum et al. "CA 15-3 (Mucin-1) and physiological characteristics of breast cancer from Lahore, Pakistan." Asian Pac J Cancer Prev 13 (2012): 5257-61.
Burke. "The role of matrix metalloproteinase 7 in innate immunity." Immunobiology 209.1-2 (2004): 51-56.
Danysh et al. "The MUC1 ectodomain: a novel and efficient target for gold nanoparticle clustering and vapor nanobubble generation." Theranostics 2.8 (2012): 777.
Dong et al. "ELISA-type assays of trace biomarkers using microfluidic methods." Wiley Interdisciplinary Reviews: Nanomedicine and Nanobiotechnology 9.5 (2017): e1457.
Ekins. "Multi-analyte immunoassay." Journal of pharmaceutical and biomedical analysis 7.2 (1989): 155-168.
Fornier et al. "Serum HER2 extracellular domain in metastatic breast cancer patients treated with weekly trastuzumab and paclitaxel: association with HER2 status by immunohistochemistry and fluorescence in situ hybridization and with response rate." Annals of Oncology 16.2 (2005): 234-239.
Goldenberg et al. "CEA (carcinoembryonic antigen): its role as a marker in the management of cancer." Journal of cancer research and clinical oncology 101.3 (1981): 239-242.
Grzywa et al. "Highly sensitive detection of cancer antigen 15-3 using novel avian IgY antibodies." ALTEX—Alternatives to animal experimentation 31.1 (2014): 43-52.
Hann et al. "Prognostic importance of serum transferrin and ferritin in childhood Hodgkin's disease." Cancer 66.2 (1990): 313-316.
Hayashi et al. "Serum HER2 levels determined by two methods in patients with metastatic breast cancer." International journal of clinical oncology 17.1 (2012): 55-62.
Jose et al. "CYFRA 21-1: An Overview." Oral & Maxillofacial Pathology Journal 4.2 (2013).
Kalousova et al. "Ferritin as an independent mortality predictor in patients with pancreas cancer. Results of a pilot study." Tumor Biology 33.5 (2012): 1695-1700.
Leung et al. "Ovarian cancer biomarkers: current state and future implications from high-throughput technologies." Advances in clinical chemistry. vol. 66. Elsevier, 2014. 25-77.
Lin et al. "Microfluidic immunoassays." JALA: Journal of the Association for Laboratory Automation 15.3 (2010): 253-274.
Locker et al. "ASCO 2006 update of recommendations for the use of tumor markers in gastrointestinal cancer." Journal of clinical oncology 24.33 (2006): 5313-5327.
Lucarelli et al. "Diagnostic and prognostic role of preoperative circulating CA 15-3, CA 125, and beta-2 microglobulin in renal cell carcinoma." Disease markers 2014 (2014).
Mattar et al. "Preoperative serum levels of CA 72-4, CEA, CA 19-9, and alpha-fetoprotein in patients with gastric cancer." Revista do Hospital das Clinicas 57.3 (2002): 89-92.
Maxim et al. "Serum ferritin as a tumor marker in patients with squamous cell carcinoma of the head and neck." Cancer 57.2 (1986): 305-311.
Melia et al. "Serum ferritin in hepatocellular carcinoma. A comparison with alphafetoprotein." Cancer 51.11 (1983): 2112-2115.
Nakata, et al. "Serum CYFRA 21-1 is one of the most reliable tumor markers for breast carcinoma." Cancer: Interdisciplinary International Journal of the American Cancer Society 89.6 (2000): 1285-1290.
Nayak et al. "Proteomics approach to identify biomarkers in neurodegenerative diseases." International review of neurobiology. vol. 121. Academic Press, 2015. 59-86.
Nimse et al. "Immobilization techniques for microarray: challenges and applications." Sensors 14.12 (2014): 22208-22229.
Olle et al. "Comparison of antibody array substrates and the use of glycerol to normalize spot morphology." Experimental and molecular pathology 79.3 (2005): 206-209.
Pepys et al. "C-reactive protein: a critical update." The Journal of clinical investigation 111.12 (2003): 1805-1812.
Reverberi et al. "Factors affecting the antigen-antibody reaction." Blood transfusion 5.4 (2007): 227.
Ricci et al. "Serum CA 15-3 is increased in pulmonary fibrosis." Sarcoidosis vasculitis and diffuse lung disease 26.1 (2009): 54-63.
Richens et al;. "Optimisation of protein microarray techniques for analysis of the plasma proteome: Minimisation of non-specific binding interactions." International immunopharmacology 24.2 (2015): 166-168.
Robertson, et al. "Prospective assessment of the role of five tumour markers in breast cancer." Cancer Immunology, Immunotherapy 33.6 (1991): 403-410.
Romero et al. "CEA, CA 15-3 and CYFRA 21-1 in serum and pleural fluid of patients with pleural effusions." European Respiratory Journal 9.1 (1996): 17-23.
Rubenstein. "Proteomic analysis of prion diseases: Creating clarity or causing confusion?." Electrophoresis 33.24 (2012): 3631-3643.
Shadfan et al. "A multiplexable, microfluidic platform for the rapid quantitation of a biomarker panel for early ovarian cancer detection at the point-of-care." Cancer Prevention Research 8.1 (2015): 37-48.
Shao et al. "Outcome prediction values of soluble human epidermal growth factor receptor-2 extracellular domain in metastatic breast cancer." International journal of clinical and experimental pathology 7.3 (2014): 1108.
Su et al. "Carbohydrate antigen 19-9 for differential diagnosis of pancreatic carcinoma and chronic pancreatitis." World Journal of Gastroenterology: WJG 21.14 (2015): 4323.

(56) References Cited

OTHER PUBLICATIONS

Tonkin et al. "Biomarkers in stable coronary heart disease, their modulation and cardiovascular risk: The LIPID biomarker study." International journal of cardiology 201 (2015): 499-507.
Xue et al. "Serial changes in high-sensitive troponin I predict outcome in patients with decompensated heart failure." European journal of heart failure 13.1 (2011): 37-42.
Yang et al. "CA72-4 combined with CEA, CA125 and CAI9-9 improves the sensitivity for the early diagnosis of gastric cancer." Clinica chimica acta 437 (2014): 183-186.
Yeh et al. "Elevated serum matrix metalloproteinase-3 and-7 in H. pylori-related gastric cancer can be biomarkers correlating with a poor survival." Digestive diseases and sciences 55.6 (2010): 1649-1657.
Yokoyama et al. "Matrilysin (MMP-7) is a novel broadly expressed tumor antigen recognized by antigen-specific T cells." Clinical Cancer Research 14.17 (2008): 5503-5511.
Zhu et al. "Protein chip technology." Current opinion in chemical biology 7.1 (2003): 55-63.
International Search Report and Written Opinion in corresponding International Patent Application No. PCT/IB2017/056047 dated Sep. 30, 2017. 11 pages.
International Preliminary Report on Patentability in corresponding International Patent Application No. PCT/IB2017/056047 dated Sep. 30, 2017. 6 pages.
Liu R H et al.: "Integrated Microfluidic Custom Array Device for Bacterial Genotyping and Identification", Journal of the Association for Laboratory Automation, Elsevier, vol. 11, No. 6, Dec. 1, 2006 (Dec. 1, 2006), pp. 360-367.
Tai L W et al: "An automated microfluidic-based immunoassay cartridge for allergen screening and other multiplexed assays", Analytical Biochemistry, Elsevier, Amsterdam, NL, vol. 391, No. 2, Aug. 15, 2009 (Aug. 15, 2009), pp. 98-105.
Extended European Search Report dated Apr. 20, 2020, issued in respect of corresponding European Patent Application No. 17855147.9. 9 pages.
Australian Examination Report dated Jul. 8, 2021 in corresponding Australian Patent Application No. 2017335710. 4 pages.

* cited by examiner

Potential Layer Stackup Illustration

MICROFLUIDIC DEVICE

CROSS-REFERENCE TO RELATED PATENT APPLICATIONS

This application is a U.S. National Stage Application under 35 U.S.C. § 371 of International Patent Application No. PCT/IB2017/056047, filed Sep. 30, 2017, which claims the benefit of priority under 35 U.S.C. Section 119(e) of U.S. Patent Application No. 62/402,087 filed Sep. 30, 2016, both of which are incorporated by reference in their entireties. The International Application was published on Apr. 5, 2018, as International Publication No. WO 2018/060973 A1.

FIELD OF INVENTION

The present invention relates to a microfluidic device. More specifically, the present invention relates to a protein microarray-integrated microfluidic system for detecting target molecules.

BACKGROUND OF THE INVENTION

Many diagnostic or other procedures suffer from the need to transport samples great distances from the point of collection to facilities where the sample can be analyzed. It would be useful to provide analytical devices that can be used closer to sample collection locations and generate analytical results in a timely fashion, for example for target molecules present in minute amounts within complex matrices.

For improved sensitivity, quantitation and throughput, ELISA has been a frequently used format, based on coating an antibody onto the solid phase of a sorbent 96-well plate, and limiting the ELISA assay to a single analyte. A large percentage of diagnostic testing is still conducted on manual or semi-automated ELISA titer plates. ELISA is extremely labor intensive and users would welcome a streamlined alternative technology. Currently, aside from cost considerations, ordering test results for two or more assays to obtain test results for multiple markers, even when requested from the same testing laboratory, tends to incur additional delays. Ordering two assays at the same time could mean sending more samples and often to different laboratories. This also incurs higher costs than the standard practice of ordering one test and waiting for results to assess if further testing is required. Multiplexing is a paradigm shift which allows more economic savings using tests that produce more diagnostic information. Multiplexing assays also improves the diagnostic power of disease markers. Often, single markers have clinical sensitivity and/or specificity limitations.

The smaller spots used in microarray surfaces, compared to those for ELISA surfaces, result in the reduced likelihood of an analyte in a test sample for a microarray assay, to be depleted or altered in the assay (Ekins, 1989). This difference also means that microarray assays have better accuracy and sensitivity, especially in low-analyte samples. Microarray assays are also associated with faster kinetics as diffusion constraints are minimized. Thus, this technology platform is much more efficient in throughput and evaluation of biomarker panels than traditional approaches.

Recently, immunoassays have been integrated with microfluidic systems. Microfluidic systems are usually referred to as "lab-on-a-chip (LOC)" or "biochips". These LOC microfluidic system miniaturize the assay in comparison with conventional lab systems. There are several advantages to integrating immunoassays into a LOC including but not limited to, less sample/reagent consumption, enhanced sensitivity, reduced risk of contamination, less unit cost, lower power consumption and higher reliability and functionality (Dong and Uede, 2017; Lin et al., 2010). A typical immunoassay performed in the lab take a large amount of time mostly due to long incubation time attributed to inefficient mass transport of the reagents to move from the solution to the surface where the immunoreaction occurs. Liquid transport during microfluidic immunoassays can assist mass transport of reagents and increase the efficiency of immunoreactions. The reagents used in immunoassays can be quite costly. Integration of immunoassays into microfluidics can greatly reduce the consumption of reagents due to miniaturization.

SUMMARY OF THE INVENTION

The present invention provides, in part, a microfluidic apparatus for detecting multiple target molecules in parallel from a small volume of sample. The target molecules include polypeptides, antibodies, small molecules, metabolites, heavy metals etc. The microfluidic apparatus may be a protein microarray-integrated microfluidic device for, for example, detection of an array of target molecules.

In one aspect, the invention provides an apparatus including a microfluidic cartridge including a protein microarray and a receptacle for receiving a fluid sample, where the fluid sample is configured to be in fluid communication with the protein microarray. The microfluidic cartridge may be in pneumatic connection with an instrument to, for example, control the motion of fluids. The instrument may be capable of detecting signals from the protein microarray.

In another aspect, the invention provides an apparatus including a microfluidic cartridge including a wet cartridge, a dry cartridge, and a protein microarray, where the wet cartridge includes a plurality of reagent reservoirs; a plurality of buffer reservoirs; a plurality of waste reservoirs; and the dry cartridge includes an aperture for detecting the protein microarray, the aperture defining an array chamber in conjunction with the protein microarray, and a plurality of microfluidic channels, the microfluidic channels including: a plurality of reagent channels; a plurality of buffer channels; a plurality of channels connecting the array chamber to the buffer reservoirs, reagent reservoirs and waste reservoirs; where the channels are configured to allow for smooth flow of fluids and minimization of cross-contamination; and where the dry cartridge is in alignment with the wet cartridge and in fluid communication with the wet cartridge and the protein microarray.

In another aspect, the invention provides a microfluidic cartridge including a wet cartridge, a dry cartridge, and a protein microarray, where the wet cartridge may include:
  i) a plurality of reagent reservoirs housing, for example, assay-specific reagents;
  ii) a plurality of buffer reservoirs, where the number of buffer reservoirs may be the same as or different from the number of reagent reservoirs;
  iii) a plurality of waste reservoirs;
  iv) a plurality of vents corresponding to each of the buffer reservoirs, reagent reservoirs and waste reservoirs;
  v) a sample well for receiving a fluid sample; and
  vi) a plurality of ports corresponding to each of the buffer reservoirs, reagent reservoirs, waste reservoirs and sample well;
and the dry cartridge may include an aperture for detecting signals from the protein microarray, the aperture defining an array chamber when in alignment with the wet cartridge, and a plurality of microfluidic channels disposed around a main junction, the microfluidic channels including:
  vii) a plurality of reagent channels, where each reagent channel corresponds to one of the reagent reservoirs of the wet cartridge;
  viii) a plurality of buffer channels, where each buffer channel corresponds to one of the buffer reservoirs of the wet cartridge;
  ix) a channel leading from the main junction to each buffer channel;
  x) a channel connecting each buffer channel with each reagent channel, to form buffer channel/reagent channel pairs;
  xi) a channel connecting the array chamber to the first waste reservoir;
  xii) a channel connecting the array chamber to the main junction;
  xiii) a channel connecting the main junction to the second waste reservoir; where the channels are configured to allow for smooth flow of fluids and minimization of cross-contamination;
  xiv) a plurality of vents corresponding to each of the buffer reservoirs, reagent reservoirs and waste reservoirs of the wet cartridge; and
  xv) a plurality of fluid-impermeable, gas-permeable barriers corresponding to each of the vents as well as the channels connecting each pair of the reagent/buffer channels from the reservoirs to the main channel;

where the dry cartridge may be in alignment with the wet cartridge and in fluid communication with the wet cartridge and the protein microarray, and the vents interface with the manifold of an instrument.

In another aspect, the invention provides a microfluidic cartridge comprising a wet cartridge, a dry cartridge, and a protein microarray, where the wet cartridge includes:
  i) a plurality of reagent reservoirs;
  ii) a plurality of buffer reservoirs, where the number of buffer reservoirs is the same as the number of reagent reservoirs;
  iii) first and second waste reservoirs;
  iv) a plurality of vents corresponding to each of the buffer reservoirs, reagent reservoirs and waste reservoirs;
  v) a sample well for receiving a fluid sample; and
  vi) a plurality of ports corresponding to each of the buffer reservoirs, reagent reservoirs, waste reservoirs and sample well;

and the dry cartridge includes an aperture for detecting the protein microarray, the aperture defining an array chamber in conjunction with the protein microarray, and a plurality of microfluidic channels disposed around a main junction, the microfluidic channels including:
  a plurality of reagent channels, where each reagent channel corresponds to one of the reagent reservoirs of the wet cartridge;
  a plurality of buffer channels, where each buffer channel corresponds to one of the buffer reservoirs of the wet cartridge and where each buffer channel connects to each corresponding reagent channel, to form buffer channel/reagent channel pairs;
  a channel leading from the main junction to each buffer channel;
  a channel connecting the array chamber to the first waste reservoir;
  a channel connecting the array chamber to the main junction;
  a channel connecting the main junction to the second waste reservoir; where the channels are configured to allow for smooth flow of fluids and minimization of cross-contamination;
  a plurality of vents corresponding to each of the buffer reservoirs, reagent reservoirs and waste reservoirs of the wet cartridge; and
  a plurality of liquid-impermeable, gas-permeable barriers corresponding to each of the vents;
  where the dry cartridge is in alignment with the wet cartridge and capable of fluid communication with the wet cartridge and the protein microarray, and the vents are capable of interfacing with the manifold of an instrument.

In another aspect, the invention provides a microfluidic cartridge comprising a wet cartridge, a dry cartridge, and a protein microarray, where the wet cartridge includes:
  i) a plurality of reagent reservoirs;
  ii) a plurality of buffer reservoirs, where the number of buffer reservoirs is the same as the number of reagent reservoirs;
  iii) first and second waste reservoirs;
  iv) a plurality of vents corresponding to each of the buffer reservoirs, reagent reservoirs and waste reservoirs;
  v) a sample well for receiving a fluid sample; and
  vi) a plurality of ports corresponding to each of the buffer reservoirs, reagent reservoirs, waste reservoirs and sample well;

and the dry cartridge includes an aperture for detecting the protein microarray, the aperture defining an array chamber in conjunction with the protein microarray, and a plurality of microfluidic channels, the microfluidic channels including:
  a plurality of reagent channels, where each reagent channel corresponds to one of the reagent reservoirs of the wet cartridge;
  a plurality of buffer channels, where each buffer channel corresponds to one of the buffer reservoirs of the wet cartridge, and wherein each buffer channel connects to each corresponding reagent channel, to form buffer channel/reagent channel pairs, and wherein each buffer channel connects to a main channel;
  a channel connecting the array chamber to the first waste reservoir;
  a channel connecting the array chamber to the main channel;
  a channel connecting the main channel to the second waste reservoir; wherein the channels are configured to allow for smooth flow of fluids and minimization of cross-contamination;
  a plurality of vents corresponding to each of the buffer reservoirs, reagent reservoirs and waste reservoirs of the wet cartridge; and
  a plurality of liquid-impermeable, gas-permeable barriers corresponding to each of the vents;
  where the dry cartridge is in alignment with the wet cartridge and capable of fluid communication with the wet cartridge and the protein microarray, and the vents are capable of interfacing with the manifold of an instrument.

In another aspect, the invention provides a wet cartridge including:
  i) a plurality of reagent reservoirs;
  ii) a plurality of buffer reservoirs, where the number of buffer reservoirs is the same as the number of reagent reservoirs;
  iii) first and second waste reservoirs;
  iv) a plurality of vents corresponding to each of the buffer reservoirs, reagent reservoirs and waste reservoirs;
  v) a sample well for receiving a fluid sample; and vi) a plurality of ports corresponding to each of the buffer reservoirs, reagent reservoirs, waste reservoirs and sample well;

where the wet cartridge is capable of alignment with a dry cartridge and a protein microarray.

In another aspect, the invention provides a dry cartridge including an aperture for detecting a protein microarray, the aperture defining an array chamber in conjunction with the protein microarray, and a plurality of microfluidic channels disposed around a main junction, the microfluidic channels including:

a plurality of reagent channels, where each reagent channel corresponds to one of the reagent reservoirs of the wet cartridge;

a plurality of buffer channels, where each buffer channel corresponds to one of the buffer reservoirs of the wet cartridge and where each buffer channel connects to each corresponding reagent channel, to form buffer channel/reagent channel pairs; a channel leading from the main junction to each buffer channel;

a channel connecting the array chamber to the first waste reservoir;

a channel connecting the array chamber to the main junction;

a channel connecting the main junction to the second waste reservoir; where the channels are configured to allow for smooth flow of fluids and minimization of cross-contamination;

a plurality of vents corresponding to each of the buffer reservoirs, reagent reservoirs and waste reservoirs of the wet cartridge; and a plurality of liquid-impermeable, gas-permeable barriers corresponding to each of the vents;

where the dry cartridge is capable of alignment with a wet cartridge and the protein microarray, and the vents are capable of interfacing with the manifold of an instrument.

In another aspect, the invention provides a dry cartridge including an aperture for detecting a protein microarray, the aperture defining an array chamber in conjunction with the protein microarray, and a plurality of microfluidic channels, the microfluidic channels including:

a plurality of reagent channels, where each reagent channel corresponds to one of the reagent reservoirs of the wet cartridge;

a plurality of buffer channels, where each buffer channel corresponds to one of the buffer reservoirs of the wet cartridge, and where each buffer channel connects to each corresponding reagent channel, to form buffer channel/reagent channel pairs, and where each buffer channel connects to a main channel;

a channel connecting the array chamber to the first waste reservoir;

a channel connecting the array chamber to the main channel;

a channel connecting the main channel to the second waste reservoir; where the channels are configured to allow for smooth flow of fluids and minimization of cross-contamination;

a plurality of vents corresponding to each of the buffer reservoirs, reagent reservoirs and waste reservoirs of the wet cartridge; and a plurality of liquid-impermeable, gas-permeable barriers corresponding to each of the vents;

where the dry cartridge is capable of alignment with a wet cartridge and the protein microarray, and the vents are capable of interfacing with the manifold of an instrument.

The protein microarray may be an antibody microarray, a protein or peptide microarray.

The fluid sample may be a biological sample or any liquid sample containing the target molecules to be detected.

The instrument may include pump, valves and optical sensor and integrated microcontrollers for controlling the above components.

The readout from the optical sensor may be interpreted using quantification software. The software may control the opening or closing of particular valves and the flow rate following a pre-set script. It may also control the optical sensor for image capturing and image analysis such as signal quantification and background subtraction.

The buffer reservoirs, reagent reservoirs and waste reservoirs may be configured to allow for pre-determined volumes.

The wet cartridge may include a laminate bottom comprising precut holes under the buffer reservoirs, reagent reservoirs and waste reservoirs for loading the reservoir.

The wet cartridge may be reusable if needed.

The dry cartridge may be disposable.

The assembled microfluidic cartridge including the protein microarray may be disposable.

This summary of the invention does not necessarily describe all features of the invention.

BRIEF DESCRIPTION OF THE DRAWINGS

These and other features of the invention will become more apparent from the following description in which reference is made to the appended drawings wherein.

Figure 12:
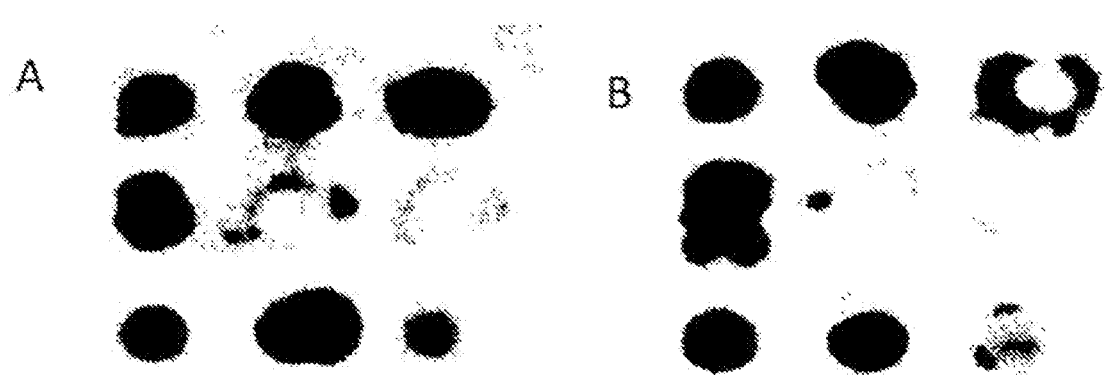
Figure 13:
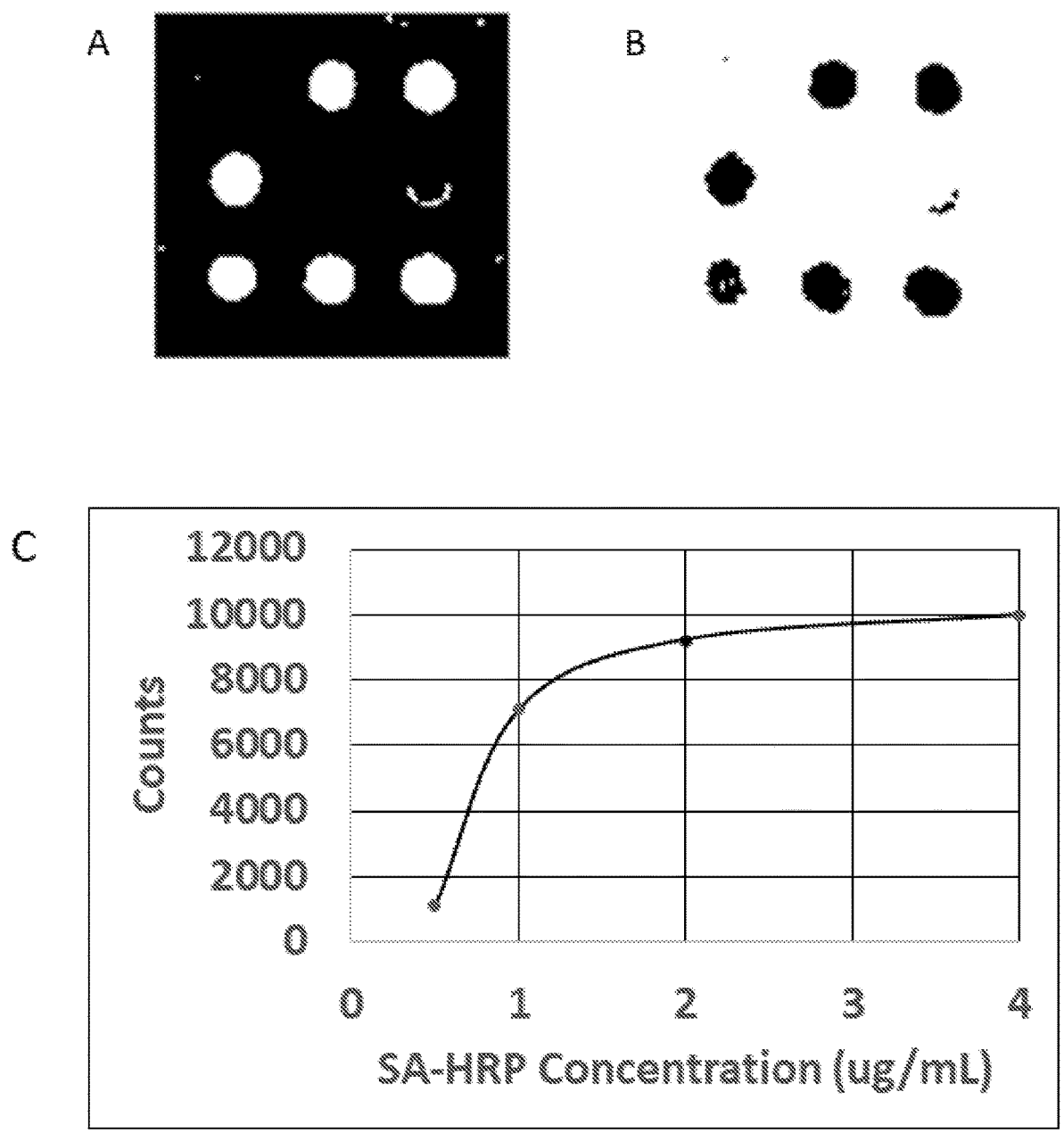
Figure 15:
Figure 16:
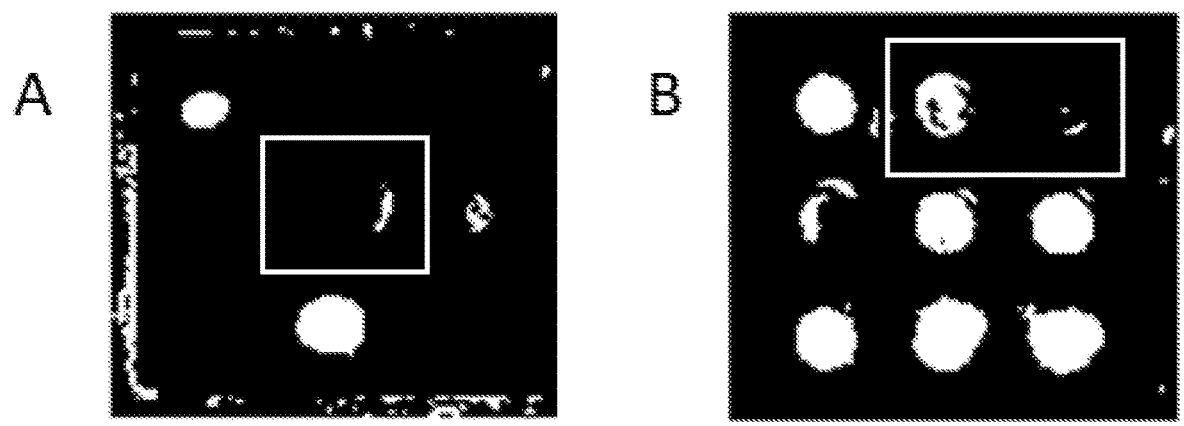
Figure 17:
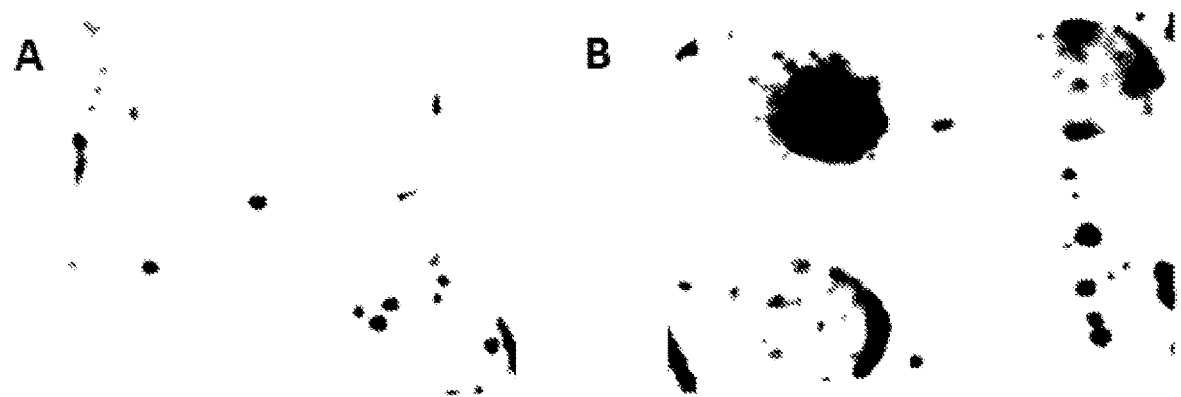
Figure 19:
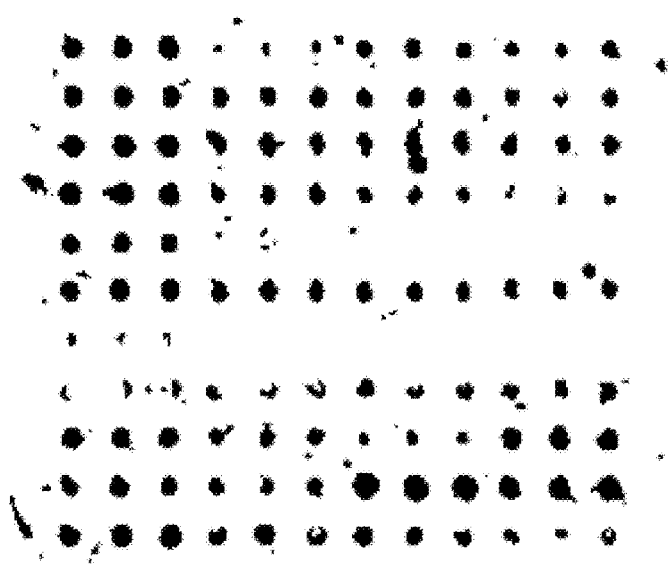
Figure 20:
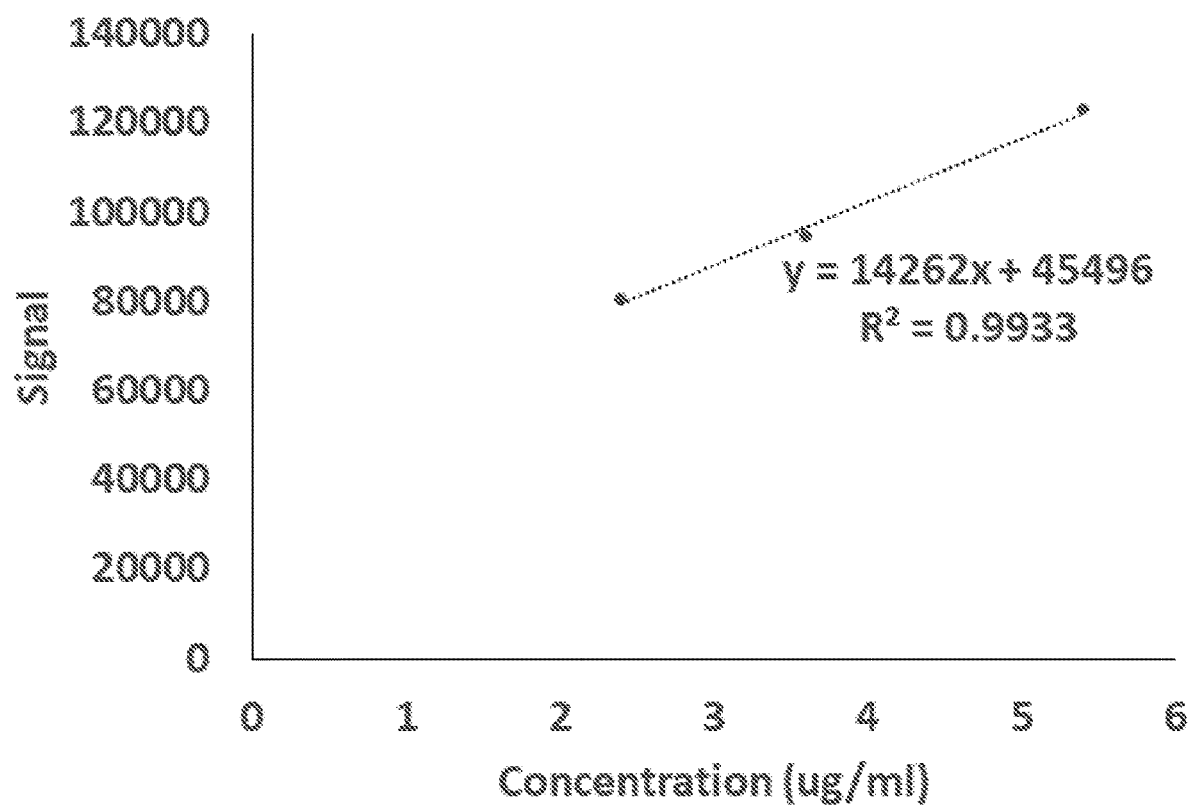
Figure 21:
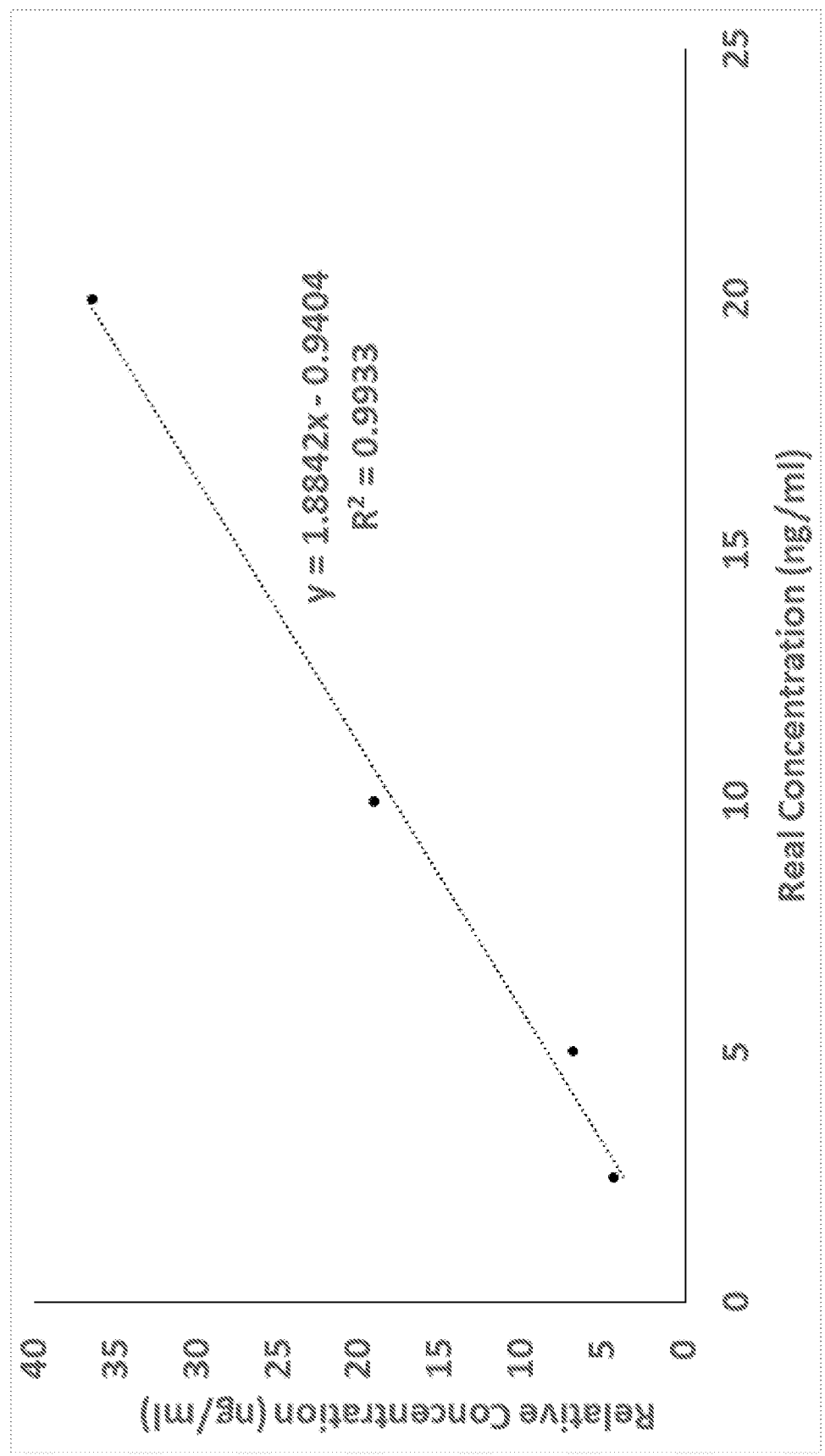
Figure 22:
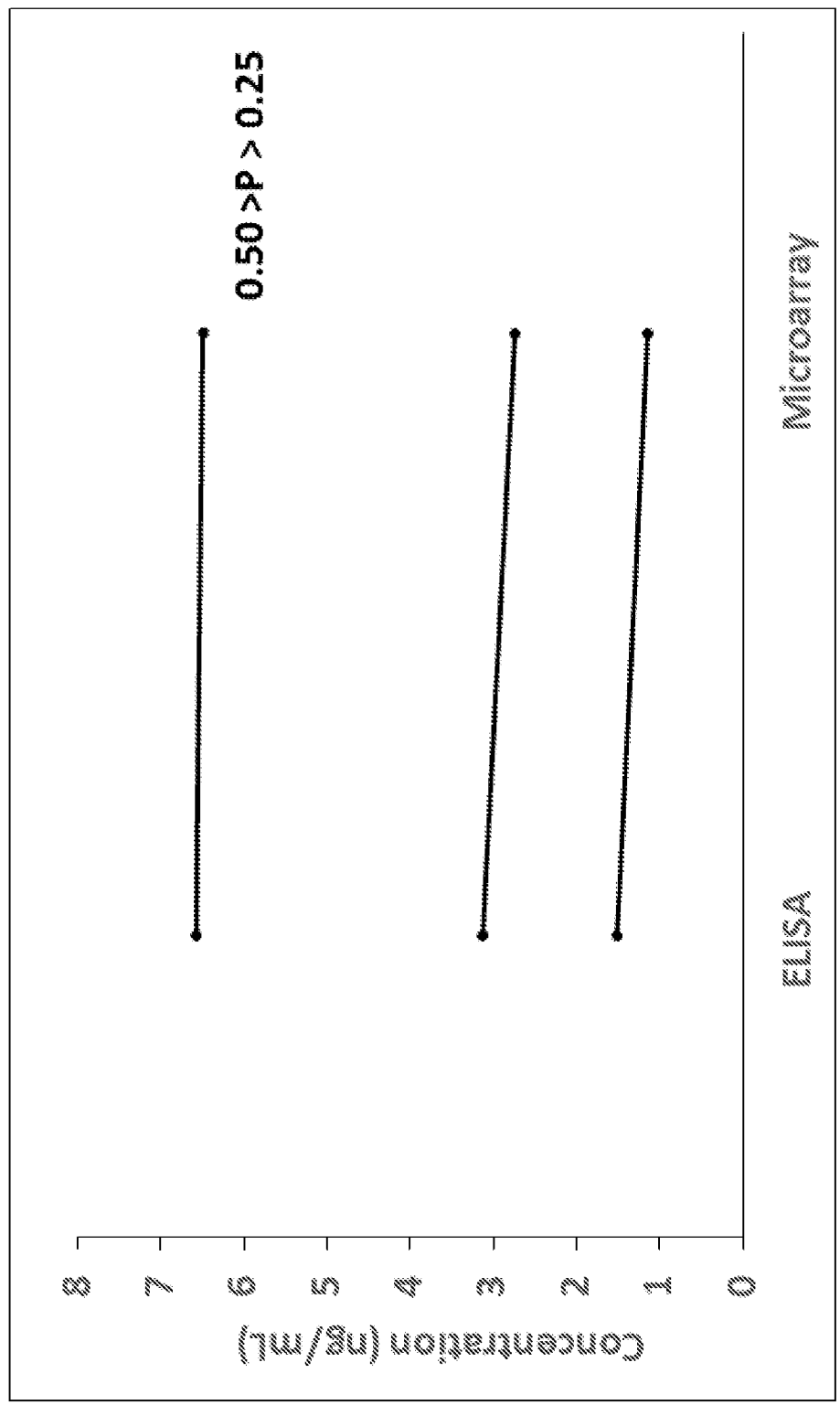
Figure 23:
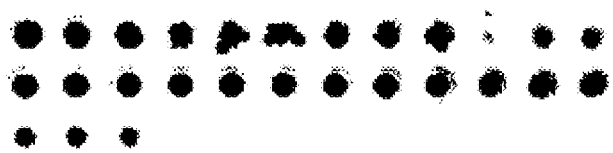
Figure 23:
Figure 24:
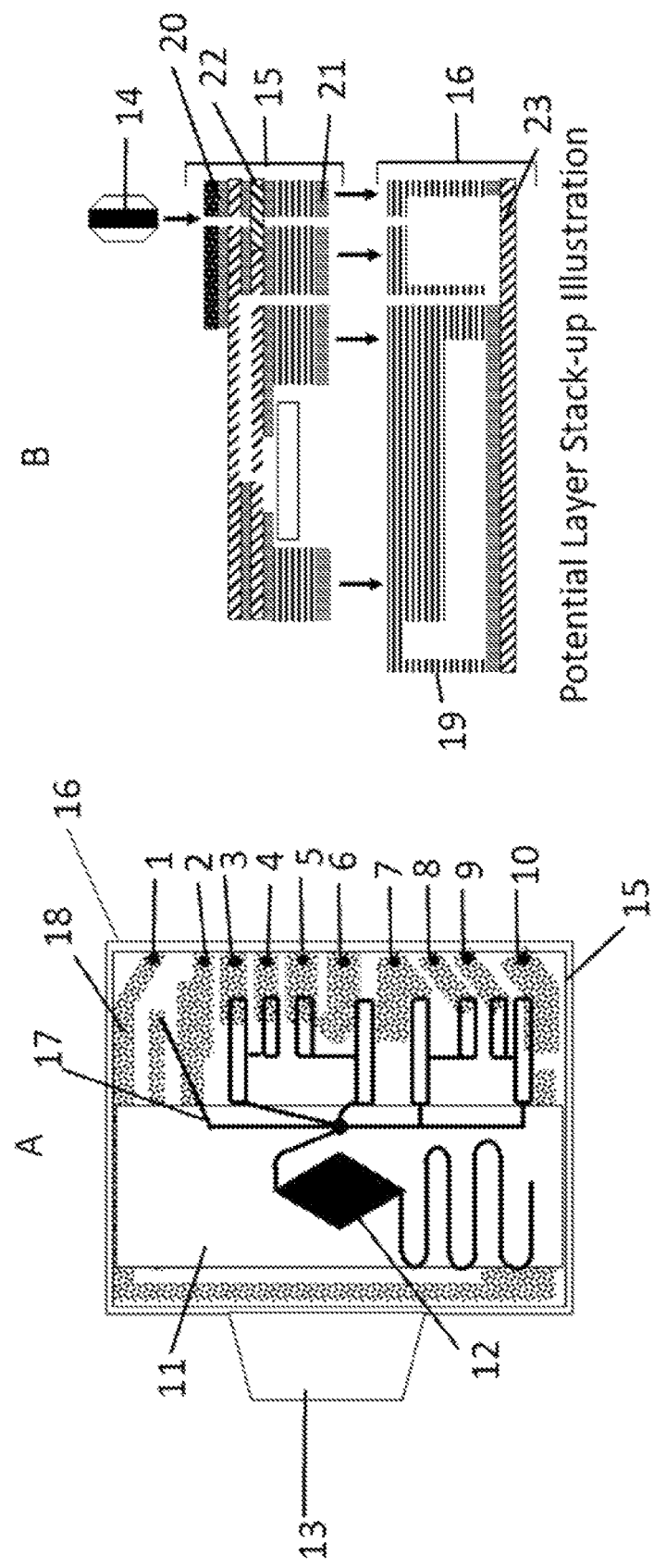

µg/mL for 10 minutes; Panels H-M: Microarray slides were printed with BSA-biotin at various concentrations in replicates of four; Row 1: BSA-biotin at 120 nM and printing buffer; Row 2: BSA-biotin at 60 nM and printing buffer; Row 3: BSA-biotin at 30 nM and printing buffer; Row 4: BSA-biotin at 20 nM and printing buffer; Row 5: BSA-biotin at 15 nM and BSA-biotin at 10 nM; Row 6: BSA-biotin at 7.5 nM and BSA-biotin at 5 nM; Row 7: BSA-biotin at 3.75 nM and BSA-biotin at 2.5 nM; Row 8: BSA-biotin at 1.875 nM and BSA-biotin at 1.25 nM; Slides were then probed with various concentrations of SA-HRP and biotin-HRP; H: probed for 10 minutes with SA-HRP at 4 µg/mL for; I: probed for 10 minutes with SA-HRP at 4 µg/mL and biotin-HRP at 2 µg/mL premixed; J: probed for 10 minutes with SA-HRP at 4 µg/mL and biotin-HRP at 4 µg/mL premixed; K: probed for 10 minutes with SA-HRP at 4 µg/mL and biotin-HRP at 6 µg/mL premixed; L: probed for 10 minutes with SA-HRP at 4 µg/mL and biotin-HRP at 8 µg/mL premixed; M: probed for 10 minutes with SA-HRP at 8 µg/mL and biotin-HRP at 4 µg/mL premixed; Panel N: Graphically representation of the data in H-M; 1: probed for 10 minutes with SA-HRP at 4 µg/mL; 2: probed for 10 minutes with 4 µg/mL SA-HRP and 2 µg/mL biotin-HRP; 3: probed for 10 minutes with 4 µg/mL SA-HRP and 4 µg/mL biotin-HRP; 4: probed for 10 minutes with 8 µg/mL SA-HRP and 4 µg/mL biotin-HRP;

FIGS. 12A-B show different incubation times for SA-HRP and biotin-HRP premix; for both panels, slides were spotted with a custom silicone isolator; Top row (left to right) BSA-biotin 4 nM, CA15-3 cAb at 50 µgµg/mL, CA15-3 antigen at 1500 U/mL; Middle row (left to right) CYFRA 21-1 cAb at 200 µgµg/mL, CEA at 975 µgµg/mL, ErbB2 cAb at 395 µgµg/mL; Bottom row (left and right) CYFRA 21-1 antigen at 100 ng/mL, CEA antigen at 15 µgµg/mL, ErbB2 antigen at 2.25 µgµg/mL Panel A shows the results at a 10 minute incubation time of SA-HRP and biotin-HRP mixture; Panel B shows the results at a 5 minute incubation time of SA-HRP/biotin-HRP mixture; Slides were scanned with the BioRad ChemDoc™ MP System;

FIGS. 13A-C show slides printed with dilutions of SA-HRP and probed with TMB-MX; slides were spotted with the custom silicone isolator; Top row (left to right) SA-HRP at 0.5 µg/mL, SA-HRP at 1 µg/mL, SA-HRP at 2 µg/mL; Middle row (left to right) SA-HRP at 4 µg/mL, buffer, SA-HRP at 0.5 µg/mL; Bottom row (left to right) SA-HRP at 1 µg/mL, SA-HRP at 2 µg/mL, SA-HRP at 4 µg/mL; Panel A shows the image of the slide after TMB-MX (Moss Substrates) development scanned with a Genepix microarray scanner; Panel B shows the optical image of the slide after TMB-MX development imaged with the instrument; Panel C is a graphical representation of the dose-dependency of the TMB-MX response illustrated in Panel B;

FIGS. 14A-D shows microarray slides testing different TMB-MX incubation times; Signals were imaged with the instrument; Slides were printed with a custom silicone isolator; Top row (left to right) CA15-3 cAb at 20 µg/mL, CA15-3 cAb at 80 µg/mL, CA15-3 antigen at 750 U/mL; Middle row (left to right) CYFRA 21-1 cAb at 100 µg/mL, CYFRA 21-1 cAb at 400 µg/mL, CYFRA 21-1 antigen at 125 ng/mL; Bottom row (left to right) ErbB2 cAb at 125 µg/mL, ErbB2 cAb at 500 µg/mL, ErbB2 antigen at 1875 ng/mL; Panel A shows the signal after 2 minutes TMB-MX incubation; Panel B shows the signal after 4 minute TMB-MX incubation; Panel C shows the signal after 6 minute TMB-MX incubation; Panel D shows the signal after 8 minute TMB-MX incubation;

FIGS. 15A-B show the spotting layout as well as the images for the two silver stained spots testing different print buffers; CA15-3 cAb at 25 µg/mL were spotted with custom silicone isolator A is spotted in 1×PBS and B is spotted in 1×PBS+20% glycerol; imaged with the BioRad ChemDoc™ MP System;

FIGS. 16A-B show the effect of printing buffers on the signal intensity of the CEA capture antibody Genepix microarray scan of silver developed microarray slide; Slides were spotted on custom silicone isolator; A: Antibodies and antigens printed with 1×PBS, 5% glycerol and 0.02% sarcosyl. Top row (left to right) BSA-biotin 4 nM, CA15-3 cAb at 50 µg/mL, CA15-3 antigen at 1500 U/mL; Middle row (left to right) CYFRA 21-1 cAb at 200 µg/mL, CEA cAb at 975 µg/mL, ErbB2 cAb at 395 µg/mL; Bottom row (left to right) CYFRA 21-1 antigen at 100 ng/mL, CEA antigen at 15 µg/mL, ErbB2 antigen at 2.25 µg/mL; B: Antibodies and antigens printed with 1×PBS. Top row (left to right) BSA-biotin 4 nM, CEA cAb at 1000 µg/mL in PBS, CEA cAb at 1000 µg/mL in PBS; Middle row (left to right) CEA antigen at 312.5 ng/mL, CEA antigen at 625 ng/mL, CEA antigen at 1250 ng/mL; Bottom row (left to right) CEA antigen at 2500 ng/mL, CEA antigen at 5000 ng/mL, CEA antigen at 10000 ng/mL; Both wells were probed with 200 ng/mL of CEA antigen (C3100-14) and 20 µg/mL of C1299-870-B detection antibody. CEA capture antibody spots of 975 µg/mL and 100 µg/mL C1299-87 W are highlighted in white boxes for comparison;

FIGS. 17A-B show the results of probing buffers of different ionic strengths. Capture antibodies were spotted onto slides with custom silicone isolator; Top row (left to right) CA15-3 cAb at 50 µg/mL, CA15-3 cAb at 25 µg/mL; Bottom row (left to right) ErbB2 cAb 500 µg/mL, ErbB2 cAb at 250 µg/mL; Results were obtained by silver development and imaged with the BioRad ChemDoc™ MP System. Panel A illustrates the results when a probing buffer of 1×PBST+5% BSA was used. Panel B illustrates the result when using a probing buffer of lower ionic strength, 0.25× PBST+5% BSA;

FIGS. 18A-L show different incubation times for antigen and detection antibody mix. Slides were printed with a microarray printer in replicates of six first row ErbB2 cAb at 500 µg/mL, second row CA15-3 cAb at 500 µg/mL; Microarray scanner images of silver developed capture antibody spots; Panels A-F Probed with antigen mix of CA15-3 antigen at 30 U/mL and ErbB2 antigen at 15 ng/mL and dAb mix at 15 minutes; A: antigen mix probed for 15 minutes, dAb mix: CA15-3 dAb at 1 µg/mL, ErbB2 dAb at 2 µg/mL B: antigen mix probed for 30 minutes, dAb mix: CA15-3 dAb at 1 µg/mL, ErbB2 dAb at 2 µg/mL C: antigen mix probed for 60 minutes, dAb mix: CA15-3 dAb at 1 µg/mL, ErbB2 dAb at 2 µg/mL; D: antigen mix probed for 15 minutes, dAb mix: CA15-3 dAb at 4 µg/mL, ErbB2 dAb at 8 µg/mL; E: antigen mix probed for 30 minutes, dAb mix: CA15-3 dAb at 4 µg/mL, ErbB2 dAb at 8 µg/mL; F: antigen mix probed for 60 minutes, dAb mix: CA15-3 dAb at 4 µg/mL, ErbB2 dAb at 8 µg/mL; Panels G-L Probed with antigen mix of CA15-3 antigen at 30 U/mL and ErbB2 antigen at 15 ng/mL and dAb mix at 30 minutes; G: antigen mix probed for 15 minutes, dAb mix: CA15-3 dAb at 1 µg/mL, ErbB2 dAb at 2 µg/mL H: antigen mix probed for 30 minutes, dAb mix: CA15-3 dAb at 1 µg/mL, ErbB2 dAb at 2 µg/mL I: antigen mix probed for 60 minutes, dAb mix: CA15-3 dAb at 1 µg/mL, ErbB2 dAb at 2 µg/mL; J: antigen mix probed for 15 minutes, dAb mix: CA15-3 dAb at 4 µg/mL, ErbB2 dAb at 8 µg/mL K: antigen mix probed for 30 minutes, dAb mix: CA15-3 dAb at 4 µg/mL, ErbB2 dAb at 8 µg/mL L: antigen mix probed for 60 minutes, dAb mix: CA15-3 dAb at 4 µg/mL, ErbB2 dAb at 8 µg/mL;

FIG. 19 shows a microarray scan of a TMB-MX developed well scanned with the Arraylt colorimetric scanner; The slide was printed with the Omnigrid Microarray printer, spots were printed in triplicate in a 12×12 grid; Row 1 (left to right): BSA-biotin 30 nM, CA15-3 cAb at 40 µg/mL, CA15-3 cAb at 30 µg/mL, CA15-3 cAb at 20 µg/mL; Row 2 (left to right): CA15-3 antigen at 1600 U/mL, CA15-3 antigen at 800 U/mL, CA15-3 antigen at 400 U/mL, CA15-3 antigen at 200 U/mL; Row 3 (left to right): CYFRA 21-1 cAb at 600 µg/mL, CYFRA 21-1 antigen at 0.25 µg/mL, CYFRA 21-1 antigen at 0.2 µg/mL, CYFRA 21-1 antigen at 0.16 µg/mL; Row 4 (left to right): CEA cAb at 580 µg/mL, CEA antigen at 5.4 µg/mL, CEA antigen at 3.6 µg/mL, CEA antigen at 2.4 µg/mL; Row 5 (left to right): ErbB2 cAb at 100 µg/mL, ErbB2 antigen at 1.35 µg/mL, ErbB2 antigen at 0.9 µg/mL, ErbB2 antigen at 0.6 µg/mL; Row 6 (left to right): MMP-7 cAb at 100 µg/mL, MMP-7 antigen at 9 µg/mL, MMP-7 antigen at 6 µg/mL, MMP-7 antigen at 3 µg/mL; Row 7 (left to right): Ferritin cAb at 40 µg/mL, Ferritin cAb at 20 µg/mL, Ferritin cAb at 10 µg/mL, Ferritin cAb at 5 µg/mL; Row 8 (left to right): Ferritin antigen at 2.7 µg/mL, Ferritin antigen at 1.8 µg/mL, Ferritin antigen at 1.2 µg/mL, Ferritin antigen at 0.8 µg/mL; Row 9 (left to right): CA19-9 cAb at 400 µg/mL, CA19-9 cAb at 200 µg/mL, CA19-9 cAb at 100 µg/mL, CA19-9 antigen at 22.5 kU/mL; Row 10 (left to right): CA19-9 antigen at 15 kU/mL, Cal 9-9 antigen at 10 kU/mL, CA72-4 cAb at 570 µg/mL, CA72-4 at 300 µg/mL; Row 11 (left to right): CA72-4 at 150 µg/mL, CA72-4 antigen at 4000 U/mL, CA72-4 antigen at 2000 U/mL, CA72-4 antigen at 1000 U/mL; Row 12 (left to right): D-Dimer cAb at 200 µg/mL, D-Dimer antigen at 100 µg/mL, D-Dimer antigen at 20 µg/mL, D-Dimer antigen at 4 µg/mL; The slide was probed with an antigen mix containing CA15-3 (60 U/mL), CYFRA 21-1 (8 ng/mL), CEA (20 ng/mL), CA72-4 (40 U/mL), CA19-9 (148 U/mL), ErbB2 (60 ng/mL), Ferritin (200 ng/mL), MMP-7 (20 ng/mL); slide was then probed with dAb mix: CA15-3 dAb (20 ng/mL), CYFRA 21-1 dAb (8 µg/mL), CEA dAb (2 µg/mL), CA72-4 dAb (5 µg/mL), CA19-9 dAb (150 ng/mL), ErbB2 dAb (0.4 µg/mL), Ferritin dAb (5 µg/mL), MMP-7 dAb (400 ng/mL);

FIG. 20 is a graphical illustration of an averaged CEA antigen curve for antigens printed on microarray slides;

FIG. 21 illustrates a standard curve for antigen response for CEA on capture antibody spots normalized with the averaged antigen curve;

FIG. 22 is a Brand-Altman plot comparing a microarray assay performed as described herein and a commercially-available ELISA kit (Fujierbio Inc);

FIG. 23 shows the results of a slide probed and imaged with the cartridge and instrument; The slide was printed with the Omnigrid Microarray printer, spots were printed in triplicate in a 12×12 grid; Row 1 (left to right): BSA-biotin 30 nM, CA15-3 cAb at 40 µg/mL, CA15-3 cAb at 30 µg/mL, CA15-3 cAb at 20 µg/mL; Row 2 (left to right): CA15-3 antigen at 1600 U/mL, CA15-3 antigen at 800 U/mL, CA15-3 antigen at 400 U/mL, CA15-3 antigen at 200 U/mL; Row 3 (left to right): CYFRA 21-1 cAb at 600 µg/mL, CYFRA 21-1 antigen at 0.25 µg/mL, CYFRA 21-1 antigen at 0.2 µg/mL, CYFRA 21-1 antigen at 0.16 µg/mL; Row 4 (left to right): CEA cAb at 1000 µg/mL, CEA antigen at 5.4 µg/mL, CEA antigen at 3.6 µg/mL, CEA antigen at 2.4 µg/mL; Row 5 (left to right): ErbB2 cAb at 100 µg/mL, ErbB2 antigen at 1.35 µg/mL, ErbB2 antigen at 0.9 µg/mL, ErbB2 antigen at 0.6 µg/mL; Row 6 (left to right): MMP-7 cAb at 100 µg/mL, MMP-7 antigen at 9 µg/mL, MMP-7 antigen at 6 µg/mL, MMP-7 antigen at 3 µg/mL; Row 7 (left to right): Ferritin cAb at 40 µg/mL, Ferritin cAb at 20 µg/mL, Ferritin cAb at 10 µg/mL, Ferritin cAb at 5 µg/mL; Row 8 (left to right): Ferritin antigen at 2.7 µg/mL, Ferritin antigen at 1.8 µg/mL, Ferritin antigen at 1.2 µg/mL, Ferritin antigen at 0.8 µg/mL; Row 9 (left to right): CA19-9 cAb at 400 µg/mL, CA19-9 cAb at 200 µg/mL, CA19-9 cAb at 100 µg/mL, CA19-9 antigen at 22.5 kU/mL; Row 10 (left to right): CA19-9 antigen at 15 kU/mL, Cal 9-9 antigen at 10 kU/mL, CA72-4 cAb at 600 µg/mL, CA72-4 at 300 µg/mL; Row 11 (left to right): CA72-4 at 150 µg/mL, CA72-4 antigen at 4000 U/mL, CA72-4 antigen at 2000 U/mL, Ca72-4 antigen at 1000 U/mL; Row 12 (left to right): D-Dimer cAb at 200 µg/mL, D-Dimer antigen at 100 µg/mL, D-Dimer antigen at 20 µg/mL, D-Dimer antigen at 4 µg/mL; The slide was probed with an antigen mix containing CA15-3 (60 U/mL), CYFRA 21-1 (8 ng/mL), CEA (20 ng/mL), CA72-4 (40 U/mL), CA19-9 (148 U/mL), ErbB2 (60 ng/mL), Ferritin (200 ng/mL), MMP-7 (20 ng/mL); slide was then probed with dAb mix: CA15-3 dAb (20 ng/mL), CYFRA 21-1 dAb (8 µg/mL), CEA dAb (2 µg/mL), CA72-4 dAb (5 µg/mL), CA19-9 dAb (150 ng/mL), ErbB2 dAb (0.4 µg/mL), Ferritin dAb (5 µg/mL), MMP-7 dAb (400 ng/mL);

FIGS. 24A-B show a schematic illustrating separate dry and wet cartridges and how they can interface with each other and an instrument manifold, according to one embodiment; Panel A shows the top view and Panel B shows a side view.

Figure 25A:
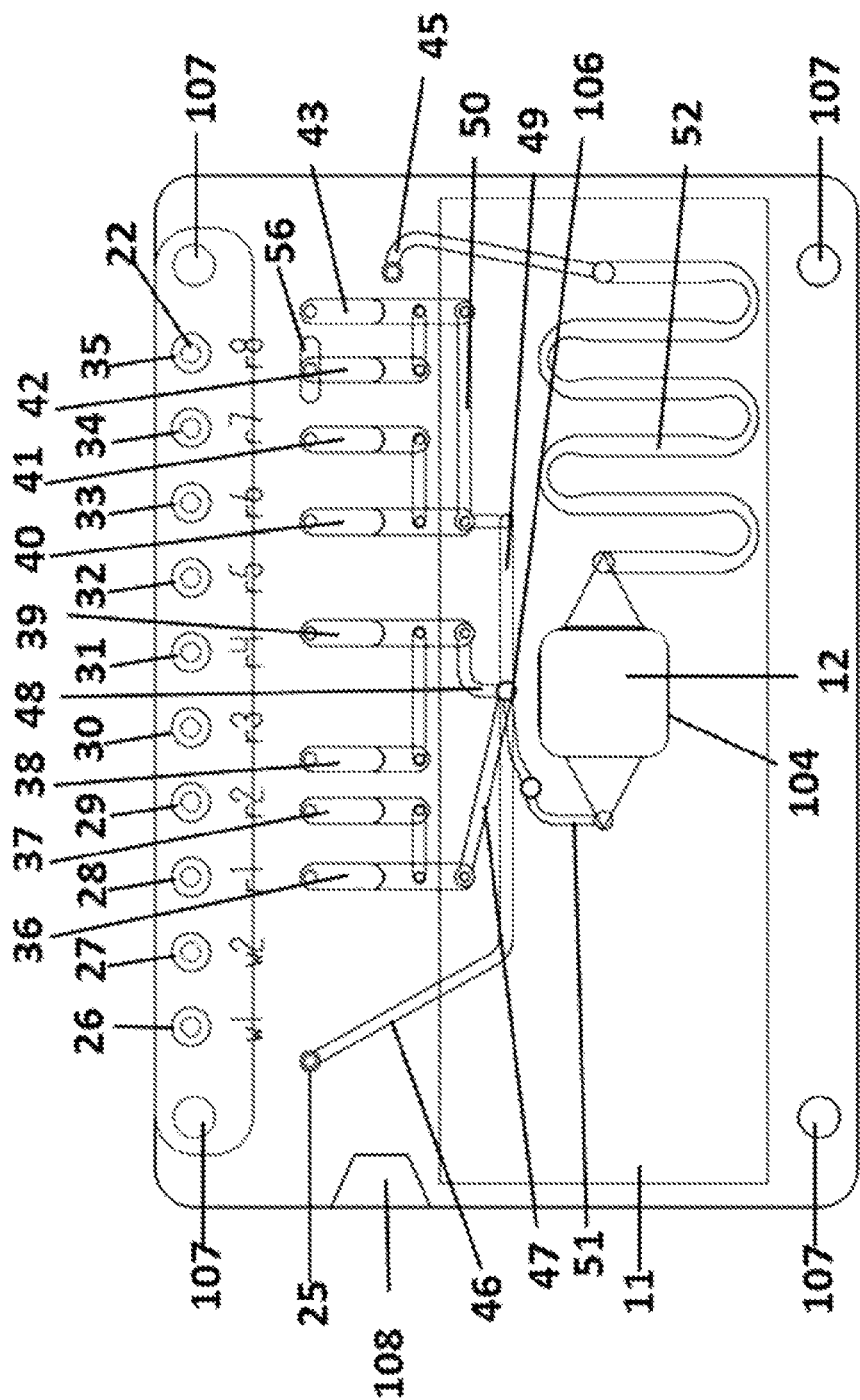
Figure 25B:
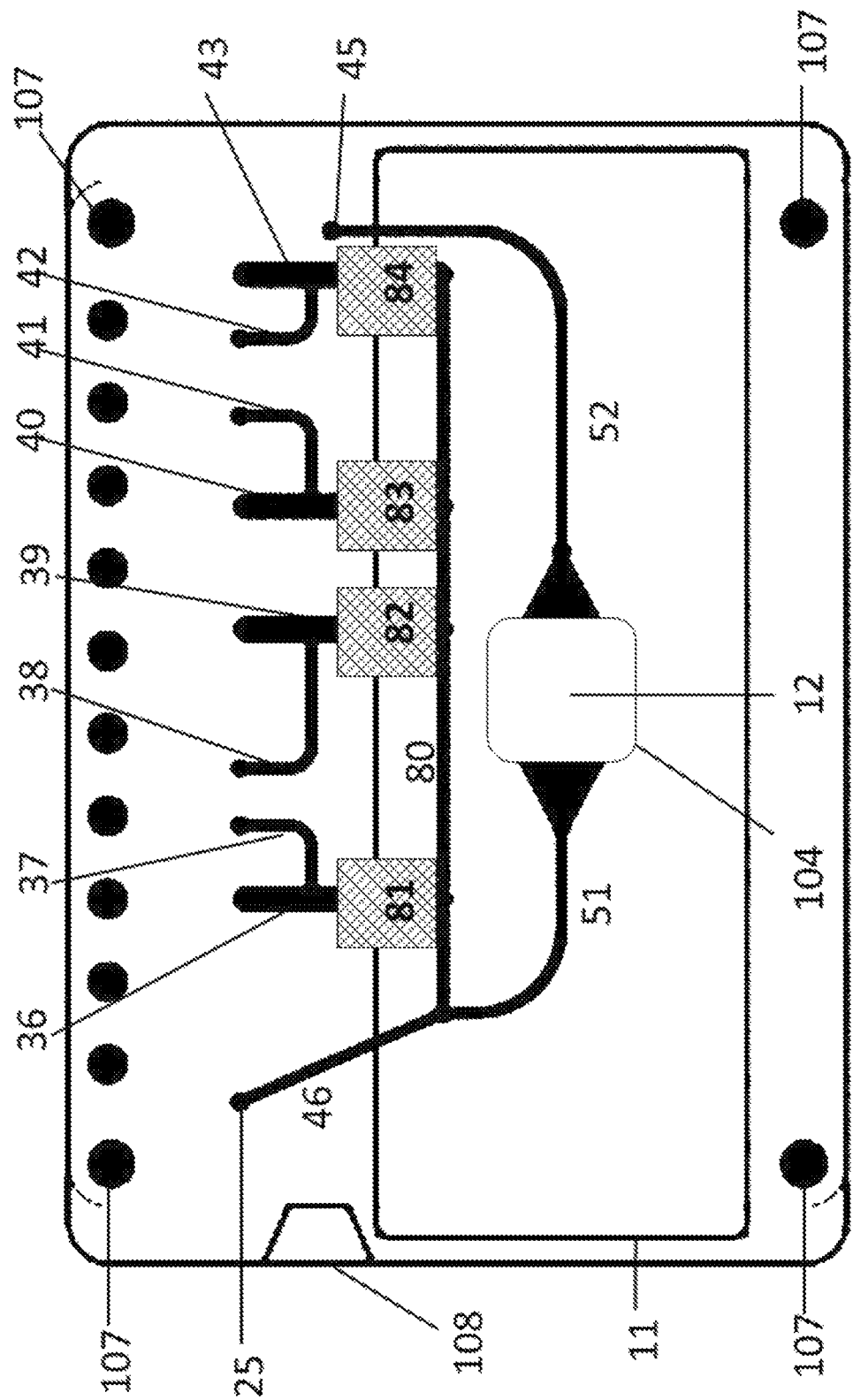
Figure 25C:
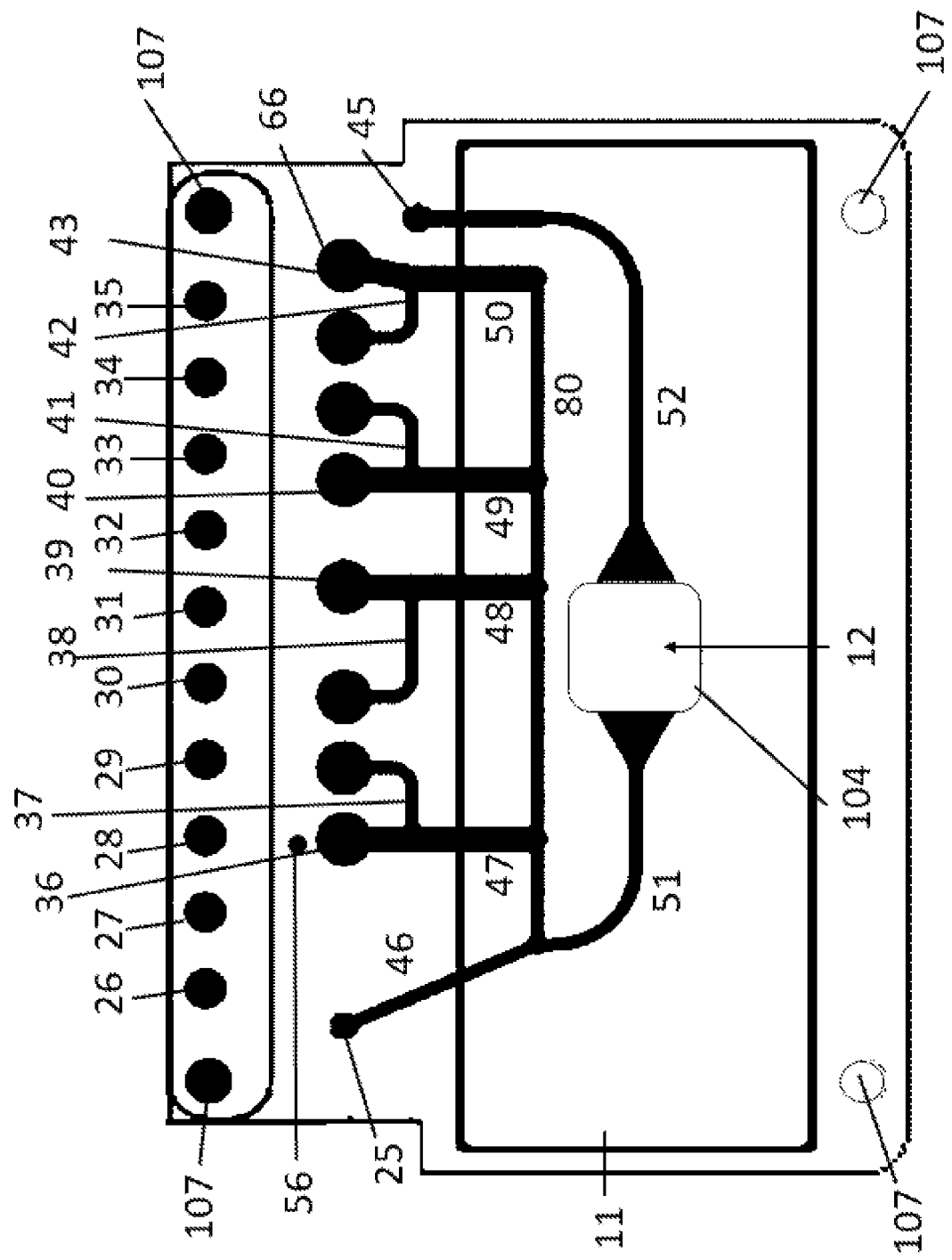
Figure 26:
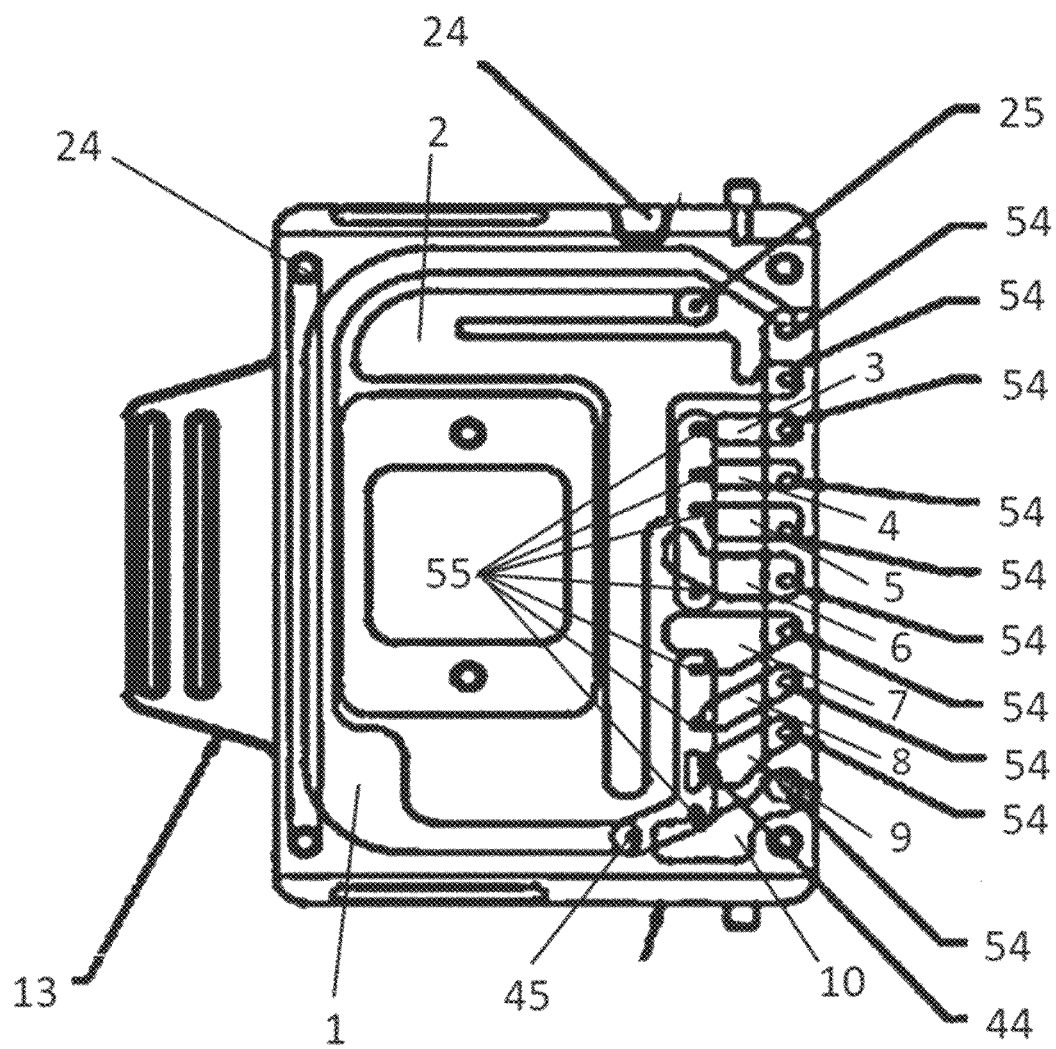
Figure 27:
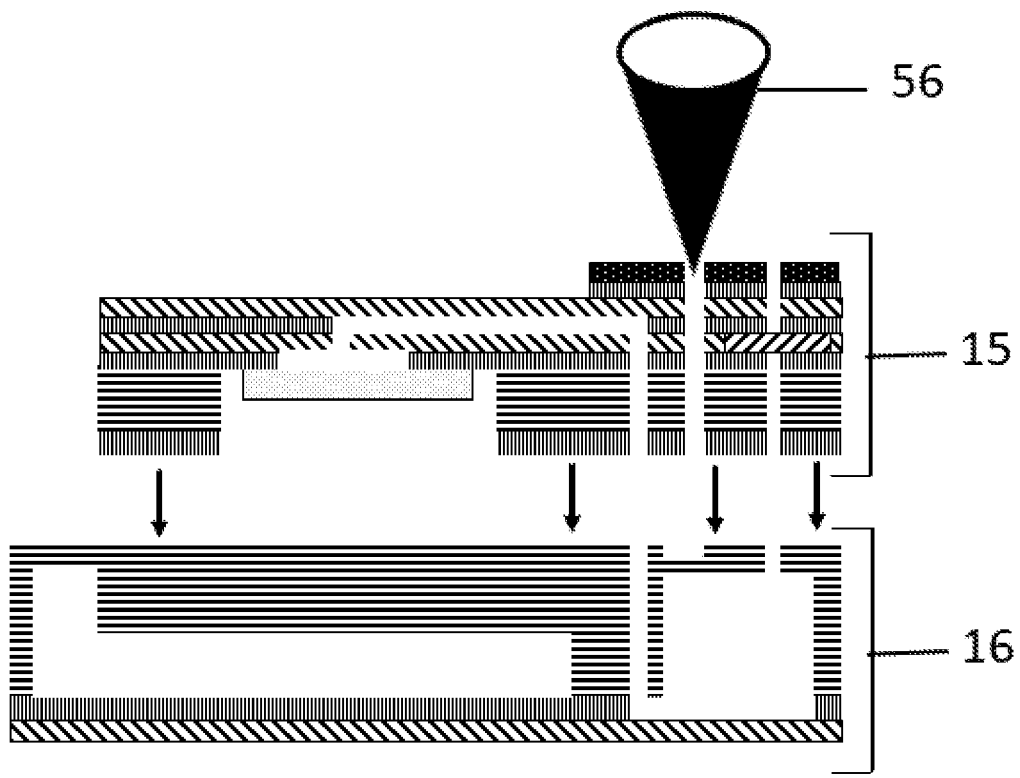
Figure 27:
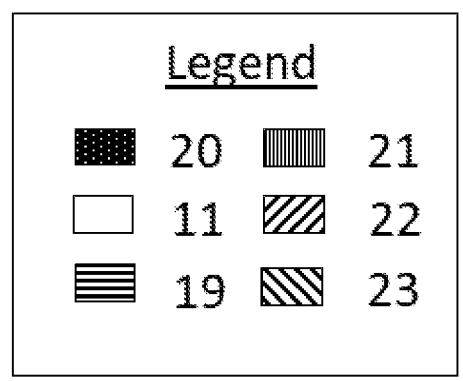
Figure 28:
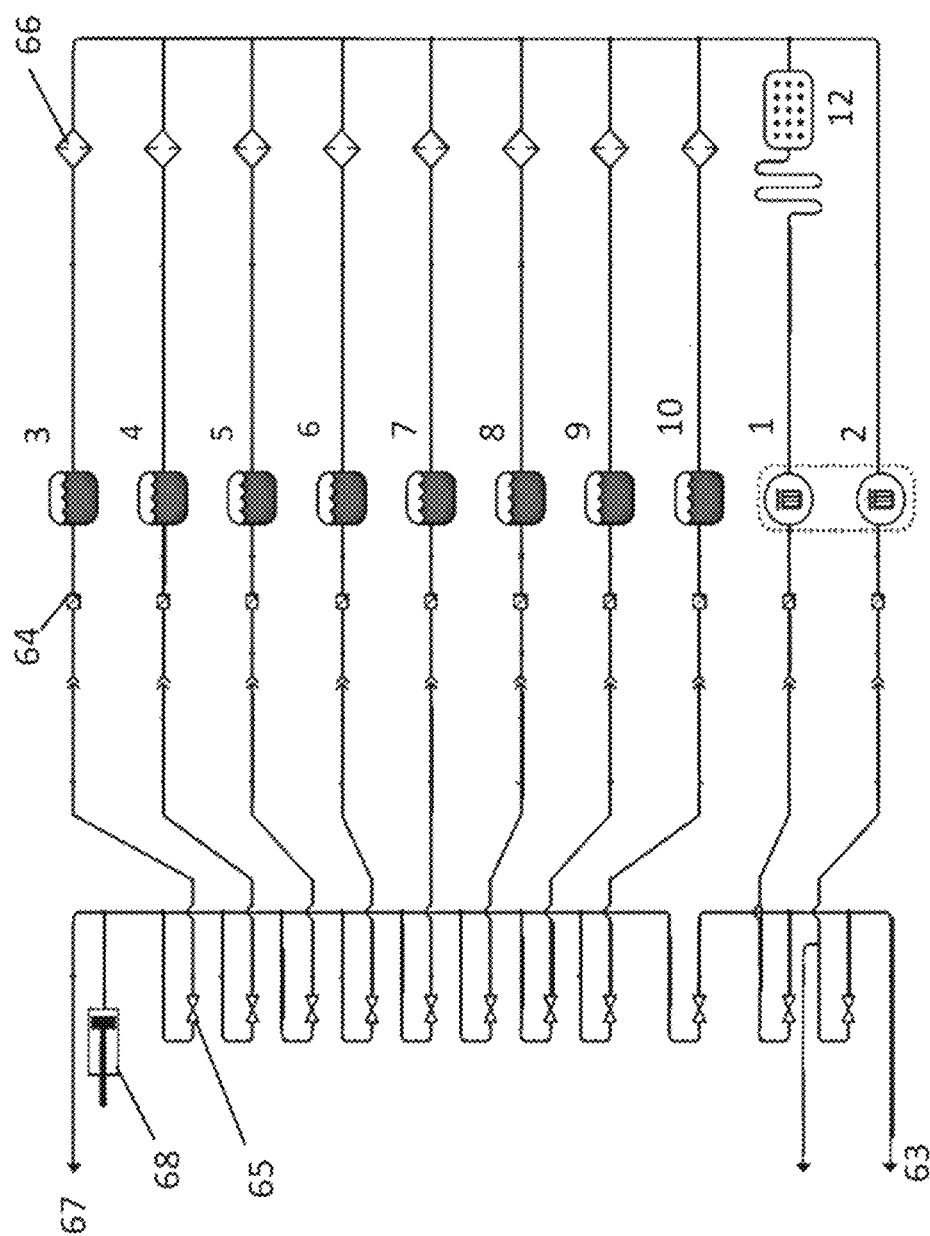
Figure 29:
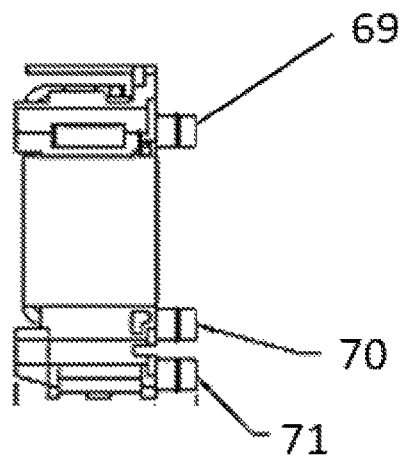
Figure 30:
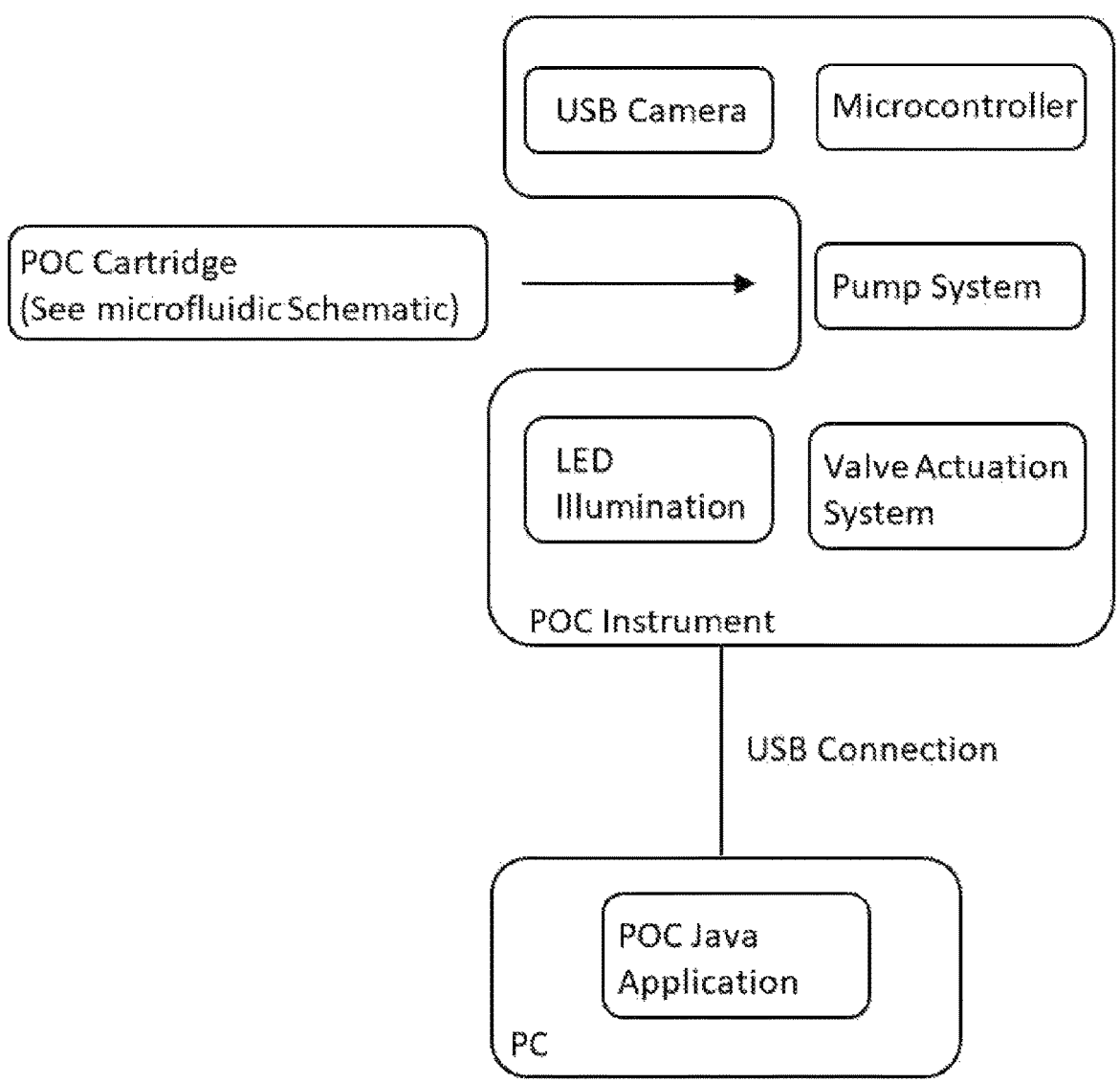
Figure 31:
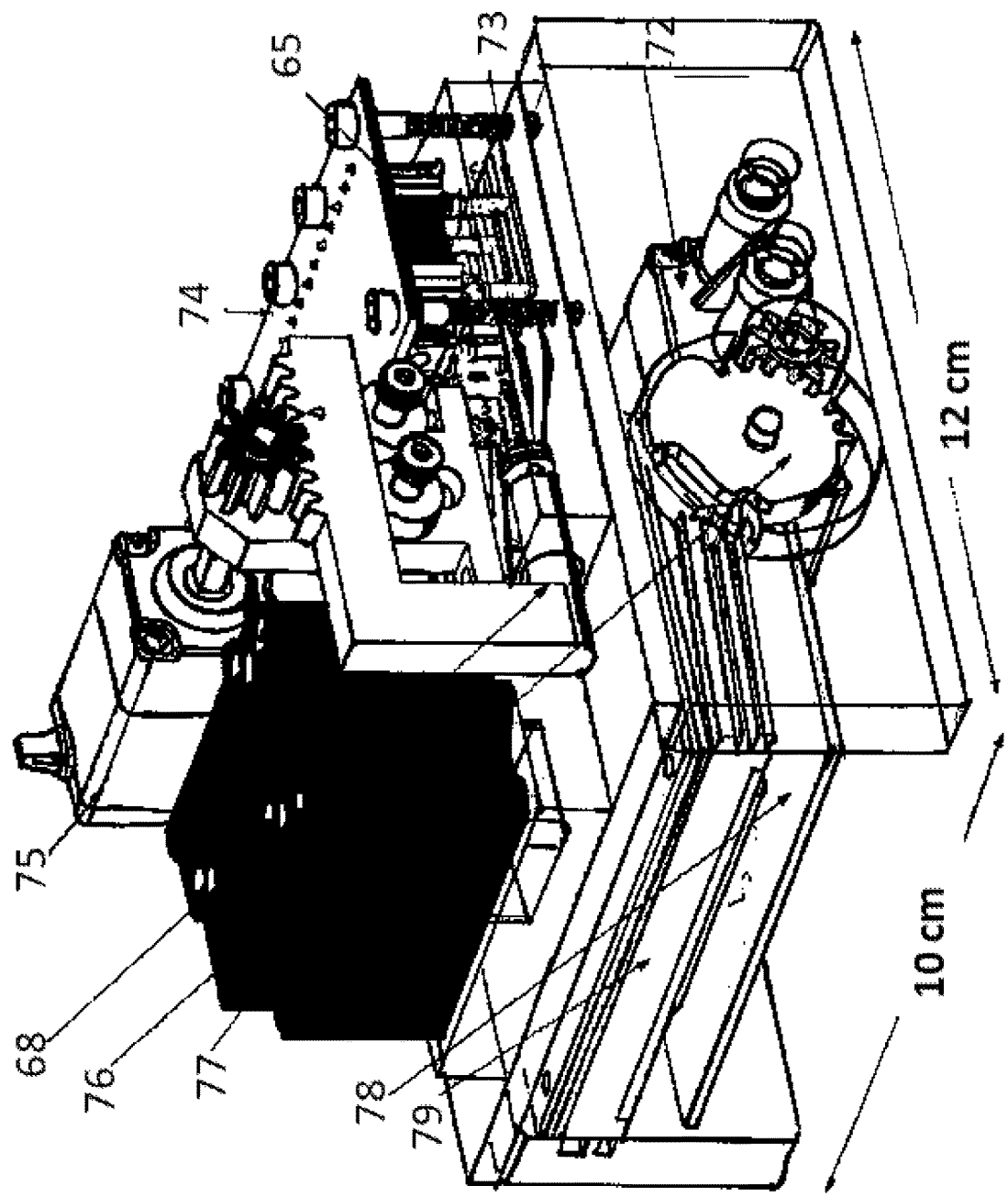
Figure 32:
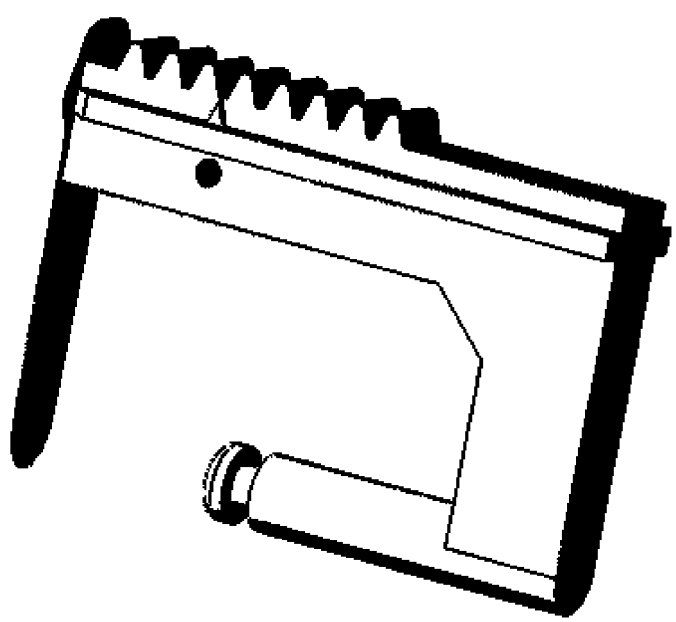
Figure 33:
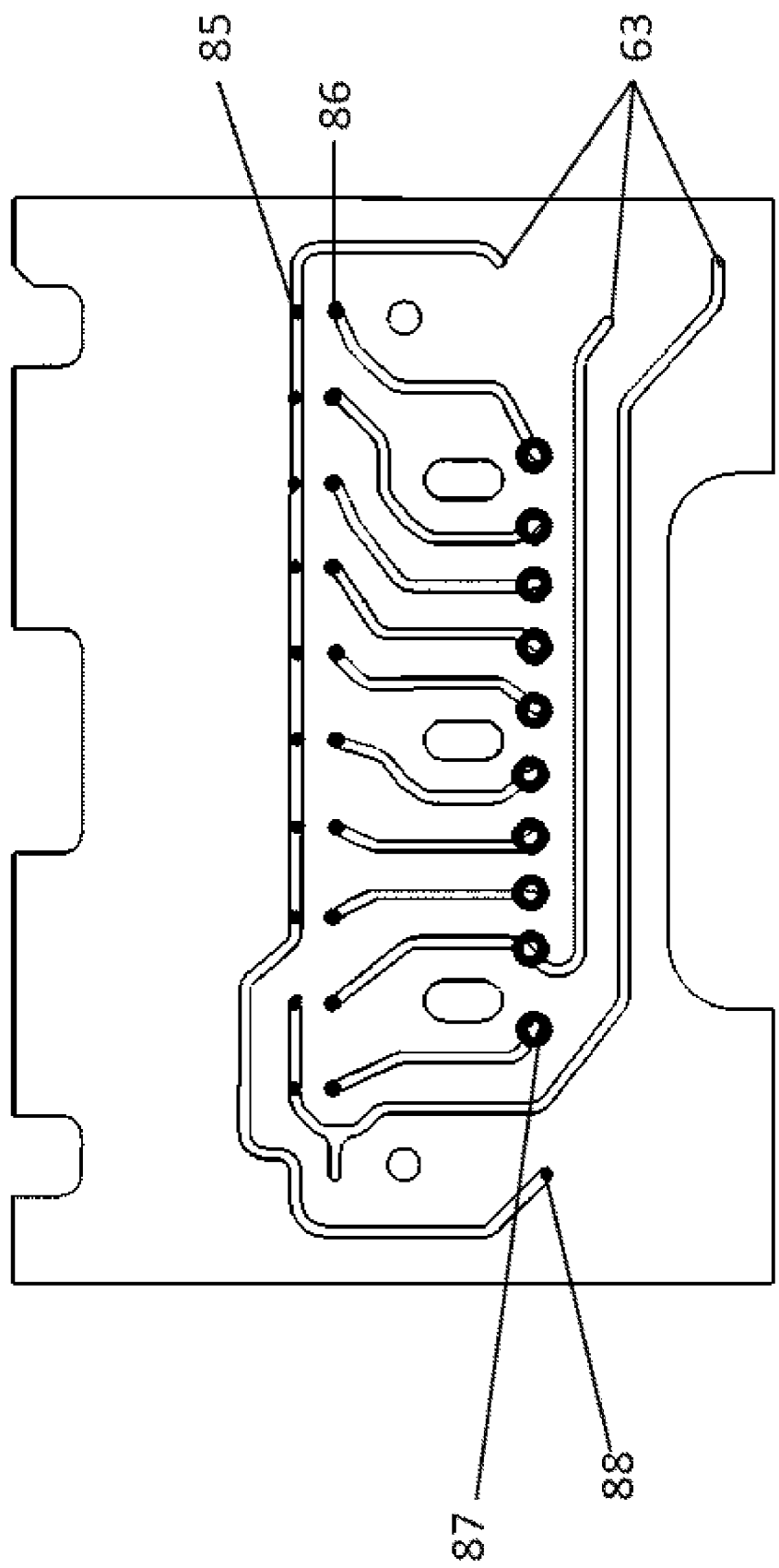
Figure 34A:
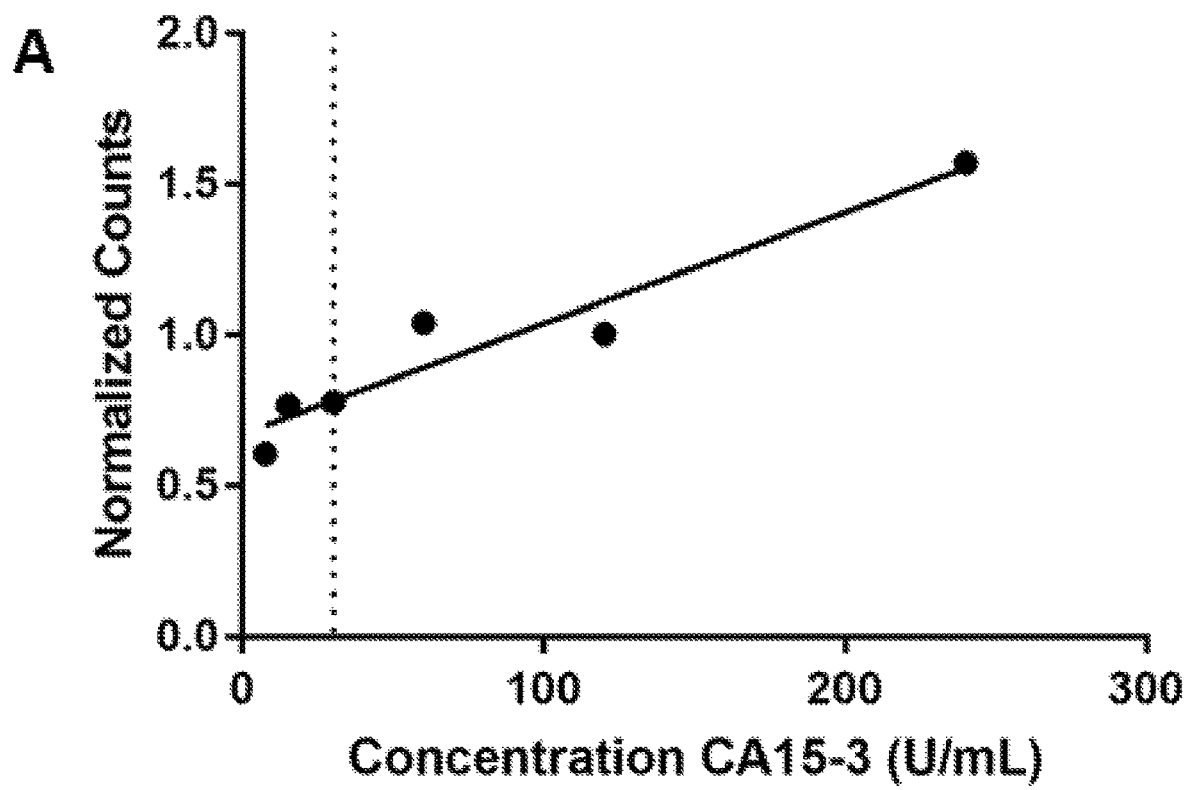
Figure 34B:
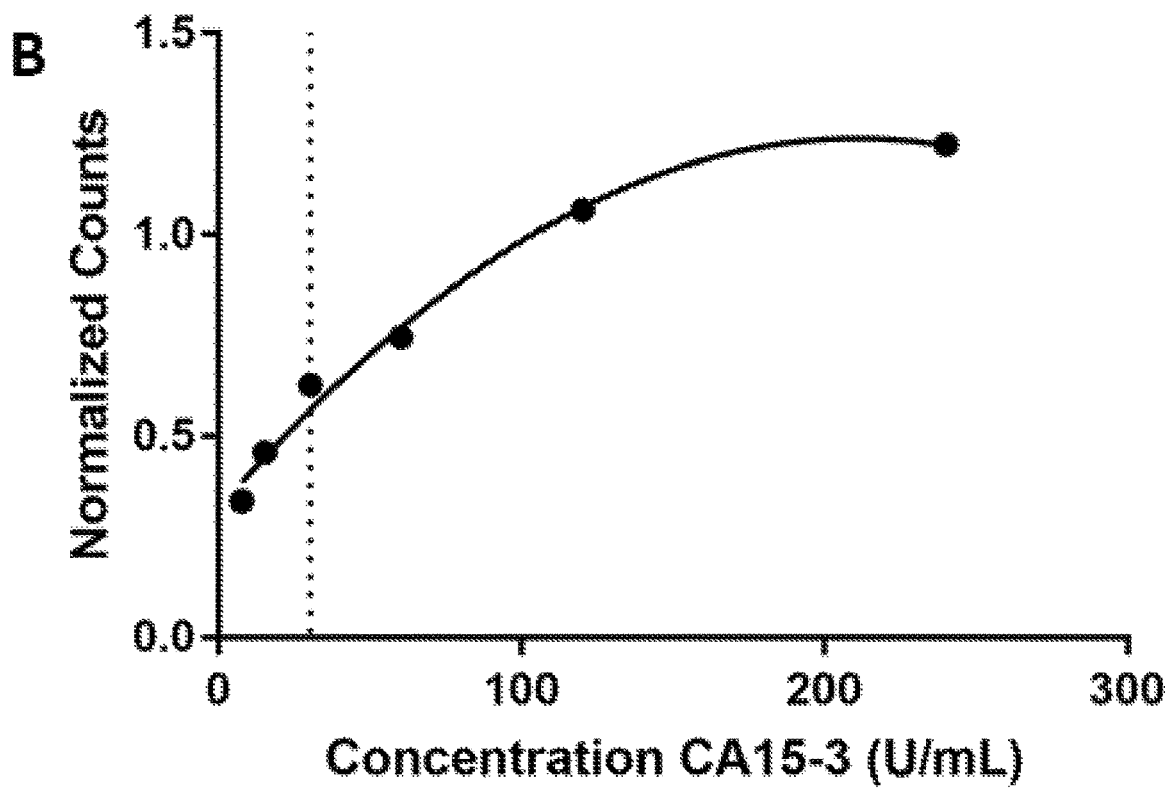
Figure 35A:
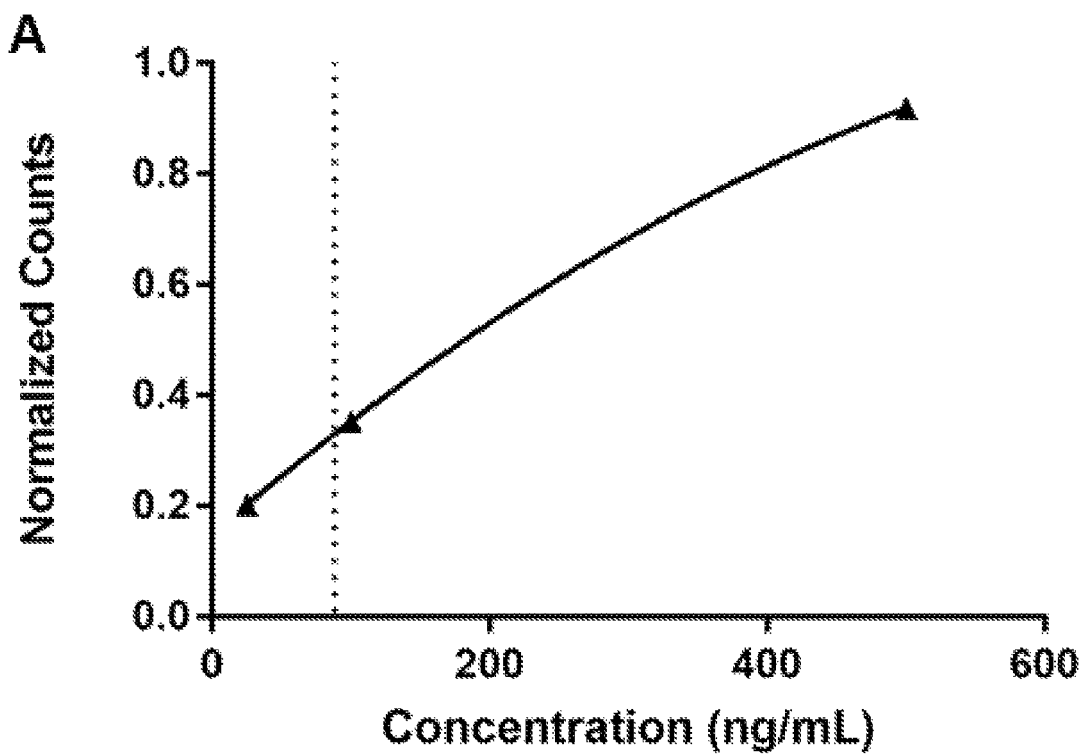
Figure 35B:
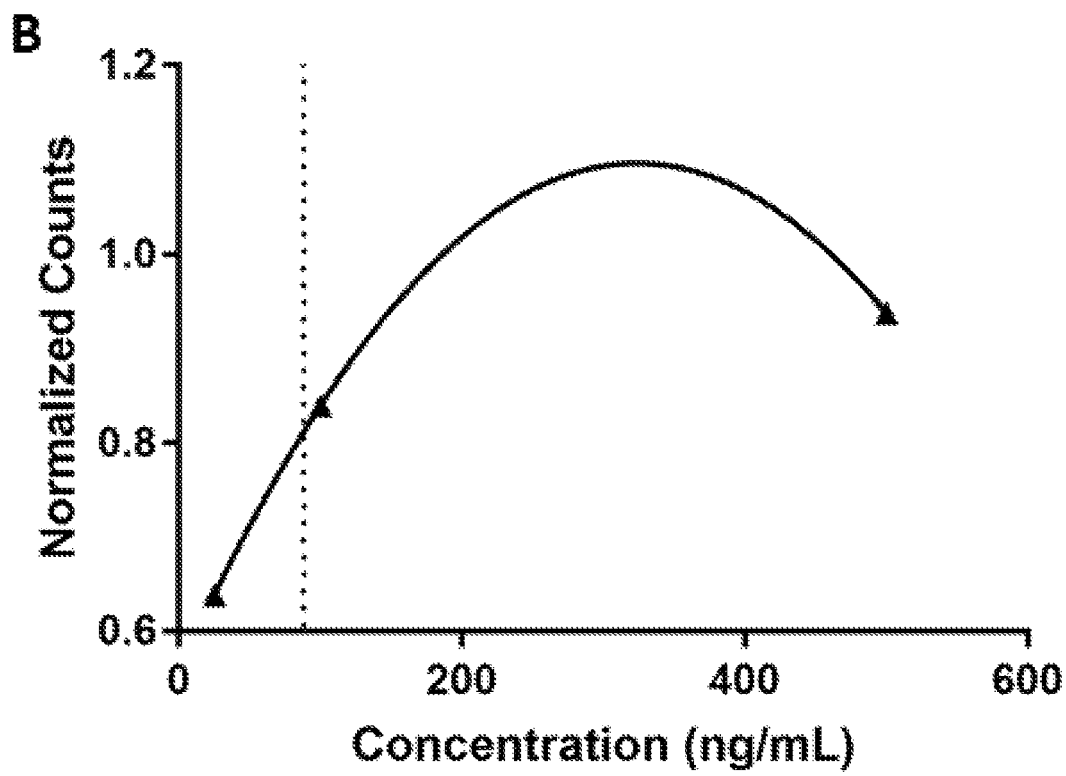
Figure 36:
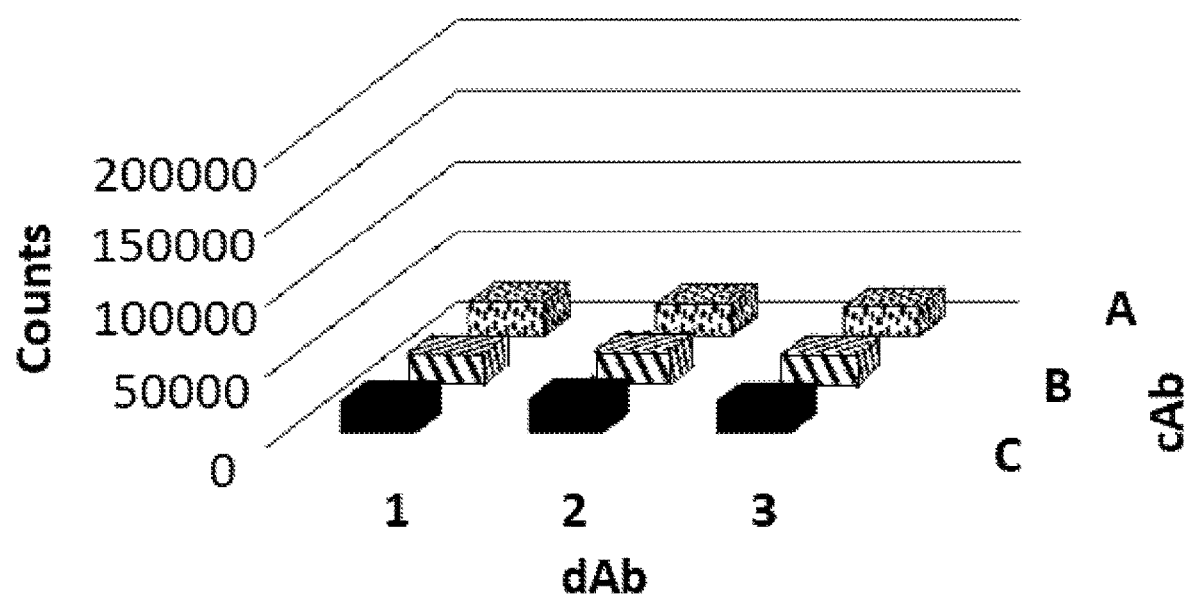
Figure 37:
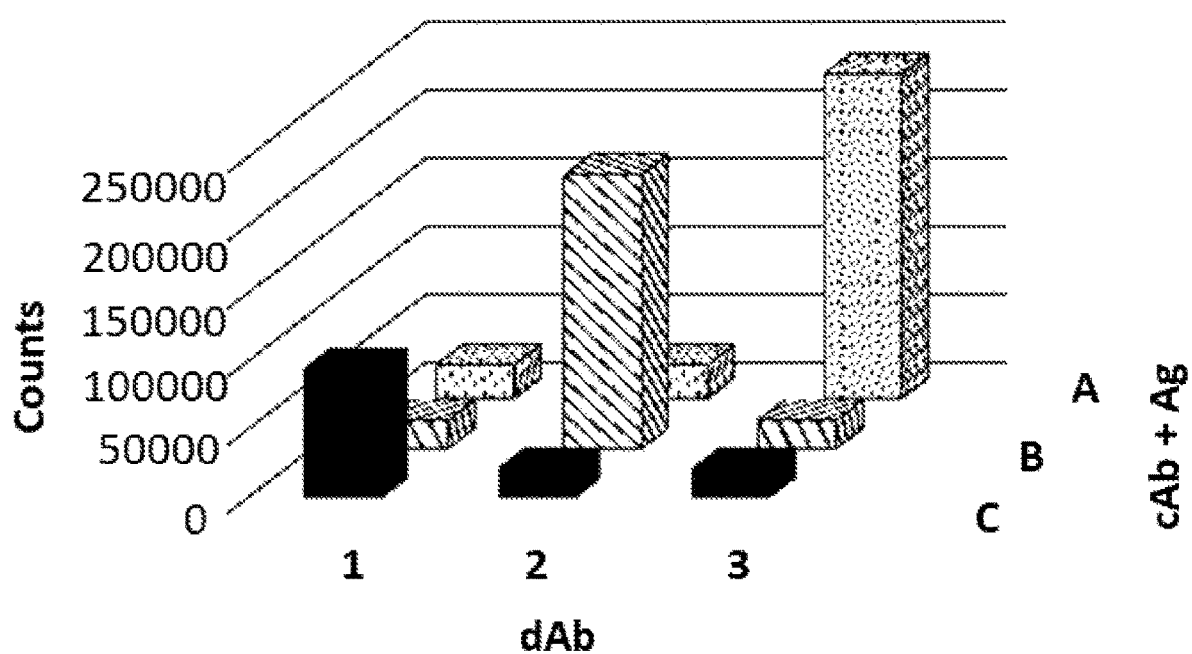
Figure 38:
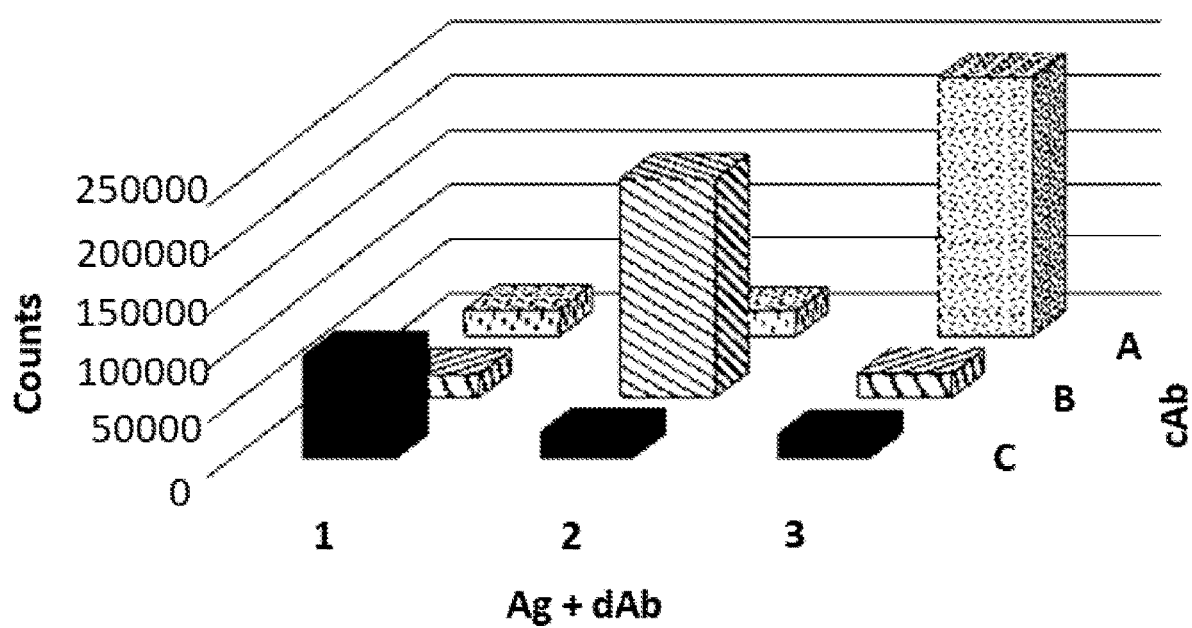
Figure 39:
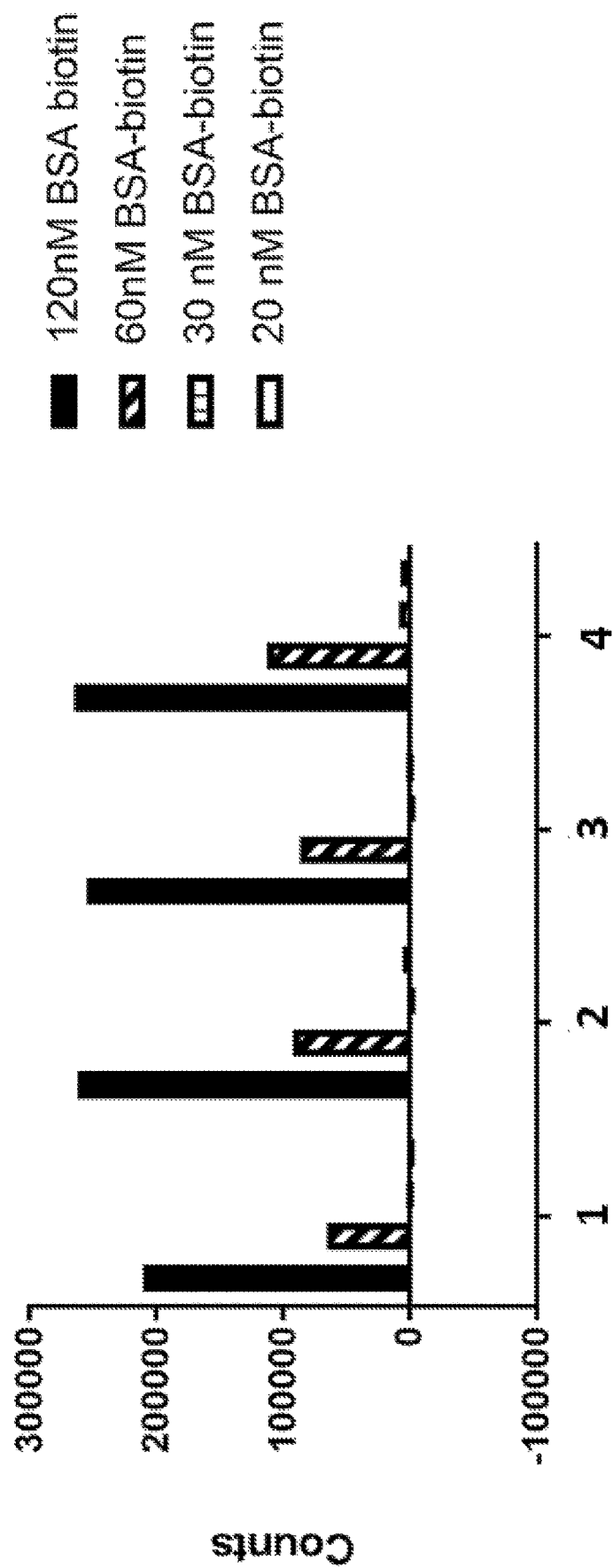
Figure 40:
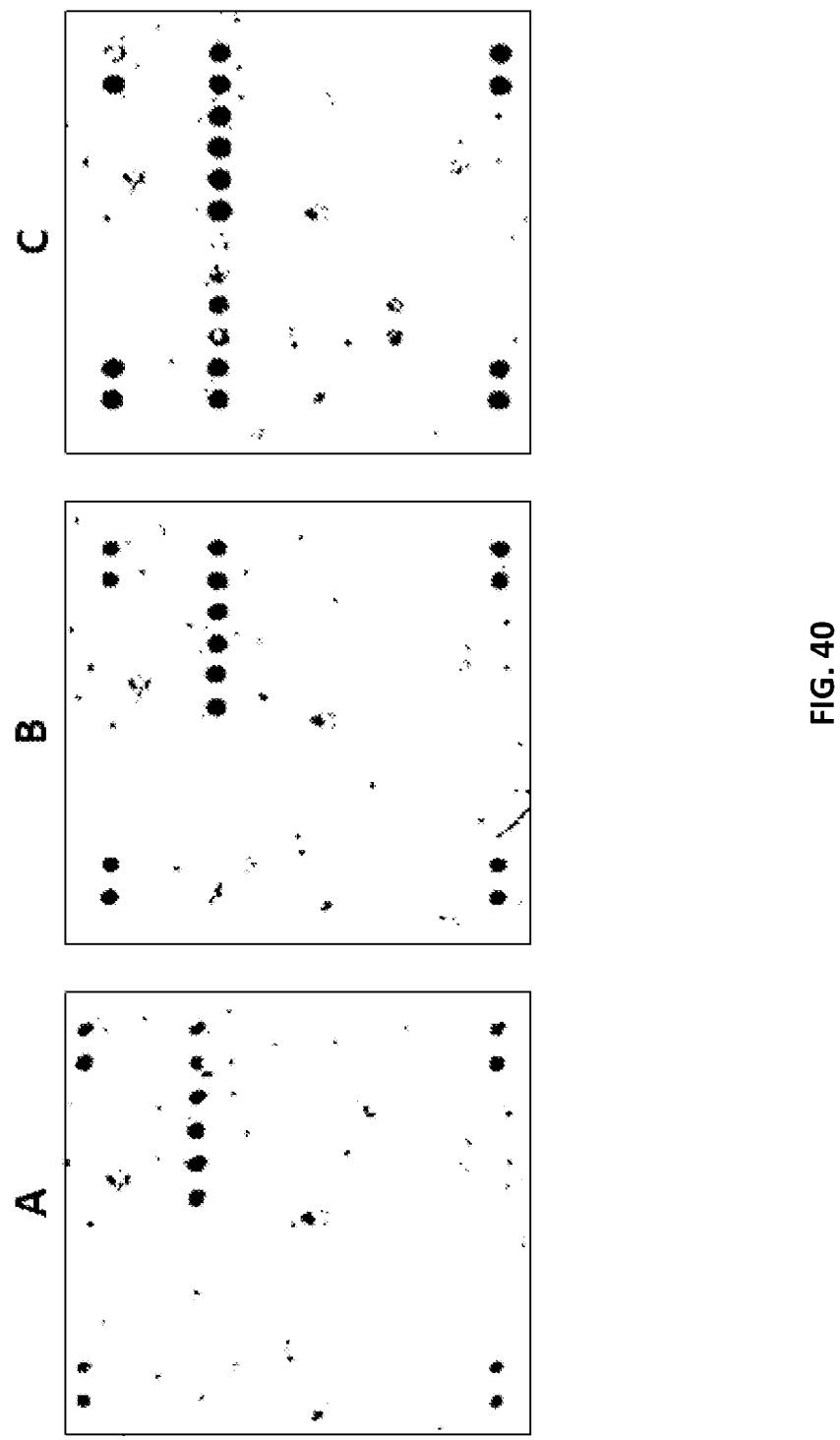
Figure 41:
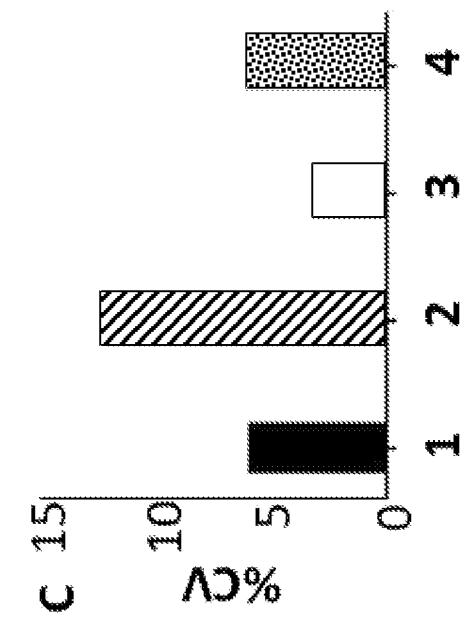
Figure 41:
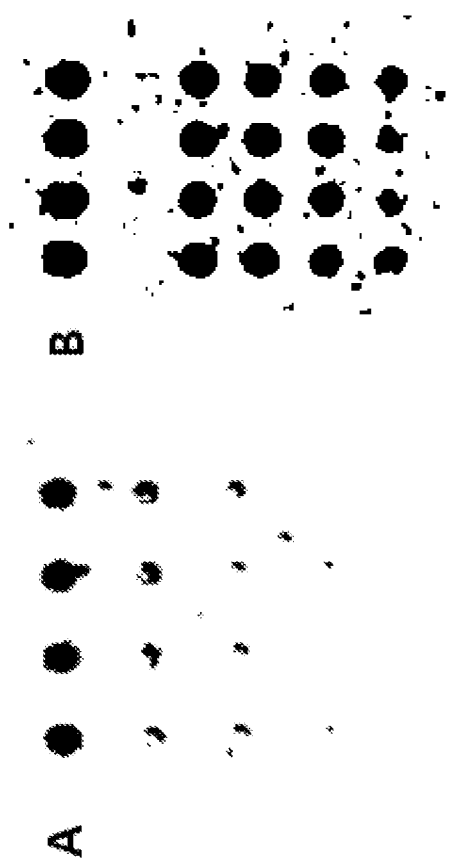
Figure 42:
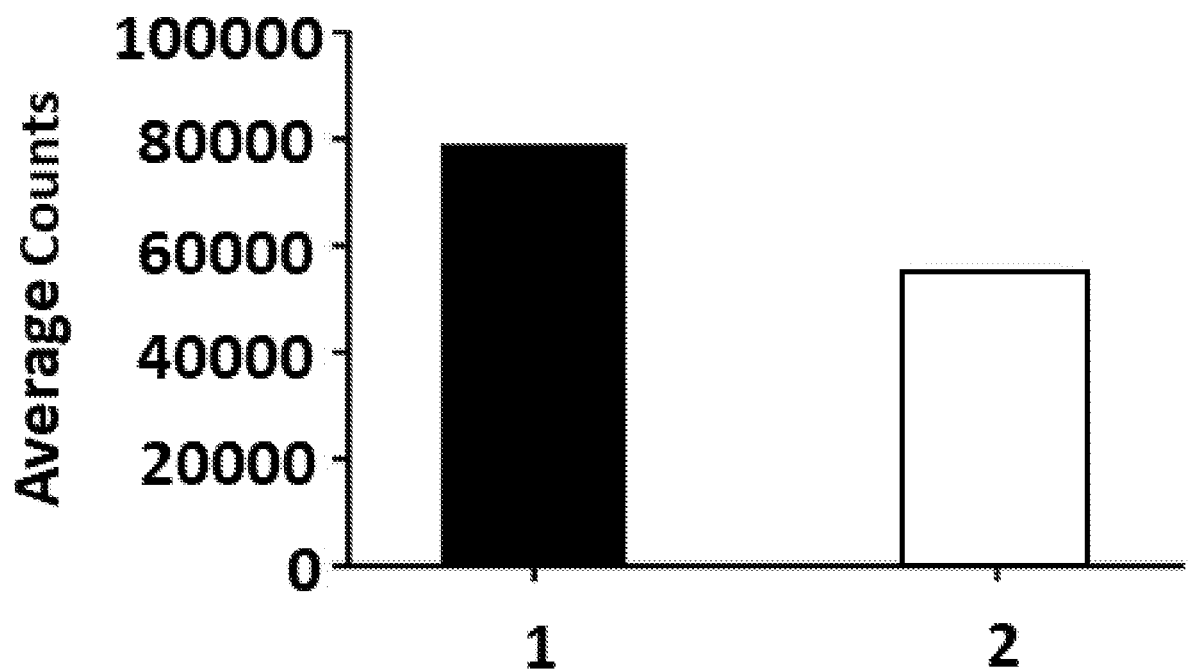
Figure 43:
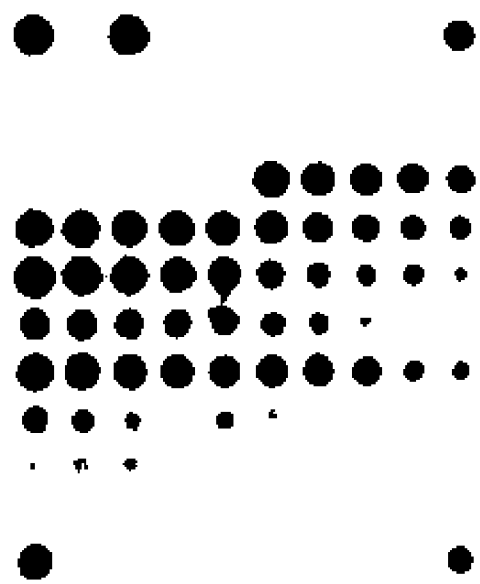
Figure 44:
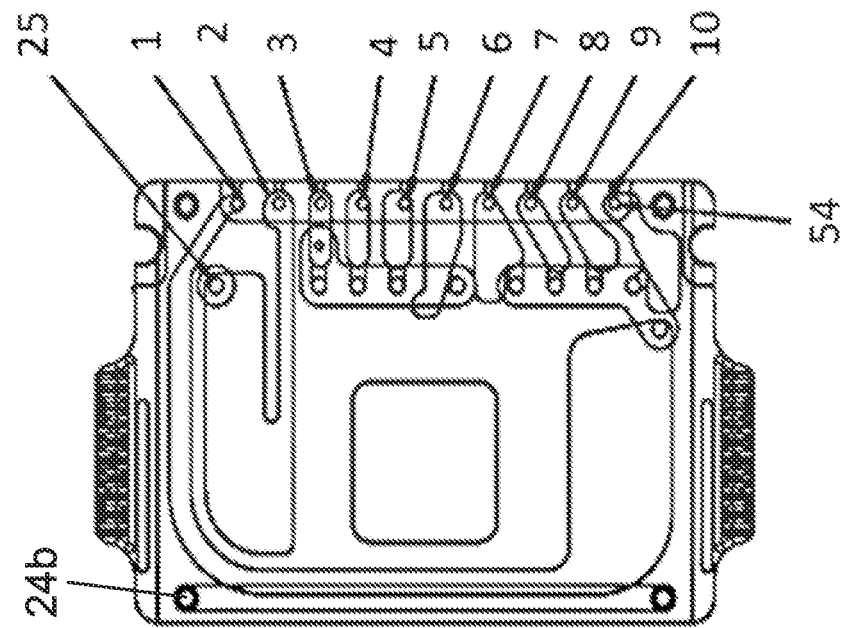
Figure 44:
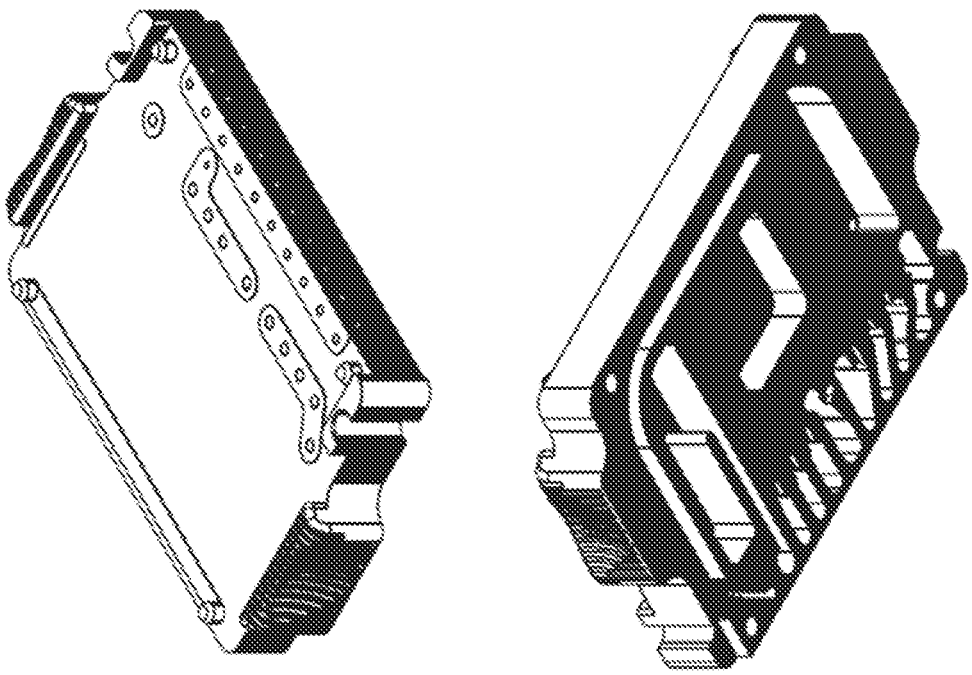
Figure 45:
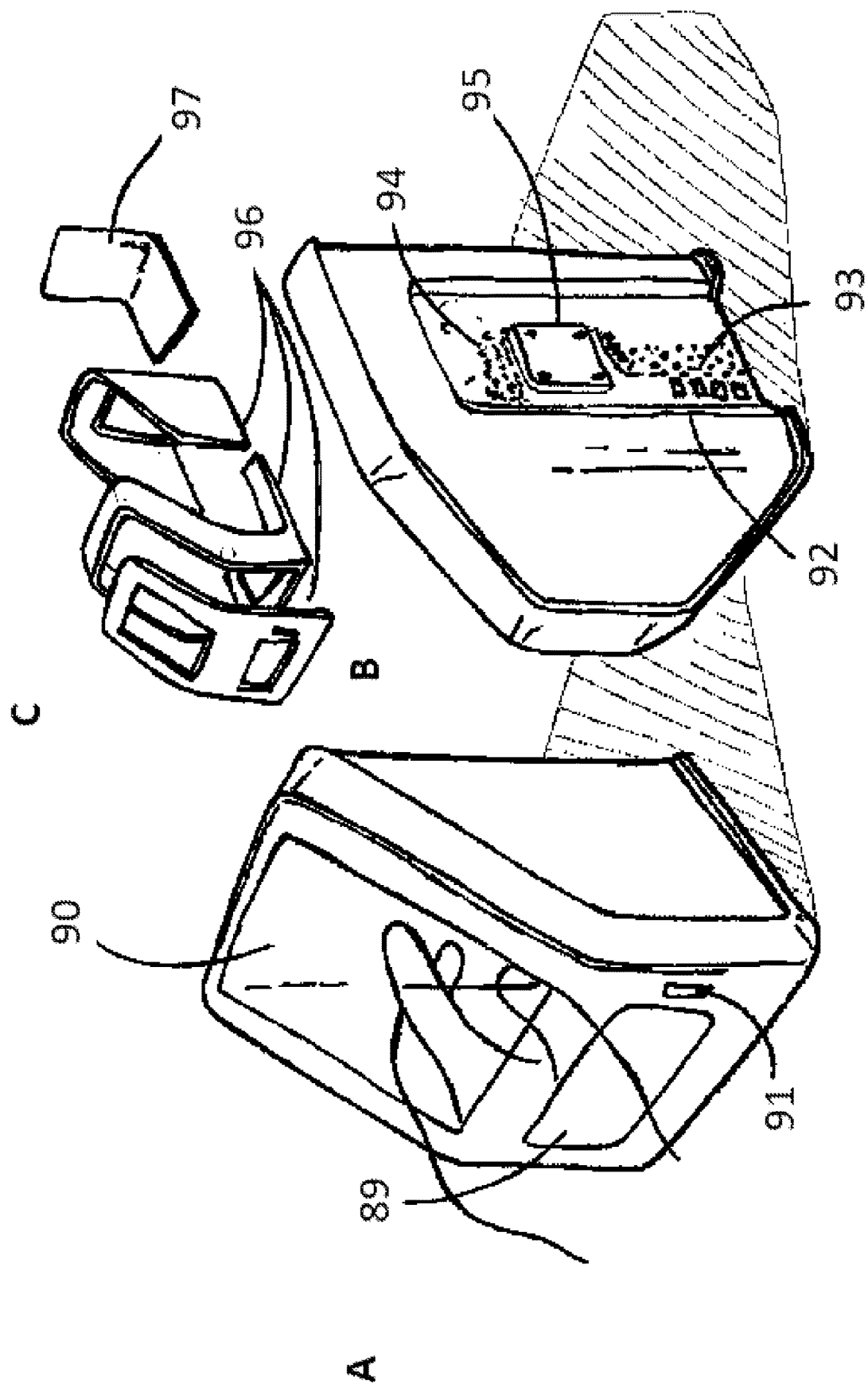
Figure 46:
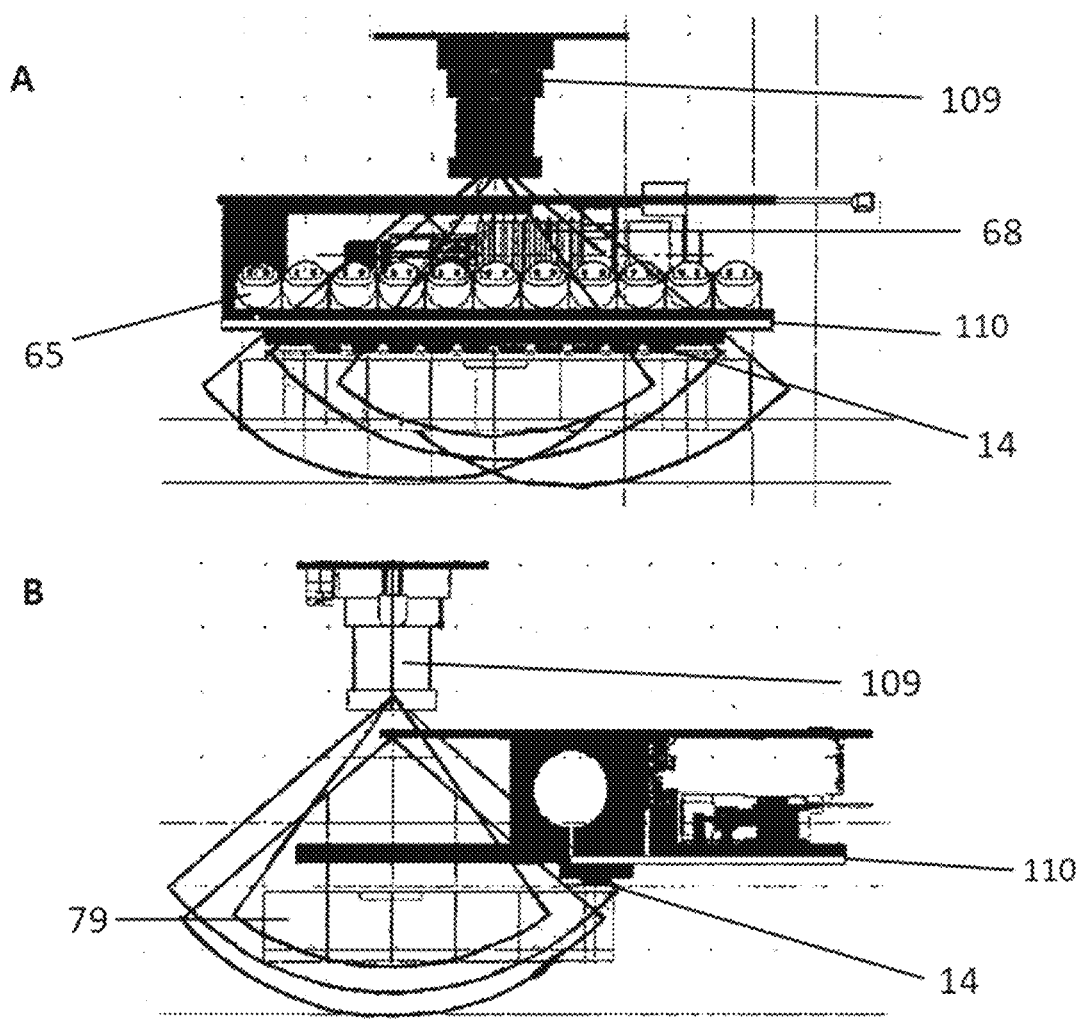
Figure 47:
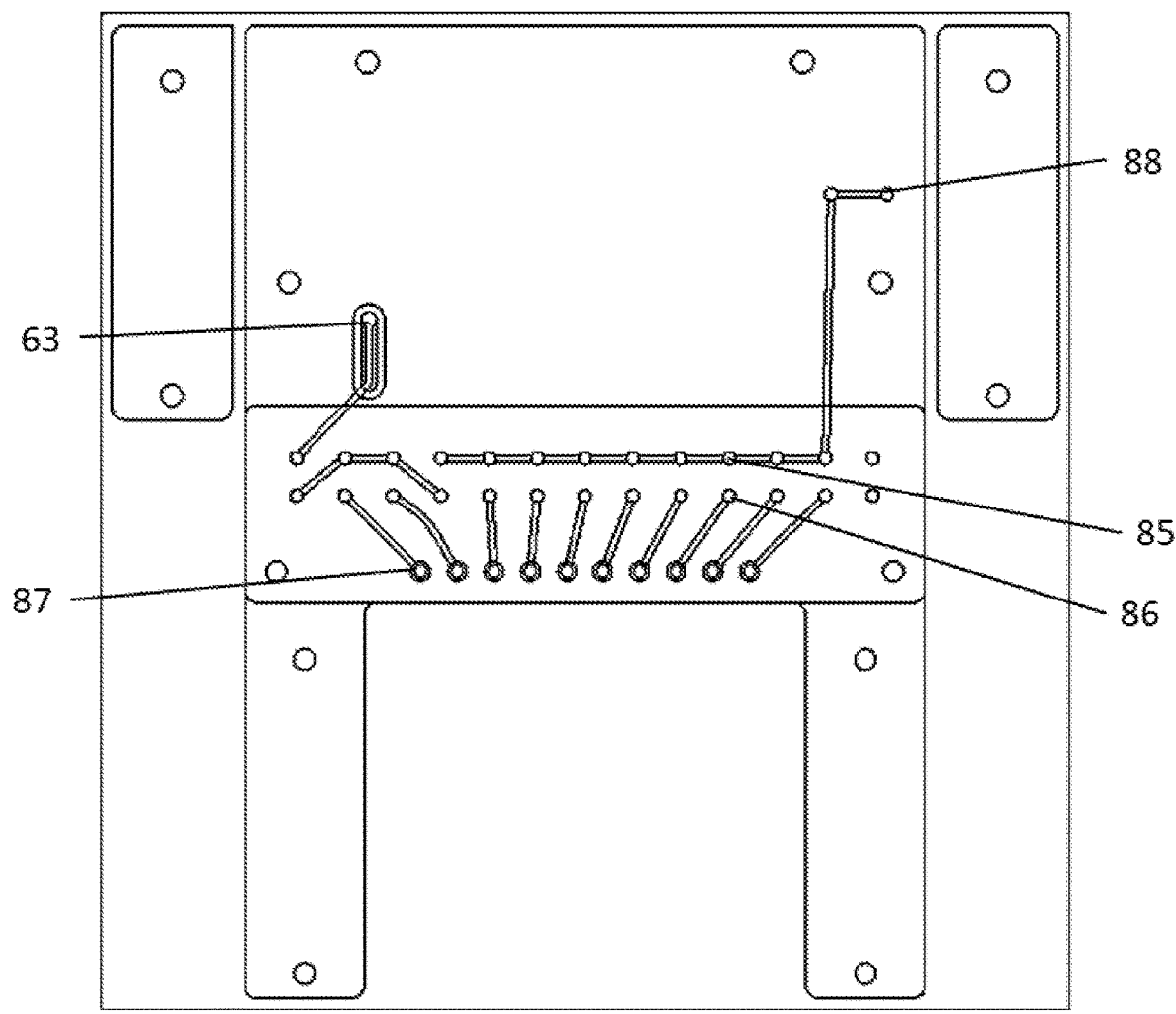

FIGS. 25A-C are schematic illustrations of different embodiments of a dry cartridge;

FIG. 26 is a schematic illustration of one embodiment of a wet cartridge;

FIG. 27 is a schematic illustration of a side view of exemplary wet and dry cartridges, showing alignment of the two;

FIG. 28 is a schematic illustration of one embodiment of a pump, valves, reservoirs and fluid paths for an instrument and cartridge;

FIG. 29 is a schematic illustration of one embodiment of solenoid valves used in the instrument;

FIG. 30 is a schematic illustration of one embodiment of an instrument, cartridge and computer/software connection;

FIG. 31 is an illustration of one embodiment of a benchtop instrument;

FIG. 32 is an illustration of one embodiment of a syringe pump;

FIG. 33 is an illustration of one embodiment of a manifold;

FIGS. 34A-B show the standard curves for CA15-3 at different detection antibody concentrations, 0.2 µg/ML (A) and 0.4 µg/ML (B), respectively;

FIGS. 35A-B show the standard curves for myoglobin at two different detection antibody concentrations, 1 µg/mL (A) and 4 µg/mL (B), respectively;

FIG. 36 shows the cross-reactivity screening results between capture and detection antibodies from microarray without antigens. Signals were detected using images from the Arraylt colorimetric scanner and quantified with ImageJ; Row A: ErbB2 cAb at 400 µg/mL, Row B: CEA cAb at 800 µg/mL, Row C: CA15-3 cAb at 160 µg/mL; Column 1: CA15-3 dAb at 40 ng/mL, Column 2: CEA dAb at 25 µg/mL, Column 3: ErbB2 dAb at 4 µg/mL;

FIG. 37 shows the cross-reactivity screening results between breast cancer panel antigens and detection antibodies on microarray. Signals were detected using images from the Arraylt colorimetric scanner and quantified with ImageJ;

Row A: ErbB2 cAb at 400 µg/mL and ErbB2 antigen, Row B: CEA cAb at 800 µg/mL and CEA antigen, Row C: CA15-3 cAb at 160 µg/mL and CA15-3 antigen; Column 1: CA15-3 dAb at 40 ng/mL, Column 2: CEA dAb at 25 µg/mL, Column 3: ErbB2 dAb at 4 µg/mL;

FIG. 38 shows the cross-reactivity screening results between breast cancer panel antigens and capture antibodies on microarray. Signals were detected using images from the ArrayIt colorimetric scanner and quantified with ImageJ; Row A: ErbB2 cAb at 400 µg/mL, Row B: CEA cAb at 800 µg/mL, Row C: CA15-3 cAb at 160 µg/mL; Column 1: CA15-3 antigen and CA15-3 dAb at 40 ng/mL, Column 2: CEA antigen and CEA dAb at 25 µg/mL, Column 3: ErbB2 antigen and ErbB2 dAb at 4 µg/mL;

FIG. 39 shows the signal of various SA-HRP/biotin-HRP conditions after the subtraction of background; 1: Counts of BSA-biotin probed with 8 ug/mL SA-HRP and 4 ug/mL biotin-HRP, 2: Counts of BSA-biotin probed with 16 ug/mL SA-HRP and 8 ug/mL biotin-HRP, 3: Counts of BSA-biotin probed with 32 ug/mL SA-HRP and 16 ug/mL biotin-HRP, 4: Counts of BSA-biotin probed with 64 ug/mL SA-HRP and 32 ug/mL biotin-HRP;

FIGS. 40A-C shows ErbB2 cAb printed, probed, and developed with TMB on three slide types; Slides imaged with ArrayIt Colorimetric scanner; BSA-biotin 30 nM were printed in duplicate in the four corners of the array; One row of ErbB2 cAb and antigen was printed in duplicate, ErbB2 cAb at max concentration, ERbB2 cAb at ½ maximum concentration, ErbB2 cAb at ¼ maximum concentration, ErbB2 antigen at 4 µg/mL, ErbB2 antigen at 2 µg/mL, ErbB2 antigen 1 µg/mL; Panel A shows the results of an Aminosilane slide; Panel B shows the results of an Aldehyde slide; Panel C shows the results of an Epoxy slide;

FIGS. 41 A-C shows improved spot morphology and reduction in CV when using printing buffer with 0.01% sarcosyl and 0.25 mg/mL BSA Panel A shows resulting image after TMB development and imaging with the ArrayIt Colorimetric scanner for samples printed in 1×PBS in replicates of four; Top row: CA15-3 cAb at 30 µg/mL, Second row: CA15-3 antigen at 400 U/mL, Third row: CA15-3 antigen at 200 U/mL, Bottom row: CA15-3 antigen at 100 U/mL; Panel B shows resulting image after TMB development and imaging with the ArrayIt Colorimetric scanner for samples printed in 1×PBS+0.01% sarcosyl+0.25 mg/mL BSA in replicates of four; Top row: CA15-3 cAb at 20 µg/mL, Second row: CA15-3 antigen at 1600 U/mL, Third row: CA15-3 antigen at 800 U/mL, Fourth row: CA15-3 antigen at 400 U/mL, Bottom row: CA15-3 antigen at 200 U/mL; Panel C is a graph illustrating the average % Coefficient of Variation (CV) of cAb and antigen of the results shown in Panels A and B; 1: % CV of cAb printed with 1×PBS, 2: % CV of antigen printed with 1×PBS, 3: % CV of cAb printed with 1×PBS+0.01% sarcosyl+0.25 mg/mL BSA, 4: % CV of antigen printed with 1×PBS+0.01% sarcosyl+0.25 mg/mL BSA;

FIG. 42 shows the results of myoglobin capture antibody after probing with 22 ng/mL of myoglobin. 1: Resulting signal of short assay time (10 minutes) with 25 ug/mL myoglobin cAb and 1 ug/mL myoglobin dAb; 2: Resulting signal of long assay time (27 minutes) with 40 ug/mL myoglobin cAb and 50 ng/mL dAb;

FIG. 43 shows an image taken from an instrument prototype after running an automatic cardiac panel immunoassay using a cartridge; Corner spots are BSA-biotin spots; cAbs and antigens were printed in replicates of five; Row 1: second half, Myoglobin cAb concentration 1, Row 2: Myoglobin cAb concentration 2, Myoglobin cAb concentration 3, Row 3: Myoglobin antigen concentration 1, Myoglobin antigen concentration 2, Row 4: CK-MB antigen concentration 1, CK-MB antigen concentration 2, Row 5: CK-MB cAb concentration 1, CK-MB cAb concentration 2, Row 6: CK-MB cAb concentration 3, NT-proBNP cAb concentration 1, Row 7: NT-proBNP cAb concentration 2, NT-proBNP cAb concentration 3;

FIGS. 44A-C are illustrations of an alternative embodiment of a wet cartridge; Panel A is an illustration of the top of an alternative embodiment of a wet cartridge; Panel B is an illustration of the bottom of an alternative embodiment of a wet cartridge; Panel C is a schematic illustration of an alternative embodiment of a wet cartridge;

FIGS. 45A-C are illustrations of one embodiment of an instrument as described herein; Panel A illustrates the front view of the instrument; Panel B illustrates the rear view of the instrument; Panel C shows the disassembly of the body of the instrument;

FIGS. 46A-B shows a schematic illustration of the manifold Panel A illustrates the rear view of the manifold Panel B illustrates the side view of the manifold;

FIG. 47 is a schematic illustration of one embodiment of a manifold laminate.

DETAILED DESCRIPTION

The present disclosure provides, in part, a microfluidic apparatus for detecting multiple target polypeptides or other target molecules in parallel. The microfluidic apparatus may be a protein microarray-integrated microfluidic device for, for example, detection of an array of disease-related protein biomarkers. In general, the microarray immunoassay described herein utilizes the same basic protocol as a conventional sandwich ELISA except that the assays are multiplexed and there is a marked reduction in the size of the assay, which reduces consumption of reagents and samples.

Target Molecules

Target molecules include, without limitation, biomarkers related to, or correlated with, human diseases, small molecules, drug metabolites, abused substances, pollutants in water or soil samples, food contaminants, and allergens in the environment. In some embodiments, the target molecules are those for which specific detection and/or recognition molecules, such as antibodies, are publicly available.

Biomarkers

Biomarkers generally refer to a measurable indicator of a biological state or condition. Accordingly, a biomarker, as used herein, can refer to any detectable molecule found in, or obtained from, a biological sample that has been correlated with, and therefore can be used to determine the existence of, a pathogenic condition, disease or disorder; predisposition to a pathogenic condition, disease or disorder; response to a therapeutic intervention, etc.

Examples of biomarkers include, without limitation, biomarkers for diseases or disorders, such as cancer, cardiovascular disease, diabetes, inflammatory diseases, or neurological conditions.

The term "cancer" includes carcinomas, which are the predominant cancers and are cancers of epithelial cells or cells covering the external or internal surfaces of organs, glands, or other body structures (e.g., skin, uterus, lung, breast, prostate, stomach, bowel), and which tend to metastasize; sarcomas, which are derived from connective or supportive tissue (e.g., bone, cartilage, tendons, ligaments, fat, muscle); and hematologic tumors, which are derived from bone marrow and lymphatic tissue. Carcinomas may be adenocarcinomas (which generally develop in organs or glands capable of secretion, such as breast, lung, colon, prostate or bladder) or may be squamous cell carcinomas (which originate in the squamous epithelium and generally develop in most areas of the body). Sarcomas may be osteosarcomas or osteogenic sarcomas (bone), chondrosarcomas (cartilage), leiomyosarcomas (smooth muscle), rhabdomyosarcomas (skeletal muscle), mesothelial sarcomas or mesotheliomas (membranous lining of body cavities), fibrosarcomas (fibrous tissue), angiosarcomas or hemangioendotheliomas (blood vessels), liposarcomas (adipose tissue), gliomas or astrocytomas (neurogenic connective tissue found in the brain), myxosarcomas (primitive embryonic connective tissue), or mesenchymous or mixed mesodermal tumors (mixed connective tissue types). Hematologic tumors may be myelomas, which originate in the plasma cells of bone marrow; leukemias which may be "liquid cancers" and are cancers of the bone marrow and may be myelogenous or granulocytic leukemia (myeloid and granulocytic white blood cells), lymphatic, lymphocytic, or lymphoblastic leukemias (lymphoid and lymphocytic blood cells) or polycythemia vera or erythremia (various blood cell products, but with red cells predominating); or lymphomas, which may be solid tumors and which develop in the glands or nodes of the lymphatic system, and which may be Hodgkin or Non-Hodgkin lymphomas. In addition, mixed type cancers, such as adenosquamous carcinomas, mixed mesodermal tumors, carcinosarcomas, or teratocarcinomas also exist.

Cancers may also be named based on the organ in which they originate i.e., the "primary site," for example, cancer of the breast, brain, lung, liver, skin, prostate, testicle, bladder, colon and rectum, cervix, uterus, etc. This naming persists even if the cancer metastasizes to another part of the body that is different from the primary site. Cancers named based on primary site may be correlated with histological classifications. For example, lung cancers are generally small cell lung cancers or non-small cell lung cancers, which may be squamous cell carcinoma, adenocarcinoma, or large cell carcinoma; skin cancers are generally basal cell cancers, squamous cell cancers, or melanomas. Lymphomas may arise in the lymph nodes associated with the head, neck and chest, as well as in the abdominal lymph nodes or in the axillary or inguinal lymph nodes.

Biomarkers for breast cancers include, without limitation, Carcinoma Antigen 15-3 (CA15-3), Carcinoembryonic Antigen (CEA), Cytokeratin Fragment 21-1 (CYFRA 21-1) and soluble human Epidermal Growth-Factor Receptor 2 (HER2/ErbB2).

CA15-3 is a commonly used tumour marker (biomarker) for breast cancer. It is derived from the MUC1 gene; therefore, CA15-3 is also known as Mucin 1 (MUC1) (Grzywa et al., 2014)). It is 1255 amino acids long and has a molecular weight of 122 kDa (Begum et al., 2012). It is a member of the mucin family and is a large transmembrane glycosylated molecule consisting of three main domains: a large extracellular region, a membrane spanning sequence and a cytoplasmic domain (Ricci et al., 2009; Lucarelli et al., 2014; Grzywa et al., 2014). The normal range for CA 15-3 in healthy individuals has been found to be 0-28 U/ml (Begum et al., 2012). When carcinomas are present, the apical orientation of CA15-3 and its glycosylation are altered (Grzywa et al., 2014) and the protein is overexpressed and distributed all over the cell surface, creating an environment which protects the cancer cells from the host immune system and promotes metastatic activity (Danysh et al., 2012). In some embodiments, CA15-3 can be used for early detection of breast cancer recurrence and/or for evaluating the efficiency of a treatment for breast cancer by, for example, comparing the level of CA15-3 in blood before and after the treatment.

| Biomarker | Antibody Type | Isotype | Clone | Supplier | Catalog Number |
|---|---|---|---|---|---|
| CA15-3 | mouse | IgG2B | M201211 | Fitzgerald | 10-CA15A |
| CA15-3 | mouse | IgG2B | M2012112 | Fitzgerald | 10-CA15B |
| CA15-3 | mouse | IgG1b | U9H3 | Biorbyt | orb195565 |
| CA15-3 | mouse | IgG2b | V2G9 | Biorbyt | orb195564 |
| CA15-3 | mouse | IgG1 | 139H2 | ProSci | 70-116 |

Carcinoembryonic Antigen (CEA) is a 180-kDa glycoprotein, which was first discovered and extracted by Gold and Freedman in 1965 from carcinoma of the colon (Gold and Freedman, 1965). Its normal function is for cell adhesion and inhibition of apoptosis. As a result, it is expressed in normal mucosal cells and over-expressed in adenocarcinoma (Beauchemin and Arabzadeh, 2013). It is present in the periphery of a tumour cell membrane where it is released into the body fluids. It is often overexpressed in breast, colorectal, and other epithelial cancer patients and released into the circulating blood stream (Goldenberg et al., 1981). The level of CEA is generally low, for example between 0 to 2.5 μg/L (micrograms per litre) in healthy adults, and tends to be slightly higher in smokers, ranging between 0 to 5 μg/L (Alexander et al., 1976). In cancer patients, for example breast cancer patients, the level of CEA can be above 10 μg/L (Romero et al., 1996). In some embodiments, CEA can be used as a marker for diagnosis, prognosis, or monitoring the response to treatment of cancers, such as breast and colorectal cancers.

| Biomarker | Species | Isotype | Clone | Supplier | Catalog Number |
|---|---|---|---|---|---|
| CEA | mouse | IgG | M12135 | Fitzgerald | 10-1131 |
| CEA | mouse | IgG | M12138 | Fitzgerald | 10-1134 |
| CEA | mouse | IgG1 | 9B35 | US Biological | C1299-87O |
| CEA | mouse | IgG1 | 9L78 | US Biological | C1299-87W |
| CEA | mouse | IgG1 | M111147 | Fitzgerald | 10-C10D |
| CEA | mouse | IgG1 | M111146 | Fitzgerald | 10-C10E |
| CEA | mouse | IgG2A | 487609 | R&D System | MAB41281 |

Cytokeratin Fragment 21-1 (CYFRA 21-1) is a soluble fragment of cytokeratin 19, the acidic type 1 subunit of cytokeratin, with a molecular weight of 40 kDa (Jose et al., 2013) and is released into the bloodstream during apoptosis (Oloomi et al., 2013). Healthy individuals do not exhibit elevated levels of serum CYFRA 21-1. In some embodiments, a cut-off value of >2.0 ng/ml for CYFRA 21-1 can be used in detection assays (Nakata et al., 2000). Monoclonal antibodies with epitopes within helix 2B of the rod domain of CYFRA 21-1 have been made (Jose et al., 2013). In some embodiments, CYFRA 21-1 can be used for detecting cancer recurrence and/or efficacy of a cancer treatment, such as a breast cancer treatment.

| Biomarker | Species | Isotype | Clone | Supplier | Catalog Number |
|---|---|---|---|---|---|
| CYFRA21-1 | rabbit | IgG1 | N/A | Biorbyt | orb48781 |
| CYFRA21-1 | rabbit | IgG1 | N/A | Biorbyt | orb78531 |
| CYFRA21-1 | rabbit | IgG1 | N/A | Biorbyt | orb156511 |
| CYFRA21-1 | sheep | IgG1 | N/A | R&D System | AF3506 |
| CYFRA21-1 | mouse | IgG1 | N/A | Enogene | E63C01003 |

-continued

| Biomarker | Species | Isotype | Clone | Supplier | Catalog Number |
|---|---|---|---|---|---|
| CYFRA21-1 | mouse | IgG1 | BA17 | R&D System | MAB3506 |
| CYFRA21-1 | mouse | IgG2A | N/A | Antibodies Online | ABIN1824073 |

Human epidermal growth-factor receptor 2 (HER2) is one of the receptors in the family of receptor tyrosine kinases (RTKs). HER2 is a 185-kDa transmembrane protein composed of 3 domains: extracellular domain (ECD), transmembrane domain, and intracellular kinase domain (Shao et al., 2014). The extracellular domain (ECD) can be cleaved from the breast cancer cell surface by matrix metalloproteases releasing the HER2-ECD into serum after cleavage (Arribase et al., (2010). In some embodiments, a level of >15 ng/ml of HER2 can be can be used in detection assays (Hyashi et al., 2012; Fornier et al., 2005). In some embodiments, HER2 can be used as a marker for diagnosis, prognosis, or monitoring the response to treatment of cancers, such as breast cancers.

| Biomarker | Species | Isotype | Clone | Supplier | Catalog Number |
|---|---|---|---|---|---|
| ErbB2 | mouse | IgG2B | 191924 | R&D System | MAB1129 |
| ErbB2 | goat | IgG1 | N/A | R&D System | BAF1129 |
| ErbB2 | goat | IgG1 | N/A | R&D System | AF1129 |

Biomarkers are capable of diagnosis, relapse or monitoring of other cancer types. CA19-9 is a sialylated Lewis blood-group antigen originally isolated from the culture medium of a colorectal cancer cell line. It is the most commonly used tumour marker for diagnosis of digestive tract cancers after CEA. Levels of CA19-9 are elevated (above 37 U/mL) in 80% of patients with advanced pancreatic cancer (Su et al., 2015). The American Society for Clinical Oncology recommends the use of monitoring CA19-9 throughout treatment of pancreatic cancer, to determine disease progression. (Locker et al., 2006).

| Biomarker | Species | Isotype | Clone | Supplier | Catalog Number |
|---|---|---|---|---|---|
| CA19-9 | mouse | IgG1 | M2012114 | Mybiosource | MBS533631 |
| CA19-9 | mouse | IgG1 | M2012113 | Mybiosource | MBS532827 |
| CA19-9 | mouse | IgG1 | 1116-NS-19-9 | ThermoFisher | MA1-34608 |
| CA19-9 | mouse | IgG1 | N/A | Biocheck | 70576 |
| CA19-9 | mouse | IgG1 | N/A | Biocheck | 70564 |

CA-125, also known as MUC-16, is another cancer antigen of the mucin family of glycoproteins. It is composed of three different domains, N-terminal, tandem repeat and C-terminal, and the extracellular region is released from cells through proteolytic cleavage. CA-125 is the most useful clinical biomarker for ovarian cancer. Rise of CA-125 levels (above 35 U/mL) correlates with the progression of ovarian cancer and is FDA-approved for the monitoring of ovarian cancer and detecting disease recurrence (Leung et al., 2014).

| Biomarker | Species | Isotype | Clone | Supplier | Catalog Number |
|---|---|---|---|---|---|
| CA-125 | mouse | IgG1 | X306 | Fitzgerald | 10R-C112c |
| CA-125 | mouse | IgG1 | X52 | Fitzgerald | 10R-C112b |
| CA-125 | mouse | IgG1 | N/A | Biocheck | 70178 |
| CA-125 | mouse | IgG1 | N/A | Biocheck | 70400 |

CA72-4, also known as Tumor-Associated glycoprotein or TAG-72, is a biomarker for gastrointestinal cancers. Similar to the other cancer antigens, it is a mucin-like molecule of over 1000 kDa. This biomarker is most useful for gastric cancer. High levels of CA72-4 (above 5 U/mL), indicates a prognosis of advanced gastric cancer or tumour recurrence (Mattar et al., 2002; Yang et al., 2014).

| Biomarker | Species | Isotype | Clone | Supplier | Catalog Number |
|---|---|---|---|---|---|
| CA72-4 | mouse | IgG1 | CC49 | Origene | CF190082 |
| CA72-4 | mouse | IgG1 | B72.3 | Origene | CF190272 |
| CA72-4 | mouse | IgG1 | N/A | Meridian | M01340M |
| CA72-4 | mouse | IgG1 | N/A | Meridian | M01341M |
| CA72-4 | mouse | IgG1 | N/A | Meridian | M01342M |

Ferritin is a mainly cytosolic protein which plays a role in the storage of intracellular iron. When overexpressed it can be secreted into serum and can be found at elevated levels in a multitude of cancers. Elevated levels of ferritin can be an indicator of worse prognosis for patients with Hodgkin's Lymphoma, Hepatocellular carcinoma, non-small-cell lung cancer or pancreatic cancer (Hann et al., 1990; Melia et al., 1982; Maxim et al., 1986; Kalousova et al., 2012). However, the cutoff values for ferritin varies with cancer type (ranging from 92-400 ng/mL). Elevated levels of ferritin can also be an indication of breast cancer relapse and pancreatic cancer patients with higher levels of ferritin have a reduced chance of survival (Robertson et al., 1991; Kalousova et al., 2012).

| Biomarker | Species | Isotype | Clone | Supplier | Catalog Number |
|---|---|---|---|---|---|
| Ferritin | mouse | IgG3 | F23 | Abcam | ab10060 |
| Ferritin | mouse | IgG2b | F31 | Abcam | ab24475 |
| Ferritin | mouse | IgG1 | N/A | Biocheck | 70226 |
| Ferritin | mouse | IgG1 | N/A | Biocheck | 70641 |

MMP-7 (matrix metalloprotease-7) is a zinc-dependent endopeptidase that cleaves proteins of the extracellular matrix. It can promote cancer invasion through proteolytic cleavage of basement membrane proteins. MMP-7 is found to be overexpressed in many cancers including ovarian carcinomas, renal carcinomas and acute myeloid leukemia (Yokohoma et al., 2008). Elevated levels of MMP-7 in serum can be useful in cancer prognostics. Ovarian cancer patients display serum MMP-7 levels above 7.4 ng/mL (Shafdan et al., 2015). In addition, in gastric cancer patients elevated levels of MMP-7 correlated with worse prognosis and reduced survival rate (Yeh et al., 2010).

| Biomarker | Species | Isotype | Clone | Supplier | Catalog Number |
|---|---|---|---|---|---|
| MMP-7 | mouse | IgG2b | 111433 | R&D | MAB9071-500 |
| MMP-7 | goat | IgG | N/A | R&D | AF907 |
| MMP-7 | mouse | IgG1 | 111439 | R&D | MAB9072-500 |

| Biomarker | Species | Isotype | Clone | Supplier | Catalog Number |
|---|---|---|---|---|---|
| MMP-7 | goat | IgG | N/A | R&D | BAF907 |
| MMP-7 | mouse | IgG1 | M72082 | Mybiosource | MBS838368 |
| MMP-7 | mouse | IgG1 | M72083 | Mybiosource | MBS838472 |

Cardiovascular diseases are diseases of the circulatory system, including the heart and blood vessels. Cardiovascular diseases include, without limitation, coronary artery diseases (e.g., angina or myocardial infarction), congestive heart failure, stroke, hypertensive heart disease, rheumatic heart disease, cardiomyopathy, arrhythmia, tachycardia, stenosis, congenital heart disease, valvular heart disease, carditis, aortic aneurysms, peripheral artery disease, venus thrombosis, atherosclerosis, etc. Biomarkers for cardiovascular diseases include, without limitation, B-type natriuretic peptide, cardiac troponin, myoglobin and D-dimer.

B-type natriuretic peptide or BNP is a cardiac marker that functions as a hormone to induce natriuresis, diuresis and vasodilation. It is initially expressed as the proBNP prohormone which is then cleaved and secreted as BNP and NT-proBNP (N-terminus proBNP). NT-proBNP has a longer half-life than BNP (2 hours vs. 20 minutes). Most healthy people have approximately 10 µg/mL of BNP. Average heart failure patients have BNP levels of 675 µg/mL, and levels of NT-proBNP of 4639 µg/mL. Both BNP and NT-proBNP is elevated in older patients, women and patients with renal failure. Conversely, BNP and NT-proBNP levels are reduced in obese people. An increase in either BNP or NT-proBNP levels correlate with an increase in disease severity and mortality. In some embodiments, BNP or NT-proBNP levels can be used to predict an increase or decrease of cardiac disease risk, such as in patients with chronic heart failure, or for establishing and/or monitoring prognosis, disease severity or guided therapy. In some embodiments, a level of about 80 µg/mL of BNP can be used for detection assays.

| Biomarker | Species | Isotype | Clone | Supplier | Catalog Number |
|---|---|---|---|---|---|
| NT-proBNP | mouse | IgG2b | 15C4 | Hytest | 4NT1-15C4 |
| NT-proBNP | mouse | IgG2b | 29D12 | Hytest | 4NT1-29D12 |
| NT-proBNP | mouse | IgG2b | 13G12 | Hyteset | 4NT1-13G12 |
| NT-proBNP | mouse | IgG2a | M72419 | Fitzgerald | 10-1710 |
| NT-proBNP | mouse | IgG2a | M72418 | Fitzgerald | 10-1709 |
| NT-proBNP | mouse | IgG1 | N/A | East Coast Bio | HM145 |
| NT-proBNP | mouse | IgG1 | N/A | East Coast Bio | HM147 |
| NT-proBNP | mouse | IgG2b | N/A | Meridian | H86451M |
| NT-proBNP | mouse | IgG2a | N/A | Meridian | H86912M |

Cardiac troponin is a cardiac specific complex consisting of troponin T, troponin I and troponin C. Troponin T (37 kDa) and Troponin I (22 kDa) have been routinely used as cardiac markers although troponin I is more common. Troponin I is 100% cardiac specific and unlike Troponin T is not elevated with renal disease or skeletal injury. Increasing levels of troponin (above 160 µg/mL) is indicative of a worsening condition (Xue et al., Tonkin et al.) In some embodiments, troponin levels can be used to predict, detect and/or determine risk of cardiovascular events (such as myocardial infarction (MI) or myocardial injury), optimization of therapy, prognosis, disease severity, clinical outcomes and/or mortality. Decrease in troponin levels is associated with better prognosis.

| Biomarker | Species | Isotype | Clone | Supplier | Catalog Number |
|---|---|---|---|---|---|
| Troponin I | mouse | IgG1 | N/A | Biocheck | 70577 |
| Troponin I | mouse | IgG1 | N/A | Biocheck | 70580 |
| Troponin I | mouse | IgG2b | N/A | Biocheck | 70344 (TPC-110) |
| Troponin I | Mouse | IgG1 | 19C7 | Hytest | 4T21-19C7 |
| Troponin I | Mouse | IgG1 | 16A11 | Hytest | 4T21-16A11 |
| Troponin I | mouse | IgG2b | M8030409 | Fitzgerald | 10-T79J |
| Troponin I | mouse | IgG1 | M805142 | Fitzgerald | 10-T79C |
| Troponin I | mouse | IgG1 | N/A | EastCoastBio | HM255 |
| Troponin 1 | mouse | IgG1 | N/A | EastCoastBio | HM256 |
| Troponin 1 | mouse | IgG1 | B1463M | Meridian | H01326M |
| Troponin 1 | mouse | IgG2b | B1462M | Meridian | H01325M |
| Troponin 1 | rabbit | IgG1 | N/A | biorbyt | orb163067 |
| Troponin 1 | goat | IgG1 | N/A | Novus | NBP2-26192 |
| Troponin 1 | goat | IgG | N/A | Novus | NBP2-26191 |

Myoglobin (17 kDa) is a heme-binding protein similar to hemoglobin except it is present in muscle tissue. Since it is in all muscle tissue it is not specific to cardiac muscle. It has been shown to be rapidly secreted from cardiac tissue 1-4 hours after acute myocardial infarction. In some embodiments, myoglobin levels above 88 ng/mL can be used to predict and/or detect mortality, myocardial necrosis or myocardial infarction.

| Biomarker | Species | Isotype | Clone | Supplier | Catalog Number |
|---|---|---|---|---|---|
| Myoglobin | mouse | IgG1 | 8.F.208 | US biological | M9800-16 |
| Myoglobin | mouse | IgG1 | 30 | US biological | M9800-16A |
| Myoglobin | goat | IgG1 | N/A | Biospacific | G125c |
| Myoglobin | mouse | IgG1 | N/A | Biospacific | A27370 |
| Myoglobin | mouse | IgG2b | N/A | Meridian | H01328M |
| Myoglobin | mouse | IgG1 | B1464M | Meridian | H01327M |
| Myoglobin | mouse | IgG1 | N/A | Biocheck | 70131 |
| Myoglobin | goat | IgG1 | N/A | Biocheck | 70196 |

D-dimer is a unique cardiac marker of fibrin degradation. It is formed through the sequential action of 3 enzymes: thrombin, factor XIIIa and plasmin. Commercial D-dimer assays detect an epitope that is present I the factor XIIIa-crosslinked fragment D domain of fibrin but not in the fibrinogen degradation products or non-crosslinked fibrin (Adam et al., 2009). In some embodiments, D-dimer measurements can be used clinically to exclude venous thromboembolism (VTE, which includes deep vein thrombosis (DVT) and pulmonary embolism (PE)) or for the diagnosis or monitoring of coagulation activation in disseminated intravascular coagulation (DIC). In some embodiments, D-dimer levels may be used to detect disease processes that initiate intravascular fibrin formation but not necessary thrombosis, such as, without limitation, activation of blood coagulation, aging, pregnancy, cancer or cancer-associated VTE (Ay et al., 2009). In some embodiments, a level of about 500 ng/mL can be used in detection assays.

| Biomarker | Species | Isotype | Clone | Supplier | Catalog Number |
|---|---|---|---|---|---|
| D-dimer | mouse | N/A | 1D2 | BBI Solutions | BM243-1D2 |

-continued

| Biomarker | Species | Isotype | Clone | Supplier | Catalog Number |
|---|---|---|---|---|---|
| D-dimer | mouse | N/A | 3B6 | BBI Solutions | BM243-3B6 |
| D-dimer | N/A | N/A | N/A | Bio-Rad | 27103 |
| D-dimer | N/A | N/A | N/A | Bio-Rad | 27102X |
| D-dimer | mouse | IgG1k | MAB<DD>M-1.2.57 | Roche | 12156903103 |
| D-dimer | mouse | IgG1k | MAB<DD>M-2.1.16 | Roche | 12045206103 |

Additional biomarkers may include but are not limited to: Calponin-h2, Fucosyltransferase IV (FUT 4), AGR3 (anterior gradient-3), AGR2 (anterior gradient-2), DJ-1, Thymidine Kinase 1 (TK1), Alpha-fetoprotein, PSA (Prostate-specific antigen), Chorionic-gonadotropin (hCG), Pro-GRP (pro gastrin-releasing peptide), NSE (Neuron-Specific Enolase), SCC-Ag (Squamous Cell Carcinoma Antigen)/TA-4, CA-242, CA-50, Pep I/I1 (pepsinogen I/I ratio), AFU (Alpha-L-fucosidase), ALP (alkaline phosphatase), HE-4 (Human epididymis protein 4/WFDC2), 12M (beta-2-microgloblin), VMA (Vanillylmandelic acid, 3-methoxy-4-hydroxymandelic acid), TPA (tissue polypeptide antigen), Galectin-3, Myeloperoxidase and hs-CRP.

Biomarkers can also be used the diagnosis and monitoring of various other medical conditions. Inflammation is a hallmark of the innate immune response, involved in pathogenic infection and tissue damage. In addition, people can suffer from chronic inflammatory diseases such as rheumatoid arthritis, asthma and irritable bowel disorders. Inflammation biomarkers assess disease activity in inflammatory conditions and diagnose and manage infections. The hallmark inflammatory biomarker is C-Reactive Protein or CRP. CRP is of the pentraxin family of proteins (110-144 kda), that is secreted by hepatocytes when activated by cytokines (Algarra et al., 2013). CRP then circulates to the site of infection or tissue damage to help recruit complement proteins to the site of inflammation. In healthy individuals, the median concentration of CRP is 0.8 µg/mL. Following an inflammatory stimulus, this increases to more than 500 µg/mL. Serum concentrations rise to above 5 µg/mL in the first 6 hours, peaking at 48 hours (Pepys and Hirschfield, 2003). CRP is also used a biomarker for risk of cardiac disease, since inflammation may be an indication of cardiovascular damage.

| Biomarker | Species | Isotype | Clone | Supplier | Catalog Number |
|---|---|---|---|---|---|
| hsCRP | mouse | IgG1 | C2 | Hytest | 4C28-C2 |
| hsCRP | mouse | IgG2a | C5 | Hytest | 4C28-C5 |
| hsCRP | mouse | IgG2a | C6 | Hytest | 4C28-C6 |

Additional biomarkers of inflammation include the aforementioned ferritin and MMP-7. Serum ferritin is recognized as an acute phase reactant and marker of acute and chronic inflammation. It is found to be elevated in a wide range of inflammatory conditions. It is thought that the rise in ferritin, reflects an increase in iron stores where it is sequestered away from the uses of pathogens (Wang et al., 2010). MMP-7 is also a biomarker of inflammation in addition to its use as marker for cancer. MMP-7 is upregulated by inflammatory cytokines as well as the presence of pathogenic bacteria (Burke, 2004). For ferritin and MMP-7 potential antibodies refer to sections [0073] and [0074].

Much work has been performed to develop biomarkers of neurologic conditions such as neurodegenerative diseases and brain injuries. Neurodegenerative diseases, such as Alzheimer's, Parkinson's and Prion disease are characterized by the formation of protein aggregates or plaques. Identifying specific biomarkers in plasma or cerebrospinal fluid (CSF) would provide physicians with a relatively non-intrusive way to diagnosis these diseases. Alzheimer's disease is a progressive neurodegenerative disease that impairs cognitive functioning affecting 20% of the population aged over 80 years (Nayak et al., 2015). It is characterized by the formation of amyloid plaques composes of amyloid β peptide 42 and the protein, tau. Interestingly, it's been found that amyloid β-42 levels are lower in the CSF of Alzheimer's patients, perhaps due to its accumulation in the brain. Conversely, tau is elevated in the CSF (Nayak et al., 2015). Utilizing a biomarker found in the plasma of Alzheimer's patients would be an even less intrusive technique in diagnosis. There is an increase in the protein Complement Factor H (CFH) in the blood of Alzheimer's patients. CFH is a negative regulator of the complement pathway and increased levels in the blood correlate with later stages of the disease. CFH is also an especially useful biomarker, since its elevation is not seen in other neurodegenerative diseases and is thus Alzheimer's specific (Nayak et al., 2015).

| Biomarker | Species | Isotype | Clone | Supplier | Catalog Number |
|---|---|---|---|---|---|
| Amyloid β 42 | Mouse | IgG1 | 12F4 | Novus | NBP2-12924 |
| Amyloid β 42 | Mouse | IgG1 | Mab1.1 | Biorad | MCA5930GA |
| Amyloid β 42 | Mouse | IgG1 | Not Given | US biologicals | 214488 |
| Amyloid β 42 | Mouse | IgG1 | 9L34 | US biologicals | A2275-75N |
| tau | Mouse | IgG1 | PHF-6 | Novus | NBP2-29676 |
| tau | Mouse | IgG1 | tau-C3 | Novus | NBP2-29847 |
| tau | Mouse | IgG1 | BT2 | Fitzgerald | 10R-T102a |
| CFH | Mouse | IgG1 | OX-24 | Biorad | MCA509G |
| CFH | Mouse | IgG1 | C18/3 | Invitrogen | GAU 018-03-02 |
| CFH | Mouse | IgG2b | 63G5 | ProSci | 70-085 |

Parkinson's disease is the most common neurodegenerative disease after Alzheimer's. It is characterized by severe motor impairment due to progressive neurodegeneration in the brainstem and cerebrum. Many of the neurons show inclusions most notably consisting of α-synuclein. Also, many proteins have been found in the CSF from Parkinson's patients, the clinical usefulness of these biomarkers remains to be determined. However, an increase in complement-related proteins have been found in sera of Parkinson's patients. Specifically, an increase in the aforementioned CFH as well as C3c, C3dg and factor B (Nayak et al., 2015).

| Biomarker | Species | Isotype | Clone | Supplier | Catalog Number |
|---|---|---|---|---|---|
| C3c | Mouse | IgG1 | 10-02A | Biorad | MCA2605 |
| C3c | Mouse | IgG1 | 10B386 | US biological | C7850-14N |
| C3dg | Mouse | IgG2a | 1H8 | Cedarlane | CL7637AP |
| C3dg | Rabbit | IgG | polyclonal | Biorbyt | orb156425 |
| FactorB | Mouse | IgG1 | 9B8 | Novus | NBP2-23508 |
| FactorB | Mouse | IgG1 | 014III-3.3.2.4.3 | Novus | NB100-64343 |
| FactorB | Mouse | IgG1 | 13A39 | US Biological | C7850-60N |
| FactorB | Mouse | IgG1 | 28A3 | Fitzgerald | 10R-8452 |

Prion diseases, also termed transmissible spongiform encephalopathies, are a unique group of diseases that can affect both humans and animals. In humans, transmission is typically genetic, resulting in abnormal accumulation of the 33-35 kDa prion protein. In its disease state, the prion protein takes on a β-sheet conformation instead of its typical α-helical conformation, leading to protein accumulation and aggregation (Nayak et al., 2015). Current diagnostic methods fail to identify prion disease so it would be greatly beneficial to have a biomarker for this disease. A few biomarkers in the CSF have been identified in prion disease sufferers. Specifically, 14-3-3, β-amyloid, tau, S100b and Neuronal Specific Enolase (NSE) (Rubenstein, 2015). One disadvantage is that these markers are not prion disease specific and can also be present in other neurodegenerative diseases. Thus, much research needs to be done to identify a prion disease specific biomarker that would be easily accessible in CSF or plasma.

| Biomarker | Species | Isotype | Clone | Supplier | Catalog Number |
|---|---|---|---|---|---|
| s100b | Mouse | IgG1 | 9A11B9 | ProSci | 49-060 |
| s100b | Mouse | IgG1 | N/A | Biorbyt | orb88955 |
| s100b | Mouse | IgG1 | 13B693 | US Biological | 30615 |
| NSE | Mouse | IgG2b | 5G10 | Biorad | 6720-0827 |
| NSE | Mouse | IgG2a | 5E2 | Invitrogen | MA1-16696 |
| NSE | Mouse | IgG2a | 1 | Biorbyt | orb243920 |

It is to be understood that any combination of biomarkers can be used. In some embodiments, for example, CYFRA 21-1 may be used to determine the recurrence and/or the efficacy of a cancer treatment, such as a breast cancer treatment along with other breast or other cancer biomarkers, such as CA15-3; troponin may be used with myoglobin or Creatine Kinase MB (CK-MB) for the early detection of myocardial infarction (MI); troponin may be used with CRP or NT-proBNP for risk assessment in patients with clinical syndrome consistent with acute coronary syndrome (ACS); etc.

Fluid Sample

A "fluid sample" can be any fluid containing, or suspected of containing, a target molecule, such as a biological sample, an environmental sample, a forensic sample, etc.

A "biological sample" can be any organ, tissue, cell, or cell extract isolated or obtained, directly or indirectly, from a subject. For example, a biological sample can include, without limitation, cells or tissue (e.g., from a biopsy or autopsy) from bone, brain, breast, colon, muscle, nerve, ovary, prostate, retina, skin, skeletal muscle, intestine, testes, heart, liver, lung, kidney, stomach, pancreas, uterus, adrenal gland, tonsil, spleen, soft tissue, peripheral blood, whole blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, urine, stool, saliva, placental extracts, amniotic fluid, a cryoprecipitate, a cryosupernatant, a cell lysate, mammalian cell culture or culture medium, products of fermentation, ascitic fluid, proteins present in blood cells, solid tumours, or any other specimen, or any extract thereof, obtained from a patient subject (human or animal), test subject, or experimental animal subject. In some embodiments, it may be desirable to separate cancerous cells from non-cancerous cells in a sample. A sample may also include, without limitation, products produced in cell culture by normal or transformed cells (e.g., via recombinant DNA or monoclonal antibody technology). A sample may also include, without limitation, any organ, tissue, cell, or cell extract isolated from a non-mammalian subject, such as an insect or a worm. A sample may also include, without limitation, plants, bacteria, mold, spores, or viruses. A "sample" may also be a cell or cell line created under experimental conditions, that is not directly isolated from a subject. A sample can also be cell-free, artificially derived or synthesized. A sample may be from a cell or tissue known to be cancerous, suspected of being cancerous, or believed not be cancerous (e.g., normal or control).

In some embodiments, a sample as used herein is substantially purified e.g., free of cells and/or cell extracts. Accordingly, in some embodiments, a sample may include a bodily fluid or extract which is substantially free of cells, such as blood plasma, serum or urine. It is to be understood that such samples may contain small amounts of cells, such as 5% or less, i.e., any value between 0% to 5%, for example, less than 1%, 2%, 3%, 4% or 5%. Alternatively, samples may contain cells, such as whole blood.

A "control" includes a sample obtained for use in determining base-line expression or activity. Accordingly, a control sample may be obtained by a number of means including from non-cancerous cells or tissue e.g., from cells surrounding a tumor or cancerous cells of a subject; from subjects not having a cancer; from subjects not suspected of being at risk for a cancer; or from cells or cell lines derived from such subjects. A control also includes a previously established standard. Accordingly, any test or assay conducted according to the invention may be compared with the established standard and it may not be necessary to obtain a control sample for comparison each time.

The sample may be analyzed to detect the presence or amount of a target molecule of interest.

Protein Microarray

Target molecules can be detected using suitable binding partners, or fragments thereof, that specifically bind the target molecules. For example, in some embodiments, biomarkers can be detected using suitable antibodies, or fragments thereof, that specifically bind the biomarkers. In alternative embodiments, autoantibodies, for example, can be detected using proteins or peptides. Any suitable detection method can be used, as described herein or known in the art.

An antibody "specifically binds" a biomarker when it recognises the biomarker, but does not substantially recognise and bind other molecules in a sample. Such an antibody has, for example, an affinity for the biomarker which is at least 10, 100, 1000 or 10000 times greater than the affinity of the antibody for another reference molecule in a sample.

In some embodiments, an antibody or fragment thereof that can specifically bind a biomarker is presented in a microarray (an "antibody microarray"). By "antibody microarray" is meant a plurality of antibodies, or fragments thereof, provided on a suitable substrate, such as a chemically functionalized or polymer-coated glass or a similar material, that are capable of binding a plurality of biomarkers.

The antibodies may be attached to or deposited on the substrate using standard techniques, such as with a microarray spotting robot.

In general, the antibodies may be provided in a region of the substrate such that they can detect the biomarkers. The region can be any suitable size, depending on the number of antibodies used and the density of the printing as well as the size of area chemically functionalized or polymer-coated.

In general, the antibody microarray will include a plurality of antibodies that are capable of specifically binding a plurality of biomarkers. For example, in some embodiments, in the antibody microarray, each distinct antibody may specifically bind a distinct biomarker. In alternative embodiments, the antibody microarray may include a plurality of antibodies capable of specifically binding a particular biomarker. Accordingly, each antibody can be different from the other antibodies present in the microarray, such that they can specifically bind different biomarkers, or specifically bind different regions of the same biomarker.

The antibody microarray can include a suitable number of antibodies, such as between about 2 to about 10,000 antibodies, or any value in between, such as about 100, 200, 300, 500, 1000, 1500, 2000, 3000, 4000, 5000, 6000, 7000, 8000, 9000 or 10000 antibodies. In some embodiments, greater numbers, such as 15000, 20000, 30000 or more, can be used, subject for example to the size of the microarray substrate, the size of the region detectable by the device, the resolution of the image afforded by the optical detection system, and the spot size of the antibodies.

It is to be understood that the number of antibodies that can be spotted on a substrate will depend on the size of the substrate, the density of the spots, cross-reactivity interactions, spot size, etc. For example, a larger number of antibodies can be spotted with an increase in the size of the region capable of detecting a biomarker, or an increase in spot density, or a decrease in spot size.

The antibodies may be provided on the substrate as spots that can be about 50 microns to about 500 microns in diameter, or any value in between, such as 60 microns, 100 microns, 200 microns or 250 microns. In some embodiments, the spots may be larger, subject for example to the size of the microarray substrate, the size of the region detectable by the biomarkers, and the density of the antibodies. The spots may of any shape, whether regular or irregular.

The antibody spots are generally discrete from each other spatially. In general, the spots are separated at least 100 microns from each other, such as at least 100, 200 or 400 microns from each other.

The spots can be arranged in any suitable fashion, whether ordered or random. In general, the spots are arranged in an ordered fashion, such that the separation of the spots is regular and pre-determined. The spots can be arranged in one, two or three dimensions. For example, the spots can be arranged in rows and columns, number from about 10 to about 1,000.

Microfluidic Cartridge

A cartridge including microfluidic circuitry, a reaction chamber or "array chamber," reservoirs for containing liquids, such as reagents, buffers, or sample (the "microfluidic cartridge") may be provided. In some embodiments, the microfluidic cartridge may include, without limitation, a plurality of reagent reservoirs and channels, a plurality of buffer reservoirs and channels, a plurality of waste reservoirs and channels, a plurality of vents, a plurality of ports, an aperture for detecting a protein microarray, as well as channels connecting the reservoirs, for example, a channel leading from a main junction or channel to a buffer channel, a channel connecting a buffer channel with a reagent channel, a channel connecting the array chamber to a waste reservoir, a channel connecting the array chamber to the main junction or channel, a channel connecting the main junction or channel to a waste reservoir, and/or a sample receptacle or well for receiving a fluid sample. In some embodiments, the sample receptacle or well may be absent, and sample may be loaded into one of the reservoirs. In some embodiments, some of the channels may be disposed around a main junction. In some embodiments, some of the channels may be connected to a main channel. The channels may be configured to allow for smooth flow of fluids by, for example, reducing or preventing air bubbles, and minimization of cross-contamination by, for example, reducing or preventing reagent and/or buffer spillover.

In some embodiments, the microfluidic cartridge may include a plurality of liquid-impermeable, gas-permeable barriers, such as liquid-impermeable, gas-permeable membranes. In some embodiments, the liquid-impermeable, gas-permeable barriers may be aqueous-liquid-impermeable. In some embodiments, the liquid-impermeable, gas-permeable barriers may be high-surface-tension-liquid-impermeable.

The microfluidic cartridge may include a receptacle for receiving the protein microarray. In some embodiments, the microfluidic cartridge may include the protein microarray. The microfluidic cartridge may be in fluid communication with the protein microarray.

In some embodiments, the microfluidic cartridge may include a "wet" portion including reservoirs for containing fluids, such as reagents or buffers (the "wet cartridge") and a "dry" portion including microfluidic circuitry and reaction chamber (the "dry cartridge"). The wet cartridge may be configured to be in alignment with the dry cartridge. The sample receptacle may be located in the wet cartridge or in the dry cartridge.

The microfluidic cartridge may be in pneumatic connection with an instrument to, for example, control the motion of fluids. The instrument may be capable of detecting the protein microarray. The vents may interface with the manifold of the instrument.

Wet Cartridge

The wet cartridge may include a plurality of reagent reservoirs and channels, a plurality of buffer reservoirs and channels, a plurality of waste reservoirs, a plurality of vents, a plurality of ports, and optionally a sample receptacle or well for receiving a fluid sample. In some embodiments, the number of buffer reservoirs may be the same as the number of reagent reservoirs. In some embodiments, the wet cartridge may include two waste reservoirs, designated first and second waste reservoirs. In some embodiments, the number of vents may correspond to each of the buffer reservoirs, reagent reservoirs and waste reservoirs. In some embodiments, the number of ports may correspond to each of the buffer reservoirs, reagent reservoirs, waste reservoirs and sample receptacle or well, if present.

In some embodiments, the wet cartridge may include a plurality of reagent reservoirs, where the number of buffer reservoirs may be the same as the number of reagent reservoirs; a plurality of waste reservoirs; a plurality of vents corresponding to each of the buffer reservoirs, reagent reservoirs and waste reservoirs; optionally a sample receptacle or well for receiving a fluid sample; and a plurality of ports corresponding to each of the buffer reservoirs, reagent reservoirs, waste reservoirs and sample receptacle or well, if present.

In some embodiments, the wet cartridge may include:
a plurality of reagent reservoirs (designed "R #" herein);
the same number of buffer reservoirs as reagent reservoirs (designed "B #" herein); the
a plurality of waste reservoirs (designated "W #" herein),
such that the buffer reservoirs, reagent reservoirs and waste reservoirs are configured to allow for specified volumes;

a plurality of vents corresponding to each of the buffer reservoirs, reagent reservoirs and waste reservoirs;

a sample receptacle or well for receiving a fluid sample;

a plurality of ports corresponding to each of the buffer reservoirs, reagent reservoirs, waste reservoirs and sample receptacle or well; and optionally, a laminate bottom which may contain precut holes under each reservoir for loading the reservoir.

In some embodiments, the wet cartridge components may have the following dimensions.

A buffer reservoir, B1 and/or a reagent reservoir, R2, may be generally oblong in shape, although other shapes such as circles, ovals, rectangles and squares can also be contemplated. B1 and/or R2 may be about 3 mm to about 40 mm, such as about 9 mm, long; about 2 mm to about 50 mm, such as about 3 mm, wide and 2 mm to about 7 mm, such as about 7 mm, deep with a volume of about 10 µl to about 2000 µl, such as about 160 µl.

In some embodiments, B1 may be generally oblong in shape, although other shapes such as circles, ovals, rectangles and squares can also be contemplated. B1 may be about 2 mm to about 40 mm, such as about 9 mm, long; about 2 mm to about 50 m, such as about 7 mm, wide and 2 mm to about 7 mm, such as about 7 mm, deep with a volume of about 10 µl to about 2000 µl, such as about 200 µl.

In some embodiments, R2 may be generally oblong in shape, although other shapes such as circles, ovals, rectangles and squares can also be contemplated. R2 may be about 2 mm to about 40 mm, such as about 9 mm, long; about 2 mm to about 50 mm, such as about 4 mm, wide and 2 mm to about 7 mm, such as about 7 mm, deep with a volume of about 10 µl to about 2000 µl, such as about 160 µl.

A reagent reservoir R3, may be generally oblong in shape, although other shapes such as circles, ovals, rectangles and squares can also be contemplated. R3 may be about 3 mm to about 40 mm long, or any value therebetween, such as about 9 mm, long; about 2 mm to about 50 mm wide, or any value therebetween, such as about 4 mm, wide and 2 mm to about 7 mm deep, or any value therebetween, such as about 7 mm, deep with a volume of about 10 µl to about 2000 µl, such as about 200 µl.

A buffer reservoir B4 may be generally bent in shape, at an angle of about 90 to about 179, such as 150 degrees to, for example, allow for specified volume and correct port alignment although other shapes such as circles, ovals, rectangles and squares can also be contemplated. B4 may be about 3 mm to about 40 mm long, or any value therebetween, such as about 13 mm, long; about 2 mm to about 50 mm wide, or any value therebetween, such as about 8 mm, wide and 2 mm to about 7 mm deep, or any value therebetween, such as about 7 mm, deep with a volume of about 10 µl to about 2000 µl, such as about 420 µl.

A buffer reservoir B5 may be generally oblong in shape, with an additional region at one side to accommodate extra volume although other shapes such as circles, ovals, rectangles and squares can also be contemplated. In some embodiments, B5 may include an extra triangular region to the side, to accommodate extra volume. B5 may be about 3 mm to about 40 mm long, or any value therebetween, such as about 13 mm, long; about 2 mm to about 50 mm wide, or any value therebetween, such as about 7 mm or about 8 mm, wide and 2 mm to about 7 mm deep, or any value therebetween, such as about 7 mm, deep with a volume of about 10 µl to about 2000 µl, such as about 420 µl.

A reagent reservoir R6 may be generally oblong in shape, although other shapes such as circles, ovals, rectangles and squares can also be contemplated. R6 may be about 3 mm to about 40 mm long, or any value therebetween, such as about 11 mm, long; about 2 mm to about 50 mm wide, or any value therebetween, such as about 3 mm, wide and 2 mm to about 7 mm deep, or any value therebetween, such as about 7 mm, deep with a volume of about 10 µl to about 2000 µl, such as about 226 µl.

A reagent reservoir R7 may be generally oblong in shape, with an additional region at one side to accommodate extra volume although other shapes such as circles, ovals, rectangles and squares can also be contemplated. In some embodiments, R7 may include a slight bulge in the base, to accommodate extra volume. R7 may be about 3 mm to about 40 mm long, or any value therebetween, such as about 11 mm, long; about 2 mm to about 50 mm wide, or any value therebetween, such as about 4 mm or about 5 mm, wide and 2 mm to about 7 mm deep, or any value therebetween, such as about 7 mm, deep with a volume of about 10 µl to about 2000 µl, such as about 260 µl.

A buffer reservoir B8 may be generally bent in shape, at an angle of about 90 to about 179 degrees, for example 150 degrees, to allow for interfacing with the dry cartridge, although other shapes such as circles, ovals, rectangles and squares can also be contemplated. In some embodiments, B8 may include a shape configured to sculpt around a notch or pin at the end of the wet cartridge for interfacing with the dry cartridge. B8 may be about 3 mm to about 40 mm long, or any value therebetween, such as about 15 mm or about 16 mm, long; about 2 mm to about 50 mm wide, or any value therebetween, such as about 6 mm or about 10 mm wide; and 2 mm to about 7 mm, or any value therebetween, such as about 7 mm, deep with a volume of about 10 µl to about 2000 µl, such as about 420 µl.

A waste reservoir W1 may be generally U-shaped, although other shapes such as circles, ovals, rectangles and squares can also be contemplated, with an additional area to allow pooling of entering fluid. In some embodiments, W1 may have a square bulge, near the bottom of the reservoir closer to the right edge. W1 may have a volume of about 100 µl to about 20000 µl, or any value therebetween, such as about 3130 µl or about 4000 µl. In W1, fluid entering the entrance port may travel through the reservoir along the right edge of the cartridge, along the bottom edge of the cartridge and then up the left edge of the cartridge until it reaches the venting port 54. This may prevent the entering fluid from shooting to end of the reservoir and clogging the venting port. In some embodiments, W1 may be expanded near the entrance to form an initial large reservoir region to for example, allow fluid to easily pool into the reservoir.

A waste reservoir W2 may be generally U-shaped, although other shapes such as circles, ovals, rectangles and squares can also be contemplated, with a volume of about 100 µl to about 20000 µl, or any value therebetween, such as about 2100 µl or about 2500 µl. Without being bound to any particular theory, the shape of W2 may allow fluid entering the W2 reservoir to be as far as possible from the venting port, thus preventing inadvertent clogging of the venting port. In some embodiments, W2 may be expanded near the entrance to form an initial large reservoir region to, for example, decrease fluid resistance.

In some embodiments, for example those including an initial large reservoir region, either or both of W1 and/or W2 may narrow to connect to the W1 or W2 corresponding port.

Indentations may be added into W1 and W2 to reduce or prevent fluid from immediately reaching the narrow region of W1 or W2 which can cause resistance and stoppage of flow.

The sample receptacle or well, if present, may be about 1 mm to about 20 mm long, or any value therebetween, such as about 1.25 mm, 1.5 mm or 3 mm long; about 1 mm to about 10 mm, or any value therebetween, such as about 1.25 mm, 2 mm or 5 mm, wide; and 2 mm to about 7 mm deep, or any value therebetween, such as about 7 mm, deep, with a capacity of about 4 µl to about 500 µl, such as about 25 µL of sample.

The bottom of the wet cartridge may be made of any suitable material. In some embodiments, the wet cartridge may have a laminate bottom. The laminate bottom may contain precut holes in alignment with and under the reservoirs to, for example, assist in reservoir loading. In some embodiments, the wet cartridge may include reagent or buffer reservoir loading ports at the side of the wet cartridge. After loading, the side ports or precut holes may be sealed with, for example, transparent tape or any other suitable sealant.

In some embodiments, the wet cartridge may include a handle at the front of the cartridge. In alternative embodiments, the wet cartridge may include grips at the sides of the wet cartridge.

In some embodiments, the wet cartridge may include alignment features, such as semi-circle cut-outs, to assist in aligning the wet cartridge with the dry cartridge.

The wet cartridge may be made of any suitable material with low protein binding properties, such as without limitation polymethyl methacrylate (PMMA), polystyrene (PS), polyethylene terephthalate (PET) and polyvinylchloride (PVC). In some embodiments, the wet cartridge may be made of polycarbonate.

In some embodiments, the wet cartridge may be reusable. In alternate embodiments, the wet cartridge may be disposable.

Dry Cartridge

The dry cartridge may include an aperture for detecting the protein microarray, a plurality of microfluidic channels including a plurality of reagent channels, a plurality of buffer channels, as well as connecting channels, for example, a channel leading from a main junction or main channel to a buffer channel, a channel connecting a buffer channel with a reagent channel, a channel leading to a waste reservoir or the main junction or main channel, etc.; a plurality of vents, optionally, a plurality of liquid-impermeable, gas-permeable barriers corresponding to the vents, and optionally a sample receptacle for receiving a fluid sample. In some embodiments, the channels may be disposed around a main junction or main channel.

In some embodiments, the dry cartridge may include an aperture for detecting the protein microarray, where the aperture defines an array chamber when in alignment with the wet cartridge, with a receptacle for receiving the protein microarray between the dry cartridge and wet cartridge defining the bottom of the array chamber, and a plurality of microfluidic channels disposed around a main junction or main channel, the microfluidic channels including a plurality of reagent channels, where each reagent channel corresponds to one of the reagent reservoirs of the wet cartridge; a plurality of buffer channels, where each buffer channel corresponds to one of the buffer reservoirs of the wet cartridge; a channel leading from the main junction to each buffer channel; a channel connecting each buffer channel with each reagent channel, to form buffer channel/reagent channel pairs; a channel connecting the array chamber to the first waste reservoir; a channel connecting the array chamber to the main junction; a channel connecting the main junction to the second waste reservoir; wherein the channels are configured to allow for smooth flow of fluids and minimization of cross-contamination; a plurality of vents corresponding to each of the buffer reservoirs, reagent reservoirs and waste reservoirs of the wet cartridge; and a plurality of liquid-impermeable, gas-permeable barriers corresponding to each of the vents.

In some embodiments, the dry cartridge may include the receptacle for receiving the protein microarray. In some embodiments, the dry cartridge may include the protein microarray. In some embodiments, the aperture may define an array chamber, with the protein microarray defining the bottom of the array chamber. In some embodiments, the aperture may define an array chamber, when in alignment with the wet cartridge, with a receptacle for receiving the protein microarray between the dry cartridge and wet cartridge defining the bottom of the array chamber. In some embodiments, the liquid-impermeable, gas-permeable barriers may be superimposed upon the vents. In some embodiments, the channels may be configured to allow for smooth flow of fluids and minimization of cross-contamination.

In some embodiments, the dry cartridge may include:
a plurality of microfluidic channels, disposed around a main junction, including:
  a plurality of reagent channels (designated "R #C" herein), such that each reagent channel corresponds to one of the reagent reservoirs of the wet cartridge;
  a plurality of buffer channels (designated "B #C" herein), such that each buffer channel corresponds to one of the buffer reservoirs of the wet cartridge;
ii) a channel leading from a main junction to each buffer channel (designated "C#/#" herein);
  a channel connecting each buffer channel with each reagent channel, to form buffer channel/reagent channel pairs;
  a channel connecting the main junction to the second waste reservoir (W2);
  a channel connecting the array chamber to the main junction (designated "PreC" herein); and
  a channel connecting the array chamber to the first waste reservoir (W1) (designated "PostC" herein);
such that the channels are configured to allow for smooth flow of fluids and minimization of cross-contamination.

In some embodiments, the dry cartridge may include:
a plurality of microfluidic channels, disposed around a main channel, including:
  a plurality of reagent channels (designated "R #C" herein), such that each reagent channel corresponds to one of the reagent reservoirs of the wet cartridge;
  a plurality of buffer channels (designated "B #C" herein), such that each buffer channel corresponds to one of the buffer reservoirs of the wet cartridge;
  a polytetrafluoroethylene (PTFE) membrane, above the buffer channels, which is exposed to the atmosphere;
  a channel connecting each buffer channel with each reagent channel, to form buffer channel/reagent channel pairs;
  a channel connecting the main junction to a waste reservoir (designated "CW2" herein);
  a channel connecting all buffer and reservoir channels to the main channel (designated "Main C" herein);
  a channel connecting the array chamber to the main channel (designated "PreC" herein); and a channel connecting the array chamber to a waste reservoir (designated "PostC" herein);

such that the channels are configured to allow for smooth flow of fluids and minimization of cross-contamination.

In some embodiments, the dry cartridge may include:

a plurality of microfluidic channels, disposed around a main channel, including:

a plurality of reagent channels (designated "R #C" herein), such that each reagent channel corresponds to one of the reagent reservoirs of the wet cartridge;

a plurality of buffer channels (designated "B #C" herein), such that each buffer channel corresponds to one of the buffer reservoirs of the wet cartridge;

a polypropylene membrane below the buffer channel and reagent channel ports (denoted "sealing membrane" herein);

a channel connecting each buffer channel with each reagent channel, to form buffer channel/reagent channel pairs;

a channel connecting all buffer and reservoir channels to the main channel (designated "Main C" herein);

a channel connecting the main channel (designated "Main C" to the first waste reservoir (designated "CW2" herein);

a channel connecting the array chamber to the main channel (designated "PreC" herein); and a channel connecting the array chamber to the second waste reservoir (designated "PostC" herein);

such that the channels are configured to allow for smooth flow of fluids and minimization of cross-contamination.

In embodiments including a sealing membrane at the dry cartridge and wet cartridge interface, and without being bound to any particular hypothesis, the sealing membrane may reduce or eliminate bubbles and/or reduce or prevent cross-contamination of reagents or buffers. In some embodiments, reagents or buffers may be prevented from entering the dry cartridge prematurely. The sealing membrane may be made of polypropylene. The sealing membrane may have a pore size of about 10 μm and may be about 51 μm thick. Upon addition of pressure from a pump, reagent fluids are able to cross the sealing membrane and enter the dry cartridge through a reagent channel that joins with a paired buffer channel, eventually joining the main channel which brings the reagent to the array chamber. The sealing membrane may be located at the valve/dry cartridge interface termed the gas-permeable membrane (GPM) or fluid block membrane and may, at this location, protect the instrument from fluid entrance by restricting the fluid to within the cartridge. The sealing membrane may also, or alternatively, be located at the entrance to the buffer and reservoir channels (for example, B1C or R2C) to, for example, reduce or prevent fluids from entering the dry cartridge prematurely and assist in the reduction or prevention of cross-contamination, for example, reagent cross-contamination.

In some embodiments, the pairing of the buffer and reagent channels allows for the flushing of the reagent channel with buffer after a reagent step, which may help reduce or prevent cross-contamination, for example, reagent cross-contamination.

In some embodiments, reagent/buffer channel pairs may join with a main channel rather than a main junction. Such a configuration may allow for fewer laminate layers in construction of the dry cartridge which, without being bound to any particular hypothesis, may reduce or prevent bubbles from becoming trapped in the junctions and reducing or preventing flow. In some embodiments, a channel to a waste reservoir, for example W2C, may reduce or prevent bubbles.

For example, before flowing to the array chamber, reagents are first primed to the corresponding waste reservoir, for example, W2. This removes any bubbles and air that may be in the channel before the reagent enters. Pushing these bubbles to W2 first before the reagent enters the array chamber, may reduce or prevent the bubbles from interfering the antibody and antigen spots located in the array chamber.

For example, in some embodiments, reagent channel for reservoir 2 (R2C) may be connected with buffer channel for Reservoir 1 (B1C); reagent channel for reservoir 3 (R3C) may be connected with buffer channel for reservoir 4 (B4C); reagent channel for reservoir 6 (R6C) may be connected with buffer channel for reservoir 5 (B5C) and reagent channel for reservoir 7 (R7C) may be connected with buffer channel for reservoir 8 (B8C) (e.g., FIG. 25A). In some embodiments, reagent/buffer channel pairs may be connected directly to the main junction or channel.

The dry cartridge may include an aperture for detecting signals from an antibody microarray (designated "Array Chamber" herein). It is to be understood that the location and dimension of the aperture, and therefore Array Chamber may change, depending on the specific geometry of the channels and reservoirs.

A sample receptacle may be introduced into the dry cartridge, to allow for sample loading into this reservoir. After sample loading, the sample receptacle may be sealed, for example with a transparent tape, to reduce or prevent leakage.

In some embodiments, the dry cartridge components may have the following dimensions.

Buffer channels B1C, B4C, B5C, and/or B8C may be about 3 mm to about 36 mm long, or any value therebetween, such as about 14 mm, 16 mm, or 25 mm long, and about 0.5 mm to about 3 mm, or any value therebetween, such as about 2 mm, wide.

Reagent channels R2C, R3C, R6C, and/or R7C may be about 3 mm to about 20 mm long, or any value therebetween, such as about 11 mm, long, and about 0.5 mm to about 3 mm, or any value therebetween, such as about 2 mm, wide.

Without being bound to any particular theory, the width and depth of the buffer and/or reagent channels may allow a pocket of air to form between the reservoirs and the channels, providing sufficient capacitance in the channels such that reagents do not exit the reservoirs accidentally.

C1/2 and/or C5/6 may be about 3 mm to about 35 mm, such as about 16 mm, long and about 0.5 mm to about 3 mm, such as about 1 mm, wide.

C3/4 may be about 3 mm to about 35 mm, such as about 8 mm, long and about 0.5 mm to about 3 mm, such as about 1 mm, wide.

C7/8 may be about 3 mm to about 50 mm, such as about 32 mm, long and about 0.5 mm to about 3 mm, such as about 1 mm, wide.

PreC may be about 3 mm to about 44 mm long, or any value therebetween, such as about 17 mm, 22 mm or 30 mm long and about 0.5 mm to about 3 mm, such as about 1 mm, wide.

PostC may be about 12 mm to about 300 mm long, or any value therebetween, such as about 70 mm or 122 mm, long and about 0.5 mm to about 3 mm, or any value therebetween, such as about 1 mm to about 1.5 mm, wide.

Main C, where present, may be about 20 mm to about 80 mm long, or any value therebetween, such as about 53 mm or 65 mm, long and about 0.5 mm to about 3 mm, or any value therebetween, such as about 1 mm, wide.

A PTFE membrane, when present, may be about 5 mm to about 27 mm, such as about 7 mm, long and about 2.5 mm to about 6 mm, such as 4 mm, wide.

The array chamber may be about 4 mm² to about 500 mm² in area, or any value therebetween, such as about 100 mm² in area, and about 100 µm to 300 µm deep, or any value therebetween, such as 250 µm deep.

A "sealing membrane", when present, may be about 5 mm to about 80 mm, such as about 3 mm, long and about 2.5 mm to about 7 mm, such as 3 mm, wide.

The dry cartridge may be made of any suitable material with low protein-binding property, such as without limitation, polymethyl methacrylate (PMMA), polycarbonate, polystyrene, or cyclic olefin polymer. In some embodiments, the dry cartridge may be made of polyethylene terephthalate.

The channels in the dry cartridge can be formed using laser, or any suitable means such as replica molding, infection molding or embossing.

In some embodiments, the dry cartridge may be disposable.

FIG. 27 shows a side view stack up of a dry cartridge 15 and a wet cartridge 16, according to an alternate embodiment. The present embodiment shown in FIG. 27 is similar to the embodiment shown in FIG. 24B, except the embodiment of FIG. 27 includes a sample port 56 in the dry cartridge 15 and the wet cartridge 16 includes a sample well for receiving a fluid sample from the sample port 56. The vents in the wet cartridge may be configured to align with the vents to the channels in the dry cartridge. In some embodiments, the vents in the wet cartridge may be aligned to the vents and gas-permeable or fluid block membranes of the dry cartridge such that air is able to flow freely (FIG. 27). In some embodiments, the vents in the wet cartridge may be aligned with the venting ports and gas-permeable or fluid block membranes of the dry cartridge such that the pressure generated by the pump in an instrument is able to pass through freely, without allowing liquids to pass through (FIG. 27).

In some embodiments, the reservoir positions in the wet cartridge may be configured to align with the ports to the channels in the dry cartridge (FIG. 27).

It is to be understood that the dimensions of the dry cartridge are sufficient to accommodate the geometry of the microfluidic channels and aperture for detecting signals from a protein microarray, such as an antibody microarray. The dimensions of the wet cartridge may be determined by those of the dry cartridge. In some embodiments, the dimensions of the assembled microfluidic cartridge may be about 8 cm×5.5 cm×1 cm.

By "about" is meant a variance (plus or minus) from a value or range of 5% or less, for example, 0.5%, 1%, 1.5%, 2.0%, 2.5%, 3.0%, 3.5%, 4.0%, 4.5%, 5.0%, etc.

Fluids, such as reagents and/or buffers, can be loaded into the appropriate reservoirs of the wet cartridge or microfluidic cartridge. In some embodiments, reagents and/or buffers, can be loaded through holes in a laminate bottom, which can be sealed after loading. In some embodiments, reagents and/or buffers, can be loaded and sealed into the appropriate reservoirs of the wet cartridge or microfluidic cartridge prior to use, and stored at for example 4° C. In alternative embodiments, reagents and/or buffers, can be loaded and sealed into the appropriate reservoirs of the wet cartridge or microfluidic cartridge immediately before use. In some embodiments, reagents and/or buffers can be provided separately from the wet and/or dry cartridges or microfluidic cartridge.

Sample can be loaded into the sample receptacle or well simultaneously or subsequently to the loading of reagents and buffers. The wet cartridge or microfluidic cartridge may include a system for purification of the fluid sample. For example, a filter or membrane may be used for, for example, blood samples. It is to be understood that the degree of purification will depend on the type of fluid sample used and that partial purification may, in many cases, be sufficient. In some embodiments, sample can be loaded into a blood filtration element. This may contain a plasma filtration filter to allow the filtering of plasma from whole blood and the removal of blood cells.

A protein microarray, such as an antibody microarray, slide can be attached to the dry cartridge such that the protein or antibody spots on the microarray are aligned within the aperture of the dry cartridge (the array chamber) and can be exposed to the fluids (such as sample, buffers, reagents) from the wet cartridge upon initiation of the analysis.

The dry cartridge and the wet cartridge may be aligned, such that the proteins or antibodies in the protein or antibody microarray are accessible to the array chamber and the microfluidic channels, ports, and/or vents in the dry cartridge align with the corresponding reservoirs, ports and/or vents in the wet cartridge. In some embodiments, notches or guides in the wet and/or dry cartridges may permit easy alignment.

In some embodiments, the wet and dry cartridges may be reversibly attached to form the assembled microfluidic cartridge, such that the wet cartridge may be re-used. In some embodiments, the wet and dry cartridges may be provided separately. In alternate embodiments, the wet and dry cartridges may be permanently attached to form the assembled microfluidic cartridge, which may be disposed of after use. In some embodiments, the wet and dry cartridges may be provided together with the protein microarray. In some embodiments, the protein microarray may be provided separately from the wet and/or dry cartridges or microfluidic cartridge.

Instrument & Operation

The microfluidic cartridge may be inserted into the cartridge receptacle of an instrument designed to hold the microfluidic cartridge. The instrument may include an alignment/ejection mechanism for the microfluidic cartridge. For example, the instrument may include a clamping feature that can clamp into a corresponding feature in the microfluidic cartridge, such as a semi-circle feature, to assist in correct alignment of the cartridge.

The microfluidic cartridge may be in pneumatic connection with an instrument to, for example, control the movement of fluids. The instrument may be capable of detecting the protein microarray using an optical sensor or other detection system (for example, a colorimetric system). The instrument may include a system for purification of the fluid sample.

In addition to the cartridge receptacle and alignment/ejection mechanism, the instrument may include, without limitation, one or more of a pump, valve system, manifold, LED excitation source, detection system, CPU, Bluetooth connectivity, LCD touchscreen, rechargeable batteries, and circuit boards, HDMI adaptor, USB connector, Ethernet connection adaptor, serial ports, ventilation fan, power switch, and/or protective enclosure.

Once inserted, the vents in the dry cartridge may interface with the manifold of the instrument, which connects the valves to the reservoir ports.

In some embodiments, the pump, valves and detection system may be integrated with a printed circuit board capable of relaying the electrical input from the software to the various components.

The pump may be used to generate pressure-driven flow of a fluid. A suitable pump may be capable of sequential fluid delivery of, for example, reagents, buffers and/or samples. In some embodiments, the pump may be a vacuum pump. It is to be understood that any suitable pump may be used, as long as it is capable of operation as desired in the context of the instrument. The instrument may be designed such that the pump is capable of pushing from the reagent reservoirs such that fluid flows towards the waste reservoirs. An exemplary syringe pump is illustrated in FIG. 32. The pump may be generally a U-shape turned on its side. The pump on the bottom may insert into the manifold of the instrument. An O-ring may fit around the end of the pump to seal the pump within the manifold, and sealing the air pressure used to drive flow. The upper part of the pump may have teeth. A ring with complementary teeth may connect the pump to the motor such that, as the motor moves, the pump will move in or out of the manifold. The pump may be operated by a motor (for example, Vex: RB-Inn-11).

The cartridge reader may include a positive displacement air pump used to push or pull a specified volume of air. Air may be displaced, for example, by a ground stainless steel pin moving axially into the pump cavity. The pin may be sealed at the cavity entrance with a stationary radial seal. The pin may be moved directly by a stepper motor driven (e.g., Haydon Kerk LC1574 W-05) linear actuator. Pump position may be measured optically with proximity sensors. The pump may be automatically calibrated to detect and correct for skipped steps and to account for variations in construction. The valves may allow automated control over connections between the pump, vent, and nozzles. Valves may mount to the manifold assembly using screws and a face seal. The manifold assembly may includes multiple valves, as well as empty sockets for additional valves. A pressure sensor may be included in the system to measure the pressure inside the pump. Air volume within the pressure sensor and sensor connection should be minimized to improve system response.

The valve may be a solenoid valve (for example, Parker: X-7 05 L-F or Lee: LHDX0532300B). Valves may be placed above every reservoir including the waste reservoirs (FIG. 29), with an additional valve for venting, or allowing the pump to re-zero without connecting into the cartridge. Opening a solenoid valve, associated with a particular reservoir, results in the fluid in that reservoir moving from the reservoir towards a waste reservoir.

The instrument may be fitted with a manifold containing channels for the passage of air between the pump, the valves and the cartridge, such that air can travel from the pump through the manifold to the valves. If the valve is open, air can travel through the specific valve, back into the manifold and into the corresponding reservoir of the cartridge. Exemplary manifolds are illustrated in FIG. 33 and FIG. 47, which function to connect the air from the pump to the valves to the cartridge. Air exits the pump through port 88, travels to the valve entrance 85, and through the open valve. The air then exits the valve through port 86 re-enters the manifold and travels to the port where the manifold interfaces with the cartridge 87. During the re-zeroing of the pump, or travel to W1 (1) or W2 (2) air exits through the port to atmosphere 63.

A Java application that allows image capture, scripting of the assay and signal quantification and uses a publicly available camera communication library, implements a publicly available controller protocol and uses standard Java graphical user interface libraries was written.

Software can be used to control the opening of the valves in the instrument, and thus the movement of fluids, for example as follows:
buffer may be pushed from a buffer reservoir through the main junction and then to the second waste reservoir (W2) to substantially reduce or purge the channels of air;
sample may be pushed from the sample well through, for example reagent reservoir R7, across the main junction and through the array chamber via PreC, and on to the first waste reservoir (W1), via PostC;
reagent may be pushed from a reagent reservoir across the main junction and through the array chamber (via PreC), and on to the first waste reservoir (W1), via PostC.

An optical sensor may be used to acquire a readout of the sample assay results, and quantification software may be used to interpret the results of the readout.

An optical sensor may be used to acquire a readout of the sample assay results, and quantification software may be used to interpret the results of the readout.

Any suitable optical sensing system may be used. In some embodiments, the instrument includes a camera, such as an USB camera (for example, Leopard Imaging: LI-OV7725) and lighting system such that the software is capable of obtaining an image of the spots. The software may then be able to compute an optical density based on the image taken by the camera.

An array of LED lights (for example, Life-on Inc.) may be placed below the field of the spots such that the illumination allows an image of the spots. The instrument imaging system may include a light source, including of 4 white LEDs which shine through a translucent acrylic diffuser and then through the back of the wet card. The wet cartridges may be made of translucent polycarbonate thereby increasing uniformity in illumination. Blinking of the LED may allow suitable software to compute gain and offset for the resulting image. The LED may illuminate the back of the slide with a time varying signal of a triangular shape. This modulation may occur at approximately 2.6 Hz. The modulation may be produced by a controller circuit that may also be used to control the valves and the pump motor. The controller circuit may produce a square-wave signal which is integrated and then used to modulate the current to the LEDs, resulting in a triangular, time-varying light output to reduce errors caused by stray light and variations in pixel gain and offset. The optical path length may be designed to be as short as possible, to reduce the size of the instrument.

The optical system may allow the TAD system to image spots in the array chamber generated by the assay, to determine the type, compatibility, orientation and successful insertion of inserted microfluidic cartridges, and to image fluid flow in the microfluidic cartridge. The camera may perform several functions including, without limitation, imaging the spots generated by the assay with sufficient resolution to quantify optical density; taking as input the blank and spot image from the Instrument; locating the fiducial spots and output of a 2-dimensional array of spots based on the selected card type's configured dimensions of the spot array; imaging features on the microfluidic cartridge that allow the cartridge type, compatibility and orientation to be determined and allowing the TAD to determine successful insertion; imaging the microfluidic channels within the microfluidic cartridge to record fluid or air position; assisting in diagnostics or provide records of the test; and/or imaging a cartridge label for barcode scanning.

An array of LEDs may illuminate the top surface of the microfluidic cartridge. The light input may be modulated by the control electronics and may be controlled by the software to support the camera functions, for example, as described above. These lights may be used for barcode scanning and potentially video recording during the assay for troubleshooting and diagnostics. The imaging LED may provide light to the base of the array chamber. Light input may be modulated by the control electronics and may be controlled by software as required for quantification of spots in the array chamber. For imaging spots in the array chamber, light from the LEDs should enter the bottom of the array chamber, pass through the viewing window, and enter the camera without reflecting off or diffusing through any other surface. Light from the imaging LED should not reflect off or diffuse through any elements of the TAD device then illuminate the array chamber from the top. A diffusing element may be included between the array imaging LEDs and the microfluidic cartridge assay chamber to evenly distribute light from the LED before it enters the assay chamber.

To obtain an image of the spots, a blank image may first be obtained, to allow the software to detect the spots by ignoring any background present before the spots are developed. Upon the development of the spots, a spots image may be obtained. At the start of image capture, two 640×480 pixel arrays are zeroed: one will accumulate the average black and white intensity of each individual pixel and the other will accumulate the intensity multiplied by the overall pixel average. The spatial pixel average may also be stored along with the time that the frame was captured. The spatial pixel average may be used as a proxy for the modulation signal in the following analysis. This is based on the assumption that the only source of 2.6 Hz periodicity is due to the modulation.

Once the total desired number of frames has been captured, the time record of average pixel intensity may be correlated with a range of frequencies of sine waves in order to identify the correct frequency, phase and amplitude of modulation. The result of this computation is a value proportional to the magnitude of the modulation. Next, a least-squares linear regression may be computed on each pixel to determine the gain and offset of each pixel with respect to the extracted modulation signal. At this point, it may be assumed that the individual pixel gain represents a proportionality factor relating to the LED output. The pixel offset is not deemed useful and discarded. In order to block out effects due to card to card variations, optical density variations due to the fluid in the chamber, and the exact modulation amplitude, an image may be captured first right before the spots are developed and then afterwards. These are termed the "blank" image and the "spot" image. The final processed image may be created by computing the ratio of each pixel gain of the spot image with those of the blank image. This image may be further scaled by the ratio of the computed modulation magnitudes of the spot image to the blank image.

Spots for quantification may be marked manually by the software user. Each spot contains a central spot region. The size of the spot can be changed by the user using the software. To quantify the spots, a new image may be computed where each pixel is equal to the ratio of each pixel of the spot and no-spot images. This removes variation due to back-lighting and inherent spatial card density, as well as pixel gain and offset. The average pixel value within the central spot circle is calculated.

The pump, valves and optical camera may be integrated into the instrument. Within the instrument, these parts may be integrated with a printed circuit board which may relay the electrical input from the software to the various components. The instrument may house the microcontroller, pump, valves and optical system. The cartridge (wet and dry together) may be inserted into the instrument and through a spring mechanism interface with the manifold, which may connect the valves to the reservoir ports. Software may be loaded on a computer connected to the instrument.

The TAD System may include a Reader that may control and quantify the results from the cartridge. This instrument may include a plastic and metal housing including without limitation, a touchscreen display, a main CPU PCB, a cartridge interface including a pump, numerous valves, a camera for quantification, various LED light sources and PCBs with an MCU, valve drivers, motor drivers and sensors to ensure the assay is performed correctly. The basic form of the reader may include a graphical touch screen display for the user interface with a drawer for cartridge insertion. The housing may use OTS antivibration feet. The TAD software may run on an ARM based CPU. The main software functionality, including all the GUI may be the result of the software application (app) written in Java. The app may rely on support by various other software libraries and packages which fall into the category of software of unknown provenance (SOUP).

The TAD may include publicly available electrical subassemblies. User interaction with the application may be accomplished through a touchscreen. Data entry may be accomplished through on-screen keypads. In some embodiments, the addition of an external barcode scanner for patient ID entry may be included.

The present invention will be further illustrated in the following examples.

EXAMPLES

1: Biomarker Assay Development and Validation (ELISA)

1a: Antibody Reactivity Validation Against Cognate Antigens (ELISA)

Sandwich immunoassay antibody pairs for each biomarker were initially selected based on manufacturer's recommendations. These included pairs for the four biomarkers: CA15-3, CEA, ErbB2 and CYFRA21.1. Antibody pairs were tested in a sandwich immunoassay to determine the quality of the pair (as described herein under Section 1 b).

More specifically, CEA (Fitzgerald: 30-AC25P) and CYFRA21.1 (Cedarlane: CLPRO350) antigens were diluted in coating buffer (0.2 M $NaHCO_3/Na_2CO_3$ pH 9.4). 50 µL of antigens in coating buffer at three concentrations (200 ng/mL, 20 ng/mL, 2 ng/mL) were coated onto the wells of a 96-well Maxisorp ELISA plate (ThermoFisher) by incubating for 2 hours at room temperature and the plate was stored at 4° C. overnight. On the following day, the ELISA plate was blocked with 200 µL of blocking buffer (1×PBST+ 2% BSA) for 1 hour. The wells were then probed with 50 µL of respective primary antibodies (1° antibodies, Table 1) for 1 hour followed by 50 µL of secondary antibody (2° antibody) (anti-IgG from various species conjugated to HRP), or 50 µL of SA-HRP was applied to the wells for 30 minutes. Subsequently, the wells were washed with 1×PBST for 6 times with 5 minutes for each wash. Signals were developed using 50 μL of TMB (VWR) for 30 minutes, and the reaction was then stopped with 50 μL of 2 M Sulphuric Acid. Plates were scanned using a Versamax microplate reader (Molecular Devices) at 450 nm.

Sample results for testing antibody reactivity towards its antigen are illustrated in Table 1. In the indirect ELISA experiment, orb48781 (Biorbyt) failed to recognize the CYFRA21.1 antigen giving low O.D. values at all antigen concentrations (Table 1). However, two other antibodies for CYFRA21.1, AF3506 and MAB3506 (R&D Systems), were able to recognize the antigen in a dose-dependent manner. Two antibodies for CEA, 10-1134B and 10-1131 (Fitzgerald) gave a low signal in a sandwich assay even at high antibody concentrations. Interestingly, they were able to recognize the CEA antigen (Table 1). It's likely that the 2 antibodies might interfere with each other in binding to the CEA antigen. Additional CEA antibodies including 10-C10D, 10-C10E and MAB41281 (R&D Systems) could recognize the CEA antigen in a dose-dependent manner. Therefore, these antibodies were further tested in sandwich assays (Section 1b).

CEA Antibodies

For CEA, three different antibodies were tested as capture antibodies (cAbs), 10-C10D, 10-C10E and 10-1134 at various concentrations ranging from 1 μg/mL to 10 μg/mL. 50 μL of antibodies diluted in coating buffer (0.2 M NaHCO$_3$/Na$_2$CO$_3$ pH 9.4) were coated onto the wells of a 96-well Maxisorp ELISA plate (ThermoFisher) individually. The plate was incubated for 2 hours at room temperature and then kept at 4° C. overnight. On the following day, the ELISA plate was blocked with 200 μL of blocking buffer (1×PBST+2% BSA) for 1 hour. The wells were washed with 200 μL of 1×PBST three times and incubated with CEA antigen at 20 ng/mL, 2 ng/mL, and 0 ng/mL for 1 hour followed by 3 times 1×PBST wash. 50 μL of different biotinylated detection antibodies (Table 2) were added for 1 hour. Each capture antibody was tested with the other two antibodies as detection antibodies (dAbs). After 1×PBST washes, wells were probed with 50 μL of SA-HRP for 30 minutes and then washed with 1×PBST for 6 times with 5 minutes each. Signals were developed using 50 μL of TMB (VWR) for 30 minutes and the reaction was stopped by

TABLE 1

Antibody reactivity screening setup and results (O.D.)

| 1° antibody | orb48781 | orb156511 | AF3506 | AF3506B | MAB3506 | MAB3506 |
| --- | --- | --- | --- | --- | --- | --- |
| [1° antibody] | 4000 ng/ml | 4000 ng/ml | 10 μg/ml | 5 μg/ml | 10 μg/ml | 5 μg/ml |
| 2° antibody | anti-Rabbit | anti-Rabbit | anti-Sheep | anti-Sheep | anti-Mouse | anti-Mouse |
| 2° antibody dilution | 1000x | 1000x | 500x | 500x | 1000x | 1000x |
| CYFRA 21-1 [200 ng/mL] | 0.6314 | 2.9014 | 3.2234 | 3.17 | 2.9705 | 3.0195 |
| CYFRA 21-1 [20 ng/mL] | 0.6226 | 1.5583 | 2.3951 | 2.4655 | 1.8275 | 2.696 |
| CYFRA 21-1 [2 ng/mL] | 0.6669 | 0.3634 | 0.4903 | 0.4884 | 1.2263 | 0.9748 |
| CYFRA 21-1 [0 ng/mL] | 0.6417 | 0.2135 | 0.1261 | 0.1035 | 1.058 | 0.4209 |
| 1° antibody | 10-C10D | 10-C10E | 10-1131 | 10-1134B | MAB41281 | MAB41281 |
| [1° antibody] | 10 μg/ml | 10 μg/ml | 10 μg/ml | 10 μg/ml | 10 μg/ml | 2 μg/ml |
| 2° antibody | anti-Mouse | anti-Mouse | anti-Mouse | SA-HRP | anti-Mouse | anti-Mouse |
| 2° antibody dilution | 1000x | 1000x | 1000x | 1000x | 1000x | 1000x |
| CEA [200 ng/ml] | 1.6453 | 2.7821 | 3.017 | 3.3022 | 1.2803 | 3.0195 |
| CEA [20 ng/ml] | 0.2083 | 0.5376 | 0.8484 | 1.1692 | 0.2376 | 2.696 |
| CEA [2 ng/ml] | 0.1015 | 0.1384 | 0.3915 | 0.2648 | 0.1036 | 0.9748 |
| CEA [0 ng/mL] | 0.0884 | 0.0809 | 0.4313 | 0.1877 | 0.0807 | 0.4209 |

1 b: Compatibility of Antibody Pairs for Sandwich Assays (ELISA)

The first sandwich antibody pairs tested for CA15-3 and ErbB2 were successful. The optimization of these antibodies can be found in Section 1c. After identifying antibodies for CEA and CYFRA21.1 that could recognize cognate antigens (section 1a), antibodies were subject to further tests for their compatibility in sandwich assays.

adding 50 μL of 2 M Sulphuric Acid. Plates were scanned using a Versamax microplate reader (Molecular Devices) at 450 nm. Sample results are shown in Table 2. The antibody pair that had the best signal to noise ratio and illustrated a dose-dependent response to CEA antigen in this study were 10-C10D capture antibody and 10-1134B detection antibody. The antibody MAB41281 exhibited high background in these tests.

TABLE 2

CEA antibody pairs compatibility test

| | | | cAb | | | | | | | | | | | |
|---|---|---|---|---|---|---|---|---|---|---|---|---|---|---|
| | 10-C10D | | 10 ug/ml | 10 ug/ml | 10 ug/ml | 5 ug/ml | 5 ug/ml | 5 ug/ml | 2.5 ug/ml | 2.5 ug/ml | 2.5 ug/ml | 1 ug/ml | 1 ug/ml | 1 ug/ml |
| | | | | | | | Antigen | | | | | | | |
| | CEA | | 20 ng/ml | 2 ng/ml | 0 | 20 ng/ml | 2 ng/ml | 0 | 20 ng/ml | 2 ng/ml | 0 | 20 ng/ml | 2 ng/ml | 0 |
| dAb | 10-C10E-B | 25 ug/ml | 0.1239 | 0.1186 | 0.0884 | 0.1338 | 0.12 | 0.1176 | 0.1301 | 0.1373 | 0.1154 | 0.7073 | 0.1117 | 0.079 |
| dAb | 10-1134-B | 10 ug/ml | 0.5877 | 0.193 | 0.141 | 0.4556 | 0.1945 | 0.142 | 0.3508 | 0.1849 | 0.1445 | 0.1444 | 0.1276 | 0.1127 |

| | | | cAb | | | | | | | | | | | |
|---|---|---|---|---|---|---|---|---|---|---|---|---|---|---|
| | 10-C10E | | 10 ug/ml | 10 ug/ml | 10 ug/ml | 5 ug/ml | 5 ug/ml | 5 ug/ml | 2.5 ug/ml | 2.5 ug/ml | 2.5 ug/ml | 1 ug/ml | 1 ug/ml | 1 ug/ml |
| | | | | | | | Antigen | | | | | | | |
| | CEA | | 20 ng/ml | 2 ng/ml | 0 | 20 ng/ml | 2 ng/ml | 0 | 20 ng/ml | 2 ng/ml | 0 | 20 ng/ml | 2 ng/ml | 0 |
| dAb | 10-1131-B | 25 ug/ml | 0.2706 | 0.2528 | 0.2356 | 0.2423 | 0.241 | 0.2321 | 0.2599 | 0.2265 | 0.2123 | 0.2375 | 0.2429 | 0.2496 |
| dAb | 10-1134-B | 10 ug/ml | 0.1843 | 0.1449 | 0.1642 | 0.1661 | 0.1538 | 0.1517 | 0.1364 | 0.1307 | 0.1372 | 0.1256 | 0.1183 | 0.1103 |

| | | | cAb | | | | | | | | | | | |
|---|---|---|---|---|---|---|---|---|---|---|---|---|---|---|
| | 10-1134 | | 10 ug/ml | 10 ug/ml | 10 ug/ml | 5 ug/ml | 5 ug/ml | 5 ug/ml | 2.5 ug/ml | 2.5 ug/ml | 2.5 ug/ml | 1 ug/ml | 1 ug/ml | 1 ug/ml |
| | | | | | | | Antigen | | | | | | | |
| | CEA | | 20 ng/ml | 2 ng/ml | 0 | 20 ng/ml | 2 ng/ml | 0 | 20 ng/ml | 2 ng/ml | 0 | 20 ng/ml | 2 ng/ml | 0 |
| dAb | 10-C10D-B | 25 ug/ml | 0.4336 | 0.2658 | 0.2487 | 0.2556 | 0.1858 | 0.1618 | 0.5771 | 0.3594 | 0.3087 | 0.4379 | 0.3134 | 0.3163 |
| dAb | 10-C10E-B | 25 ug/ml | 0.3816 | 0.2075 | 0.206 | 0.2365 | 0.1504 | 0.1366 | 0.1787 | 0.1605 | 0.1621 | 0.1621 | 0.16 | 0.1756 |

CYFRA21.1 Antibodies

Initial antibody testing for CYFRA21.1 identified two antibodies that recognized cognate antigen well, MAB3506 and AF3506. These antibodies were tested in a sandwich assay in two combinations, one with MAB3506 as the capture antibody and AF3506 as the detection antibody and vice versa. An ELISA assay was performed as previously described with the capture antibody coated at various concentrations (Table 3) and then probed with CYFRA21.1 antigen at 20 ng/mL, 2 ng/mL and 0 ng/mL respectively (Table 3). Wells were then probed with biotinylated detection antibodies at various concentrations (Table 3) followed by SA-HRP. Signals were developed with TMB. Plates were then scanned with a Versamax (Molecular Devices) plate reader at 450 nm. The O.D. results are illustrated in Table 3. Sandwich assays performed using MAB3506 as the capture antibody and AF3506-B as the detection antibody worked well, detecting CYFRA21.1 antigen in a dose-dependent manner. However, the reverse sandwich assay with AF3506 as the capture antibody and MAB3506 as the detection antibody failed to result in a strong CYFRA21.1 signal in these tests.

TABLE 3

CYFRA21.1 antibody pairs compatibility test

| | | | Capture antibody dilutions | | | | | | | | | | | | |
|---|---|---|---|---|---|---|---|---|---|---|---|---|---|---|---|
| | Biotin-- AF3506 | CK19 | 25 ug/ml 1 | 25 ug/ml 2 | 25 ug/ml 3 | 5 ug/ml 4 | 5 ug/ml 5 | 5 ug/ml 6 | 1 ug/ml 7 | 1 ug/ml 8 | 1 ug/ml 9 | 0.2 ug/ml 10 | 0.2 ug/ml 11 | 0.2 ug/ml 12 | MAB3506 |
| Detection antibody | 10 ug/ml | A | 20 ng/ml | 2 ng/ml | 0 | 20 ng/ml | 2 ng/ml | 0 | 20 ng/ml | 2 ng/ml | 0 | 20 ng/ml | 2 ng/ml | 0 | |
| | 5 ug/ml | B | 20 ng/ml | 2 ng/ml | 0 | 20 ng/ml | 2 ng/ml | 0 | 20 ng/ml | 2 ng/ml | 0 | 20 ng/ml | 2 ng/ml | 0 | |
| | 1 ug/ml | C | 20 ng/ml | 2 ng/ml | 0 | 20 ng/ml | 2 ng/ml | 0 | 20 ng/ml | 2 ng/ml | 0 | 20 ng/ml | 2 ng/ml | 0 | |
| | 0.2 ug/ml | D | 20 ng/ml | 2 ng/ml | 200 ng/ml | 20 ng/ml | 2 ng/ml | 0 | 20 ng/ml | 2 ng/ml | 0 | 20 ng/ml | 2 ng/ml | 0 | |

TABLE 3-continued

CYFRA21.1 antibody pairs compatibility test

| | 10 ug/ml | E | 20 ng/ml | 2 ng/ml | 0 | 20 ng/ml | 2 ng/ml | 0 | 20 ng/ml | 2 ng/ml | 0 | 20 ng/ml | 2 ng/ml | 0 | |
|---|---|---|---|---|---|---|---|---|---|---|---|---|---|---|---|
| | 5 ug/ml | F | 20 ng/ml | 2 ng/ml | 0 | 20 ng/ml | 2 ng/ml | 0 | 20 ng/ml | 2 ng/ml | 0 | 20 ng/ml | 2 ng/ml | 0 | |
| | 1 ug/ml | G | 20 ng/ml | 2 ng/ml | 0 | 20 ng/ml | 2 ng/ml | 0 | 20 ng/ml | 2 ng/ml | 0 | 20 ng/ml | 2 ng/ml | 0 | |
| | 0.2 ug/ml | H | 20 ng/ml | 2 ng/ml | 200 ng/ml | 20 ng/ml | 2 ng/ml | 0 | 20 ng/ml | 2 ng/ml | 0 | 20 ng/ml | 2 ng/ml | 0 | |
| Biotin--MAB3506 | | | 25 ug/ml | 25 ug/ml | 25 ug/ml | 5 ug/ml | 5 ug/ml | 5 ug/ml | 1 ug/ml | 1 ug/ml | 1 ug/ml | 0.2 ug/ml | 0.2 ug/ml | 0.2 ug/ml | AF3506 |

| | 200 ng/ml | | | | Highest Capture Ab and Highest Detection Ab | | | | | | | | |
|---|---|---|---|---|---|---|---|---|---|---|---|---|---|
| Temperatu | 1 | 2 | 3 | 4 | 5 | 6 | 7 | 8 | 9 | 10 | 11 | 12 | |
| 25.5 | 1.8361 | 0.3798 | 0.1854 | 1.8492 | 0.4121 | 0.2291 | 1.1758 | 0.2595 | 0.1225 | 0.5126 | 0.1459 | 0.0787 | |
| | 1.255 | 0.2449 | 0.1251 | 1.278 | 0.2839 | 0.161 | 0.8812 | 0.1759 | 0.0962 | 0.3466 | 0.0871 | 0.062 | |
| | 0.4387 | 0.0968 | 0.0651 | 0.4047 | 0.0936 | 0.0668 | 0.2405 | 0.0727 | 0.059 | 0.1222 | 0.0552 | 0.0484 | |
| | 0.1282 | 0.0585 | 3.7239 | 0.1287 | 0.057 | 0.0472 | 0.0925 | 0.0505 | 0.0463 | 0.0618 | 0.0478 | 0.0455 | |
| | 0.7608 | 0.3104 | 0.2108 | 0.9948 | 0.3015 | 0.2249 | 0.759 | 0.2166 | 0.1378 | 0.4316 | 0.1666 | 0.1207 | |
| | 0.5278 | 0.2023 | 0.141 | 0.6152 | 0.19 | 0.1322 | 0.478 | 0.1412 | 0.0937 | 0.2573 | 0.1237 | 0.0875 | |
| | 0.158 | 0.076 | 0.061 | 0.1707 | 0.0726 | 0.0588 | 0.1312 | 0.0635 | 0.0523 | 0.0845 | 0.0587 | 0.0501 | |
| | 0.0637 | 0.0517 | 2.819 | 0.0628 | 0.049 | 0.0463 | 0.0576 | 0.0473 | 0.0455 | 0.0491 | 0.0451 | 0.045 | |

1c: Antibody Titrations (ELISA)

The optimal concentration for both capture antibody and detection antibody was tested. These experiments are commonly referred to as checkerboard titrations. 2-fold serial dilutions were prepared for capture and detection antibodies for each biomarker. Two concentrations of the antigen were prepared with one above and one below its physiological cut-off value, in addition to a blank control. To determine the optimal concentrations for each antibody pair, a signal-to-noise ratio was calculated by dividing the reading from the antigen wells by that from wells with no antigen. The optimal concentration of capture and detection antibodies was determined with the highest signal-to-noise ratio and lowest background reading.

Biomarker: ErbB2

Sandwich assay ELISA was performed as previously described. The capture antibody, MAB1129 (R&D systems), was tested at 4 different concentrations: 8 μg/mL, 4 μg/mL, 2 μg/mL and 1 μg/mL. Similarly, the detection antibody, BAF1129 (R&D systems) was tested at 160 ng/mL, 80 ng/mL, 32 ng/mL and 16 ng/mL. Since the ErbB2 cut-off is 15 ng/mL, the ErbB2 antigen (R&D systems: 1129-ER-050) was tested at 25 ng/mL, 5 ng/mL and 0 ng/mL. Each combination was performed in duplicate. The results and experimental setup are illustrated in Table 4. The signal-to-noise ratios were calculated and the highest signal-to-noise ratio was observed for 4 μg/ml cAb and 80 ng/ml dAb, respectively. Therefore, these two optimal concentrations would be used for later experiments.

TABLE 4

ErbB2 antibody titration

ErbB2 Assay Development - Stage 1

| | | | Capture antibody dilutions | | | | | | | | | | | |
|---|---|---|---|---|---|---|---|---|---|---|---|---|---|---|
| | | | 8 ug/ml | 8 ug/ml | 8 ug/ml | 4 ug/ml | 4 ug/ml | 4 ug/ml | 2 ug/ml | 2 ug/ml | 2 ug/ml | 1 ug/ml | 1 ug/ml | 1 ug/ml |
| Detection Antibody dilutions | | ErbB2 protein | 1 | 2 | 3 | 4 | 5 | 6 | 7 | 8 | 9 | 10 | 11 | 12 |
| | 160 ng/ml | A | 25 ng/ml | 5 ng/ml | 0 | 25 ng/ml | 5 ng/ml | 0 | 25 ng/ml | 5 ng/ml | 0 | 25 ng/ml | 5 ng/ml | 0 |
| | 160 ng/ml | B | 25 ng/ml | 5 ng/ml | 0 | 25 ng/ml | 5 ng/ml | 0 | 25 ng/ml | 5 ng/ml | 0 | 25 ng/ml | 5 ng/ml | 0 |
| | 80 ng/ml | C | 25 ng/ml | 5 ng/ml | 0 | 25 ng/ml | 5 ng/ml | 0 | 25 ng/ml | 5 ng/ml | 0 | 25 ng/ml | 5 ng/ml | 0 |
| | 80 ng/ml | D | 25 ng/ml | 5 ng/ml | 0 | 25 ng/ml | 5 ng/ml | 0 | 25 ng/ml | 5 ng/ml | 0 | 25 ng/ml | 5 ng/ml | 0 |
| | 32 ng/ml | E | 25 ng/ml | 5 ng/ml | 0 | 25 ng/ml | 5 ng/ml | 0 | 25 ng/ml | 5 ng/ml | 0 | 25 ng/ml | 5 ng/ml | 0 |
| | 32 ng/ml | F | 25 ng/ml | 5 ng/ml | 0 | 25 ng/ml | 5 ng/ml | 0 | 25 ng/ml | 5 ng/ml | 0 | 25 ng/ml | 5 ng/ml | 0 |
| | 16 ng/ml | G | 25 ng/ml | 5 ng/ml | 0 | 25 ng/ml | 5 ng/ml | 0 | 25 ng/ml | 5 ng/ml | 0 | 25 ng/ml | 5 ng/ml | 0 |
| | 16 ng/ml | H | 25 ng/ml | 5 ng/ml | 0 | 25 ng/ml | 5 ng/ml | 0 | 25 ng/ml | 5 ng/ml | 0 | 25 ng/ml | 5 ng/ml | 0 |

TABLE 4-continued

ErbB2 antibody titration

| Plate: | Plate #1 | 1.3 | PlateFormat | Endpoint | Absorbance | Raw | FALSE | 1 | | | | |
|---|---|---|---|---|---|---|---|---|---|---|---|---|
| | Temperature (°  | 1 | 2 | 3 | 4 | 5 | 6 | 7 | 8 | 9 | 10 | 11 | 12 |
| | 25.4 | 2.926 | 1.5704 | 0.1081 | 2.8899 | 1.6191 | 0.0949 | 2.6848 | 1.0223 | 0.0905 | 1.7348 | 0.4279 | 0.0881 |
| | | 2.9634 | 1.4901 | 0.0943 | 2.8877 | 1.2978 | 0.0961 | 2.7791 | 1.057 | 0.0782 | 1.6071 | 0.4422 | 0.076 |
| | | 2.8506 | 1.0778 | 0.0652 | 2.7587 | 1.0387 | 0.0628 | 2.4599 | 0.7712 | 0.0637 | 1.2841 | 0.2967 | 0.0612 |
| | | 2.8641 | 1.1405 | 0.0768 | 2.7367 | 1.0426 | 0.068 | 2.4358 | 0.7837 | 0.0595 | 1.2891 | 0.2958 | 0.0752 |
| | | 2.0844 | 0.5963 | 0.0632 | 1.9066 | 0.5483 | 0.0526 | 1.473 | 0.4229 | 0.0517 | 0.5098 | 0.1221 | 0.0608 |
| | | 1.9005 | 0.6973 | 0.06 | 1.8896 | 0.5847 | 0.0552 | 1.5705 | 0.4081 | 0.0521 | 0.4318 | 0.1106 | 0.0586 |
| | | 1.2943 | 0.3544 | 0.0523 | 1.1558 | 0.3447 | 0.0531 | 0.7942 | 0.2283 | 0.0497 | 0.2071 | 0.0758 | 0.05 |
| | | 1.2758 | 0.379 | 0.0525 | 1.22 | 0.3378 | 0.0585 | 0.7263 | 0.2523 | 0.0602 | 0.2187 | 0.1186 | 0.068 |

Biomarker: CA15-3

A sandwich assay ELISA experiment was performed as previously described. The capture antibody, 10-CA153A (Fitzgerald), was tested at 4 different concentrations: 5 µg/mL, 2.5 µg/mL, 1.25 µg/mL and 0.625 µg/mL. Similarly, the detection antibody, 10-CA153B-B was tested at 200 ng/mL, 100 ng/mL, 50 ng/mL and 25 ng/mL. Since the CA15-3 cut-off is 30 U/mL, the CA15-3 antigen 30C-CP9064 (Fitzgerald) was tested at 100 U/mL, 10 U/mL and 0 U/mL. Each combination was performed in duplicate. The results and experimental setup are illustrated in Table 5. The signal-to-noise ratios were calculated and the optimal concentrations of cAb and dAb for CA15-3 was determined as 1.25 µg/ml and 100 ng/ml, respectively.

TABLE 5

Antibody titrations for CA15-3

CA15-3 Assay Development - Stage 1

| | | | Capture antibody dilutions | | | | | | | | | | | |
|---|---|---|---|---|---|---|---|---|---|---|---|---|---|---|
| 20140811 | Biotin- | | 5 ug/ml | 5 ug/ml | 5 ug/ml | 2.5 ug/ml | 2.5 ug/ml | 2.5 ug/ml | 1.25 ug/ml | 1.25 ug/ml | 1.25 ug/ml | 0.625 ug/ml | 0.625 ug/ml | 0.625 ug/ml | 10-CA15A |
| | 10-CA15B | CA15-3 | 1 | 2 | 3 | 4 | 5 | 6 | 7 | 8 | 9 | 10 | 11 | 12 |
| Detection antibody | 200 ng/ml | A | 100 U/ml | 10 U/ml | 0 | 100 U/ml | 10 U/ml | 0 | 100 U/ml | 10 U/ml | 0 | 100 U/ml | 10 U/ml | 0 |
| | 200 ng/ml | B | 100 U/ml | 10 U/ml | 0 | 100 U/ml | 10 U/ml | 0 | 100 U/ml | 10 U/ml | 0 | 100 U/ml | 10 U/ml | 0 |
| | 100 ng/ml | C | 100 U/ml | 10 U/ml | 0 | 100 U/ml | 10 U/ml | 0 | 100 U/ml | 10 U/ml | 0 | 100 U/ml | 10 U/ml | 0 |
| | 100 ng/ml | D | 100 U/ml | 10 U/ml | 0 | 100 U/ml | 10 U/ml | 0 | 100 U/ml | 10 U/ml | 0 | 100 U/ml | 10 U/ml | 0 |
| | 50 ng/ml | E | 100 U/ml | 10 U/ml | 0 | 100 U/ml | 10 U/ml | 0 | 100 U/ml | 10 U/ml | 0 | 100 U/ml | 10 U/ml | 0 |
| | 50 ng/ml | F | 100 U/ml | 10 U/ml | 0 | 100 U/ml | 10 U/ml | 0 | 100 U/ml | 10 U/ml | 0 | 100 U/ml | 10 U/ml | 0 |
| | 25 ng/ml | G | 100 U/ml | 10 U/ml | 0 | 100 U/ml | 10 U/ml | 0 | 100 U/ml | 10 U/ml | 0 | 100 U/ml | 10 U/ml | 0 |
| | 25 ng/ml | H | 100 U/ml | 10 U/ml | 0 | 100 U/ml | 10 U/ml | 0 | 100 U/ml | 10 U/ml | 0 | 100 U/ml | 10 U/ml | 0 |
| Capture antibody | | 1.1 mg/ml | | | | | | | | | | | | |
| Antigen | | 9 U/ul | | | | | | | | | | | | |
| Detection Antibody-biotin | | 0.4 mg/ml | | | | | | | | | | | | |

| Plate: | Plate #1 | 1.3 | PlateFormat | Endpoint | Absorbance | Raw | FALSE | 1 | | | | |
|---|---|---|---|---|---|---|---|---|---|---|---|---|
| | Temperature | 1 | 2 | 3 | 4 | 5 | 6 | 7 | 8 | 9 | 10 | 11 | 12 |
| | 24.6 | 2.7708 | 2.8805 | 0.1104 | 2.924 | 2.421 | 0.0681 | 2.8369 | 2.8508 | 0.0613 | 2.7069 | 2.556 | 0.0558 |
| | | 3.0535 | 2.8995 | 0.0981 | 3.036 | 2.897 | 0.0761 | 2.9814 | 2.9028 | 0.0617 | 2.8332 | 2.5688 | 0.0563 |
| | | 2.9155 | 2.6893 | 0.0783 | 2.9606 | 2.6252 | 0.0687 | 2.8099 | 2.6647 | 0.0612 | 2.4167 | 1.7991 | 0.0565 |
| | | 2.9612 | 2.5738 | 0.0748 | 2.9605 | 2.6778 | 0.103 | 2.8451 | 2.6473 | 0.0613 | 2.3007 | 2.0668 | 0.0555 |
| | | 2.3977 | 1.8726 | 0.058 | 2.2009 | 1.8146 | 0.0563 | 2.1146 | 1.8047 | 0.0515 | 1.4797 | 1.075 | 0.0468 |
| | | 2.3149 | 1.8024 | 0.0833 | 2.2361 | 1.8766 | 0.0659 | 2.0431 | 1.6832 | 0.0592 | 1.4003 | 0.8475 | 0.0545 |
| | | 1.3487 | 0.09864 | 0.0729 | 1.2964 | 0.9726 | 0.0748 | 1.0895 | 0.9413 | 0.0526 | 0.7547 | 0.5606 | 0.0509 |
| | | 1.2987 | 0.9862 | 0.0699 | 1.2557 | 0.09913 | 0.0672 | 1.205 | 0.8888 | 0.0606 | 0.7743 | 0.395 | 0.051 |
| End | | | | | | | | | | | | | |

TABLE 5-continued

Antibody titrations for CA15-3

| Average | | 5 ug/ml | 5 ug/ml | 5 ug/ml | 2.5 ug/ml | 2.5 ug/ml | 2.5 ug/ml | 1.25 ug/ml | 1.25 ug/ml | 1.25 ug/ml | 0.625 ug/ml | 0.625 ug/ml | 0.625 ug/ml | 10-CA15A |
|---|---|---|---|---|---|---|---|---|---|---|---|---|---|---|
| | | 1 | 2 | 3 | 4 | 5 | 6 | 7 | 8 | 9 | 10 | 11 | 12 | |
| | 200 ng/ml | 2.91215 | 2.89 | 0.10425 | 2.98 | 2.659 | 0.0721 | 2.90915 | 2.8768 | 0.0615 | 2.77005 | 2.5624 | 0.05605 | |
| | 100 ng/ml | 2.93835 | 2.63155 | 0.07655 | 2.96055 | 2.6515 | 0.08585 | 2.8275 | 2.656 | 0.06125 | 2.3587 | 1.93295 | 0.056 | |
| | 50 ng/ml | 2.3563 | 1.8375 | 0.07065 | 2.2185 | 1.8456 | 0.0611 | 2.07885 | 1.74395 | 0.05535 | 1.44 | 0.96125 | 0.05065 | |
| | 25 ng/ml | 1.3237 | 0.9863 | 0.0714 | 1.27605 | 0.98195 | 0.071 | 1.14723 | 0.91505 | 0.0566 | 0.7645 | 0.4778 | 0.05095 | |

| SNR | | 5 ug/ml | 5 ug/ml | 5 ug/ml | 2.5 ug/ml | 2.5 ug/ml | 2.5 ug/ml | 1.25 ug/ml | 1.25 ug/ml | 1.25 ug/ml | 0.625 ug/ml | 0.625 ug/ml | 0.625 ug/ml | 10-CA15A |
|---|---|---|---|---|---|---|---|---|---|---|---|---|---|---|
| | | 1 | 2 | 3 | 4 | 5 | 6 | 7 | 8 | 9 | 10 | 11 | 12 | |
| | 200 ng/ml | 27.93429 | 27.72182 | | 41.33148 | 36.87933 | | 47.30325 | 46.77724 | | 49.42105 | 45.71632 | | |
| | 100 ng/ml | 38.38472 | 34.37688 | | 34.48515 | 30.88526 | | 46.16327 | 43.36327 | | 42.11964 | 34.51696 | | |
| | 50 ng/ml | 33.35173 | 26.00849 | | 36.30933 | 30.20622 | | 37.55827 | 31.50768 | | 28.4304 | 18.97828 | | |
| | 25 ng/ml | 18.53922 | 13.81373 | | 17.97254 | 13.83028 | | 20.26943 | 16.16696 | | 15.00491 | 9.377821 | | |

Biomarker: CYFRA21.1

A sandwich assay ELISA experiment was performed as previously described. The capture antibody, MAB3506 (R&D Systems), was tested at 4 different concentrations: 6.4 μg/mL, 3.2 μg/mL, 1.6 μg/mL and 0.8 μg/mL. Similarly, the detection antibody, AF3506-B (R&D Systems) was tested at 10 μg/mL and 5 μg/mL. Since the CYFRA21.1 cut-off is 2 ng/mL, the CYFRA21.1 antigen (Cedarlane: CLPRO350) was tested at 20 ng/mL, 2 ng/mL and 0 ng/mL. Each combination was performed in duplicate. The results and experimental setup are illustrated in Table 6. The signal-to-noise ratios were calculated and the optimal concentrations of cAb and dAb for CYFRA21.1 were determined as 6.25 μg/ml and 5 μg/ml, respectively.

TABLE 6

CYFRA21.1 antibody titrations

| | | | 6.4 ug/ml | 6.4 ug/ml | 6.4 ug/ml | 3.2 ug/ml | 3.2 ug/ml | 3.2 ug/ml |
|---|---|---|---|---|---|---|---|---|
| Detection antibody | AF3506B | KRT19 | 1 | 2 | 3 | 4 | 5 | 6 |
| | 10 ug/ml | A | 20 ng/ml | 2 ng/ml | 0 | 20 ng/ml | 2 ng/ml | 0 |
| | 10 ug/ml | B | 20 ng/ml | 2 ng/ml | 0 | 20 ng/ml | 2 ng/ml | 0 |
| | 5 ug/ml | C | 20 ng/ml | 2 ng/ml | 0 | 20 ng/ml | 2 ng/ml | 0 |
| | 5 ug/ml | D | 20 ng/ml | 2 ng/ml | 0 Note | 20 ng/ml | 2 ng/ml | 0 D3 and D4 wells are swapped |
| | | | 2.1359 | 1.0413 | 0.8921 | 1.8803 | 1.0184 | 0.9053 |
| | | | 2.1036 | 1.0538 | 0.8233 | 1.925 | 0.9894 | 0.8237 |
| | | | 1.5373 | 0.5942 | 0.1907 | 1.4092 | 0.576 | 0.4565 |
| | | | 1.5402 | 0.6026 | 1.5258 Note | 0.4439 | 0.5596 | 0.4336 D3 and D4 wells are swapped |

| | | | 1.6 ug/ml | 1.6 ug/ml | 1.6 ug/ml | 0.8 ug/ml | 0.8 ug/ml | 0.8 ug/ml | MAB3506 |
|---|---|---|---|---|---|---|---|---|---|
| Detection antibody | | | 7 | 8 | 9 | 10 | 11 | 12 | |
| | | | 20 ng/ml | 2 ng/ml | 0 | 20 ng/ml | 2 ng/ml | 0 | |
| | | | 20 ng/ml | 2 ng/ml | 0 | 20 ng/ml | 2 ng/ml | 0 | |
| | | | 20 ng/ml | 2 ng/ml | 0 | 20 ng/ml | 2 ng/ml | 0 | |
| | | | 20 ng/ml D3 and D4 wells are swapped | 2 ng/ml | 0 | 20 ng/ml | 2 ng/ml | 0 | |
| | | | 1.3594 | 0.7317 | 0.5884 | 0.6569 | 0.4386 | 0.4313 | |
| | | | 1.3077 | 0.6497 | 0.5954 | 0.6776 | 0.4112 | 0.387 | |

TABLE 6-continued

CYFRA21.1 antibody titrations

|  |  | 0.9565<br>0.8716 |  | 0.4095<br>0.3937 |  | 0.3325<br>0.3484 |  | 0.3809<br>0.3871 |  | 0.2374<br>0.2236 |  | 0.2233<br>0.2183 |  |
|---|---|---|---|---|---|---|---|---|---|---|---|---|---|
|  | D3 and D4 wells are swapped |  |  |  |  |  |  |  |  |  |  |  |  |
|  |  | 6.4 ug/ml |  | 6.4 ug/ml |  | 6.4 ug/ml |  | 3.2 ug/ml |  | 3.2 ug/ml |  | 3.2 ug/ml |  | 1.6 ug/ml |
| Average | AF3506B | 1 |  | 2 |  | 3 |  | 4 |  | 5 |  | 6 |  | 7 |
|  | 10 ug/ml | 2.11975 |  | 1.04755 |  | 0.8577 |  | 1.90265 |  | 1.0039 |  | 0.8645 |  | 1.33355 |
|  | 5 ug/ml | 1.53875 |  | 0.5984 |  | 0.3173 |  | 1.4675 |  | 0.5678 |  | 0.44505 |  | 0.91405 |
|  |  | 1.6 ug/ml |  | 1.6 ug/ml |  | 0.8 ug/ml |  | 0.8 ug/ml |  | 0.8 ug/ml |  |  |  | MAB3506 |
|  | Average | 8 |  | 9 |  | 10 |  | 11 |  | 12 |  |  |  |  |
|  |  | 0.6907 |  | 0.5919 |  | 0.66725 |  | 0.4249 |  | 0.40915 |  |  |  |  |
|  |  | 0.4016 |  | 0.34045 |  | 0.384 |  | 0.2305 |  | 0.2208 |  |  |  |  |

| SNR | Biotin-- | 6.4 ug/ml | 6.4 ug/ml | 6.4 ug/ml | 3.2 ug/ml | 3.2 ug/ml | 3.2 ug/ml | 1.6 ug/ml | 1.6 ug/ml | 1.6 ug/ml | 0.8 ug/ml | 0.8 ug/ml | 0.8 ug/ml | MAB3506 |
|---|---|---|---|---|---|---|---|---|---|---|---|---|---|---|
|  | AF3506 | 1 | 2 | 3 | 4 | 5 | 6 | 7 | 8 | 9 | 10 | 11 | 12 |  |
|  | 10 ug/ml | 2.47144 | 1.22135 |  | 2.20087 | 1.16125 |  | 2.253 | 1.16692 |  | 1.63082 | 1.03849 |  |  |
|  | 5 ug/ml | 4.84951 | 1.88591 |  | 3.29738 | 1.27581 |  | 2.68483 | 1.17962 |  | 1.73913 | 1.04393 |  |  |

Biomarker: CEA

A sandwich assay ELISA experiment was performed as previously described. The capture antibody, 10-C10D (Fitzgerald), was tested at 4 different concentrations: 20 µg/mL, 10 µg/mL, 5 µg/mL and 2.5 µg/mL. Unlike the other biomarkers, two detection antibodies were tested for CEA; 10-1134B (Fitzgerald) and 10-1134B (Fitzgerald). Both of these detection antibodies were tested at 4 different concentrations: 10 µg/mL, 5 µg/mL, 2.5 µg/mL and 1.25 µg/mL. Since the CEA cut-off is 5 ng/mL, the CEA antigen (Fitzgerald: 30-AC25P) was tested at 20 ng/mL, 2 ng/mL and 0 ng/mL. Each combination was performed in duplicate. The results and experimental setup are illustrated in Table 7. The signal-to-noise ratios were calculated and the optimal concentrations of cAb and dAb for CEA were determined as 10 µg/ml and 1.25 µg/ml, respectively. Both detection antibodies performed similarly well.

TABLE 7

CEA Antibody titrations

CEA Assay Development - Stage 1

Capture antibody dilutions

| | | 1 | 2 | 3 | 4 | 5 | 6 | 7 | 8 | 9 | 10 | 11 | 12 |
|---|---|---|---|---|---|---|---|---|---|---|---|---|---|
| | Biotin- | 20 ug/ml | 20 ug/ml | 20 ug/ml | 10 ug/ml | 10 ug/ml | 10 ug/ml | 5 ug/ml | 5 ug/ml | 5 ug/ml | 2.5 ug/ml | 2.5 ug/ml | 2.5 ug/ml |
| | 10-1134 | | | | | | | | | | | | |
| Detection antibody | CEA | | | | | | | | | | | | |
| 10 ug/ml | A | 20 ng/ml | 2 ng/ml | 0 | 20 ng/ml | 2 ng/ml | 0 | 20 ng/ml | 2 ng/ml | 0 | 20 ng/ml | 2 ng/ml | 0 |
| 5 ug/ml | B | 20 ng/ml | 2 ng/ml | 0 | 20 ng/ml | 2 ng/ml | 0 | 20 ng/ml | 2 ng/ml | 0 | 20 ng/ml | 2 ng/ml | 0 |
| 2.5 ug/ml | C | 20 ng/ml | 2 ng/ml | 0 | 20 ng/ml | 2 ng/ml | 0 | 20 ng/ml | 2 ng/ml | 0 | 20 ng/ml | 2 ng/ml | 0 |
| 1.25 ug/ml | D | 20 ng/ml | 2 ng/ml | 0 | 20 ng/ml | 2 ng/ml | 0 | 20 ng/ml | 2 ng/ml | 0 | 20 ng/ml | 2 ng/ml | 0 |
| 10 ug/ml | E | 20 ng/ml | 2 ng/ml | 0 | 20 ng/ml | 2 ng/ml | 0 | 20 ng/ml | 2 ng/ml | 0 | 20 ng/ml | 2 ng/ml | 0 |
| 5 ug/ml | F | 20 ng/ml | 2 ng/ml | 0 | 20 ng/ml | 2 ng/ml | 0 | 20 ng/ml | 2 ng/ml | 0 | 20 ng/ml | 2 ng/ml | 0 |
| 2.5 ug/ml | G | 20 ng/ml | 2 ng/ml | 0 | 20 ng/ml | 2 ng/ml | 0 | 20 ng/ml | 2 ng/ml | 0 | 20 ng/ml | 2 ng/ml | 0 |
| 1.25 ug/ml | H | 20 ng/ml | 2 ng/ml | 0 | 20 ng/ml | 2 ng/ml | 0 | 20 ng/ml | 2 ng/ml | 0 | 20 ng/ml | 2 ng/ml | 0 |
| Biotin--10-1131 | | | | | | | | | | | | | |

Coating time: 2 hours @ RT
Blocking time: O/N @ 4 C.
Antigen: 1 hour @ RT
Detection-Ab: 1 Hour @ RT

| Plate: | Plate #1 | 1.3 | Plate Format | End point | Absorbance | Raw | FALSE | | | | | | |
|---|---|---|---|---|---|---|---|---|---|---|---|---|---|
| | Temperature 22.8 | 1 | 2 | 3 | 4 | 5 | 6 | 7 | 8 | 9 | 10 | 11 | 12 |
| | | 1.6884 | 0.9437 | 0.7141 | 1.5561 | 0.8414 | 0.7052 | 1.394 | 0.7583 | 0.6071 | 0.6678 | 0.4493 | 0.5239 |
| | | 1.3511 | 0.4634 | 0.362 | 0.4537 | 0.4341 | 0.5373 | 1.046 | 0.442 | 0.319 | 0.3744 | 0.2252 | 0.2489 |
| | | 1.1343 | 0.3029 | 0.2315 | 0.9573 | 0.2592 | 0.2315 | 0.731 | 0.2379 | 0.1801 | 0.2701 | 0.1372 | 0.1359 |
| | | 0.6991 | 0.1662 | 0.1256 | 0.6501 | 0.1608 | 0.1142 | 0.5147 | 0.1445 | 0.1379 | 0.1835 | 0.0897 | 0.1109 |
| | | 1.3145 | 0.6173 | 0.559 | 1.1932 | 0.6053 | 0.4848 | 1.0047 | 0.6024 | 0.9273 | 0.4696 | 0.32 | 0.351 |
| | | 1.0844 | 0.3605 | 0.2919 | 0.933 | 0.34 | 0.2966 | 0.7601 | 0.2956 | 0.2625 | 0.352 | 0.1881 | 0.2987 |
| | | 0.8328 | 0.2087 | 0.1738 | 0.7761 | 0.2075 | 0.1623 | 0.5629 | 0.1832 | 0.1624 | 0.228 | 0.1141 | 0.1266 |
| End | | 0.6976 | 0.1419 | 0.1052 | 0.61 | 0.1378 | 0.1031 | 0.4552 | 0.1271 | 0.0973 | 0.1831 | 0.0927 | 0.0776 |

TABLE 7-continued

CEA Antibody titrations

| SNR | 20 Biotin-10-1134 | 20 ug/ml 1 | 20 ug/ml 2 | 20 ug/ml 3 | 10 ug/ml 4 | 10 ug/ml 5 | 10 ug/ml 6 | 5 ug/ml 7 |
|---|---|---|---|---|---|---|---|---|
| 10 ug/ml | | 2.364375 | 1.321524 | | 2.206608 | 1.193137 | | 2.296162 |
| 5 ug/ml | | 3.73232 | 1.28011 | | 2.705565 | 0.807929 | | 3.278997 |
| 2.5 ug/ml | | 4.899784 | 1.308423 | | 4.135205 | 1.119654 | | 4.058856 |
| 1.25 ug/ml | | 5.566083 | 1.323248 | | 5.692644 | 1.408056 | | 3.732415 |
| 10 ug/ml | | 2.351521 | 1.104293 | | 2.461221 | 1.248556 | | 1.083468 |
| 5 ug/ml | | 3.714971 | 1.235012 | | 3.145651 | 1.146325 | | 2.895619 |
| 2.5 ug/ml | | 4.791715 | 1.200806 | | 4.781885 | 1.278497 | | 3.466133 |
| 1.25 ug/ml Biotin-10-1131 | | 6.631179 | 1.348859 | | 5.916586 | 1.336566 | | 4.678314 |

| SNR | 5 ug/ml 8 | 5 ug/ml 9 | 2.5 ug/ml 10 | 2.5 ug/ml 11 | 2.5 ug/ml 12 | 10-C10D |
|---|---|---|---|---|---|---|
| | 1.249053 | | 1.274671 | 0.857606 | | |
| | 1.38558 | | 1.504219 | 0.904781 | | |
| | 1.320933 | | 1.987491 | 1.009566 | | |
| | 1.047861 | | 1.654644 | 0.808837 | | |
| | 0.649628 | | 1.337892 | 0.911681 | | |
| | 1.126095 | | 1.17844 | 0.629729 | | |
| | 1.128079 | | 1.800948 | 0.901264 | | |
| | 1.306269 | | 2.359536 | 1.194588 | | |

1d: Antibody Cross-Reactivity (ELISA)

ELISA tests were conducted to determine if cross-reactions occurred between antibodies and the biomarkers.

Cross-Reactivity: Between Capture Antibodies and Detection Antibodies (Experiments with No Antigen)

Figure 1:
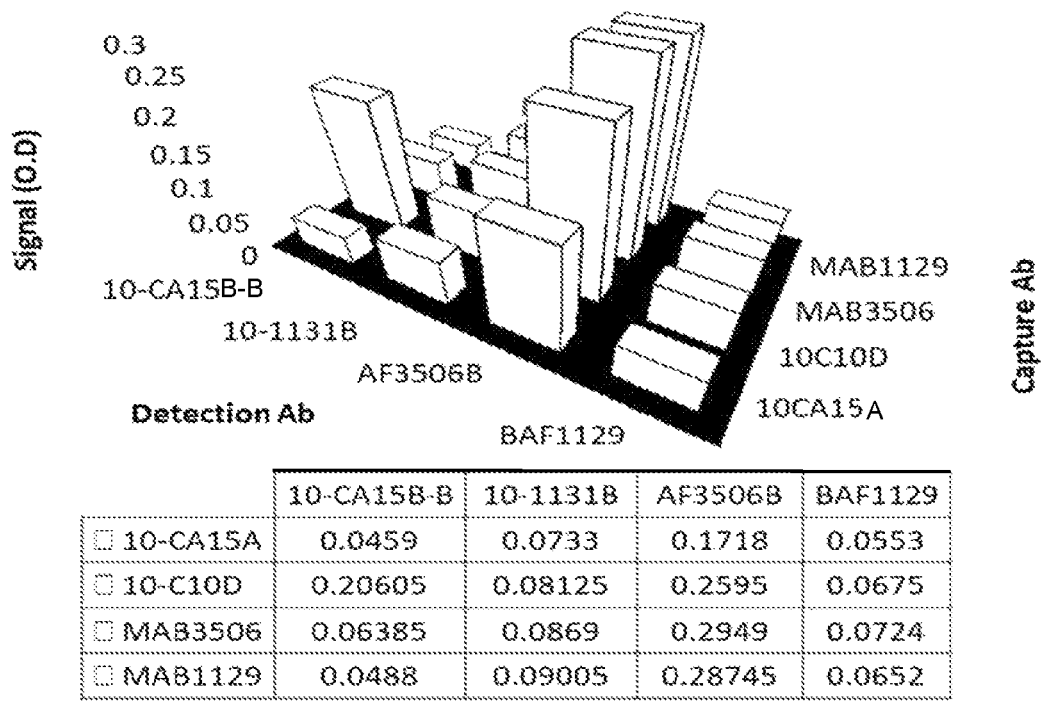
FIG. 1 shows cross-reactivity screening results between capture and detection antibodies from ELISA without antigens. All the detection antibodies were biotinylated. Signals were detected using streptavidin-HRP (SA-HRP) and the numbers shown in the table embedded were optical density readings (O.D.)

ELISA experiments were performed as previously described. Instead of antigens, wells were incubated with blocking buffer (1×PBST+2% BSA) for 1 hour. The biotinylated detection antibody for CA15-3, 10-CA153B-B, displayed some cross-reactivity with 10-C10D, the capture antibody for CEA with an O.D reading of 0.20605 (FIG. 1). The biotinylated detection antibody for CYFRA21.1, AF3506B, displayed cross-reactivity with all capture antibodies including its paired capture antibody, MAB3506. The biotinylated detection antibodies for CEA and ErbB2 (10-1131B and BAF1129) did not display significant levels of cross-reactivity with any of the capture antibodies.

Cross-Reactivity Between Detection Antibodies and Antigens

Figure 2:
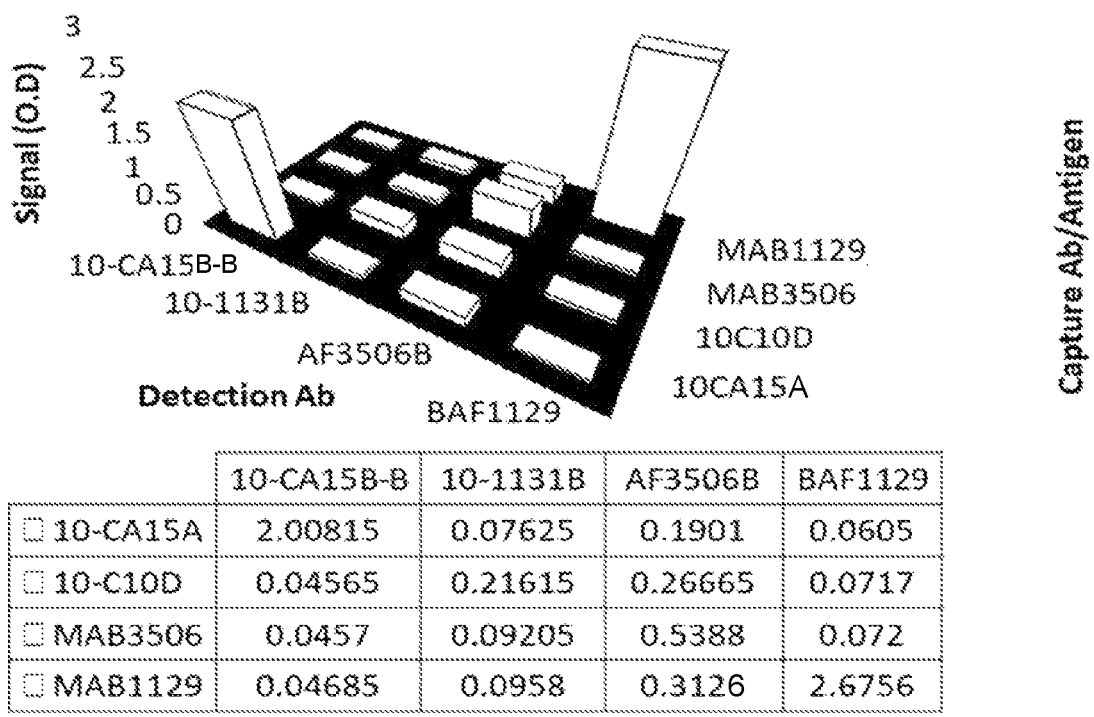
FIG. 2 shows cross-reactivity screening results between antigens and detection antibodies from ELISA. After incubation of the antigen corresponding to the capture antibody in the well, all the detection antibodies were individually applied to distinct wells for detecting cross-reactivity between each antigen and the other 3 detection antibodies.
Figure 3:
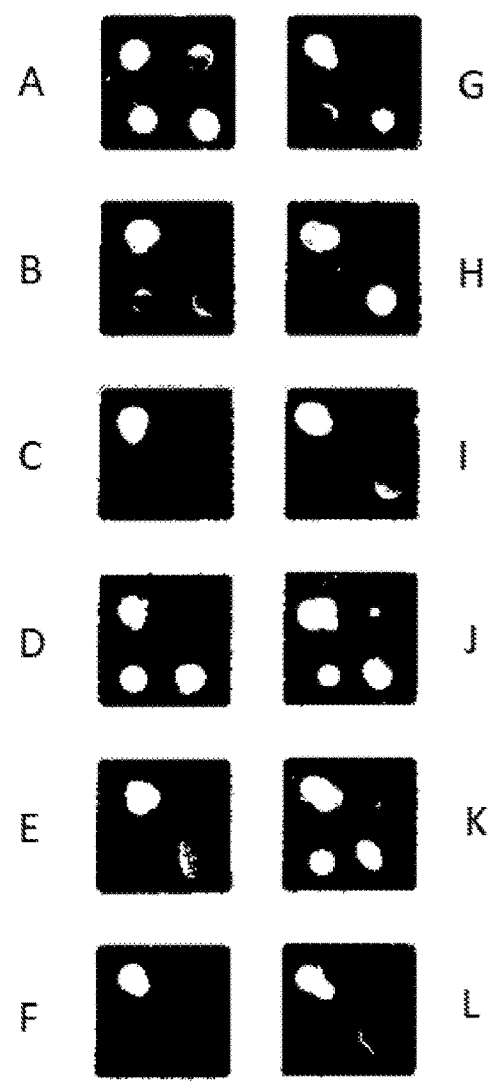
FIGS. 3A-L show the setup and results for testing various capture antibody concentrations and their response in a microarray format, where the slide was scanned with a Genepix microarray scanner; A-C: four spots were spotted, from top-left, clockwise: BSA-Biotin: 13.2 µg/mL, CA15-3 cAb 1.25 µg/mL, CA15-3 cAb 125 µg/mL, CA15-3 cAb 12.5 µg/mL; A: probed with CA15-3 Antigen at 3000 U/mL and CA15-3 dAb at 1 µg/mL; B: probed with CA15-3 antigen at 300 U/mL and CA15-3 dAb at 1 µg/mL; C: probed with CA15-3 at 30 U/mL and CA15-3 dAb at 1 µg/mL; D-F: four spots were spotted, from top-left, clockwise: BSA-Biotin: 13.2 µg/mL, CEA cAb 20 µg/mL, CEA cAb 2000 µg/mL, CEA cAb cAb 200 µg/mL; D: probed with CEA antigen 500 ng/mL and CEA dAb at 10 µg/mL; E: probed with CEA antigen at 50 ng/mL and CEA dAb at 10 µg/mL; F: probed with CEA antigen at 5 ng/mL and CEA dAb at 10 µg/mL; G-I: four spots were spotted, from top-left, clockwise: BSA-biotin: 13.2 µg/mL, CYFRA 21-1 cAb at 5 µg/mL, CYFRA 21-1 cAb at 500 µg/mL, CYFRA 21-1 cAb at 50 µg/mL; G: probed with CYFRA 21-1 antigen at 200 ng/mL and CYFRA 21-1 dAb at 10 µg/mL; H: probed with CYFRA 21-1 antigen at 20 ng/mL and CYFRA 21-1 dAb at 10 µg/mL; I: probed with CYFRA 21-1 antigen at 2 ng/mL and CYFRA 21-1 dAb at 10 µg/mL; J-L: four spots were spotted, from top-left, clockwise: BSA-biotin: 13.2 µg/mL, ErbB2 cAb at 5 µg/mL, ErbB2 cAb at 500 µg/mL, ErbB2 at 50 µg/mL; J: probed with ErbB2 at 1500 ng/mL at ErbB2 dAb at 4 µg/mL; K: ErbB2 at 150 ng/mL at ErbB2 dAb at 4 µg/mL; L: ErbB2 at 15 ng/mL at ErbB2 dAb at 4 µg/mL.

To determine unspecific interactions between antigens and detection antibodies, ELISA experiments were performed as previously described. Each well was coated with a capture antibody, blocked and incubated with its corresponding antigen. However, instead of being probed with its paired detection antibody, it was probed with a detection antibody unrelated to the antigen. As shown in FIG. 2, no cross-reactivity was found between antigens and other detection antibodies. The relatively high readings with the wells in which CYFRA21.1 detection antibody was applied might stem from the cross-reactivity observed earlier (FIG. 1) between this detection antibody and all capture antibodies.

Cross-Reactivity Between Capture Antibodies and Antigens

All capture antibodies were probed with antigen mixes of decreasing CA15-3 concentration (the concentrations of the other 3 antigens remained constant) and detected with a mixture of all detection antibodies. As expected there was a decrease of signal seen for the CA15-3 capture antibody, 10-CA15-3A. Surprisingly, there was also a decrease of signal for the CEA capture antibody, 10-C10D and the CYFRA21.1 capture antibody, MAB3506 (Table 8). It was found that the CA15-3 antigen, 30C-CP9064 (Fitzgerald) contained CEA and CYFRA21.1 contaminants. Therefore, the CEA and CYFRA21.1 capture antibodies were not non-specifically binding CA15-3 antigen but their cognate antigens present in the CA15-3 antigen solution. There was no interaction with MAB1129, the ErbB2 capture antibody and the CA15-3 antigen. Similar experiments were performed for the remaining three biomarkers. For ErbB2, a dose-dependent response was only seen with the ErbB2 capture antibody, MAB1129 (Table 8). Since CEA and CYFRA21.1 were presence as contaminants in CA15-3, CA15-3 was omitted from the antigen mix for testing CEA and CYFRA21.1. Without CA15-3 in the antigen mix, the CEA and CYFRA21.1 capture antibodies only recognized their respective antigens (Table 8).

TABLE 8

Summary of cross-reactivity experiment: interactions between capture antibodies and antigens

[CA15-3] + 5 ng/mL CEA + 2 ng/mL CK19 + 15 ng/mL ErbB2

|  | 120 U/mL | 60 U/mL | 30 U/mL | 15 U/mL | 7.5 U/mL | 0 U/mL | cAb | dAb | mix |
|---|---|---|---|---|---|---|---|---|---|
| Average | 1.9636 | 2.0043 | 1.8166 | 1.59205 | 1.3887 | 0.28805 | 10-CA153A | 10-CA153-B | 50 ng/ml |
|  | 2.7148 | 2.09075 | 1.2392 | 0.85565 | 0.649 | 0.46185 | 10-C10D | 10-1131B | 1.25 ug/ml |
|  | 1.8538 | 1.30635 | 0.84265 | 0.71065 | 0.5895 | 0.5245 | MAB3506 | AF3506-B | 2.5 ug/ml |
|  | 2.3206 | 2.3887 | 2.20925 | 2.26125 | 2.12485 | 2.10865 | MAB1129 | BAF1129 | 160 ng/ml |

[ErbB2] + 5 ng/mL CEA + 2 ng/mL CK19 + 30 U/mL CA15-3

|  | 60 ng/mL | 30 ng/mL | 15 ng/mL | 7.5 ng/mL | 3.75 ng/mL | 0 ng/mL | cAb | dAb | mix |
|---|---|---|---|---|---|---|---|---|---|
| Average | 1.89925 | 1.94595 | 1.8105 | 1.815 | 1.85135 | 1.7258 | 10-CA153A | 10-CA153-B | 50 ng/ml |
|  | 1.30575 | 1.2313 | 1.2051 | 1.1939 | 1.1638 | 1.01605 | 10-C10D | 10-1131B | 1.25 ug/ml |
|  | 0.8798 | 0.8321 | 0.8411 | 0.838 | 0.8315 | 0.767 | MAB3506 | AF3506-B | 2.5 ug/ml |
|  | 2.84935 | 2.65065 | 2.21285 | 1.57895 | 1.0512 | 0.4971 | MAB1129 | BAF1129 | 160 ng/ml |

[CK19] + 5 ng/mL CEA + 15 ng/mL ErbB2

|  | 16 ng/mL | 8 ng/mL | 4 ng/mL | 2 ng/mL | 1 ng/mL | 0 ng/mL | cAb | dAb | mix |
|---|---|---|---|---|---|---|---|---|---|
| Average | 0.22905 | 0.19345 | 0.16975 | 0.16725 | 0.15795 | 0.16885 | 10-CA153A | 10-CA153-B | 50 ng/ml |
|  | 0.4042 | 0.36525 | 0.3448 | 0.33825 | 0.3365 | 0.32315 | 10-C10D | 10-1131B | 2.5 ug/ml |
|  | 1.418 | 0.3077 | 0.5183 | 0.36285 | 0.2865 | 0.2342 | MAB3506 | AF3506-B | 2.5 ug/ml |
|  | 2.17565 | 1.93115 | 1.8714 | 2.05165 | 1.91455 | 1.95865 | MAB1129 | BAF1129 | 160 ng/ml |

[CEA] + 2 ng/mL CK19 + 15 ng/mL ErbB2

|  | 20 ng/mL | 10 ng/mL | 5 ng/mL | 2.5 ng/mL | 1.25 ng/mL | 0 ng/mL | cAb | dAb | mix |
|---|---|---|---|---|---|---|---|---|---|
| Average | 0.17685 | 0.1658 | 0.1626 | 0.1593 | 0.15305 | 0.17455 | 10-CA153A | 10-CA153-B | 50 ng/ml |
|  | 0.822 | 0.4672 | 0.3483 | 0.2688 | 0.2366 | 0.199 | 10-C10-D | 10-1131B | 2.5 ug/ml |
|  | 0.3552 | 0.3341 | 0.36555 | 0.35375 | 0.33025 | 0.3249 | MAB3506 | AF3506-B | 2.5 ug/ml |
|  | 1.85815 | 1.5945 | 1.6068 | 1.4888 | 1.89425 | 1.9442 | MAB1129 | BAF1129 | 160 ng/ml |

1e: Antibody Affinity

To determine how well the capture and detection antibodies recognized their respective antigens, we performed antibody affinity experiments with ELISA. We incubated antigen and detection antibodies for various amounts of time to see how incubation time affects the signal readings. An example of such an experiment is illustrated in Table 9: left, Wells were coated with capture antibodies for CA15-3 (10-CA153A) at 1.25 μg/mL. After blocking, wells were incubated with CA15-3 antigen at the cut off level of 30 U/mL for incubation time ranging from 5 minutes to 60 minutes. No-antigen controls were included for each time point. Wells were then probed with 100 ng/mL CA15-3 detection antibody (10-CA153B-B) for varying amounts of time from 5 minutes to 60 minutes. The results are shown on the lower, left hand side. As expected, longer incubation time with the antigen or detection antibody produced stronger signals. An increase in detection antibody incubation time did not appear to affect the background signal. For detection antibody incubation times of 60 minutes, the signal became saturated at 15 minutes of antigen incubation time with longer antigen incubation times not resulting in higher signal. It was found that 10 minutes of antigen incubation time appeared sufficient for reliable signal.

A similar experiment was performed finessing the detection antibody incubation time and seeing the effect of detection antibody concentration. Antigen was probed at the cutoff level of 30 U/mL for CA15-3 and incubation times were kept stable at 10 minutes (Table 9: right). The detection antibody, 10-CA153B-B was tested at 4 different concentrations: 100 ng/mL, 200 ng/mL, 400 ng/mL and 800 ng/mL and at varying incubation times from 5 minutes to 1 hour. For concentrations of 100 ng/mL and 200 ng/mL, the signal increased with incubation time as expected. For 400 ng/mL and 800 ng/mL, the signal became saturated after only 5 or 10 minutes of incubation time and further incubation time did not result in stronger signals. Therefore, a concentration of 100 ng/mL for detection antibody appeared sufficient for a reliable signal. Experiments similar to these were performed for the remaining biomarkers to refine antigen and detection antibody incubation times as well as detection antibody concentration.

TABLE 9

Setup and results of an antibody affinity ELISA test for CA15-3.

| antigen incubation time | | | | | | | CA15-3 1.25 ug/ml | 100 ng/ml |
|---|---|---|---|---|---|---|---|---|
| 5' | 10' | 15' | 20' | 40' | 60' | | | |
| 7 | 8 | 9 | 10 | 11 | 12 | | CA15-3 1.25 ug/ml | |
| 30 U/ml 0 | 30 U/ml 0 | 30 U/ml 0 | 30 U/ml 0 | 30 U/ml 0 | 30 U/ml 0 | | A | 5' |
| 30 U/ml 0 | 30 U/ml 0 | 30 U/ml 0 | 30 U/ml 0 | 30 U/ml 0 | 30 U/ml 0 | | B | 5' |
| 30 U/ml 0 | 30 U/ml 0 | 30 U/ml 0 | 30 U/ml 0 | 30 U/ml 0 | 30 U/ml 0 | | C | 10' |
| 30 U/ml 0 | 30 U/ml 0 | 30 U/ml 0 | 30 U/ml 0 | 30 U/ml 0 | 30 U/ml 0 | | D | 10' |
| 30 U/ml 0 | 30 U/ml 0 | 30 U/ml 0 | 30 U/ml 0 | 30 U/ml 0 | 30 U/ml 0 | | E | 30' |
| 30 U/ml 0 | 30 U/ml 0 | 30 U/ml 0 | 30 U/ml 0 | 30 U/ml 0 | 30 U/ml 0 | | F | 30' |
| 30 U/ml 0 | 30 U/ml 0 | 30 U/ml 0 | 30 U/ml 0 | 30 U/ml 0 | 30 U/ml 0 | | G | 60' |
| 30 U/ml 0 | 30 U/ml 0 | 30 U/ml 0 | 30 U/ml 0 | 30 U/ml 0 | 30 U/ml 0 | | H | 60' |
| 7 | 8 | 9 | 10 | 11 | 12 | | | |
| 0.3318 | 0.4944 | 0.5488 | 0.5992 | 0.6773 | 0.7041 | | | |
| 0.0767 | 0.08 | 0.0791 | 0.0786 | 0.0577 | 0.0756 | | | |
| 0.5019 | 0.7166 | 0.8602 | 0.9463 | 1.1722 | 1.0793 | | | |
| 0.077 | 0.0726 | 0.0821 | 0.0816 | 0.0745 | 0.0778 | | | |
| 1.2266 | 1.804 | 1.8284 | 1.8864 | 2.064 | 2.1057 | | | |
| 0.0725 | 0.1386 | 0.0881 | 0.0732 | 0.0699 | 0.0835 | | | |
| 1.7176 | 1.9856 | 2.3296 | 2.2325 | 2.3294 | 2.3329 | | | |
| 0.0568 | 0.0634 | 0.0607 | 0.0849 | 0.0808 | 0.0667 | | | |

| detection antibody incubation time (antigen incubated for 10 minutes) | | | | | | | CA15-3 1.25 ug/ml | |
|---|---|---|---|---|---|---|---|---|
| 5' | 10' | 15' | 20' | 30' | 60' | | | |
| 7 | 8 | 9 | 10 | 11 | 12 | | CA15-3 1.25 ug/ml | |
| 30 U/ml 0 | 30 U/ml 0 | 30 U/ml 0 | 30 U/ml 0 | 30 U/ml 0 | 30 U/ml 0 | | A | 100 ng/ml |
| 30 U/ml 0 | 30 U/ml 0 | 30 U/ml 0 | 30 U/ml 0 | 30 U/ml 0 | 30 U/ml 0 | | B | 100 ng/ml |
| 30 U/ml 0 | 30 U/ml 0 | 30 U/ml 0 | 30 U/ml 0 | 30 U/ml 0 | 30 U/ml 0 | | C | 200 ng/ml |
| 30 U/ml 0 | 30 U/ml 0 | 30 U/ml 0 | 30 U/ml 0 | 30 U/ml 0 | 30 U/ml 0 | | D | 200 ng/ml |
| 30 U/ml 0 | 30 U/ml 0 | 30 U/ml 0 | 30 U/ml 0 | 30 U/ml 0 | 30 U/ml 0 | | E | 400 ng/ml |
| 30 U/ml 0 | 30 U/ml 0 | 30 U/ml 0 | 30 U/ml 0 | 30 U/ml 0 | 30 U/ml 0 | | F | 400 ng/ml |
| 30 U/ml 0 | 30 U/ml 0 | 30 U/ml 0 | 30 U/ml 0 | 30 U/ml 0 | 30 U/ml 0 | | G | 800 ng/ml |
| 30 U/ml 0 | 30 U/ml 0 | 30 U/ml 0 | 30 U/ml 0 | 30 U/ml 0 | 30 U/ml 0 | | H | 800 ng/ml |
| 7 | 8 | 9 | 10 | 11 | 12 | | | |
| 0.4002 | 0.7607 | 1.0326 | 1.2955 | 1.6597 | 2.1056 | | | |
| 0.0478 | 0.0441 | 0.0455 | 0.0499 | 0.0467 | 0.0501 | | | |
| 0.9704 | 1.4875 | 1.7821 | 2.0452 | 2.3859 | 2.5561 | | | |
| 0.0421 | 0.044 | 0.0461 | 0.0453 | 0.0483 | 0.0558 | | | |
| 1.6134 | 2.4243 | 2.5344 | 2.914 | 4 | 4 | | | |
| 0.045 | 0.0448 | 0.0449 | 0.0479 | 0.0519 | 0.0507 | | | |
| 2.1712 | 2.6419 | 2.7834 | 2.7314 | 2.824 | 2.7381 | | | |
| 0.0457 | 0.0452 | 0.0492 | 0.048 | 0.0521 | 0.0486 | | | |

2: Antibody Microarray Assay Development

2a: Antibody Titration

Various concentrations for each capture antibody were tested to determine the optimal concentration for microarrays. The capture antibodies for all four biomarkers were spotted in 10-fold serial dilutions epoxysilane slides. Three concentrations for an individual capture antibody were spotted per well, as well as a BSA-biotin spot at 13.2 µg/mL for orientation. Three wells were spotted with each capture antibody set (FIGS. 3A-L). Each well was then probed with three 10-fold concentrations of each antigen: CA15-3 at 30 U/mL, 300 U/mL and 3000 U/mL; CEA at 5 ng/mL, 50 ng/mL and 500 ng/mL; CYFRA21.1 at 2 ng/mL, 20 ng/mL and 200 ng/mL and ErbB2 at 15 ng/mL, 150 ng/mL and 1500 ng/mL. Each well was probed with its corresponding detection antibody: 10-CA153B-B at 1 µg/mL, 10-1131B at 10 µg/mL, AF3506B at 10 µg/mL and BAF1129 at 4 µg/mL. All wells were probed with streptavidin (SA)-Alexa 546 (ThermoFisher) and scanned with the Genepix microarray scanner at 532 nm. For 10-CA153B-B, none of the capture antibody concentrations were able detect CA15-3 at the cutoff level of 30 U/mL, (FIGS. 3A-L). For 10-C10D, 2000 µg/mL was able to detect CEA at cutoff levels of 5 ng/mL but the signal was weak. For both MAB3506 and MAB1129, 500 µg/mL of capture antibody was able to detect cutoff levels of both CYFRA21.1 at 2 ng/mL and ErbB2 at 15 ng/mL.

Figure 4:
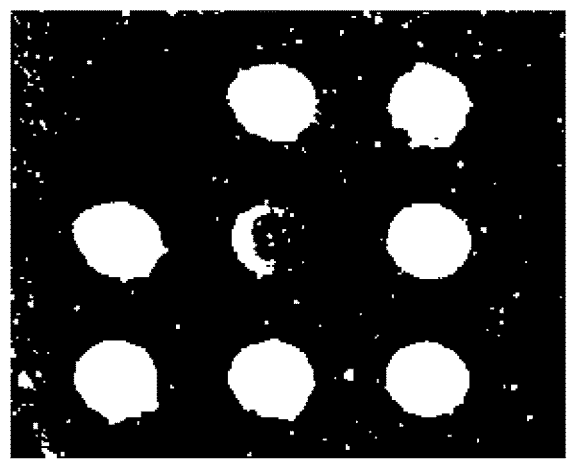
FIG. 4 shows the microarray layout and results illustrating the effect of varying a CA15-3 capture antibody concentration on signals, Signals were developed with TMB-MX and scanned with a Genepix microarray scanner; Spotted on slide with isolator; Top row (from left to right): BSA-biotin (8 nM), CA15-3 cAb at 500 µg/mL, CA15-3 cAb at 200 µg/mL; Middle row (from left to right): CA15-3 cAb at 80 µg/mL, CA15-3 at 32 µg/mL, CA15-3 antigen at 750 U/mL; Bottom row (from left to right): CA15-3 antigen at 375 U/mL, CA15-3 antigen at 187.5 U/mL and CA15-3 antigen at 93.75 U/mL; Probed with CA15-3 antigen at 30 U/mL and CA15-3 dAb at 1 µg/mL.

Multiple concentrations of the CA15-3 capture antibody, 10-CA153A. 0.4 µL of the capture antibody at four concentrations: 500 µg/mL, 200 µg/mL, 80 µg/mL and 32 µg/mL were spotted onto epoxysilane slides using a custom silicone isolator (See: Section 3 Antibody Microarray Construction). CA15-3 antigen spots were also spotted for use in a different experiment. The slide was blocked and probed with 30 U/mL of CA15-3 antigen as well as the detection antibody 10-CA153B-B at 1 µg/mL. The results were developed with TMB-MX (Moss) and scanned with the Genepix microarray scanner. This probing was performed at minimal volume as we were testing the limits of volume for our probing conditions. As shown in FIG. 4, a good signal was detected when 10-CA153A was at 80 µg/mL. At the higher capture antibody concentrations of 200 µg/mL and 500 µg/mL the signal was lower. This suggests that these higher concentrations of capture antibody might interfere with antigen binding. The signal was also low for 32 µg/mL of capture antibody; however, this might be attributed to the minimal volume used in this experiment and its location in the middle of the well, which resulted in poor coverage of the antigen solution during the incubation step. Similar experiments were performed for the other biomarker capture antibodies to determine the optimal capture antibody concentration that elicits the best density for antigen capture.

Detection antibody concentrations were determined empirically. Chemically-modified microarray slides were printed with dilutions of capture antibodies for CA15-3 and CEA with a microarray printer such as the Genemachines Omnigrid300. Dilutions of antigens for CA15-3 and CEA were also printed for data normalization purposes. Antibodies and antigens were diluted in 1×PBS+0.01% sarcosyl+0.25 mg/mL BSA printing buffer. After slide printing and immobilization, slides were blocked with blocking buffer. 16 microarray grids were probed with varying amounts of CA15-3 and CEA antigens followed by dilutions of CA15-3 and CEA detection antibodies. Two different dilutions of both CA15-3 and CEA detection antibodies probed 7 different antigen concentrations to generate standard curves for both detection antibody dilutions. For CA15-3, detection antibody was tested at 0.2 µg/mL and 0.4 µg/mL. CEA detection antibody was tested at 20 µg/mL and 25 µg/mL. After signal development with SA-HRP/biotin-HRP and TMB, slides were imaged with the ArrayIt Colorimetric scanner and quantified with ImageJ. Background (cAb count value at zero antigen) was subtracted from the capture antibody counts. Capture antibody spots were then normalized with the antigen spots (cAb counts/Ag counts). Normalized Counts were then plotted vs. probed antigen concentrations to generate standard curves. Standard curves for the CA15-3 capture antibody at 80 µg/mL at both 0.2 µg/mL and 0.4 µg/mL detection antibody is shown in FIGS. 34A-B. Using detection antibody at 0.2 µg/mL generated a linear standard curve while the detection antibody at 0.4 µg/mL caused saturation of counts at higher antigen concentrations. Based on these studies, 0.2 µg/mL was selected as the detection antibody concentration for CA15-3. Similar experiments were also performed with CEA and resulted in the selection of 20 µg/mL as the detection antibody concentration.

Similar experiments were performed for cardiovascular biomarkers. Detection antibody concentrations were determined empirically. Epoxy-coated slides were printed with dilutions of capture antibodies for myoglobin. Dilutions of myoglobin were also printed for data normalization purposes. Antibodies and antigens were diluted in 1×PBS+0.01% sarcosyl+0.25 mg/mL BSA printing buffer. After slide printing and immobilization, slides were blocked with blocking buffer. Sixteen microarray grids were probed with varying amounts of myoglobin antigen followed by dilutions of myoglobin detection antibodies. For myoglobin, detection antibody was tested at 0.5 µg/mL, 1 µg/mL, 2 µg/mL and 4 µg/mL. Standard curves for the myoglobin capture antibody at 100 µg/mL at both 1 µg/mL and 4 µg/mL detection antibody is shown in FIGS. 35A-B. Using detection antibody at 1 µg/mL generated a linear standard curve while the detection antibody at 4 µg/mL caused saturation of counts at higher antigen concentrations. Based on these studies, 1 µg/mL was selected as the detection antibody concentration for myoglobin. Similar experiments were also performed with the other cardiovascular biomarkers, CK-MB, NT-proBNP and Troponin I and resulted in the selection of 5 µg/mL, 10 µg/mL and 100 µg/mL, respectively, as the detection antibody concentrations for these biomarkers.

2b: Antigen Titrations

Figure 5:
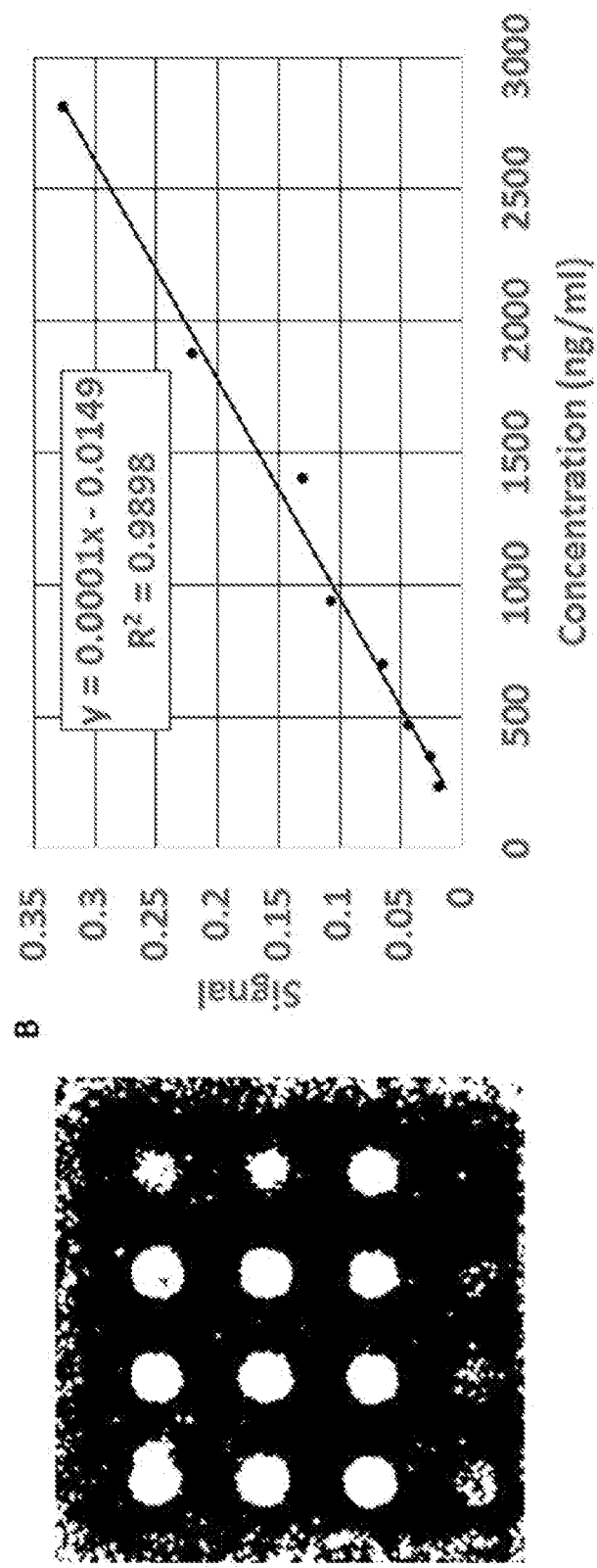
FIGS. 5A-B show immobilized antigen titration of ErbB2 (A) and corresponding antigen titration curve from a microarray assay (B); A: spotted on a slide with isolator; Top row (from left to right): ErbB2 cAb at 500 µg/mL, ErbB2 cAb at 250 µg/mL, ErbB2 cAb at 125 µg/mL, ErbB2 cAb at 62.5 µg/mL; Second row (from left to right): same as top row; Third row (from left to right): ErbB2 antigen at 2812.5 ng/mL, ErbB2 antigen at 1875 ng/mL, ErbB2 antigen at 1406.25 ng/mL, ErbB2 antigen at 937.5 ng/mL; Bottom row (from left to right): ErbB2 antigen at 703.13 ng/mL, ErbB2 antigen at 468.75 ng/mL, ErbB2 antigen at 351.56 ng/mL, ErbB2 antigen at 234.38 ng/mL
Figure 6:
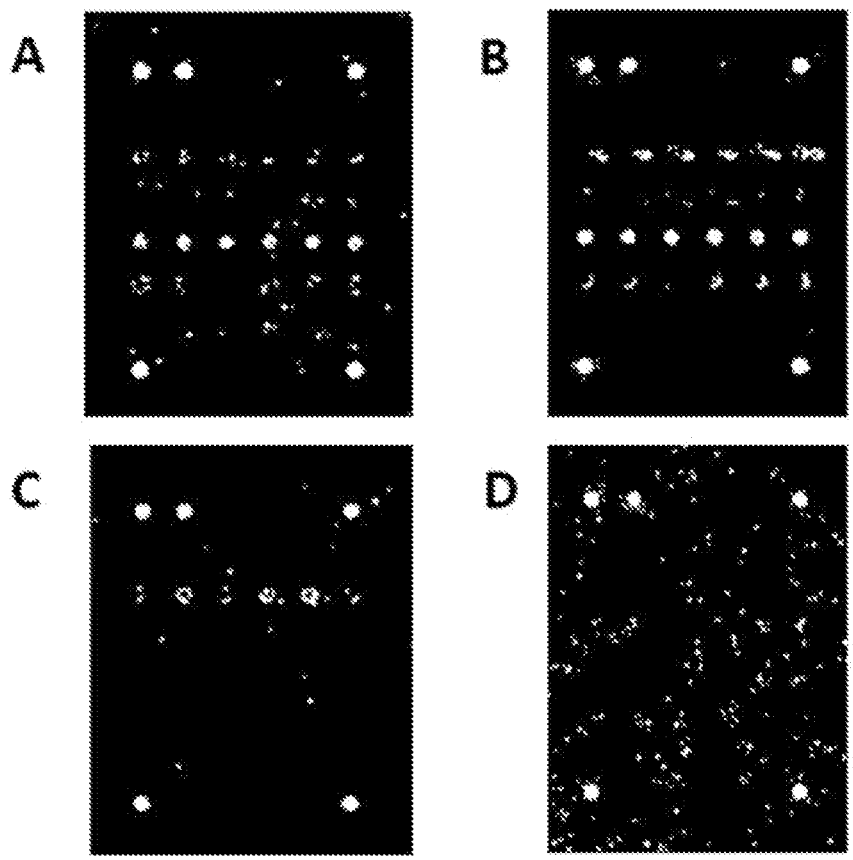
FIGS. 6A-D show the results for microarray slides printed using a robotic microarray printer with capture antibodies in replicates of six probed with single detection antibodies; The bright corner spots are BSA-biotin for orientation; The first row is ErbB2 cAb at 500 µg/mL; the second row is CYFRA 21-1 cAb at 500 µg/mL; the third row is CA15-3 cAb at 500 µg/mL; the fourth row is CEA cAb1 at 2000 µg/mL; the fifth row is CEA cAb2 at 2000 µg/mL; A: probed with CA15-3 dAb at 2 µg/mL; B: probed with ErbB2 dAb at 4 µg/mL; C: probed with CEA dAb at 20 µg/mL; D: probed with CYFRA 21-1 dAb 10 µg/mL.

To determine the optimal antigen concentration to be spotted for potential signal quantification purposes, antigen standard curves were performed on microarray slides. 8 different antigen concentrations were spotted onto slides in addition to four duplicate capture antibody concentrations. An example of this experiment for ErbB2 is shown in FIGS. 5A-B. Each well was probed with a different concentration of ErbB2 antigen to obtain a standard curve for a different experiment. Wells were then probed with the ErbB2 detection antibody, BAF1129, at 20 µg/mL, followed by SA-HRP/biotin-HRP, and signals were developed with TMB-MX. Spots were quantified with the instrument camera. Since the amount of antigen used for incubation in sandwich assays should not affect the antigen spotted, each well was considered a replicate for each antigen spot. Averages were obtained for each antigen concentration and plotted in a graph of signal vs. concentration to obtain a standard curve for the antigen titration (FIGS. 5A-B). Similar experiments were performed for the other biomarkers to obtain standard curves for antigen titration.

2c: Antibody Conjugation

Detection antibodies were modified with biotin, allowing use of the common secondary detection reagent carrying streptavidin (SA) for signal detection. Biotin has a very small size (244 Da) and can be conjugated to antibodies and proteins without affecting their activity. The biotin molecule would bind tightly to SA-HRP through SA such that HRP would catalyze its colorimetric substrates to develop into a visible signal. The conjugation typically allows more than one biotin molecule to conjugate onto the antibody and thus amplifies the signal by increasing the number of HRP molecules able to bind to one antibody. To conjugate biotin to the detection antibodies we used N-hydroxysuccinimide (NHS) ester-activated biotins (ThermoFisher). The NHS esters react with the primary amines on the antibodies as well as the side chain of lysine residues to form amide bonds. For the biotinylation reaction, a 10 mM solution of NHS ester-activated biotin was prepared. For every 20 µg of detection antibody, 0.5 µL of 10 mM NHS-ester-activated biotin was used. The detection antibody-biotin solution was incubated at room temperature on a rotator for 1 hour. Following incubation, the solution was placed in a 10,000 MW cut-off dialysis tube (ThermoFisher). The dialysis tubing with the solution was placed in cold 1×PBS and left in the 4° C. overnight. This allowed for the removal of any unconjugated biotin while keeping the detection antibody in the dialysis tubing. This also allowed the exchange of the conjugation buffer for 1×PBS. The following day, solution was removed from the dialysis tube and the final concentration of the resulting detection antibody was quantified with Bradford method.

2d: Antibody Cross-Reactivity on Microarray

Cross-Reactivity Between Capture and Detection Antibodies

Cross-reactivity experiments performed with ELISA were further verified in the microarray format. A microarray slide was printed with a printing robot. These slides had all capture antibodies printed in replicates of six. Wells containing all the capture antibodies were blocked with blocking buffer and probed with a single detection antibody to determine if there was cross-reactivity between capture and detection antibodies. The results are illustrated in FIGS. 6A-D. The detection antibody for CA15-3, 10-CA153B-B was found to cross-react mildly with MAB3506, MAB1129 and its own capture antibody, 10-CA153A. The detection antibodies for both CYFRA21.1 and ErbB2, AF3506 and BAF1129, also cross-reacted slightly with these same capture antibodies.

Figure 7:
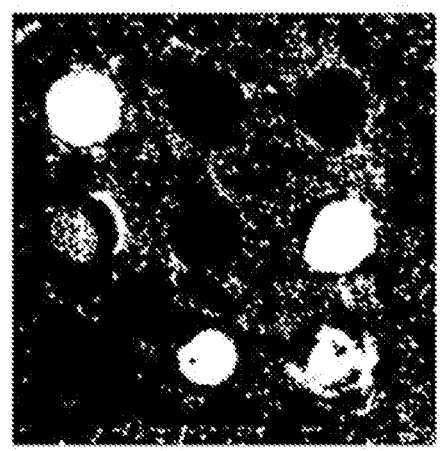
FIG. 7 shows the cross-reactivity between capture and detection antibodies on microarray slide hand spotted with custom silicone isolator; Top row (from left to right) BSA-biotin at 8 nM, CA15-3 cAb at 25 µg/mL, ErbB2 cAb at 250 µg/mL; Middle row (from left to right) CYFRA 21-1 cAb at 50 µg/mL, CEA cAb at 500 µg/mL, CA15-3 antigen at 1500 U/mL; Bottom row (from left to right) ErbB2 antigen at 7.5 µg/mL, CYFRA 21-1 antigen at 100 ng/mL, CEA at 15 µg/mL; It was then probed with a dAb mix of CA15-3 dAb at 2 µg/mL, CEA dAb at 20 µg/mL, ErbB2 dAb at 8 µg/mL, CYFRA 21-1 dAb at 5 µg/mL.

Cross-reactivity between capture antibodies and detection antibodies was also examined with slides spotted with custom-made silicon isolators (Grace Biolabs). Slides were spotted with both capture antibodies and antigens for all four biomarkers. The wells were incubated with blocking buffer instead of antigen. Wells were probed with a detection antibody mix containing detection antibodies for all four biomarkers (CA15-3B-B at 2 µg/mL, C1299-870-B at 20 µg/mL, BAF1129 at 8 µg/mL and AF3506 at 5 µg/mL). Detection antibodies were premixed with SA-HRP (dAb: 5×SA-HRP) for 1 hour before probing. Spots were developed with EnzMet silver developer from Nanoprobes and scanned with the Genepix microarray scanner. The results are illustrated in FIG. 7. As expected, the spotted antigens developed with the exception of ErbB2. No signal was seen for capture antibodies CA15-3A at 25 µg/mL, MAB1129 at 250 µg/mL and C1299-87 W at 500 µg/mL. A low level of cross-reactivity was observed for MAB3506 at 50 µg/mL.

Cross-reactivity was examined for the breast cancer panel between capture and detection antibodies. Capture antibodies and antigens for CA15-3, CEA and ErbB2 were printed with the Genemachines Omnigrid300 onto epoxy-coated slides. Slides were then probed with detection antibodies without any antigen and imaged with the Arraylt Colorimetric scanner. Unless there is cross-reactivity, in the absence of antigen there should be no capture antibody signal when probed with detection antibody. FIG. 36 graphically illustrates the experimental results. Each bar represents a different capture antibody/detection antibody combination. There was no signal above background for any of the capture antibody/detection antibody combinations illustrating no cross-reactivity between breast cancer panel capture antibodies and detection antibodies under the tested conditions.

Cross-Reactivity Between Antigen and Detection Antibodies

Figure 8:
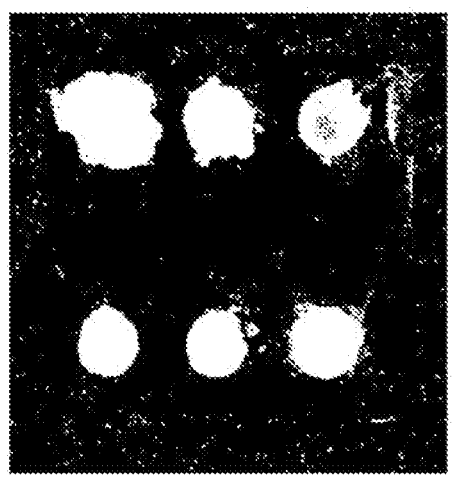
FIG. 8 shows a microarray experiment to examine potential contaminants in a new CA15-3 antigen (Fitzgerald: 30C-CP9064 U), where the microarray was probed with SA-HRP and EnzMet silver developer and signals developed were scanned with a Genepix microarray scanner; A microarray slide was spotted with custom silicone isolate; Top row (from left to right) BSA-biotin 8 nM, CA15-3 cAb at 25 µg/mL, CA15-3 antigen at 1500 U/mL; Middle row (from left to right) CYFRA 21-1 cAb at 50 µg/mL, CEA cAb at 650 µg/mL, ErbB2 cAb at 250 µg/mL; Bottom row (from left to right) CYFRA 21-1 antigen at 100 ng/mL, CEA antigen at 15 µg/mL, ErbB2 antigen at 7.5 µg/mL; Probed with new CA15-3 antigen at 30 U/mL and a dAb mix of CA15-3 dAb at 1 µg/mL, CEA dAb at 20 µg/mL, ErbB2 dAb at 8 µg/mL and CYFRA 21-1 dAb at 5 µg/mL.
Figure 9:
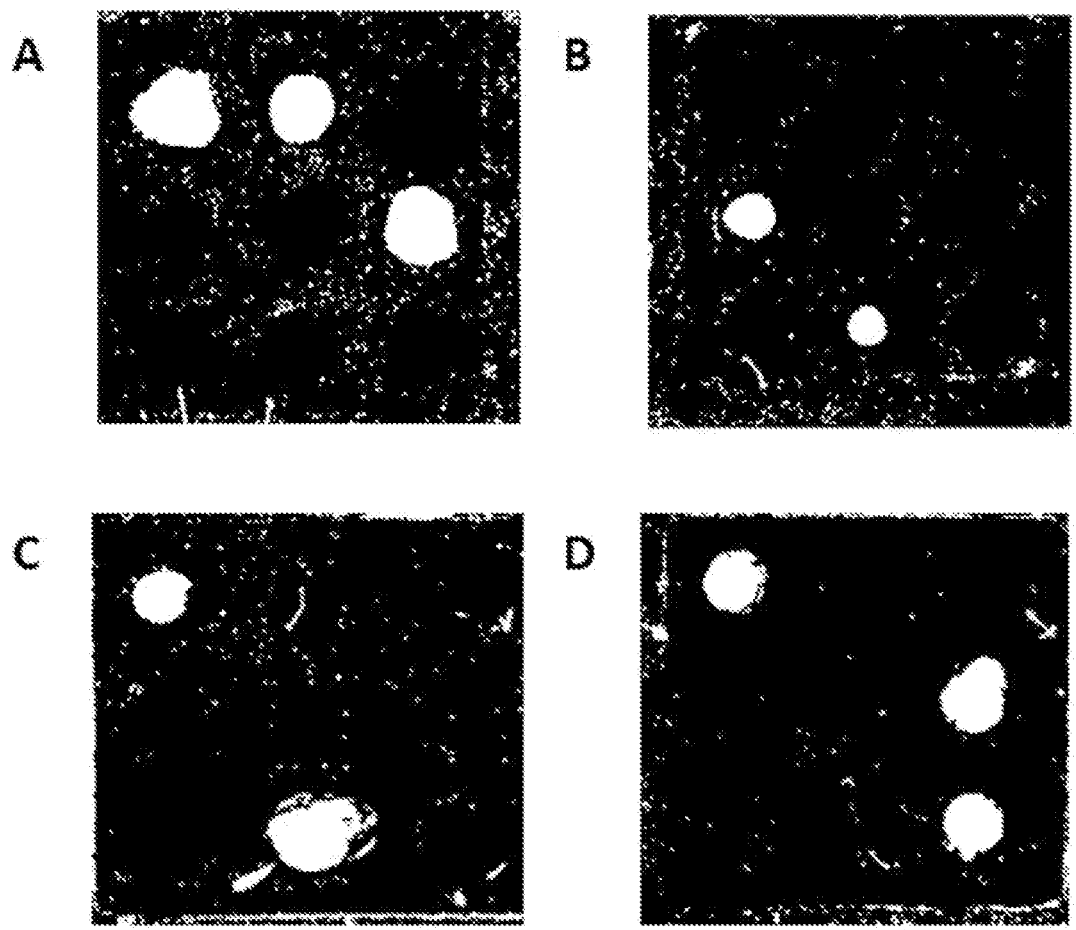
FIGS. 9A-D show the results from microarray experiments examining cross-reactivity between antigen and detection antibodies; Panel A-B: printed with custom silicone isolator; Top row (from left to right) BSA-biotin 8 nM, CA15-3 cAb at 25 µg/mL, ErbB2 cAb at 250 µg/mL; Middle row (from left to right) CYFRA 21-1 cAb at 50 µg/mL, CEA cAb at 500 µg/mL, CA15-3 antigen at 1500 U/mL; Bottom row (from left to right) ErbB2 antigen at 7.5 µg/mL, CYFRA 21-1 antigen at 100 ng/mL, CEA antigen at 15 µg/mL; Panel C-D: printed with custom silicone isolator; Top row (from left to right) BSA-biotin 4 nM, CA15-3 cAb at 50 µg/mL, CA15-3 antigen at 1500 U/mL; Middle row (from left to right) CYFRA 21-1 cAb at 200 µg/mL, CEA cAb at 975 µg/mL, ErbB2 cAb at 395 µg/mL; Bottom row (from left to right) CYFRA 21-1 antigen at 100 ng/mL, CEA antigen at 15 µg/mL, ErbB2 antigen at 2.25 µg/mL; A: probed with CA15-3 antigen at 30 U/mL and CA15-3 dAb at 2 µg/mL; B: probed with CYFRA 21-1 antigen at 8 ng/mL and CYFRA 21-1 dAb at 5 µg/mL; C: probed with CEA antigen at 200 ng/mL and CEA dAb at 20 µg/mL; D: probed with ErbB2 antigen at 120 ng/mL and ErbB2 dAb at 8 µg/mL.
Figure 10:
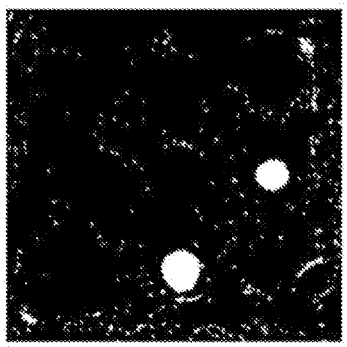
FIGS. 10 A-D show the results from microarray experiments examining cross-reactivity between antigens and capture antibodies Panel A-C: spotted with custom silicone isolator; Top row (left to right) BSA-biotin 8 nM, CA15-3 cAb at 25 µg/mL, ErbB2 cAb at 250 µg/mL; Middle row (left to right) CYFRA 21-1 cAb at 50 µg/mL, CEA cAb at 500 µg/mL, CA15-3 antigen at 1500 U/mL; Bottom row (left to right) ErbB2 antigen at 7.5 µg/mL, CYFRA 21-1 antigen at 100 ng/mL, CEA antigen at 15 µg/mL; Panel D: spotted with custom silicon isolator; Top row (left to right) BSA-biotin 10 nM, CA15-3 cAb at 25 µg/mL, ErbB2 at 200 µg/mL; Middle row (left to right) CYFRA 21-1 cAb at 250 µg/mL, CYFRA 21-1 cAb at 125 µg/mL, CYFRA 21-1 antigen at 250 µg/mL; Bottom row (left to right) CEA cAb at 500 µg/mL, CEA cAb at 250 µg/mL, CEA cAb at 125 µg/mL; A: probed with CA15-3 antigen at 30 U/mL and CA15-3 dAb at 2 µg/mL; B: probed with CEA antigen at 50 ng/mL and CEA dAb at 20 µg/mL; C: probed with CYFRA 21-1 antigen at 8 ng/mL and CYFRA 21-1 dAb at 5 µg/mL; D: probed with ErbB2 antigen at 30 ng/mL and ErbB2 dAb at 8 µg/mL.
Figure 10:
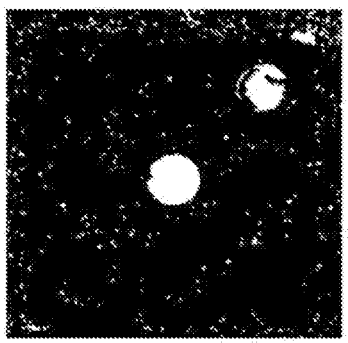
Figure 10:
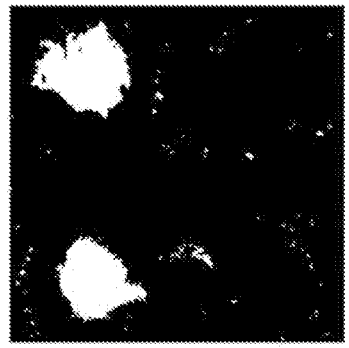
Figure 10:
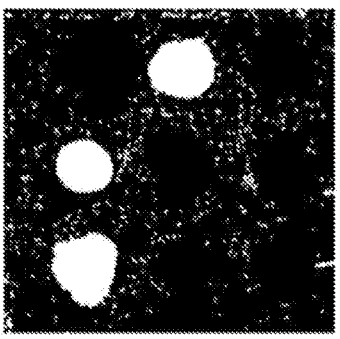

We had found with our cross-reactivity experiments with ELISA that the original CA15-3 antigen contained impurities of CEA and CYFRA21.1 antigen as well. A new CA15-3 antigen (Fitzgerald: 30C-CP9064 U) was acquired and tested on microarray to ensure that there was no longer any contamination. Capture antibodies and antigens were spotted using the silicone isolator onto microarray slides. A well was probed with CA15-3 antigen (new) at 30 U/mL and probed with a detection antibody mix for all biomarkers. The well was probed with SA-HRP and EnzMet silver developer. The resulting slide was scanned with the Genepix microarray scanner at 532 nm. However, no signal was found at the CYFRA21.1 and CEA capture antibodies (MAB3506 and C1299-87 W) (FIG. 8). Thus, we concluded that this new CA15-3 antigen did not have contaminants that would interfere with our multiplexed immunoassay.

To examine potential cross-reactions between antigens and detection antibodies, antigen was spotted onto microarray slides. The slides were blocked with blocking buffer (1×PBST+5% BSA), and probed with antigens and their corresponding detection antibodies. The wells were probed with antigen because the slides were also spotted with capture antibodies for another experiment. Wells were probed with SA-HRP and biotin-HRP premix (4 µg/mL and 2 µg/mL respectively) and developed with EnzMet silver developer. The results are illustrated in FIGS. 9A-D. A well spotted with all four antigens was probed with CA15-3B-B at 2 µg/mL. The only antigen signal developed was that of CA15-3 as expected. The CA15-3B-B detection antibody failed to cross-react with the other three biomarkers. All four antigen spots were also probed with the remaining three detection antibodies in three separate wells (AF3506B at 5 µg/mL, C1299-870-B at 20 µg/mL and BAF1129 at 8 µg/mL). There failed to be any signal with an unrelated antigen. This confirmed no cross-reactive interactions between detection antibodies and non-cognate antigens.

Potential cross-reactivity was examined between antigens and the detection antibodies of the breast cancer panel. The CA15-3, CEA and ErbB2 capture antibodies were spotted onto epoxy-coated slides with the Genemachines Omnigrid 300 as above. Individual microarray grids were probed with either CA15-3, CEA and ErbB2 antigens. Wells were then probed with detection antibodies of the other biomarkers, ie. a well probed with CA15-3 antigen would then be probed with CEA and ErbB2 detection antibodies. After signal development, slides were scanned with the Arraylt Colorimetric scanner. The antigen should bind its respective capture antibody but since the antigen does not have its cognate detection antibody, there should be no signal at the capture antibody spots. Capture antibody/antigen spots did not display signal that well was probed with the corresponding detection antibody (FIG. 37). This indicates that there was no cross-reactivity between antigens and detection antibodies in the breast cancer panel.

Cross-Reactivity Between Antigen and Capture Antibodies

To examine interactions between antigens and capture antibodies, microarray slides were spotted with capture antibodies and antigens using the custom silicone isolators. Slides were incubated overnight and blocked in blocking buffer (1×PBST+5% BSA) for 1 hour. Wells were then probed with a single antigen and its corresponding detection antibody. The results are illustrated in FIGS. 10A-D. A well probed with CA15-3 at 30 U/mL and CA15-3B-B detection antibody at 2 µg/mL only displayed a signal at the 10-CA15-3A capture antibody and CA15-3 spotted antigen as expected. A well probed with CEA at 50 ng/mL and C1299-870-B detection antibody (20 µg/mL) only had a signal at the CEA capture antibody (C1299-87 W) and the CEA spotted antigen. Similarly, the well probed with CYFRA21-1 at 8 ng/mL and its detection antibody (AF3506B) at 5 µg/mL only showed a signal for CYFRA21-1 capture antibody, MAB3506, and the CYFRA21-1 spotted antigen. The well probed with ErbB2 30 ng/mL and its detection antibody, BAF1129 at 8 µg/mL was spotted with only capture antibodies in a separate experiment. It only displayed a signal at the ErbB2 capture antibody (MAB1129) as expected. These results illustrate that there are not any strong cross-reactive interactions between antigen and other capture antibodies within the panel that could interfere with our multiplexed immunoassay.

To examine interactions between antigens and capture antibodies, capture antibodies were spotted onto epoxy-coated slides with the Genemachines Omnigrid300. Microarray grids were then probed with either CA15-3, CEA or ErbB2 followed by their cognate detection antibody. After signal development, the slides were scanned with the Arraylt Colorimetric scanner. If there was an interaction between the antigen and capture antibody, there should be signal at that capture antibody. Without cross-reactivity, an antigen should only display signal at its corresponding capture antibody. There was no signal seen at any unspecific capture antibody indicating no cross-reactivity between antigens and the capture antibodies under the tested conditions (FIG. 38)

2d: Signal Amplification

Different amounts of streptavidin-horseradish peroxidase (SA-HRP) were tested, as was combining the detection antibody and SA-HRP steps into one. The detection antibodies were biotinylated such that they can be recognized by the SA-HRP.

Shortening of Assay Time with the Pre-Mixture of Detection Antibodies and SA-HRP We initially tried to increase signal and shorten assay time by combining the biotinylated detection antibody and SA-HRP incubations into one by premixing the two components. Detection antibodies were premixed with either 5 times SA-HRP in molarity, with rotation for 1 hour before probing. Capture antibodies for CA15-3 (10-CA15-3A), CYFRA 21-1 (MAB3506), CEA (C1299-87 W) and ErbB2 (MAB1129) were hand-spotted onto microarray slides. Antigens for all four biomarkers were hand-spotted as well. The spots were then probed with CA15-3, CYFRA21-1, CEA and ErbB2 antigen at 1× cut-off: 30 U/mL, 5 ng/mL, 2.5 ng/mL and 15 ng/mL respectively for 30 minutes. Different wells were then incubated with the dAb mixed 5×SA-HRP (FIGS. 11A-G). Detection antibody mix for 15 minutes was followed by SA-HRP for 15 minutes. The results indicated that detection antibodies mixed with 5 times SA-HRP probed for 15 minutes was sufficient to get good signals. Some wells were also probed with detection antibody mix for 15 minutes followed by a mixture of SA-HRP and biotin-HRP in various combinations (FIGS. 11H-M). It was found that having premixing SA-HRP and biotin-HRP and probing this separately from detection antibody mix increased signals compared to detection antibody, SA-HRP premix.

The Use of Biotin-HRP and SA-HRP in Combination

The use of biotin-HRP in combination with SA-HRP was explored with the goal to enhance the sensitivity of signal detection on the microarray. We first attempted different ratios of SA-HRP to biotin-HRP that were premixed for 30 minutes before being used for probing. Capture antibodies and antigens were spotted onto microarray slides as seen in FIGS. 11A-G. The different SA-HRP/biotin-HRP combinations are shown in FIGS. 11H-M. Wells were blocked and then probed with an antigen mix consisting of CA15-3 at 30 U/mL, CYFRA21.1 at 2 ng/mL, ErbB2 at 15 ng/mL and CEA at 50 ng/mL. Wells were probed with a detection antibody mix consisting of CA15-3B-B at 1 µg/mL, C1299-870-B at 20 µg/mL, BAF1129 at 8 µg/mL and AF3506B at 5 µg/mL. Detection mixes were either probed separately or premixed with SA-HRP before probing. Slides were developed using the EnzMet silver development protocol of 2 minutes/2 minutes/8 minutes. The results illustrate that wells that were probed with SA-HRP/biotin-HRP premix had higher signal than the SA-HRP alone or the dAb mix/5× SA-HRP premix. In addition, the optimal concentration of SA-HRP/biotin-HRP premix was 4 µg/mL and 2 µg/mL, respectively. There was not higher signal achieved with higher concentrations of either reagent.

Figure 11:
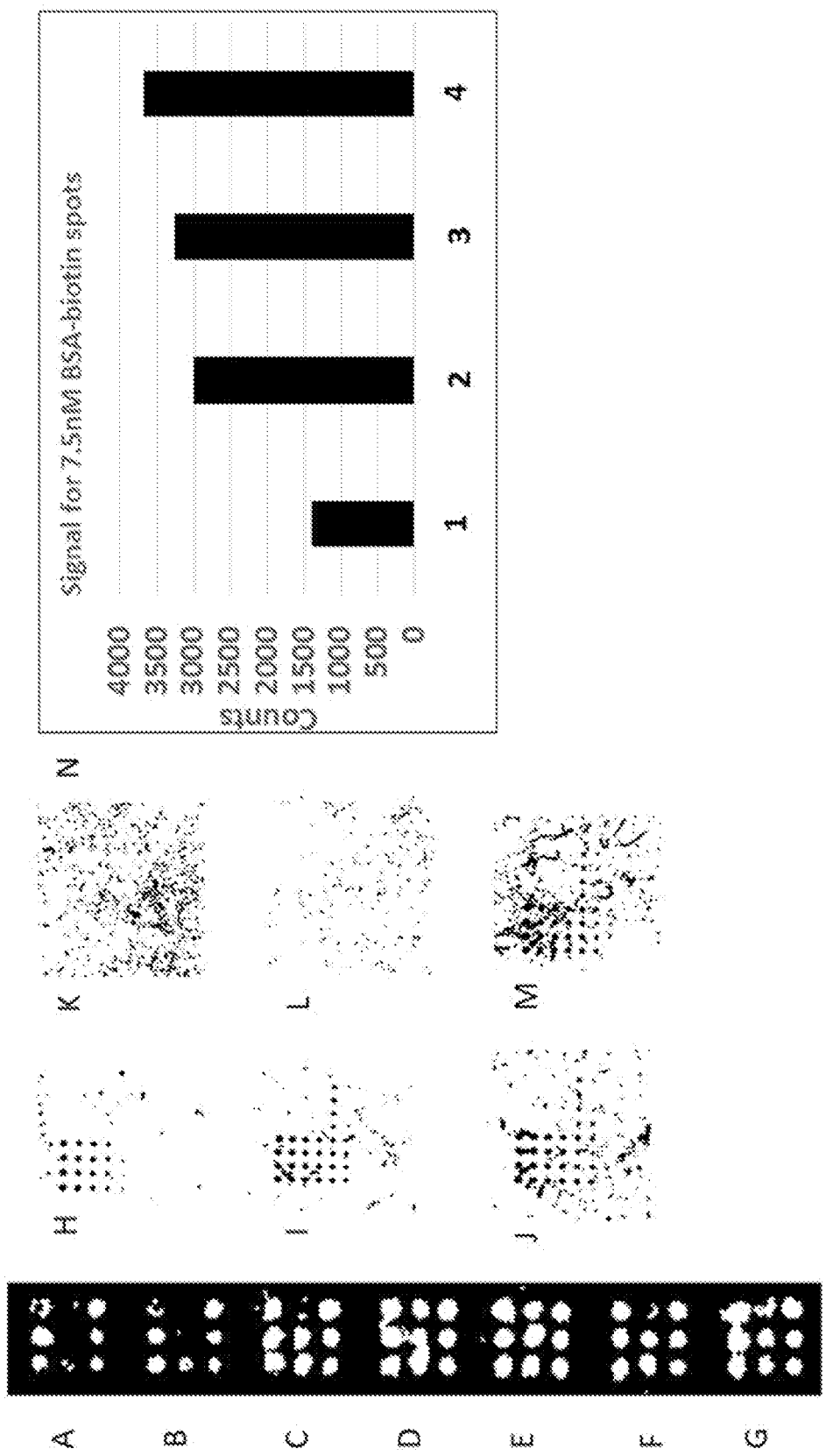
FIGS. 11A-N show signal amplification with either pre-mixing dAb and streptavidin-horseradish peroxidase (SA-HRP) or with SA-HRP/biotin-HRP; Panels A-G shows the results of a sandwich antibody microarray assay probed with various combinations of SA-HRP and biotin-HRP, where the probed slide was scanned with a Genepix microarray scanner; Slides were spotted with a custom silicone isolator; Top row (left to right) BSA-biotin 8 nM, CA15-3 cAb at 25 µg/mL, CA15-3 antigen at 1500 U/mL; Middle row (left to right) CYFRA 21-1 cAb at 50 µg/mL, CEA cAb at 650 µg/mL, ErbB2 cAb at 250 µg/mL; Bottom row (left to right) CYFRA 21-1 antigen at 100 ng/mL, CEA antigen at 15 µg/mL, ErbB2 at 7.5 µg/mL; A-G were all probed with an antigen mix consisting of CA15-3, CEA, ErbB2 and CYFRA 21-1. A: probed with dAb mix with 5× molar amount of SA-HRP for 15 minutes; B: probed with dAb mix with 5× molar amount of SA-HRP for 15 minutes plus addition biotin-HRP at 4 µg/mL for 10 minutes; C: probed with dAb mix for 15 minutes plus SA-HRP at 4 µg/mL premixed with biotin-HRP at 1 µg/mL for 10 minutes; D: probed with dab mix for 15 minutes plus SA-HRP at 4 µg/mL premixed with biotin-HRP at 2 µg/mL for 10 minutes; E: probed with dAb mix for 15 minutes plus SA-HRP at 4 µg/mL premixed with biotin-HRP at 4 µg/mL for 10 minutes; F: probed with dAb mix for 15 minutes plus SA-HRP at 20 µg/mL with biotin-HRP at 5 µg/mL for 10 minutes; G: probed with dAb mix for 15 minutes plus SA-HRP at 100 µg/mL with 25 µg/mL biotin-HRP at 25

The combined use of SA-HRP/biotin-HRP premix was also explored with slides printed with the Omingrid 300 Microarray Printer on which the TMB-MX detection method was used. Various concentrations of BSA conjugated to biotin were spotted onto microarray slides as seen in FIG. 11N. Wells were blocked and then probed with the various SA-HRP/biotin-HRP combinations for 10 minutes. Slides were developed with TMB-MX for 4 minutes. The spot signals were quantified and the results illustrated that wells that were probed with SA-HRP/biotin-HRP premix had higher signal than the SA-HRP alone. In addition, the optimal concentration of SA-HRP/biotin-HRP premix was 4 µg/mL and 4 µg/mL, respectively. SA-HRP/biotin-HRP premix at 8 µg/mL and 4 µg/mL had slightly higher signal but also higher background.

Once appropriate concentrations of SA-HRP and biotin-HRP were determined, we also tested to see if we could shorten the incubation time for the SA-HRP/biotin-HRP mixture illustrated in FIGS. 12A-B. Slides were spotted with capture antibodies and their corresponding antigens side by side (FIG. 12A). Wells were then probed with an antigen mixture consisting of CA15-3 at 60 U/mL, CYFRA21.1 at 4 ng/mL, CEA at 50 ng/mL and ErbB2 at 30 ng/mL for 30 minutes. Wells were washed with PBST and then probed with a detection antibody mixture consisting of 10-CA15-3B-B at 1 µg/mL, AF3506B at 5 µg/mL, C1299-870-B at 20 µg/mL and BAF1129 at 8 µg/mL for 15 minutes. After PBST washes, the wells were then probed with 4 µg/mL SA-HRP/2 µg/mL biotin-HRP for either 10 or 5 minutes. Slides were then developed using EnzMet silver development protocol of 2 minutes/2 minutes/8 minutes. The results are shown in FIG. 12B. We found a reduction in signal after probing with SA-HRP/biotin-HRP for only 5 minutes. As a result, we used a 10 minutes SA-HRP/biotin-HRP incubation time for subsequent experiments.

To reduce the SA-HRP/b-HRP incubation time, higher concentrations of the two reagents were increased. BSA-biotin at varying concentrations was printed onto epoxy-coated slides as seen in FIGS. 11A-G. The slide was probed with SA-HRP/b-HRP at concentrations of 64 µg/mL/32 µg/mL, 32 µg/mL/16 µg/mL, 16 µg/mL/8 µg/mL, 8 µg/mL/4 µg/mL respectively for 2 minutes. Spots were developed with TMB for 2 minutes and imaged on the Arraylt Colorimetric scanner. The results can be seen in FIG. 39. After the background was subtracted from the average counts, 64 µg/mL/32 µg/mL SA-HRP/b-HRP had the highest signal at all concentrations of BSA-biotin. As a result, a mixture of 64 µg/mL SA-HRP and 32 µg/mL b-HRP were used for all subsequent assays at 2 minutes' SA-HRP/b-HRP incubation time.

2e: Signal Development

Colorimetric Detection

Initial work was performed using silver development, a colorimetric detection method in which HRP catalyzes the reduction of silver ions in the presence of a reduction agent and hydrogen peroxide. This method, termed EnzMet, required the addition of three solutions, silver nitrate, hydroquinone and hydrogen peroxide sequentially and in strict molar ratio. Implementing the silver development proved to be difficult when we tested the assays in our microfluidic cartridges using the instrument prototype. First, the silver development requires three separate reagents that need to be released into the assay chamber in order and in defined volumes. In addition, any contamination between reagents would result in pre-mature silver deposition in the reservoirs and channels. The reagents are also very sensitive to ions as any contact with ions could also lead to pre-mature unspecific silver deposition. Considering all the other reagents contain ions, this could potentially lead to a problem. As a result, we explored other colorimetric detection methods such as TMB-MX.

TMB-MX for Signal Development

TMB (3,3',5,5'-Tetramethylbenzidine) is a substrate for horseradish peroxidase (HRP) and is very commonly used in ELISA. We adapted this substrate for use in microarray by using TMB-MX, a peroxidase substrate which produces an insoluble blue precipitate at the reaction site with little or no background (Moss substrates).

Our initial test of TMB-MX involved a microarray on which SA-HRP was spotted onto a microarray slide in various concentrations (0.5 µg/mL, 1 µg/mL, 2 µg/mL and 4 µg/mL) in duplicate (FIG. 13A). After blocking and washing, the array was incubated with TMB-MX for 8 minutes followed by a rinse with distilled water to stop the reaction. The slide was scanned in a Genepix microarray scanner and the image was quantified. The TMB-MX produced a strong and dose-dependent signal (FIGS. 13B, 13C). This dose-dependency is illustrated graphically in FIG. 13C; however, the signal appears to become saturated at 2 µg/mL SA-HRP.

Figure 14:
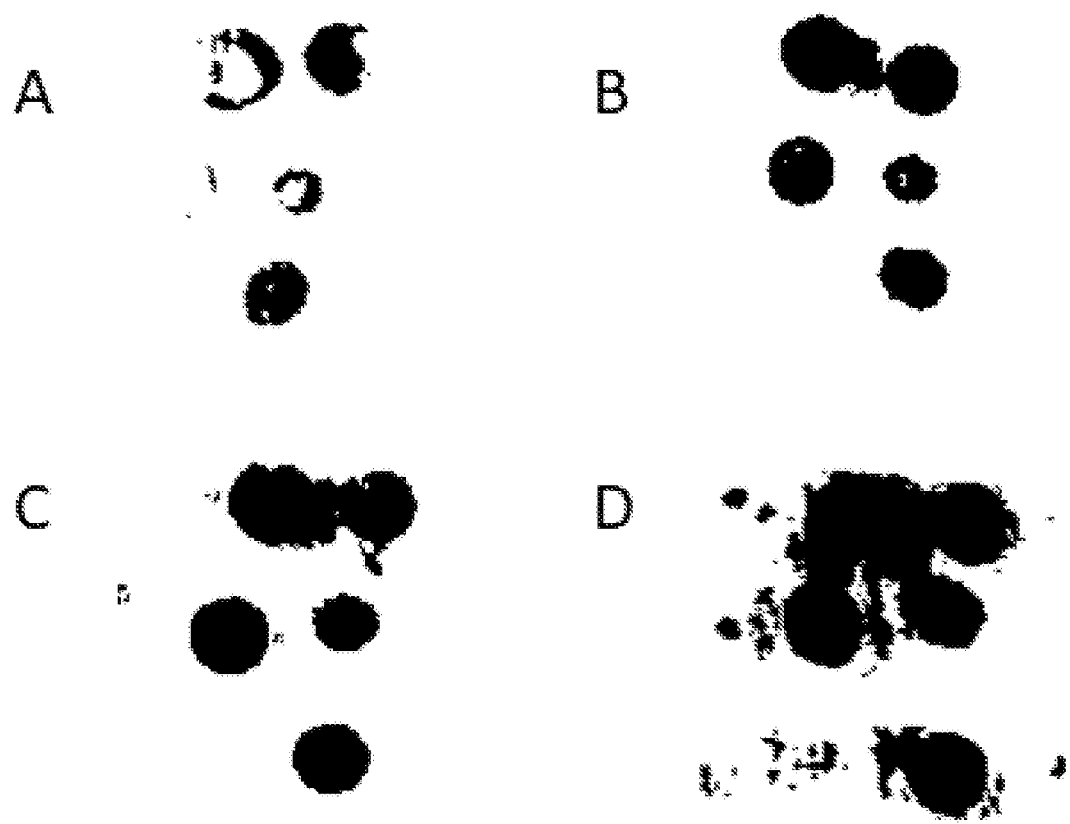

Capture antibodies and antigens were hand-spotted onto microarray slides to see if we could reduce the time of TMB-MX exposure (FIGS. 14A-D). All four wells were probed with antigen mixture consisting of CA15-3 (30 U/mL), CYFRA21.1 (2 ng/mL) and ErbB2 (15 ng/mL) for 30 minutes. After PBST rinses, all four wells were probed with a detection antibody mix consisting of 10-CA15-3B-B 1 µg/mL, AF3506B 5 µg/mL, and AF1129B 8 µg/mL for 15 minutes. After PBST rinses, all four wells were probed with a SA-HRP/biotin-HRP mixture of 4 µg/mL and 2 µg/mL respectively for 10 minutes. After PBST rinses, the wells were then probed with TMB-MX for either 2 minutes, 4 minutes, 6 minutes or 8 minutes. The results are illustrated in FIGS. 14A, B, C, and D. Qualitatively, 2 minutes of TMB-MX exposure was not sufficient for high signals, however, 4 minute, 6 minutes or 8 minutes of TMB-MX exposure gave equivalent signals.

3: Antibody Microarray Construction

3a: Microarray Substrates

An antibody microarray requires antibody immobilization onto a surface. This can occur through adsorption or covalent immobilization. The function of these surfaces is not only to provide support onto which antibodies can be immobilized, but also should demonstrate maximal binding properties and maintain the antibodies native conformation and activity. It also needs to display minimal nonspecific binding to minimize background noise in the detection system.

Immobilization through molecular adsorption occurs via intermolecular forces, mainly ionic bonds and hydrophobic and polar interactions. This results in an antibody layer that is heterogenous and randomly oriented, since each molecule can form any contacts in different orientations for minimizing repulsive interactions with the substrate and previously adsorbed proteins. Adsorption is thus limited by the geometric size of the immobilized proteins, high-density packing may sterically block active sites of the antibodies, interfering with their binding capacities. Antibodies and proteins can also be adsorbed onto slides coated with nitrocellulose or gel. Hydrogels are three-dimensional supports in which capture molecules diffuse into a porous structure. This leads to improved adsorption capacity but the antibodies are still randomly orientated and weakly attached. Moreover, problems relating to mass transport effects and high background signals from nonspecific interactions can interfere with assay accuracy and sensitivity (Nimse et al., 2014).

During covalent immobilization, antibodies or proteins are covalently bound to the immobilization support through accessible functional groups of exposed amino acids. This results in irreversible binding and produces high surface coverage. Chemical binding via side chains of amino acids is often random, since it is based upon residues typically present on the exterior of the protein. The attachment may occur simultaneously through many residues, enhancing heterogeneity in the population of immobilized proteins. Many different functional groups may be targeted including amines, thiols, carboxyls and hydroxyls. Amine groups can be covalent attached to supports through NHS, aldehyde or epoxy coated slides. The supports react with the NH2 groups forming a strong amide bond. Typically, lysine side-chains react but the reaction can also occur with N-termini. Thiol groups located in exterior exposed cysteines can react with maleimide coated slides. The maleimide double bond undergoes and addition reaction with thiol groups to form stable thioether bonds. However, this linkage is reversible by exposure to reducing reagents. Carboxyl groups located on exterior exposed glutamic and aspartic acids can reacted with amine-coated slides with the use of carbodiimide. Hydroxyls on serine and threonine side chains can react with epoxy coated slides, thus making epoxy coated slides able to react not only with amines but hydroxyls as well (Zhu and Snyder, 2003).

To identify which would be the best slide surface for antigen spotting, we tested 3 types of microarray surfaces of different physiochemical properties. epoxysilane slides (such as Slide E from Schott and SuperEpoxy slides from Arrayit), as well as slides coated with either a thin film of polymer or a 3-D polymer that is functionalized with N-Hydroxysuccinimide (NHS) esters were tested. Various amounts of the four antigens (CA15-3, CYFRA21.1, ErbB2 and CEA) were spotted onto each type of the surfaces. Despite the similarities in signal intensity and spot morphologies amongst the three slides, the epoxysilane coated slides from a reputable microarray supplier were selected as the array substrate, due to its superior stability at the room temperature in comparison with the polymer coated surfaces.

Additional tests were performed to confirm that epoxycoated slides were suitable for our microarray assay. Alternative slides coated in aminosilane and aldehyde were tested. Aminosilane coated slides display an amine group that covalently binds to carboxyl groups on the antibody. Aldehyde coated slides display an aldehyde group that covalently binds to amine groups on the antibody. ErbB2 capture antibody and antigen were printed onto all three slide types. After blocking, slides were probed with ErbB2 antigen at 15 ng/mL and ErbB2 detection antibody (4 μg/mL). After signal development with SA-HRP/b-HRP and TMB, slides were imaged with the Arraylt Colorimetric scanner. The printing layout and the resulting images are shown in FIGS. 40A-C. ErbB2 cAb displayed the highest signal when printed on epoxy-coated slides. ErbB2 cAb had no signal on aminosilane slides and only weak signal on aldehyde-coated slides. ErbB2 antigen spots had signal on all slide types, however the epoxy-coated slides had the highest signal. This confirmed that epoxy-coated slides were suitable for high assay signals.

3b: Spotting Buffers

Initially, our spotting onto microarray slides was performed by diluting antibodies and antigens in 1× phosphate buffer saline (PBS). We tested other spotting buffers to determine spreading of antibodies and antigens for better homogeneity of the spot. Glycerol has been shown to help maintain spot size and morphology previously (Olle et al., 2005; Richens et al., 2015). We spotted the capture antibody 10-CA15-3A at 25 μg/mL in either 1×PBS or 1×PBS+20% glycerol, and then probed the spotted array with CA15-3 antigen at 30 U/mL for 1 hour as well as its biotinylated detection antibody 10-CA15-3B-B at 20 μg/mL for 30 minutes. Signals were detected with SA-HRP for 30 minutes and developed using the EnzMet Silver developer (2 minutes/2 minutes/8 minutes). The results are illustrated in FIGS. 15A-B. The addition of 20% glycerol to the spotting buffer allowed more uniform spreading of the antibody. It also resulted in a more circular spot shape. We also explored alternative additives to spot buffer such as detergents and 2'3'-butanediol. The addition of 1% Tween-20 or 30% 2'3-butanediol improved signal strength, antibody spreading or spot morphology.

We used a spotting buffer containing 1×PBS, 5% glycerol and 0.02% sarcosyl (TAD Printing buffer) for most of the capture antibodies, except that for CEA, C1299-87 W which afforded an improved signal when printed in 1×PBS. As shown in FIGS. 16A-B, C1299-87 W was printed in either 1×TAD printing buffer (FIG. 16A) or 1×PBS (FIG. 16B). In both experiments C1299-87 W was printed at a concentration of approximately 1000 μg/mL, probed with 200 ng/mL of CEA antigen (C3100-14), detected with 20 μg/mL of CEA biotinylated detection antibody (C1299-870-B), SA-HRP/biotin-HRP (4 μg/mL and 2 μg/mL respectively) and EnzMet silver detection (2 minutes/2 minutes/8 minutes). The C1299-87 W spots are highlighted. Compared to the spot on the left (FIG. 16A), spotting C1299-87 W in 1×PBS increased signal significantly (FIG. 16B).

We found that some antibodies didn't print well using glycerol or TAD printing buffer under some conditions, for example, when using with the Omnigrid300 microarray. The majority of the antibodies and antigens printed well in PBS. However, some antibodies and antigens at low concentrations failed to print in PBS because the total concentration of protein was very low. As a result, we printed antibodies and antigens in 1×PBS+0.25 mg/mL BSA. This increased the total concentration of protein for low concentration antibodies and antigens and improved printing. Thus, 1×PBS+0.25 mg/mL BSA was used as our printing buffer for microarray experiments printed with the Omnigrid300.

Initially capture antibodies and antigens were spotted in 1×PBS with the Genemachines Omnigrid300. Additional spotting buffers including Bovine Serum Albumin (BSA) and/or Sarcosyl, an ionic surfactant, were tested. The results are illustrated in FIGS. 41A-B. CA15-3 capture antibodies and antigens were printed on epoxy-coated slides using either 1×PBS or 1×PBS+0.01% Sarcosyl+0.25 mg/mL BSA as the print buffer. Slides were then probed with 30 U/mL CA15-3 antigen and CA15-3 detection antibodies. After signal development, slides were imaged with the Arraylt Colorimetric scanner. The addition of Sarcosyl and BSA improved signal intensity of both capture antibody and antigens (FIG. 41A). These print buffer additives also increase spot diameter and reduced variation among capture antibody and antigen replicate spots, respectively (FIG. 41B). FIG. 41C shows the average % Coefficient of Variation (CV) of cAb and antigen of the results shown in Panels A and B.

3c: Printing Methods

For microarray printing, multiple strategies have been employed, depending on the configuration and size of the array required for different stages of the assay development. Robotic systems such as Arraylt SpotBot3 (Arrayit) and MicroGrid II Microarrayer (BioRobotics) have been successfully used for printing microarrays when a wide range of conditions were tested or when printing parameters have been finalized where high spot density and uniform morphology were required. To reduce array printing costs and shorten the turnaround time, arrays used for preliminary microarray experiments were spotted manually with custom made silicone isolators featuring 16 (8×2) wells of approximately 7 mm×7 mm in dimension each. They can be adhered to the surface of array substrates by surface tension and thus be removed easily. Each well contains either 9 (3×3) or 16 (4×4) spots. The spot diameter for the 9-spot isolator is 1 mm while that of the 16-spot isolator is 0.75 mm.

Due to the relatively larger droplets produced on hand-spotted slides and the presence of glycerol in the printing buffer, no complete drying of the spots occurred after overnight incubation in a humidity chamber at room temperature necessary for the epoxy-amine reaction to occur, and therefore, some proteins in the droplet could not be in direct contact with the surface of the substrate, resulting in signal loss. As a result, after overnight incubation in the humidity chamber at room temperature, slides were taken out and dried at 4C for 24 hours followed by multiple rinses in 1×PBST. Slides were then blocked for 1 hour in blocking buffer.

In order to compare the signal generated from the slides printed between the silicone isolators and the microarray printer, different samples were sent to different microarray printers located at Applied Microarray Inc. in Arizona and NRC-BRI in Montreal for printing multiple batches of slides. At last, a Gene Machines Omni Grid 300 MicroArray printer was set up in-house to provide high capacity (up to 308 slides) and robust performance in a well-controlled GUI software for easy experiment design. Along with the provided SMP3B pins from Arraylt, 144 spots (approximately 220 microns in diameter for each spot) were able to be printed in a single well. In 16-well format, total of 2304 spots were printed in a single slide. Multiple batches of slides were printed with different biomarkers' samples. The signal generated from the printed slides was satisfactory. Further optimization in the printing parameters (loading parameters, cleaning procedures, and contact time) were needed.

Although hand spotting with isolators was useful for preliminary experiments, they had too much variability between replicates. As a result, the Genemachines Omnigrid300, a robotic microarray printer capable of printing up to 300 slides at a time, was used to robotically print slides. The Omnigrid300 also allowed printing of either 8×2 arrays per slide for benchtop processing, or single field slides for use in the microfluidic cartridge. Slides were printed with the microarray quill pin, SMB3B (Telechem), resulting in spots with a diameter of approximately 150-400 um. Slides were printed with the Omnigrid300 at approximately 50% humidity. After printing, slides remained in the printer overnight at 70% humidity, to allow for antibody/antigen immobilization. Slides were then dried the following day and followed by multiple rinses with 1×PBST. Slides were then blocked for 1 hour in blocking buffer.

3d: Blocking and Incubation Buffers

Preliminary microarrays were blocked with 1×PBS+ 0.05% Tween (PBST)+2% BSA, the same buffer as the one used in our ELISA assays. After 1-h blocking at room temperature with shaking, a high unspecific background was observed. An increase in concentration of BSA from 2 to 5% improved the background noise, as had been was attempted shown previously (Richens et al., 2009).

Initially, incubation steps subsequent to the blocking were carried out in blocking buffer containing 1×PBST and 5% BSA. To facilitate antigen-antibody interactions, we attempted the assays in an incubation buffer of lower ionic strength (Reverberi and Reverberi, 2007). Two capture antibodies were spotted, 10-CA15-3A at 50 µg/mL and 25 µg/mL and MAB1129 at 500 µg/mL and 250 µg/mL. The wells were then probed with CA15-3 at 30 U/mL and ErbB2 at 15 ng/mL diluted in either 1×PBST+5% BSA or 0.25× PBST+5% BSA for 30 minutes. Wells were then probed with a detection antibody/5×SA-HRP mix diluted in either probing buffer for 15 minutes. The detection antibodies included were 10-CA15-3B-B at 1 µg/mL and BAF1129 at 4 µg/mL. Signals were then developed with the EnzMet silver developer (2 minutes/2 minutes/8 minutes). The results can be seen in FIGS. 17A-B. Much higher signals were obtained for both CA15-3 and ErbB2 when the lower ionic strength buffer was used. Thus, we concluded that lowering ionic strength can assist antibody-antigen interactions and was therefore used in subsequent experiments.

3d: Microarray Incubation Times

Figure 18:
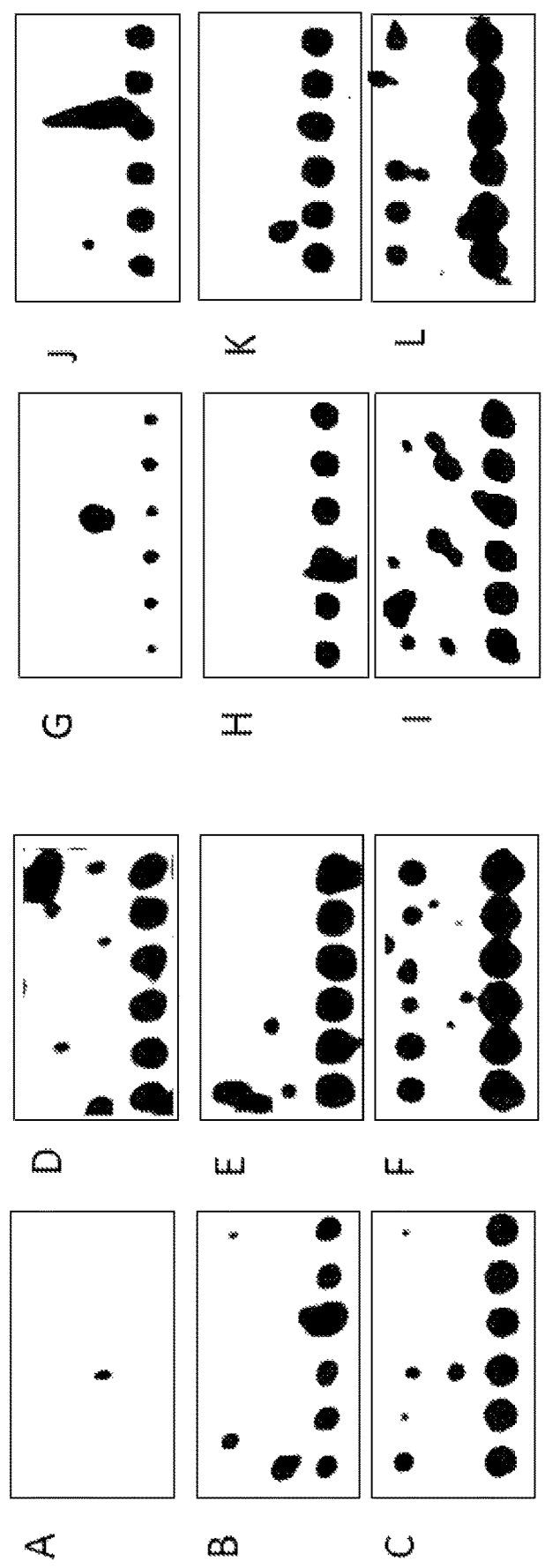

We initially began microarray experiments incubating reagents with similar times to those used in ELISA experiments, typically 1 hour for each incubation step. However, since the end product would be an assay performed in as little time as possible, we began experimenting with shorter incubation times. One example of such experiments shown here was performed on a robot-printed capture antibody slide (Applied Microarrays). The capture antibodies 10-CA15-3A and MAB1129 were spotted at 500 µg/mL respectively. An antigen mixture of CA15-3 at 30 U/mL and ErbB2 at 15 ng/mL was incubated for either 15, 30 or 60 minutes (FIGS. 18A-F). Subsequently, the detection antibody mixture of 10-CA15-3B-B at 1 µg/mL and BAF1129 at 4 µg/mL was applied onto the slide for either 15, 30 or 60 minutes (FIGS. 18G-I). Following these steps, wells were probed with SA-HRP at 4 µg/mL for 30 minutes. Spots were then developed with EnzMet silver developer (2 minutes/2 minutes/8 minutes). As shown by the CA15-3 spots, the shortest incubation time for antigen mixture that produced signals adequate for quantification was 30 minutes, respectively (FIGS. 18A-F). For detection antibody, 15 minutes of incubation was required for a detectable signal (FIGS. 18G-I).

3e: Resulting Microarray Assay

An optimized microarray assay example well is illustrated in FIG. 19. 144 capture antibodies and antigens were printed onto epoxy-coated slides using the Omnigrid 300 and left to immobilize overnight. The following day, slides were blocked for an hour in 1×PBS+5% BSA. The well was then probed for 30 minutes with an antigen mix containing 8 cancer biomarkers: CA15-3 (60 U/mL), CYFRA21-1 (8 ng/mL), CEA (20 ng/mL), CA72-4 (40 U/mL), CA19-9 (148 U/mL), ErbB2 (60 ng/mL), Ferritin (200 ng/mL) and MMP7-4 (20 ng/mL). After washing briefly with PBST, the well was probed with a detection antibody mix for 15 minutes. All detection antibodies were biotinylated to allow for recognition by SA-HRP. The well was again briefly washed with PBST and probed with a mixture of 4 µg/mL SA-HRP and 4 µg/mL biotin-HRP for 10 minutes. After washing with 1×PBST for 5 minutes, the reaction spots were developed with TMB-MX for 4 minutes. The slide was scanned using the Arraylt colorimetric scanner and quantified with ImageJ.

In addition to the printing of capture antibodies, antigens were also printed to normalize differences in detection antibody amounts. Antigens were printed in at least three different concentrations to generate an antigen standard curve. In experiments in which multiple wells were probed, the averages of each antigen spot were used to generate the averaged standard curve (FIG. 20). These normalized small variations in detection antibody concentrations and resulting signals and could be used in turn to normalize capture antibody signals.

To generate standard curves for each biomarker, each well was probed with known concentrations of antigen. The resulting capture antibody signal (FIG. 19), was normalized with the averaged antigen curve for a given biomarker. By using the slope of the averaged antigen curve, the signal was converted into a relative concentration (FIG. 20). This relative concentration was then plotted against the known concentration of antigen as seen in FIG. 21. These curves were generated for all 8 biomarkers.

Variation can occur between two wells even when probed with the same concentration of antigen. The level of variation can be quantified with the coefficient of variation (CV). To determine the coefficient of variation, the standard deviation of the signal of replicates for a capture antibody is divided by the average of the signal of replicates for a capture antibody and multiplied by 100, giving a % CV. For immunoassays, a coefficient of variation below 20% is deemed an acceptable level of variation. Intra-variation is the average % CV for multiple wells probed with the same concentration on the same slide. Inter-variation is the average % CV for multiple wells probed with the same concentration on different slides on potentially different days. The intra-variation was calculated for all biomarkers. The intra-variations for CA15-3 and CA19-9 are illustrated in Table 12. The intra-variations for CA15-3 and CA19-9 are both below 20% within the realm of acceptable variation.

TABLE 12

Intra-variation of CA15-3 and CA19-9

| Biomarker | Antigen mix in 50% plasma | Capture antibody | N (wells) | Intra-well CV % |
|---|---|---|---|---|
| CA15-3 | 20 U/mL | 10-CA15-3A (30 µg/ml) | 6 | 13.41% |
| CA19-9 | 18.5 U/mL | 70576 (400 µg/mL) | 6 | 12.16% |

Inter-variation was also examined for the biomarkers. Wells were probed with the same concentration of antigen on three separate days in three separate experiments. The CV % was calculated from replicate spots for the indicated capture antibodies (Table 13). The CV % s from these three experiments were then averaged to generate the inter-variation for each biomarker. The results are indicated in Table 13. The inter-variation for each biomarker fell below 15% indicating that the assay is precise.

TABLE 13

Inter-variation of biomarkers

| Biomarker | Antigen concentration in 50% plasma | Capture Antibody | N (wells) | Inter-variation (CV %) |
|---|---|---|---|---|
| CA15-3 | 7.5 U/mL | 10-CA153A (30 µg/mL) | 3 | 10.12 |
| CYFRA 21-1 | 1 ng/mL | AF3506 (600 µg/mL) | 3 | 5.75 |
| CEA | 2.5 ng/mL | C129987W (580 µg/mL) | 3 | 10.73 |
| CA72-4 | 5 U/mL | CF190272 (570 µg/mL) | 3 | 8.89 |
| CA19-9 | 18.5 U/mL | 70576 (400 µg/mL) | 3 | 7.94 |
| ErbB2 | 7.5 ng/mL | AF1129 (100 µg/mL) | 3 | 12.82 |
| Ferritin | 25 ng/mL | 70641 (40 µg/mL) | 3 | 9.20 |

Our assay was also compared with FDA-approved or CE-marked ELISA kits for each biomarker to determine how our assay compared with FDA-approved assays. A standard curve was generated using the ELISA kit and our microarray. Three known concentrations for each biomarker was also assayed with both the ELISA kit and microarray. These concentrations spanned the standard curve at the low, medium and high range. Using the standard curve generated by each assay, the concentrations of these three "unknowns" was determined and compared. An example using CYFRA21-1 is shown in FIG. 22. For CYFRA2-1, we compared our assay to the FDA-approved ELISA kit from Fujierbio Inc. The two detection methods were compared using paired t-tests and visually represented in Bland-Altman plots. The concentrations determined by our assay had 95% agreeability with the Fujierbio's ELISA assay.

Time is of the essence in the diagnosis of a heart attack. Any delay in treatment decreases the patient's chance of a good outcome. As a result, we wished to decrease the total assay time especially for the cardiovascular biomarker panel. Initially, the total assay time for the cardiovascular panel was 27 minutes: 10 minutes antigen incubation, 10 minutes detection antibody incubation, 5 minutes SA-HRP/biotin-HRP incubation and 2 minutes TMB incubation. We reduced the total assay time to 10 minutes: 4 minutes sample incubation, 2 minutes detection antibody incubation, 2 minutes SA-HRP/biotin-HRP incubation and 2 minutes TMB incubation. Even with reduced total assay time, we could maintain high levels of signal and sensitivity.

To reduce the total assay time, some variables of the assay had to be changed. Specifically, we raised the concentrations of the capture and detection antibodies. For example, for the detection of myoglobin, in the longer assay the capture antibody (cAb) concentration ranged from 80 µg/mL to 10 µg/mL. After reducing the assay time to 10 minutes, the myoglobin capture antibody concentration was raised to a span of 800 µg/mL to 12.5 µg/mL. Similarly, in the longer myoglobin assay of 27 minutes, a detection antibody (dAb) concentration of 50 ng/mL was sufficient for the detection of myoglobin antigen. After the reduction of assay time, the myoglobin detection antibody concentration was raised to 1 µg/mL. However, with the change of these conditions, we maintained the myoglobin signal. FIG. 42 illustrates the averaged signal for capture antibodies when probed with 22 ng/mL of myoglobin and the different detection antibody concentrations. Even though the assay is substantially shorter than the longer assay, the shorter assay displays higher signal with the altered conditions. Thus, we concluded that a 10-minute assay time would be sufficient for detection of the cardiovascular biomarkers tested.

3f: Immunoassay Performed with Microfluidic Cartridge and Instrument.

We implemented our antibody microarray assay into our microfluidic cartridge and instrument. An epoxy-coated slide was printed with the Omnigrid300 in the center of the slide for correct alignment with the microfluidic cartridge. After immobilization, the slide was blocked and adhered to the microfluidic cartridge. The wet cartridge was loaded with reagents for the immunoassay in separate reservoirs; Antigen mix consisting of CA15-3 calibrator (40 U/mL), detection antibody mix consisting of CA15-3 detection antibody (10-CA153B-B: 0.5 µg/mL), SA-HRP/biotin-HRP (4 µg/mL/4 µg/mL). Other reagents loaded into the wet cartridge include: 1×PBS, distilled water and TMB-MX. The dry cartridge and wet cartridge were assembled and inserted into the instrument. A script was run to perform the assay automatically as well as take the final image which is shown in FIG. 23. The assay was able to develop results for CA15-3 capture antibody spots and antigen spots. There were additional cross-reactivity spots due to the high concentration of detection antibody used.

Once the assay was optimized in the lab, we integrated the microarray assay into the microfluidic cartridge. Reagents such as antigen, detection antibody mix, SA-HRP/biotin-HRP, TMB and buffers such as PBST and dH$_2$O were pre-loaded into a wet cartridge (FIG. 44C). A slide spotted with cardiac marker capture antibodies and antigens was adhered to the dry cartridge. The wet cartridge was pre-loaded with reagents. R1 was loaded with TMB, R2 with dH$_2$O, R3 with SA-HRP/biotin-HRP, R4 with PBST, R5 with PBST, R6 with antigen sample, R7 with detection antibody mix and R8 with PBST. The cartridge was then put into one of our initial instrument prototypes and a script was run through the instrument software. The instrument automatically acquired a blank and spots image (FIG. 43). These spots can then be quantified into optical density with the instrument. The results indicated that the machine is capable of automatically processing a microarray assay and developing colorimetric quantifiable results.

4: Development of Microfluidic Cartridges for Microarray Assays

4a: Design of Separate Wet and Dry Cartridges

The wet components and the dry components were separated into two separate cartridges (FIGS. 24A-B), where FIG. 24A shows a top plan view of a dry cartridge 15 and a wet cartridge 16 with a glass slide 11 interposed between the two cartridges. FIG. 24B shows a side view stack up of a dry cartridge 15 and a wet cartridge 16. The dry cartridge contains the aperture defining the array chamber 12 as well as microfluidic channels 17 that carry the reagents and/or buffers from reservoirs in the wet cartridge through the array chamber 12 to the waste reservoirs, also in the wet cartridge, and instrument manifold port 14. A fluid block membrane 22 may be interposed between the channels and the instrument manifold port. An elastomer seal 20 may be adhered to the top of the dry cartridge, around the instrument manifold port, with a pressure sensitive adhesive 21. The glass microarray slide 11 containing the capture antibodies can be adhered to the dry cartridge with the pressure sensitive adhesive 21, which may be also attached to the bottom of the dry cartridge to adhere it to the wet cartridge.

The wet cartridge 16 contains reservoirs 18 (individual reservoirs 3 to 10 for the reagents and buffer, as well as waste reservoirs 1 and 2) for the used reagents after passing through the array chamber, as well as tab 13, for ease of handling.

The dry cartridge 15 and wet cartridge 16 can be made from the same or different types of materials. In some embodiments, a portion of the dry cartridge may be laser cut out of polyethylene terephthalate 23, with polycarbonate 19 portions, while the wet cartridge may be made out of polycarbonate 19.

The separation of the dry cartridge 15 allows the insertion of the microarray glass slide immediately before assembly, as well as customization of the cartridge according to the specific biochemical assay and flexibility with respect to timing of the assay. Similarly, separation of the wet cartridge 16 allows simplicity and flexibility for reagent loading.

For the dry cartridge, each reagent channel was connected with a buffer channel to flush out any residual reagent remaining in the channel during use. One embodiment of the dry cartridge is illustrated in FIG. 25A. In FIG. 25A, the numbered elements are referred to herein as follows:
a. 11: glass slide;
b. 12: array chamber;
c. 22: gas permeable membrane
d. 25: port from the waste reservoir 2 (W2) to channel in dry cartridge (CW2)
e. 26: vent for waste reservoir 1 (W1)
f. 27: vent for waste reservoir 2 (W2)
g. 28: vent for buffer reservoir 1 (B1V)
h. 29: vent for reagent reservoir 2 (R2V)
i. 30: vent for reagent reservoir 3 (R3V)
j. 31: vent for buffer reservoir 4 (B4V)
k. 32: vent for buffer reservoir 5 (B5V)
l. 33: vent for reagent reservoir 6 (R6V)
m. 34: vent for reagent reservoir 7 (R7V)
n. 35: vent for buffer reservoir 8 (B8V)
o. 36: channel for buffer reservoir 1 (B1C)
p. 37: channel for reagent reservoir 2 (R2C)
q. 38: channel for reagent reservoir 3 (R3C)
r. 39: channel for buffer reservoir 4 (B4C)
s. 40: channel for buffer reservoir 5 (B5C)
t. 41: channel for reagent reservoir 6 (R6C)
u. 42; channel for reagent reservoir 7 (R7C)
v. 43: channel for buffer reservoir 8 (B8C)
w. 45: port from W1 to channel in dry cartridge (PostC)
x. 46: channel to waste reservoir 2 (CW2)
y. 47: channel from B1C and R2C to main junction (C1/2)
z. 48: channel from B4C and R3C to main junction (C3/4)
aa. 49: channel from B5C and R6C to main junction (C5/6)
bb. 50: channel from B8C and R7C to main junction (C7/8)
cc. 51: pre-array chamber channel (PreC)
dd. 52: post-array chamber channel (PostC)
ee. 56: sample receptacle;
ff. 104: aperture
gg. 106: main junction
hh. 107: notch for alignment with the wet cartridge;
ii. 108: poke yoke for alignment with wet cartridge The position and size of the channels and apertures in the dry cartridge illustrated in FIG. 25A were as follows:
a. B1C, B4C, B5C, B8C: 14 mm in length, 2 mm wide;
b. R2C, R3C, R6C, R7C: 11 mm in length, 2 mm wide;
c. C1/2: 16 mm in length, 1 mm wide;
d. C3/4: 8 mm in length, 1 mm wide;
e. C5/6: 16 mm in length, 1 mm wide;
f. C7/8: 32 mm in length, 1 mm wide;
g. PreC: 17 mm in length, 1 mm wide;
h. PostC: 122 mm in length, 1-1.5 mm wide;
i. Aperture: 100 mm$^2$ in area;
j. Array chamber with glass slide: 25 mm$^2$ in volume.

In operation, reagent channel R2C (37) for reservoir 2 is connected with buffer channel B1C (36) for reservoir 1; reagent channel R3C (38) for reservoir 3 is connected with buffer channel B4C (39) for reservoir 4; reagent channel R6C (41) for reservoir 6 is connected with buffer channel B5C (40) for reservoir 5 and reagent channel R7C (42) for reservoir 7 is connected with buffer channel B8C (43) for reservoir 8 (FIG. 25A). Once a reagent is pushed from a specified reservoir, pushing buffer from its buffer reservoir pair allows the remaining reagent in the channels to be flushed (C1/2 (47) for example). These configurations may reduce or prevent cross-contamination between reagents. We also connected all reagent/buffer channel pairs with the main junction to reduce or prevent cross-contamination between reagents. Once a reagent or buffer is pushed from its reservoir, through its channel (for example, either R2C (37) or B1C (36) and C1/2 (47)), the fluid arrives at main junction 106. From here, the fluid can be pushed to either first or second waste reservoirs, W2 (27) or W1 (26). All reagents are pushed to W2 first, to "prime" the reservoir and clear any air bubbles into the W2 (26). One the reagent is "primed" the entire channel from the reservoir to the main junction is filled with the specified fluid. Then a push is made to W1 (27) which allows the fluid to fill the array chamber with the specified solution. This allows any interactions to be made between the reagent and the antibodies printed on the slide or in the case of buffer allows any unspecific interactions to be cleared from the array chamber and into W1 (27).

An alternative embodiment of the dry cartridge is illustrated in FIG. 25B. In FIG. 25B, the numbered elements are referred to herein as follows:
a. 11: glass slide;
b. 12: array chamber;
c. 25: port from the waste reservoir 2 (W2) to channel in dry cartridge (CW2);
d. 36: channel for buffer reservoir 1 (B1C)
e. 37: channel for reagent reservoir 2 (R2C)
f. 38: channel for reagent reservoir 3 (R3C)
g. 39: channel for buffer reservoir 4 (B4C)

h. 40: channel for buffer reservoir 5 (B5C)
i. 41: channel for reagent reservoir 6 (R6C)
j. 42; channel for reagent reservoir 7 (R7C)
k. 43: channel for buffer reservoir 8 (B8C)
l. 45: port from W1 to Post C
m. 46: channel to waste reservoir 2 (CW2)
n. 51: pre-array chamber channel (PreC)
o. 52: post-array chamber channel (PostC)
p. 80: main channel (MainC)
q. 81: polytetrafluoroethylene membrane M1/2
r. 82: polytetrafluoroethylene membrane M3/4
s. 83: polytetrafluoroethylene membrane M5/6
t. 84: polytetrafluoroethylene membrane M7/8
u. 104: aperture
v. 107: notch for alignment with the wet cartridge
w. 108: poke yoke for alignment with wet cartridge The position and size of the channels and apertures in the dry cartridge illustrated in FIG. 25B were as follows:
a. 25: port from W2 0.79 mm$^2$
b. 36: B1C 15 mm
c. 37: R2C 11 mm
d. 38: R3C 21 mm
e. 39: B4C 15 mm
f. 40: B5C 15 mm
g. 41: R6C 12 mm
h. 42; R7C 11 mm
i. 43: B8C 15 mm
j. 45: port from W1 to PostC channel in dry cartridge 0.79 mm$^2$
k. 46: CW2 11 mm
l. 51: PreC 20 mm
m. 52: PostC 37 mm
n. 80 MainC 52 mm
o. 81: M1/2 28 m mm$^2$
p. 82: M3/4 28 mm$^2$
q. 83: M5/6 28 mm$^2$
r. 84: M7/8 28 mm$^2$
s. 104: aperture 100 mm$^2$ In operation, reagent will be pushed from a reagent reservoir 4, 5, 8 or 9 in the wet cartridge through its respective channel 37, 38, 41 or 42 to the main channel 80. As the reagent passes through the channel it will pass under the membrane 81, 82, 83 or 84. The membrane exposes the reagent to air, allowing any air bubbles within the reagent to pass to the atmosphere. Once in the main channel 80 the reagent will be pushed first through CW2 (46) to the port of W2 (25). This allows entrance of waste reagent into W2 (2). As the reagent passes through the channel it will pass under the membrane 81, 82, 83 or 84. The membrane exposes the reagent to air, allowing any air bubbles within the reagent to pass to the atmosphere. Once in the main channel 80 the reagent will be pushed first through CW2 (46) to W2 (2). This will ensure all air has been removed from the reagent. The reagent will then be pushed through PreC (51) to the aperture (104) which when interfaced with the glass slide (11) creates the array chamber (12). The reagent will continue in PostC (52) to the port of W1 (45) and enter W1 (1). This will ensure all air has been removed from the reagent. The reagent will then be pushed through PreC (51) to the aperture (104) which when interfaced with the glass slide (11) creates the array chamber (12). The reagent will continue in PostC (52) to W1 (1). After reagent incubation in the array chamber, remaining reagent is flushed out with its paired buffer reagent. Buffer will be pushed from its buffer reservoir 3, 6, 7, or 10 through its respective channel 36, 39, 40, or 43. As the buffer passes through the channel it will pass under the membrane 81, 82, 83 or 84. The membrane exposes the buffer to air, allowing any air bubbles within the buffer to pass to the atmosphere. Once in the main channel 80 the buffer will be pushed first through CW2 (46) to the port of W2 (25) and enter W2 (2). This will ensure all air has been removed from the buffer. The buffer will then be pushed through PreC (51) to the aperture (104), which when interfaced with the glass slide (11) creates the array chamber (12). The buffer will continue in PostC (52) to the port of W1 (45) and enter W1 (1).

An alternative embodiment of the dry cartridge is illustrated in FIG. 25C. In FIG. 25C, the numbered elements are referred to herein as follows:
a. 11: glass slide;
b. 12: array chamber;
c. 25: port from the waste reservoir 2 (W2) to CW2 channel in dry cartridge;
d. 26: vent for waste reservoir 1 (W1)
e. 27: vent for waste reservoir 2 (W2)
f. 28: vent for buffer reservoir 1 (B1V)
g. 29: vent for reagent reservoir 2 (R2V)
h. 30: vent for reagent reservoir 3 (R3V)
i. 31: vent for buffer reservoir 4 (B4V)
j. 32: vent for buffer reservoir 5 (B5V)
k. 33: vent for reagent reservoir 6 (R6V)
l. 34: vent for reagent reservoir 7 (R7V)
m. 35: vent for buffer reservoir 8 (B8V)
n. 36: channel for buffer reservoir 1 (B1C)
o. 37: channel for reagent reservoir 2 (R2C)
p. 38: channel for reagent reservoir 3 (R3C)
q. 39: channel for buffer reservoir 4 (B4C)
r. 40: channel for buffer reservoir 5 (B5C)
s. 41: channel for reagent reservoir 6 (R6C)
t. 42; channel for reagent reservoir 7 (R7C)
u. 43: channel for buffer reservoir 8 (B8C)
v. 45: port from W1 to PostC channel in dry cartridge;
w. 46: channel to waste reservoir 2 (CW2)
x. 47: channel from B1C and R2C to main junction (C1/2)
y. 48: channel from B4C and R3C to main junction (C3/4)
z. 49: channel from B5C and R6C to main junction (C5/6)
aa. 50: channel from B8C and R7C to main junction (C7/8)
bb. 51: pre-array chamber channel (PreC)
cc. 52: post-array chamber channel (PostC)
dd. 56: sample port
ee. 66: sealing membrane
ff. 80: main channel (MainC)
gg. 104: aperture 100 mm$^2$
hh. 107: notch for alignment with the wet cartridge In this embodiment, the dry cartridge components illustrated in FIG. 25C may have the following dimensions:
a. 25: port from the waste reservoir 2 (W2) to CW2 channel in dry cartridge; 0.79 mm$^2$
b. 26: vent for waste reservoir 1 (W1) 1.13 mm$^2$
c. 27: vent for waste reservoir 2 (W2) 1.13 mm$^2$
d. 28: vent for buffer reservoir 1 (B1V) 1.13 mm$^2$
e. 29: vent for reagent reservoir 2 (R2V) 1.13 mm$^2$
f. 30: vent for reagent reservoir 3 (R3V) 1.13 mm$^2$
g. 31: vent for buffer reservoir 4 (B4V) 1.13 mm$^2$
h. 32: vent for buffer reservoir 5 (B5V) 1.13 mm$^2$
i. 33: vent for reagent reservoir 6 (R6V) 1.13 mm$^2$
j. 34: vent for reagent reservoir 7 (R7V) 1.13 mm$^2$
k. 35: vent for buffer reservoir 8 (B8V) 1.13 mm$^2$
l. 36: channel for buffer reservoir 1 (B1C) 5 mm
m. 37: channel for reagent reservoir 2 (R2C) 10 mm
n. 38: channel for reagent reservoir 3 (R3C) 18 mm
o. 39: channel for buffer reservoir 4 (B4C) 5 mm
p. 40: channel for buffer reservoir 5 (B5C) 5 mm q. 41: channel for reagent reservoir 6 (R6C) 10 mm
r. 42; channel for reagent reservoir 7 (R7C) 9 mm
s. 43: channel for buffer reservoir 8 (B8C) 5 mm
t. 45: port from W1 to PostC channel in dry cartridge; 0.79 mm$^2$
u. 46: channel to waste reservoir 2 (CW2) 15 mm
v. 47: channel from B1C and R2C to main junction (C1/2) 10 mm
w. 48: channel from B4C and R3C to main junction (C3/4) 10 mm
x. 49: channel from B5C and R6C to main junction (C5/6) 10 mm
y. 50: channel from B8C and R7C to main junction (C7/8) 10 mm
z. 51: pre-array chamber channel (PreC) 18 mm
aa. 52: post-array chamber channel (PostC) 27 mm
bb. 56: sample port 0.79 mm$^2$
cc. 66: sealing membrane 9.62 mm$^2$
dd. 80: main channel (MainC) 51 mm
ee. 104: aperture 100 mm$^2$.

In operation, the sample will first be loaded through the sample port (56) into the reagent reservoir. Reagent will be pushed from a reagent reservoir 4, 5, 8 or 9 in the wet cartridge through its respective sealing membrane (66) into its respective channel 37, 38, 41 or 42. The reagent will pass into its respective buffer/reagent channel 47, 48, 49 or 50 to the main channel 80. Once in the main channel 80 the reagent will be pushed first through CW2 (46) to the port of W2 (25). This allows entrance of waste reagent into W2 (2). This will ensure all air has been removed from the reagent. The reagent will then be pushed through PreC (51) to the aperture (104) which when interfaced with the glass slide (11) creates the array chamber (12). The reagent will continue in PostC (52) to the port of W1 (45) and enter W1 (1). This will ensure all air has been removed from the reagent. The reagent will then be pushed through PreC (51) to the aperture (104) which when interfaced with the glass slide (11) creates the array chamber (12). The reagent will continue in PostC (52) to W1 (1). After reagent incubation in the array chamber, remaining reagent is flushed out with its paired buffer reagent. Buffer will be pushed from its buffer reservoir 3, 6, 7, or 10 through its respective sealing membrane (66) to its respective channel 36, 39, 40, or 43. The reagent will pass into its respective buffer/reagent channel 47, 48, 49 or 50 to the main channel 80. Once in the main channel 80 the buffer will be pushed first through CW2 (46) to the port of W2 (25) and enter W2 (2). This will ensure all air has been removed from the buffer. The buffer will then be pushed through PreC (51) to the aperture (104), which when interfaced with the glass slide (11) creates the array chamber (12). The buffer will continue in PostC (52) to the port of W1 (45) and enter W1 (1).

The position and size of the reservoirs in the wet cartridge are optimized such that they allow for specified volumes. In FIGS. 26 and 44C, which illustrate embodiments of wet cartridges, the numbered elements, where present, are referred to herein as follows:

i) 1: waste reservoir 1 (W1)
ii) 2: waste reservoir 2 (W2)
iii) 3: buffer reservoir 1 (B1)
iv) 4: reagent reservoir 2 (R2)
v) 5: reagent reservoir 3 (R3)
vi) 6: buffer reservoir 4 (B4)
vii) 7: buffer reservoir 5 (B5)
viii) 8: reagent reservoir 6 (R6)
ix) 9: reagent reservoir 7 (R7)
x) 10: buffer reservoir 8 (B8)
xi) 13: handling tab
xii) 24a: notch for alignment with dry cartridge 107
xiii) 24b: poke yoke feature for alignment with dry cartridge 108
xiv) 25: port from W2 to dry cartridge
xv) 44: sample well
xvi) 45: port from W1 to dry cartridge
xvii) 54: ports to valves
xviii) 55: ports to dry cartridge In FIG. 26, the dimensions of the reservoirs are as follows:

B8 (10): A reservoir of 420 μl in volume. B8 is of a bent shape to sculpt around the notch at the end of the wet cartridge for interfacing with the dry cartridge. This reservoir covers an area of 15 mm in length, 10 mm wide and is 7 mm deep.

R7 (9): A reservoir of 260 μl in volume. R7 is of a generally oblong shape with a slight bulge in the base to allow extra volume. This reservoir covers an area of 11 mm in length, 4 mm wide and 7 mm deep.

sample receptacle (44): 5 mm wide, 1.5 mm in length and 7 mm in depth. This holds approximately 25 μl of sample.

R6 (8): A reservoir of 226 μl in volume. R6 is generally oblong in shape. This reservoir covers an area of 11 mm in length, 3 mm wide and 7 mm deep.

B5 (7): A reservoir of 420 μl in volume. This reservoir is generally oblong in shape with an extra triangular region to the side to accommodate extra volume. This reservoir covers an area of approximately 13 mm in length, 7 mm in wide and 7 mm deep.

B4 (6): A reservoir of 420 μl in volume. This reservoir is generally bent in shape to allow specified volume and have correct port alignment. This reservoir covers an area of approximately 13 mm in length, 8 mm in wide and 7 mm deep.

R3 (5): A reservoir of 200 μl in volume. This reservoir is generally oblong in shape. This reservoir covers an area of 9 mm length, 4 mm wide and 7 mm deep.

R2 (4): A reservoir of 160 μl in volume. This reservoir is generally oblong in shape. This reservoir covers an area of 9 mm in length, 3 mm wide and 7 mm deep.

B1 (3): A reservoir of 160 μl in volume. This reservoir is generally oblong in shape. This reservoir covers an area of 9 mm in length, 3 mm wide and 7 mm deep.

W2 (2): A reservoir approximately 2100 μl in volume. This reservoir has a U-shape. This design allows the fluid entering the W2 reservoir to be as far as possible from the venting port. This prevents any inadvertent clogging of the venting port.

W1 (1): A waste reservoir approximately 3129 μl in volume. This reservoir has a U shape. Fluid entering the entrance port travels through the reservoir along the right edge of the cartridge, along the bottom edge of the cartridge (near the handle) and then up the left edge of the cartridge until it reaches the venting port. In addition, a square bulge was added near the bottom of the reservoir closer to the right edge. This was added to allow pooling of entering to fluid. This prevents the entering fluid from shooting to end of the reservoir and clogging the venting port.

In FIG. 44C, the dimensions of the reservoirs are as follows:

B8 (10): A reservoir of 475 μl in volume. B8 is of a bent shape to sculpt around the notch at the end of the wet cartridge for interfacing with the dry cartridge. This reservoir covers an area of about 19 mm in length, about 6 mm width and about 9 mm depth.

R7 (9): A reservoir of 300 µl in volume. R7 is of a generally oblong shape with a slight bulge in the base to allow extra volume. This reservoir covers an area of about 11 mm in length, about 4 mm width and about 9 mm depth.

R6 (8): A reservoir of 275 µl in volume. R6 is generally oblong in shape. This reservoir covers an area of about 11 mm in length, about 3 mm width and about 9 mm depth.

B5 (7): A reservoir of 450 µl in volume. This reservoir is generally oblong in shape with an extra triangular region to the side to accommodate extra volume. This reservoir covers an area of about 13 mm in length, about 6 mm width and about 9 mm depth.

B4 (6): A reservoir of 450 µl in volume. This reservoir is generally bent in shape to allow specified volume and have correct port alignment. This reservoir covers an area of about 15 mm in length, about 4.5 mm width and about 9 mm depth.

R3 (5): A reservoir of 250 µl in volume. This reservoir is generally oblong in shape. This reservoir covers an area of about 9 mm in length, about 3 mm width and about 9 mm depth.

R2 (4): A reservoir of 300 µl in volume. This reservoir is generally oblong in shape. This reservoir covers an area of about 10 mm in length, about 4 mm width and about 9 mm depth.

B1 (3): A reservoir of 175 µl in volume. This reservoir is generally oblong in shape. This reservoir covers an area of about 9 mm in length, about 3 mm width and about 9 mm depth.

W2 (2): A reservoir approximately 2000 µl in volume. This reservoir has a U-shape. This design allows the fluid entering the W2 reservoir to be as far as possible from the venting port. This reduces or prevents any inadvertent clogging of the venting port.

W1 (1): A waste reservoir approximately 2000 µl in volume. This reservoir has a U shape. Fluid entering the entrance port travels through the reservoir along the right edge of the cartridge, along the bottom edge of the cartridge (near the handle) and then up the left edge of the cartridge until it reaches the venting port. In addition, a square bulge was added near the bottom of the reservoir closer to the right edge. This was added to allow pooling of entering to fluid. This reduces or prevents the entering fluid from shooting to end of the reservoir and clogging the venting port.

Bottom laminate: The wet cartridges illustrated in FIGS. 26 and 44C have a laminate bottom. The laminate contains precut holes under the reservoirs, used for reservoir loading.

Microarray Antibody Slide

Antibodies were printed onto a glass slide such that the printed spots were aligned with the array chamber. The location of the array chamber and the printed spots may change as long as they align with one another. The antibodies can be printed in spot sizes ranging from 50 µm to 300 µm.

5: Instrument Design

5a: Pump and Solenoid Valve System

Pressure-driven flow is generated by a pump (68). The pump moves in a desired direction, by opening the valve above a selected reservoir from which fluid movement is desired, and by opening the waste reservoir to atmospheric air, such that the fluid in the selected reservoir is pushed towards atmospheric air, and allows sequential reagent delivery. Our instrument was designed such that the pump would push from the reagent reservoirs. By opening a solenoid valve (65) at the reservoir of the reagent which we would want to move (ex. 3), the fluid would move from the reservoir towards either Waste 1 or Waste 2 (FIG. 28). The fluid trap (64) ensures that no liquid from the reservoir is able to enter the manifold or valves. The sealing membrane (66) prevents the liquid from leaving the reservoir prematurely into the array chamber or dry cartridge channels. However, upon pressure from the pump (68) and the opening of the specific valve (65), liquid can cross the sealing membrane towards W1 (1) or W2 (2). If we wished to prime the reservoir, we move the solution the solution to Waste 2 (2). This would reduce or eliminate any air bubbles present in the reservoir and bring the reagent to the main junction. This would be followed by a push towards Waste 1 (1) which would bring the reagent across the array chamber (12) and into the Waste 1 reservoir (1). The pump is operated by a motor (Vex: RB-Inn-11). Both of the valves for Waste 1 (1) and Waste (2) are open to atmosphere (63), allowing the air to escape the cartridge. Alternatively, the luer port (67) seals the manifold such that air only travels within the manifold and cartridge. The rotation of the motor causes the pump to move in and out leading to the movement of the fluid.

The cartridge reader includes a positive displacement air pump used to push or pull a specified volume of air. Air is displaced by a ground stainless steel pin moving axially into the pump cavity. The pin is sealed at the cavity entrance with a stationary radial seal. The pin is moved directly by a stepper motor driven (Haydon Kerk LC1574 W-05) linear actuator. Pump position is measured optically with proximity sensors. The pump can be automatically calibrated to detect and correct for skipped steps and to account for variations in construction. The valves allow automated control over pneumatic connections between the pump, vent, and nozzles. Valves mount to the manifold assembly using screws and a face seal. The manifold assembly includes eleven valves and will include empty sockets for two additional valves to facilitate future cartridge iterations. A pressure sensor is included in the system to measure the pressure inside the pump. Air volume within the pressure sensor and sensor connection should be minimized to improve system response.

To control which reservoir is open at a given time, we employed solenoid valves (Parker: X-7 05 L-F). Solenoid valves are electromechanically actuated to open by the software. Without any actuation, the valves are closed. The opening of the valve allows air to come into the reservoir, if the pump pushes the fluid from the reagent reservoir towards the waste reservoir open to atmospheric pressure. A schematic of a valve is illustrated in FIG. 29, showing blocked port 69, common port 70, and normally-closed port 71. When the valve is activated, ports 70 and 71 open allowing the passage of air through the valve. When the valve is no longer activated, or turned off, these ports close. Valves were placed above every reservoir including the waste reservoirs (FIG. 28). An additional valve was also placed for venting, or allowing the pump to re-zero without connecting into the cartridge.

5b: Optical Sensing

Any suitable optical sensing system may be used. In some embodiments, the instrument includes a camera, such as an USB camera (for example, Leopard Imaging: LI-OV7725) and lighting system such that the software is capable of obtaining an image of the spots. The software may then be able to compute an optical density based on the image taken by the camera.

An array of LED lights may be placed below the field of the spots such that the illumination allows an image of the spots (for example, Life-on Inc.). The instrument imaging system consists of a light source, consisting of 4 white LEDs which shine through a translucent acrylic diffuser and then through the back of the wet card. The wet cartridges are made of translucent polycarbonate thereby increasing uniformity in illumination. Blinking of the LED may allow suitable software to compute gain and offset for the resulting image. The LED illuminates the back of the slide with a time varying signal of a triangular shape. This modulation occurs at approximately 2.6 Hz. The modulation is produced by the controller circuit that is also used to control the valves and the pump motor. The controller circuit produces a square-wave signal which is integrated and then used to modulate the current to the LEDs, resulting in a triangular, time-varying light output. The optical path length may be designed to be as short as possible, to reduce the size of the instrument.

The optical system allows the TAD system to image spots in the array chamber generated by the assay, to determine the type, compatibility, orientation and successful insertion of inserted microfluidic cartridges, and to image fluid flow in the microfluidic cartridge. The camera preforms several functions. It images the spots generated by the assay with sufficient resolution to quantify optical density. It will take as input the blank and spot image from the Instrument. It will also locate the fiducial spots and output a 2-dimensional array of spots based on the selected card type's configured dimensions of the spot array. It images features on the microfluidic cartridge that allow the cartridge type, compatibility and orientation to be determined and allows the TAD to determine successful insertion. It may image all microfluidic channels within the microfluidic cartridge to record fluid or air position and assist in diagnostics or provide records of the test. The camera is also able to image the cartridge label for barcode scanning.

An array of LEDs illuminates the top surface of the microfluidic cartridge. The light input is modulated by the control electronics and can be controlled by the software to support the camera functions described above. These lights are used for barcode scanning and potentially video recording during the assay for troubleshooting and diagnostics. The imaging LED provides light to the base of the array chamber. Light input is modulated by the control electronics and can be controlled by software as required for quantification of spots in the array chamber. For imaging spots in the array chamber, light from the LEDs must enter the bottom of the array chamber, pass through the viewing window, and enter the camera without reflecting off or diffusing through any other surface. Light from the imaging LED must not reflect off or diffuse through any elements of the TAD device then illuminate the array chamber from the top. A diffusing element is included between the array imaging LEDs and the microfluidic cartridge assay chamber to evenly distribute light from the LED before it enters the assay chamber.

To obtain an image of the spots, a blank image may first be obtained, to allow the software to detect the spots by ignoring any background present before the spots are developed. Upon the development of the spots, a spots image may be obtained. At the start of image capture, two 640×480 pixel arrays are zeroed: one will accumulate the average black and white intensity of each individual pixel and the other will accumulate the intensity multiplied by the overall pixel average. The spatial pixel average is also stored along with the time that the frame was captured. The spatial pixel average is used as a proxy for the modulation signal in the following analysis. This is based on the assumption that the only source of 2.6 Hz periodicity must be due to the modulation.

Once the total desired number of frames has been captured, the time record of average pixel intensity is correlated with a range of frequencies of sine waves in order to identify the correct frequency, phase and amplitude of modulation. The result of this computation is a value proportional to the magnitude of the modulation. Next, a least-squares linear regression is computed on each pixel to determine the gain and offset of each pixel with respect to the extracted modulation signal. At this point, it is assumed that the individual pixel gain represents a proportionality factor relating to the LED output. The pixel offset is not deemed useful and discarded. In order to block out effects due to card to card variations, optical density variations due to the fluid in the chamber, and the exact modulation amplitude, an image is captured first right before the spots are developed and then afterwards. These are termed the "blank" image and the "spot" image. The final processed image is created by computing the ratio of each pixel gain of the spot image with those of the blank image. This image is further scaled by the ratio of the computed modulation magnitudes of the spot image to the blank image.

Spots for quantification may be marked manually by the software user. Each spot contains a central spot region. The size of the spot can be changed by the user using the software. To quantify the spots, a new image may be computed where each pixel is equal to the ratio of each pixel of the spot and no-spot images. This removes variation due to back-lighting and inherent spatial card density, as well as pixel gain and offset. The average pixel value within the central spot circle is calculated. The instrument was designed to contain a camera and lighting system such that the software would be able to take an image of the spots developed from the TMB-MX. The software would then be able to compute an optical density based on the image taken by the camera. The camera is a USB camera (Leopard Imaging: LI-OV7725). An array of LED lights is below the field of the spots and its illumination allows an image of the spots (Life-on Inc.). The LED light blinks which allows the software to compute gain and offset for the resulting image. The optical path length was designed to be as short as possible, to make the unit as compact as possible.

5c: Instrument Integration

The pump, valves and optical camera would all be integrated into the instrument. Within the instrument, these parts are integrated with a printed circuit board. This circuit board would relay all of the electrical input from the software to the various components.

The instrument would house the microcontroller, pump, valves and optical system. The cartridge (wet and dry together) would be inserted into the instrument and through a spring mechanism interface with the manifold. The manifold is what connects the valves to the reservoir ports. The software currently loaded on a PC laptop connects to the instrument through two USB cables, one controlling the instrument and the other controlling the camera. A schematic illustrating how the instrument, cartridge and software come together is illustrated in FIG. 30.

The TAD System may include a Reader that controls and quantifies the results from the cartridge. This instrument consists of a plastic and metal housing containing a touchscreen display, a main CPU PCB, a cartridge interface including a pump, numerous valves, a camera for quantification, various LED light sources and PCBs with an MCU, valve drivers, motor drivers and sensors to ensure the assay is performed correctly. The basic form of the reader will consist of a graphical touch screen display for the user interface with a drawer for cartridge insertion. The housing may use OTS antivibration feet. It is assumed that the reader will be used on a sufficiently flat surface that there is no need for adjustment. The reader may indicate to the user if it is not sufficiently flat. The TAD software will run on an ARM based CPU. The main software functionality, including all the GUI may be the result of the software application (app) written in Java. The app will rely on support by various other software libraries and packages which fall into the category of software of unknown provenance (SOUP). The software that runs in the microcontroller in the TAD will be referred to as the TAD firmware. This is intended to imply that this software cannot be significantly reconfigured at runtime and that it will begin execution at power up. The Firmware of the TAD will run on a microcontroller in the cartridge interface. This firmware will be implemented using a real-time architecture consisting of two threads: a continuous, infinite main loop and a constant interval timer interrupt. The interrupt may be referred to as fast code and the main loop will be referred to as slow code. As a rule of thumb, the MCU is expected to spend close to half of its time executing fast code and half on slow code.

The TAD may consist of many custom and off-the-shelf electrical subassemblies. The main UI for the TAD may be based on a 7" touchscreen LCD. This may be an OTS component with a parallel interface and I2C touchscreen controller based on the FT5x06 controller. All user interaction with the application will be accomplished through the touchscreen. Any data entry will be accomplished through on-screen keypads. In some embodiments, the addition of an external barcode scanner for patient ID entry may be included. The GUI may consist of a home screen to allow the user to initiate a wizard-style guided process for running assays and access to instrument setting, depending on user authorization level. The TAD may contain a NiMH battery for battery backup purposes. Four MiMH cells of approximately 4A*h may give enough energy to run the device at 8 W for approximately 2 hours. The reader may use four to six cells. The CPU PCB houses all the GUI and communication of the TAD. The manifold PCB contains the driving components for the top LEDS, valves, and pump motor. It also contains the ADC for the pressure sensor. The cartridge interface PCV manages all the functionality of the cartridge interface. This board provides mounting for the illumination LEDs for up-lighting the array chamber. It also contains all input power conversion including battery charging and monitoring. The battery PCB mechanically mounts the batteries, the battery thermistor and the battery monitor circuit.

The manifold assembly (FIGS. 46A-B, conceptual renderings) may include the cartridge interface PCB; the camera (109) and cartridge imaging LEDs described in the optical sensing system; the manifold ports (14), optical window, and alignment features described in the microfluidic cartridge interface; and the pump (68), valves (65), pressure sensor, and laminate stack (110). The pump (68), valves (65), and assembled cartridge (79) must all interface with the laminate stack (110) of the manifold. In addition, the camera (109) must be positioned to correctly image the results of the array chamber (12). FIGS. 33 and 47 show two exemplary detailed laminate stacks of the manifold, which function to connect the air from the pump to the valves to the cartridge. Air exits the pump through port 88, travels to the valve entrance 85, and through the open valve. The air then exits the valve through port 86 re-enters the manifold and travels to the port where the manifold interfaces with the cartridge 87. During the re-zeroing of the pump, or travel to W1 (1) or W2 (2) air exits through the port to atmosphere 63.

The cartridge interface contains the connectivity features that the instrument expects to correctly couple the cartridge. This interface is intended to provide sufficient flexibility in cartridge design and construction so that the cartridge design can be iterated independently of the instrument. The cartridge reader includes 10 nozzles, each 0.9 mm high with a 3 mm ID, 3.5 mm OD, and a 60° chamfer. The 3 mm ID is 0.9 mm deep to accept flex in the nozzle gasket, then it transitions to a 0.5 mm diameter hole to minimize internal air volume. Nozzles are spaced 5.8 mm apart. The reader includes space for adding two additional nozzles with minimal modification to support future cartridge iterations.

Nozzles and cartridge alignment features are machined from a single aluminum billet and screwed to the manifold assembly. The nozzles interface with 10 ports on the microfluidic cartridge. The ports are spaced 5.8 mm apart, centered on the cartridge midline, and 2.72 mm from the front edge of the cartridge. Each nozzle/port pair provides an independent pneumatic connection between the cartridge reader and the microfluidic cartridge. A 0.03-inch-thick silicone elastomer gasket is bonded above the pneumatic ports. The gasket contains 1.5 mm holes aligned with each pneumatic port. When clamped, the gasket provides a seal between the pneumatic ports and the nozzles. The nozzle and nozzle gasket of the microfluidic cartridge interface are clamped together with a spring or actuator driven mechanism. Clamping will be accomplished with no input force from the user. The mechanism provides even clamping force to all nozzles with a total clamping force of 30+/-5N. The mechanism can maintain acceptable clamping force for cartridges that are 12 mm to 17 mm high. This will ensure that sufficient local pressure is applied between the cartridge's elastomer surface and the reader's nozzle to provide an adequate seal without applying too much pressure, which could distort the gasket and interfere with sealing. There will be alignment features on the cartridge reader at the sides of the nozzles that will engage with features on the sides of the top of the wet cartridge. These are used for precise cartridge alignment. They may consist of rectangular protrusions with chamfers on 3 edges of the end. The features will take up 1-2 mm of misalignment in the horizontal plane.

The laminate stack provides microfluidic air channels to connect the vent/intake, the pump, the valves, and the nozzles. The stack can be easily removed and replaced to refurbish the instrument or to reconfigure the microfluidic connections. The stack interfaces with other components through circular channels that exit the top or bottom of the stack, and seals to other components with exposed islands of adhesive that provide 2-4 mm of seal around each channels. The stack is aligned by features (pins, etc.) on the manifold assembly and it includes features so it can only be installed in the correct orientation. The system includes a path for potentially humid air to be moved through the microfluidic cartridge and safely rejected to the environment. This path doubles as an air intake for the pump. The vent port opening points down to prevent dust from collecting in the port. The vent is capped with a GPM to prevent dust from entering the air system. The vent discharges into the body of the cartridge reader. Small volumes of air must be allowed to flow freely into and out of the cartridge reader to prevent pressure/vacuum building inside the cartridge reader.

The cartridge can be placed into a drawer that extends from the cartridge reader (89) (FIG. 45A). It should be easy to hold the cartridge horizontally during insertion. It is desired that the drawer cannot be closed without properly inserting the cartridge (e.g. the cartridge collides with the reader). The drawer closing mechanism may be force-limited to prevent damage to the cartridge if the drawer is closed with the cartridge not properly inserted. The drawer design may minimize pinch points and may include force laminating to prevent injury to the user. When accepted by the cartridge reader, the microfluidic cartridge is held within a removable drip tray which may have the capacity to hold the entire volume of fluid held within the microfluidic cartridge. The moving drawer element may be the tray. The tray is removable for cleaning. The tray accepts cartridges that are up to 80 mm wide and up to 70 mm long and can replaced with a tray that accepts cartridges up to 95 mm wide and 85 mm long to allow for future cartridge iterations. The intent is to include space for two additional pneumatic ports. The tray may include finger clearance pockets to allow easy installation and removal of the microfluidic cartridge. The tray may include features such that the cartridge cannot be inserted upside down or in an incorrect orientation. An illustration of the final instrument is shown in FIGS. 45A-C, in which the internal elements including pump, CPU, motors and manifold assembly are surrounded by plastic housing (96) and metal components (94). The front of the instrument consists of a 7-inch LCD screen (90) and an ejectable tray (89) for housing the inserted cartridge. A heat-dissipating metal plate is located at the back of the instrument to help cool the instrument (95). Various USB and electrical connections are located on the front and rear of the instrument (91, 93). The instrument is powered on by an ON button located at the rear of the instrument 92.

5d: Operating Script

The script in the software is used to command the instrument which reservoirs to push from and to. The script can be written in a text file and loaded into the instrument a user-friendly Java-based script was developed specifically for the use in our system. Some simple commands are used for re-zeroing the pressure in the cartridge (vent all) and the pump (vent in, vent out, vent mid). Another simple command for script control is "break" which simply pauses the script until the user wishes to continue. Finally, image control "grab blank" grabs a blank image used for background and "grab spots" grabs an image when the spots have finished developing. To control the fluidics of the machine, one command line contains all the information required to move the fluid to the desired location. Exemplary pump commands include "vent all" which opens and closes all valves to re-zero the pressure in the cartridge, "vent in" which moves the pump all the way out so it can push, "vent out" moves the pump all the way in so it can pull, "vent mid" moves the pump to halfway; exemplary fluid commands include "Draw" the pump pulls fluid towards the reagents reservoirs, "Push" the pump pushes fluid from the reagent reservoir; and exemplary imaging commands include "Grab blank" which grabs a blank image, "Grab spots" which grabs spots image; exemplary other script commands include "Break" which pauses the script and instrument and "//" makes any text after it a comment and not a command. A pump command is that beginning of the script line, either "push" which pushes fluid from the reservoir to waste or "draw" which pushes fluid in the opposite direction. Following draw or push is the volume you would like pushed, for example 100 µL. The next part of the command is the reservoir which you would like fluid pushed from, for example "R1" (one can choose from any of the buffer or reagent reservoirs). Following this, is the reservoir you would like the fluid pushed to, for example "W1" (pick either W1 or W2). The last part of the command is the amount of time it the use would like the fluid to be pushed in, i.e. "100 s". The amount of volume and the amount of time determines the flow rate i.e. how fast the fluid is moving.

The script is stored in a plain text file with a .txt file extension. None of the file content are case sensitive. Each line of the script is assumed to contain a comment, a single command or both. If a line contains a command then the command name will begin at the first non-blank character of the line. Blank characters (spaces and tabs) at the beginning of a line will be ignored. Comments are text that is not processed by the script parser. These can be used to convey human-readable information to aid the human understanding of a script. Comments begin with //. Any text after the comment delimiter will be ignored by the script parser. If the first non-blank characters of a line are a comment delimiter then the whole line will be ignored. Parameters must occur in the order specified in the command definition unless unambiguously indicated with units. Parameters are separated from the command and each other with spaces. Many commands require the specification of one or more valves. Valid valve descriptors are: R1, R2, R3, R4, R5, R6, R7, R8, W1, W2, ALL, VENT, NONE. All numerical parameters can be specified in scientific notation e.g. 1.4e-9 and are assumed to be positive unless specified with a negative sign. Numerical parameters can be followed by units for convenience such as: s, µl, g/ml. If present, specified units will override the defined parameter order for that command unless there are also unitless parameters required. Time values are assumed to be in seconds. Volume values are assumed to be in micro-litres. Concentration values are assumed to be in grams per millilitre. Some commands require a name to be specified, for instance to indicate that the parameters refer to a specific protein. All references to that name must be typed the same. Names are written in the script beginning and ending with double quotes.

Operation of the Cartridge and Instrument

Assembling the Dry Cartridge

The wet and dry cartridges are supplied separately although this is not necessary. The antibody printed slide is placed face down into the dry cartridge onto a layer of adhesive. The slide and are clamped together to ensure good sealing of the channels against the slide.

Assembling the Wet Cartridge

Reagents may be loaded into the reservoirs through the precut holes in the bottom laminate. To ensure the reagents do not spill out of the channel port or vent port, a piece of tape is placed over the top of the wet cartridge sealing these ports. Once reagents are loaded a piece of tape is placed over the precut holes of the laminate to seal the reservoirs. In a final product, the reagents would be loaded during manufacturing and the sealing would occur through more appropriate mechanisms. Sample can be added to the sample port through the top of the wet cartridge at this time. Alternatively, a sample mechanism can be installed such that sample can be added after the entire cartridge is assembled.

Assembling the Wet and Dry Cartridge

An adhesive cover is removed from the back of the dry cartridge exposing the adhesive. The dry cartridge and the wet cartridge are aligned using the poke yoke and notches. The dry cartridge is pressed down onto the wet cartridge. The dry and wet cartridge are sealed with a clamp.

Cartridge/Instrument Interface

The assembled cartridge is slid into the cartridge entry port. Some force is applied to override the spring mechanism on the cartridge platform. Once the cartridge is completely inserted into the instrument, the release of pressure on the platform allows the venting ports of the cartridge to spring up and interface correctly with the manifold port.

Software and Assay Protocol

An embodiment of a bench-top instrument (FIG. 31) is connected to a personal computer through two USB cables. The final product may have the software, instrument and imaging screen all integrated into one product. For the bench-top instrument, the software is loaded on a personal computer. A script containing the protocol of the assay is loaded into the app. The script can begin by going to the first line of the script and pressing play. An assembled microfluidic cartridge (79) is loaded into the front of the instrument. With the script, the clamping motor (72) is engaged and through the cartridge clamping CAM (76) the cartridge can be clamped to interface with the manifold (73). The instrument can automatically control (through the script) the opening of the valves (65) through the Valve PCB (74) in the instrument. Simultaneously, the script activates the pump motor (75) moving the pump (68). This results in fluid moving from the specified reagent or buffer reservoir to the specified waste reservoir. Reagents are pushed sequentially across the array chamber until the entire assay is complete. Before the spot development with TMB, the software can activate the LEDs through the lower PCBs (78) and the camera located in the camera shroud (77). This creates a blank image for the assay. After TMB, the camera takes a spots image. The camera grabbing is also controlled through the script. The spots can be quantified by loading the specific setting file. The spots will be automatically quantified and a results file can be saved. The final product may illustrate the results in a user-friendly format and indicate whether the results indicate biomarker levels higher than cut-off.

REFERENCES

Adam, S. S., Key, N. S., and Greenberg, C. S. (2009). D-dimer antigen: current concepts and future prospects. *Blood*, 113.13, 2878-2887. [00340] Alexander, J. C., Silverman, N. A. and Chretien, P. B. (1976). Effect of Age and Cigarette Smoking on Carcinoembryonic Antigen Levels. *Journal of the American Medical Association*, 235 (18), 1975-1979.

Algarra, M., Gomes, D., & da Silva, J. C. E. (2013). Current analytical strategies for C-reactive protein quantification in blood. *Clinica Chimica Acta*, 415, 1-9.

Arribas J., Parra-Palau J. L., and Pedersen K. (2010). HER2 Fragmentation and Breast Cancer Stratification. *Clin Cancer Res*; 16(16); 4071-4073.

Ay, C., Vormittag, R., Dunkler, D., Simanek, R., Chiriac, A. L., Drach, J., . . . and Pabinger, I. (2009). D-dimer and prothrombin fragment 1+2 predict venous thromboembolism in patients with cancer: results from the Vienna Cancer and Thrombosis Study. *Journal of clinical oncology*, 27(25), 4124-4129.

Beauchemin, N. and Arabzadeh, A. (2013). Carcinoembryonic antigen-related cell adhesion molecules (CEACAMs) in cancer progression and metastasis. *Cancer Metastasis Reviews*, 32: 643-671.

Begum, M., Karim, S., Malik, A., Khurshid, R., Asif, M., Salim, A., . . . and Alqahtani, M. H. (2012). CA 15-3 (Mucin-1) and physiological characteristics of breast cancer from Lahore, Pakistan. *Asian Pacific Journal of Cancer Prevention*, 13(10), 5257-5261.

Burke, B. (2004). The role of matrix metalloproteinase 7 in innate immunity. *Immunobiology*, 209:51-56.

Danysh, B. P., Constantinou, P. E., Lukianova-Hleb, E. Y., Lapotko, D. O., and Carson, D. D. (2012). The MUC1 ectodomain: a novel and efficient target for gold nanoparticle clustering and vapor nanobubble generation. *Theranostics*, 2(8), 777.

Dong, J. and Ueda, H. (2017). ELISA-type assays of trace biomarkers using microfluidic methods. *WIREs Nanomedicine and Nanobiotechnology*, e1457.

Ekins. R. P (1989). Multi-analyte immunoassay. *J Pharm Biomed Anal*. 1989; 7(2): 155-68.

Fornier, M. N., Seidman, A. D., Schwartz, M. K., Ghani, F., Thiel, R., Norton, L., and Hudis, C. (2005). Serum HER2 extracellular domain in metastatic breast cancer patients treated with weekly trastuzumab and paclitaxel: association with HER2 status by immunohistochemistry and fluorescence in situ hybridization and with response rate. *Annals of Oncology*; 16; 234-239

Goldenberg, D. M., Neville, A. M., Carter, A. C., Go, V. L. W., Holyoke, E. D., Isselbacher, K. J., . . . and Schwartz, M. (1981). CEA (carcinoembryonic antigen): its role as a marker in the management of cancer. *Journal of cancer research and clinical oncology*, 101(3), 239-242.

Grzywa R, Lupicka-Slowik A, Walczak, M, et al. (2014). Highly Sensitive Detection of Cancer Antigen 15-3 Using Novel Avian IgY Antibodies. *Altex*; 31(1); 43-52

Hann, H. L., et al. (1990). Prognostic importance of serum transferrin and ferritin in childhood Hodgkin's disease, 66.2:313-316.

Jose, J., Sunil, P. M., Madhavan Nirmal, R., and Varghese, S. S. (2013). CYFRA 21-1: AN OVERVIEW. *Oral &Maxillofacial Pathology Journal*, 4(2).

Kalousova, M., Krechler, T., Jachymova, M., Kubena, A. A., ák, A., & Zima, T. (2012). Ferritin is an independent mortality predictor in patients with pancreas cancer. Results of a pilot study. *Tumor Biology*, 33.5: 1695-1700.

Leung, F., Diamanis, E. P. and Kulasingam, V. (2014). Ovarian Cancer Biomarkers: Current State and Future Implications from High-Throughput Technologies. *Advances in Clinical Chemistry*, 66, 25-77.

Lin, C. et al. (2010). Microfluidic immunoassays. *Journal for Laboratory Automation*. 15(3). 253-274.

Locker, G. Y., Hamilton, S., Harris, J., Jessup, J. M., Kemeny, N., Macdonald, J. S., . . . and Bast, R. C. (2006). ASCO 2006 Update of Recommendations for the Use of Tumor Markers in Gastrointestinal Cancer. *Journal of Clinical Oncology*, 24(33), 5313-5327.

Lucarelli, G., Ditonno, P., Bettocchi, C., Vavallo, A., Rutigliano, M., Galleggiante, V., . . . and Selvaggi, F. P. (2014). Diagnostic and prognostic role of preoperative circulating CA 15-3, CA 125, and beta-2 microglobulin in renal cell carcinoma. *Disease markers*, 689795.

Mattar, R., Andrade, C. R. A. D., DiFavero, G. M., Gama-Rodrigues, J. J., & Laudanna, A. A. (2002). Preoperative serum levels of CA72-4, CEA, CA19-9 and alpha-fetoprotein in patients with gastric cancer. *Revista do Hospital das Clinicas* 57.3: 89-92.

Maxim, Peter E. and Robert W. Veltri. (1986). Serum ferritin as a tumor marker in patients with squamous cell carcinoma of the head and neck. *Cancer*, 57.2: 305-311.

Melia, W. M., Bullock, S., Johnson, P. J., & Williams, R. (1983). Serum ferritin in hepatocellular carcinoma. A comparison with alphafetoprotein. *Cancer*, 51.11: 2112-2115.

Nakata, B., Ogawa, Y., Ishikawa, T., Ikeda, K., Kato, Y., Nishino, H., and Hirakawa, K. (2000). Serum CYFRA 21-1 is one of the most reliable tumor markers for breast carcinoma. *Cancer*, 89(6), 1285-1290.

Nayak, A., Salt, G., Verma, S. K., and Kishore, U. (2015). Proteomics Approach to Identify Biomarkers of Neurodegenerative Diseases. *Int Rev Neurobiol.* 121: 59-86.

Olle, E. W., Messamore, J., Deogracias, M. P., McClintock, S. D., Anderson, T. D., & Johnson, K. J. (2005). Comparison of antibody array substrates and the use of glycerol to normalize spot morphology. *Experimental and Molecular Pathology.* 79(3): 206-209

Pepys, M. B. and Hirschfield, G. M. (2003). C-reactive protein: a critical update. *Journal for Clinical Investigation.* 111:1805-1812.

Reverberi, R and Reverberi, L. (2007). Factors affecting the antigen-antibody reaction. *Blood Transfusion.* 5: 227-240.

Ricci, A., Mariotta, S., and Bronzetti, E. (2009). Serum CA 15-3 is increased in pulmonary fibrosis. *Sarcoidosis vasculitis and diffuse lung disease,* 26(1), 54-63.

Richens, J. L., Lunt, E. A., and O'Shea, P. (2015). Optimisation of protein microarray techniques for analysis of the plasma proteome: Minimisation of non-specific binding interactions. *International immunopharmacology,* 24(2), 166-168.

Howell, A. (1991). Prospective assessment of the role of five tumour markers in breast cancer. *Cancer Immunology, Immunotherapy.* 33.6: 403-410.

Romero, S., Fernandez, C., Arriero, J. M., Espasa, A., Candela, A., Martin, C. and Sanchez-Paya, J. (1996). CEA, CA15-3 and CYFRA21-1 in serum and pleural fluid of patients with pleural effusions. *Euro Respir J,* 9, 17-23.

Rubenstein, R. (2015). Proteomic analysis of prion diseases: Creating clarity or causing confusion. *Electrophoresis,* 33: 3631-3643.

Shao, X., Wang, X., Xu, X., Feng, J., Han, M., Zhang, H., ... and Jin, H. (2014). Outcome prediction values of soluble human epidermal growth factor receptor-2 extracellular domain in metastatic breast cancer. *Int J Clin Exp Pathol;* 7(3); 1108-1113

Su, S. B., Qin, S. Y., Chen, W., Luo, W., and Jiang, H. X. (2015). Carbohydrate antigen 19-9 for differential diagnosis of pancreatic carcinoma and chronic pancreatitis. *World J. Gastroenterol.* 21(14): 4323-4333.

Tonkin, A. (2015). Biomarkers in stable coronary heart disease, their modulation and cardiovascular risk: the LIPID biomarker study. *International Journal of Cardiology.* 201: 499-507.

Xue, Y., Clopton, P., Peacock, W. F., & Maisel, A. S. (2011). Serial Changes in high-sensitive troponin I predict outcome in patients with decompensated heart failure. *European Journal of Heart Failure.* 13: 37-42.

Yang, A. P., Liu, J., Lei, H. Y., Zhang, Q. W., Zhao, L., and Yang, G. H. (2014). CA72-4 combined with CEA, CA15 and CA19-9 improves the sensitivity for the early diagnosis of gastric cancer. *Clinica Chimica Acta,* 437: 183-186.

Yeh, Y. C., Sheu, B. S., Cheng, H. C., Wang, Y. L., Yang, H. B., and Wu, J. J. (2010). Elevated serum matrix metalloproteinase-3 and -7 in *H. pylori*-related gastric cancer can be biomarkers correlating with a poor survival. *Digestive diseases and sciences,* 55.6: 1649-1657.

Zhu, H. and Snyder, M. (2003). Protein chip technology. *Current Opinion in Chemical Biology.* 7: 55-63.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. An apparatus comprising a microfluidic cartridge comprising a wet cartridge, a dry cartridge, and a protein microarray, wherein the wet cartridge comprises:
   i) at least one reagent reservoir for storing a reagent fluid;
   ii) at least one buffer reservoir for storing a buffer fluid; and
   iii) a plurality of waste reservoirs for receiving the reagent fluid or the buffer fluid;
   and the dry cartridge comprises an aperture for detecting the protein microarray, the aperture defining an array chamber in conjunction with the protein microarray, and a plurality of microfluidic channels, the microfluidic channels comprising:
   i) a main channel coupled to the array chamber
   ii) at least one reagent channel configured to transfer the reagent fluid from each of the at least one reagent reservoir to the main channel;
   iii) at least one buffer channel configured to transfer the buffer fluid from each of the at least one buffer reservoir to the main channel to flush the reagent fluid from the main channel; and
   iv) a plurality of channels configured to transfer the reagent fluid or the buffer fluid to the waste reservoirs;
   wherein the channels are configured to allow for smooth flow of fluids and minimization of cross-contamination;
   wherein the dry cartridge is in alignment with and positioned above the wet cartridge and reagent fluid and buffer fluid in the reservoirs of the wet cartridge are pushed up against gravity into the channels of the dry cartridge and onto the protein microarray.

2. The apparatus of claim 1, wherein the wet cartridge includes,
   i) a plurality of reagent reservoirs;
   ii) a plurality of buffer reservoirs, wherein the number of buffer reservoirs is the same as the number of reagent reservoirs;
   iii) first and second waste reservoirs;
   iv) a plurality of vents corresponding to each of the buffer reservoirs, reagent reservoirs and waste reservoirs
   v) a sample well for receiving a fluid sample; and
   vi) a plurality of ports corresponding to each of the buffer reservoirs, reagent reservoirs, waste reservoirs and sample well;
   the dry cartridge includes an aperture for detecting the protein microarray, the aperture defining an array chamber in conjunction with the protein microarray, the main channel includes a main junction and a plurality of microfluidic channels are disposed around the main junction, the microfluidic channels comprising:
   i) a plurality of reagent channels, wherein each reagent channel corresponds to one of the reagent reservoirs of the wet cartridge;
   ii) a plurality of buffer channels, wherein each buffer channel corresponds to one of the buffer reservoirs of the wet cartridge and wherein each buffer channel connects to each corresponding reagent channel, to form buffer channel/reagent channel pairs;
   iii) a channel leading from the main junction to each buffer channel;
   iv) a channel connecting the array chamber to the first waste reservoir;
   v) a channel connecting the array chamber to the main junction;
   vi) a channel connecting the main junction to the second waste reservoir; wherein the channels are configured to allow for smooth flow of fluids and minimization of cross-contamination;

vii) a plurality of vents corresponding to each of the buffer reservoirs, reagent reservoirs and waste reservoirs of the wet cartridge; and viii) a plurality of liquid-impermeable, gas-permeable barriers corresponding to each of the vents;

and the dry cartridge is in alignment with and positioned above the wet cartridge and reagent fluid and buffer fluid in the reservoirs of the wet cartridge are pushed up against gravity into the channels of the dry cartridge, and the vents of the dry cartridge are capable of interfacing with a manifold of an instrument.

3. The apparatus of claim 1, wherein the wet cartridge includes, i) a plurality of reagent reservoirs;

ii) a plurality of buffer reservoirs, wherein the number of buffer reservoirs is the same as the number of reagent reservoirs iii) first and second waste reservoirs;

iv) a plurality of vents corresponding to each of the buffer reservoirs, reagent reservoirs and waste reservoirs;

v) a sample well for receiving a fluid sample; and vi) a plurality of ports corresponding to each of the buffer reservoirs, reagent reservoirs, waste reservoirs and sample well;

the dry cartridge comprises an aperture for detecting the protein microarray, the aperture defining an array chamber in conjunction with the protein microarray, and a plurality of microfluidic channels, the microfluidic channels comprising:

i) a plurality of reagent channels, wherein each reagent channel corresponds to one of the reagent reservoirs of the wet cartridge;

ii) a plurality of buffer channels, wherein each buffer channel corresponds to one of the buffer reservoirs of the wet cartridge, and wherein each buffer channel connects to each corresponding reagent channel, to form buffer channel/reagent channel pairs, and wherein each buffer channel connects to the main channel;

iii) a channel connecting the array chamber to the first waste reservoir;

iv) a channel connecting the array chamber to the main channel;

v) a channel connecting the main channel to the second waste reservoir; wherein the channels are configured to allow for smooth flow of fluids and minimization of cross-contamination;

vi) a plurality of vents corresponding to each of the buffer reservoirs, reagent reservoirs and waste reservoirs of the wet cartridge; and vii) a plurality of liquid-impermeable, gas-permeable barriers corresponding to each of the vents;

and wherein the dry cartridge is in alignment with and positioned above the wet cartridge and reagent fluid and buffer fluid in the reservoirs of the wet cartridge are pushed up against gravity into the channels of the dry cartridge, and the vents of the dry cartridge are capable of interfacing with a manifold of an instrument.

4. The apparatus of claim 3, wherein the fluid sample is a biological sample.

5. The apparatus of claim 1, wherein the protein microarray is an antibody microarray.

6. The apparatus of claim 2, wherein the instrument comprises an integrated microcontroller, pump, valves and optical sensor.

7. The apparatus of claim 6, wherein the optical sensor is configured to capture an image from the aperture of the dry cartridge of the protein microarray, the image being a readout from the optical sensor which can be interpreted using quantification software.

8. The apparatus of claim 1, wherein the at least one buffer reservoir, reagent reservoir and the waste reservoirs are configured to allow for pre-determined volumes.

9. The apparatus of claim 1, wherein the wet cartridge comprises a laminate bottom.

10. The apparatus of claim 9 wherein the laminate bottom comprises precut holes in alignment with each of the buffer reservoirs, reagent reservoirs and waste reservoirs for loading the reservoirs.

11. The apparatus of claim 1 wherein the wet cartridge is reusable.

12. The apparatus of claim 1 wherein the dry cartridge is disposable.

13. The apparatus of claim 1 wherein the microfluidic cartridge is disposable.

14. An instrument comprising the microfluidic apparatus of claim 1, the instrument further comprising a pump, a plurality of valves, a microcontroller and an optical system.

15. A microfluidic cartridge comprising a wet cartridge, a dry cartridge, and a protein microarray, wherein the wet cartridge comprises:

i) at least one reagent reservoir for storing a reagent fluid;

ii) at least one buffer reservoir for storing a buffer fluid; and iii) a plurality of waste reservoirs for receiving the reagent fluid or the buffer fluid;

and the dry cartridge comprises an aperture for detecting the protein microarray, the aperture defining an array chamber in conjunction with the protein microarray, and a plurality of microfluidic channels, the microfluidic channels comprising:

i) a main channel coupled to the array chamber;

ii) at least one reagent channel configured to transfer the reagent fluid from each of the at least one reagent reservoir to the main channel;

iii) at least one buffer channel configured to transfer the buffer fluid from each of the at least one buffer reservoir to the main channel to flush the reagent fluid from the main channel; and iv) a plurality of channels configured to transfer the reagent fluid or the buffer fluid to the waste reservoirs;

wherein the channels are configured to allow for smooth flow of fluids and minimization of cross-contamination;

wherein the dry cartridge is in alignment with and positioned above the wet cartridge and reagent fluid and buffer fluid in the reservoirs of the wet cartridge are pushed up against gravity into the channels of the dry cartridge and onto the protein microarray.

16. The microfluidic cartridge of claim 15 wherein the wet cartridge includes, i) a plurality of reagent reservoirs;

ii) a plurality of buffer reservoirs, wherein the number of buffer reservoirs is the same as the number of reagent reservoirs;

iii) first and second waste reservoirs;

iv) a plurality of vents corresponding to each of the buffer reservoirs, reagent reservoirs and waste reservoirs;

v) a sample well for receiving a fluid sample; and vi) a plurality of ports corresponding to each of the buffer reservoirs, reagent reservoirs, waste reservoirs and sample well the dry cartridge comprises an aperture for detecting the protein microarray, the aperture defining an array chamber in conjunction with the protein microarray, the main channel includes a main junction and a plurality of microfluidic channels are disposed around a main junction, the microfluidic channels comprising:
  i) a plurality of reagent channels, wherein each reagent channel corresponds to one of the reagent reservoirs of the wet cartridge;
  ii) a plurality of buffer channels, wherein each buffer channel corresponds to one of the buffer reservoirs of the wet cartridge and wherein each buffer channel connects to each corresponding reagent channel, to form buffer channel/reagent channel pairs;
  iii) a channel leading from the main junction to each buffer channel;
  iv) a channel connecting the array chamber to the first waste reservoir;
  v) a channel connecting the array chamber to the main junction;
  vi) a channel connecting the main junction to the second waste reservoir; wherein the channels are configured to allow for smooth flow of fluids and minimization of cross-contamination;
  vii) a plurality of vents corresponding to each of the buffer reservoirs, reagent reservoirs and waste reservoirs of the wet cartridge; and
  viii) a plurality of liquid-impermeable, gas-permeable barriers corresponding to each of the vents;
and wherein the dry cartridge is in alignment with and positioned above the wet cartridge and reagent fluid and buffer fluid in the reservoirs of the wet cartridge are pushed up against gravity into the channels of the dry cartridge, and the vents are capable of interfacing with a manifold of an instrument.

17. The microfluidic cartridge of claim 15, wherein the wet cartridge includes,
i) a plurality of reagent reservoirs;
ii) a plurality of buffer reservoirs, wherein the number of buffer reservoirs is the same as the number of reagent reservoirs;
iii) first and second waste reservoirs
iv) a plurality of vents corresponding to each of the buffer reservoirs, reagent reservoirs and waste reservoirs;
v) a sample well for receiving a fluid sample; and
vi) a plurality of ports corresponding to each of the buffer reservoirs, reagent reservoirs, waste reservoirs and sample well;
  the dry cartridge comprises an aperture for detecting the protein microarray, the aperture defining an array chamber in conjunction with the protein microarray, and a plurality of microfluidic channels, the microfluidic channels comprising:
    i) a plurality of reagent channels, wherein each reagent channel corresponds to one of the reagent reservoirs of the wet cartridge;
    ii) a plurality of buffer channels, wherein each buffer channel corresponds to one of the buffer reservoirs of the wet cartridge, and wherein each buffer channel connects to each corresponding reagent channel, to form buffer channel/reagent channel pairs, and wherein each buffer channel connects to a main channel;
    iii) a channel connecting the array chamber to the first waste reservoir;
    iv) a channel connecting the array chamber to the main channel;
    v) a channel connecting the main channel to the second waste reservoir; wherein the channels are configured to allow for smooth flow of fluids and minimization of cross-contamination;
    vi) a plurality of vents corresponding to each of the buffer reservoirs, reagent reservoirs and waste reservoirs of the wet cartridge; and
    vii) a plurality of liquid-impermeable, gas-permeable barriers corresponding to each of the vents;
  and wherein the dry cartridge is in alignment with and positioned above the wet cartridge and reagent fluid and buffer fluid in the reservoirs of the wet cartridge are pushed up against gravity into the channels of the dry cartridge, and the vents are capable of interfacing with a manifold of an instrument.

18. A wet cartridge comprising:
i) at least one reagent reservoir for storing a reagent fluid;
ii) at least one buffer reservoir for storing a buffer fluid;
iii) first and second waste reservoirs;
iv) a plurality of vents corresponding to each of the at least one buffer reservoir, at least one reagent reservoir and waste reservoirs;
v) a sample well for receiving a fluid sample; and
vi) a plurality of ports corresponding to each of the at least one buffer reservoir, at least one reagent reservoir, waste reservoirs and sample well;
wherein the wet cartridge is configured for alignment with and below a dry cartridge and a protein microarray, and configured to push reagent fluid and buffer fluid up against gravity through the corresponding ports.

19. A dry cartridge comprising an aperture for detecting a protein microarray, the aperture defining an array chamber in conjunction with the protein microarray, and a plurality of microfluidic channels disposed around a main junction, wherein:
A) the microfluidic channels are disposed around a main junction and comprise:
  i) at least one reagent channel, wherein each reagent channel corresponds to one reagent reservoir of a wet cartridge;
  ii) at least one buffer channel, wherein each buffer channel corresponds to one buffer reservoir of the wet cartridge and wherein each buffer channel connects to each corresponding reagent channel, to form a buffer channel/reagent channel pair;
  iii) a channel leading from the main junction to each buffer channel;
  iv) a channel connecting the array chamber to a first waste reservoir;
  v) a channel connecting the array chamber to the main junction;
  vi) a channel connecting the main junction to a second waste reservoir; wherein the channels are configured to allow for smooth flow of fluids and minimization of cross-contamination;
  vii) a plurality of vents corresponding to each of the buffer reservoirs, reagent reservoirs and waste reservoirs of the wet cartridge; and viii) a plurality of liquid-impermeable, gas-permeable barriers corresponding to each of the vents; or B) the microfluidic channels comprise:
  i) at least one reagent channel, wherein each reagent channel corresponds to one reagent reservoir of the wet cartridge;
  ii) at least one buffer channel, wherein each buffer channel corresponds to one buffer reservoir of the wet cartridge, and wherein each buffer channel connects to each corresponding reagent channel, to form a buffer channel/reagent channel pair, and wherein each buffer channel connects to a main channel;
  iii) a channel connecting the array chamber to the first waste reservoir;
  iv) a channel connecting the array chamber to the main channel;
  v) a channel connecting the main channel to the second waste reservoir; wherein the channels are configured to allow for smooth flow of fluids and minimization of cross-contamination; and
  vi) a plurality of vents corresponding to each of the buffer reservoirs, reagent reservoirs and waste reservoirs of the wet cartridge;

wherein the dry cartridge is configured for alignment with and above the wet cartridge, and the vents of the dry cartridge are configured for interfacing with a manifold of an instrument that pushes fluid from the reagent and buffer reservoirs of the wet cartridge up against gravity into corresponding channels of the dry cartridge.

* * * * *